(12) United States Patent
Nabel et al.

(10) Patent No.: US 7,635,688 B2
(45) Date of Patent: Dec. 22, 2009

(54) DEVELOPMENT OF A PREVENTIVE VACCINE FOR FILOVIRUS INFECTION IN PRIMATES

(75) Inventors: Gary J. Nabel, Washington, DC (US); Zhi-yong Yang, Potomac, MD (US); Nancy Sullivan, Kensington, MD (US); Anthony Sanchez, Lilburn, GA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 358 days.

(21) Appl. No.: 10/491,121

(22) PCT Filed: Sep. 24, 2002

(86) PCT No.: PCT/US02/30251

§ 371 (c)(1),
(2), (4) Date: Aug. 23, 2004

(87) PCT Pub. No.: WO03/028632

PCT Pub. Date: Apr. 10, 2003

(65) Prior Publication Data

US 2004/0259825 A1 Dec. 23, 2004

Related U.S. Application Data

(60) Provisional application No. 60/326,476, filed on Oct. 1, 2001.

(51) Int. Cl.
*A61K 31/70* (2006.01)
*A61K 49/00* (2006.01)
*A01N 65/00* (2006.01)
*A61K 48/00* (2006.01)
*C12N 5/00* (2006.01)
*C12N 15/00* (2006.01)
*C07H 21/02* (2006.01)

(52) U.S. Cl. ........................ 514/44; 424/93.1; 424/93.2; 424/9.2; 435/320.1; 435/325; 435/455; 536/23.1

(58) Field of Classification Search ........................ None
See application file for complete search history.

(56) References Cited

U.S. PATENT DOCUMENTS 6,171,596 B1    1/2001    Earl et al.
6,200,959 B1    3/2001    Haynes et al.

FOREIGN PATENT DOCUMENTS

WO    WO 97/42320    11/1997
WO    WO 99/32147    7/1999
WO    WO 01/16183    3/2001

OTHER PUBLICATIONS

Baize, Nature Medicine 11(7): 720-721, 2005.*
Hampton, JAMA 294(2):163-164, 2005.*
Australian Patent Office Communication dated Oct. 25, 2006, pursuant to Australia Patent Application No. 2002327049.
Australian Patent Office Communication dated Nov. 21, 2006, pursuant to Australia Patent Application No. 2005244541.
Sullivan, N.J. et al. 2003 "Accelerated vaccination for Ebola virus haemorrhagic fever in non-human primates." *Nature* 424:681-684.
Yang, Z.Y. et al. 2003 "Overcoming immunity to a viral vaccine by DNA priming before vector boosting." *J. Virol.* 77(1):799-803.
Geisbert, T.W. et al. 2002 "Evaluation in nonhuman primates of vaccines against Ebola virus." *Emerg. Infect. Dis.* 8(5):503-507.
Sullivan, N.J. et al. 2000 "Development of a preventive vaccine for Ebola virus infection in primates." *Nature* 408:605-609.
Pushko, P. et al. 2001 "Individual and bivalent vaccines based on alphavirus replicons protect guinea pigs against infection with Lassa and Ebola viruses." *J. Virol.* 75(23):11677-11685.
Aoki, K. et al. 1999 "Efficient generation of recombinant adenoviral vectors by Cre-lox recombination in vitro," *Mol. Med.* 5:224-231.
Baize, S. et al. 1999 "Defective humoral responses and extensive intravascular apoptosis are associated with fatal outcome in Ebola virus-infected patients," *Nature Med.* 5:423-426.
Bray, M. et al. 1998 "A mouse model for evaluation of prophylaxis and therapy of Ebola hemorrhagic fever," *J. Infect. Dis.* 178:651-661.
Connolly, B.M. et al. 1998 "Pathogenesis of experimental Ebola virus infection in guinea pigs," *J. Infect. Dis.* 179:S203-S217.
Davis, A.R. et al. 1985 "Expression of hepatitis B surface antigen with a recombinant adenovirus," *PNAS USA* 82:7560-7564.
Feldmann, H. et al. 1994 "Characterization of filoviruses based on differences in structure and antigenicity of the virion glycoprotein," *Virology* 199:469-473.
Fisher-Hoch, S.P. et al. 1985 "Pathophysiology of shock and hemorrhage in a fulminating viral infection (Ebola)," *J. Infect. Dis.* 152:887-894.
Hanke, T. et al. 1998 "Enhancement of MHC class I-restricted peptide-specific T cell induction by a DNA prime/MVA boost vaccination regime," *Vaccine* 16:439-445.
Kiley, M.P. et al. 1980 "Ebola virus: identification of virion structural proteins," *J. Gen. Virol.* 49:333-341.
Krieg, A.M. et al. 1995 "CpG motifs in bacterial DNA trigger direct B-cell activation," *Nature* 374:546-549.
Ksiazek, T.G. et al. 1992 "Enzyme immunosorbent assay for Ebola virus antigens in tissues of infected primates," *J. Clin. Microbiol.* 30:947-950.
Letvin, N.L. et al. 1997 "Potent, protective anti-HIV immune responses generated by bimodal HIV envelope DNA plus protein vaccination," *PNAS USA* 94:9378-9383.
Maryuama, T. et al. 1999 "Ebola virus can be effectively neutralized by antibody produced in natural human infection," *J. Virol.* 73:6024-6030.

(Continued)

*Primary Examiner*—Sumesh Kaushal
(74) *Attorney, Agent, or Firm*—Townsend and Townsend and Crew LLP

(57) ABSTRACT

The present invention relates generally to viral vaccines and, more particularly, to filovirus vaccines and methods of eliciting an immune response against a filovirus or disease caused by infection with filovirus.

9 Claims, 51 Drawing Sheets

OTHER PUBLICATIONS

Natuk, R.J. et al. 1992 "Adenovirus-human immunodeficiency virus (HIV) envelope recombinant vaccines elicit high-titered HIV-neutralizing antibodies in the dog model," *PNAS USA* 89:7777-7781.

Ohno, T. et al. 1994 "Gene therapy for vascular smooth muscle cell proliferation after arterial injury," *Science* 265:781-784.

Robinson, H.L. et al. 1999 "Neutralizing antibody-independent containment of immunodeficiency virus challenges by DNA priming and recombinant pox virus booster immunizations," *Nature Med.* 5:526-534.

Sanchez, A. et al. 1996 "The virion glycoproteins of Ebola viruses are encoded in two reading frames and are expressed through transcriptional editing," *PNAS USA* 93:3602-3607.

Sanchez A. et al. 1998 "Biochemical analysis of the secreted and virion glycoproteins of Ebola virus" *J. Virol.* 72:6442-6447.

Sato, Y. et al. 1996 "Immunostimulatory DNA sequences necessary for effective intradermal gene immunization," *Science* 273:352-354.

Schneider, J. et al. 1998 "Enhanced immunogenicity for CD8 + T cell induction and complete protective efficacy of malaria DNA vaccination by boosting with modified vaccinia virus Ankara," *Nature Med.* 4:397-402.

Sedegah, M. et al. 1994 "Protection against malaria by immunization with plasmid DNA encoding circumsporozoite protein," *PNAS USA* 91:9866-9870.

Sedegah, M. et al. 1998 "Boosting with recombinant vaccinia increases immunogenicity and protective efficacy of malaria DNA vaccine," *PNAS USA* 95:7648-7653.

Sullivan, N.J. et al. 2000 "Ebola virus pathogenesis and vaccine development" Symposium on Marburg and Ebola Viruses, Marburg, Germany, Oct. 1-4, 2000, Abstract 23, p. 35.

Tang, D.C. et al. 1992 "Genetic immunization is a simple method for eliciting an immune response," *Nature* 356:152-154.

Ulmer, J.B. et al. 1993 "Heterologous protection against influenza by injection of DNA encoding a viral protein," *Science* 259:1745-1749.

Vanderzanden, L. et al. 1998 "DNA vaccines expressing either the GP or NP genes of Ebola virus protect mice from lethal challenge," *Virology* 246:134-144.

Wang, B. et al. 1993 "Gene inoculation generates immune responses against human immunodeficiency virus type 1," *PNAS USA* 90:4156-4160.

Wilson, J. et al. 2000 "Epitopes involved in antibody-mediated protection from Ebola virus," *Science* 287:1664-1666.

Xiang, Z.Q. et al. 1996 "A replication-defective human adenovirus recombinant serves as a highly efficacious vaccine carrier," *Virology* 219:220-227.

Xiang, Z.Q. et al. 1999 "Induction of genital immunity by DNA priming and intranasal booster immunization with a replication-defective adenoviral recombinant," *J. Immunol.* 162:6716-6723.

Xu, L. et al. 1998 "Immunization for Ebola virus infection," *Nature Med.* 4:37-42.

Yang, Z. et al. 1998 "Distinct cellular interactions of secreted and transmembrane Ebola virus glycoproteins" *Science* 279:1034-1037.

Yang, Z. et al. 2000 "Identification of the Ebola virus glycoprotein as the main viral determinant of vascular cell cytotoxicity and injury" *Nature Med.* 6:886-889.

\* cited by examiner pVR1012x/s Ebola GP(Z)

Dra III (6986)
Xho I (6850)
Xma I (6576)
Kan r
Pvu I (6454)
Hin d III (6330)
Nde I (185)
Nde I (571)
CMV enhancer
Nco I (697)
Sac II (992)
CMV IE 5' UTR
Sph I (1092)
CMV IE Intron
Hpa I (1755)
Nco I (1848)
Sal I (1875)
Pml I (1882)
Eco RV (1894)
Not I (1899)
Xba I (1906)
Sal I (2081)

VRC6001
7188 bp

Sfi I (4747)
TbGH
Sph I (4377)
Eco RV (2597)
Ebola GP (Z)

FIG. 2 pVR1012-GP(Z) delta MUC delta FUR

Plasmid map of pVRC 6003, 6561 bp, showing the following features and restriction sites:

- Nde I (185)
- Nde I (571)
- CMV enhancer
- Sac II (992)
- CMV IE 5' UTR
- Sph I (1092)
- CMV IE Intron
- Hpa I (1755)
- Pst I (1865)
- Sal I (1875)
- Pml I (1882)
- Bcl I (1886)
- Eco RV (1894)
- Not I (1899)
- Xba I (1906)
- Sal I (2081)
- Eco RV (2597)
- Ebola GP Zaire delta MUC, delta FUR
- EarI/3436bp
- Pst I (3130)
- Bcl I (3215)
- Kpn I (3565)
- Sph I (3784)
- Kpn I (3812)
- bovine growth hormone poly A
- Hin d III (5703)
- Pvu I (5827)
- kanamycin resistance
- Xho I (6223)
- Dra III (6359)

FIG. 4 pVR1012-GP(Z) delta GP2 pVRC 6004
6724 bp

- Dra III (6522)
- Xho I (6386)
- kanamycin resistance
- Pvu I (5990)
- Hind III (5866)
- Nde I (185)
- Msc I (248)
- Nde I (571)
- CMV enhancer
- Sac II (992)
- CMV IE 5' UTR
- Sph I (1092)
- CMV IE Intron
- Pvu II (1701)
- Hpa I (1755)
- Pst I (1865)
- Sal I (1875)
- Pml I (1882)
- Bcl I (1886)
- Eco RV (1894)
- Not I (1899)
- Xba I (1906)
- Sal I (2081)
- Eco RV (2597)
- Pvu II (2704)
- Ebola GP Zaire
- Pst I (3022)
- delta GP2(BclI/BspEI)
- Bsp MI (3460)
- Kpn I (3728)
- Sph I (3947)
- Kpn I (3975)
- bovine growth hormone poly A
- Bst XI (4062)

FIG. 5 pVR1012-GP(Z) delta GP2 delta C-term B

- Dra III (6842)
- Xho I (6706)
- kanamycin resistance
- Pvu I (6310)
- Hind III (6186)
- Nde I (185)
- Msc I (248)
- Nde I (571)
- CMV enhancer
- Sac II (992)
- CMV IE 5' UTR
- Sph I (1092)
- Bsp EI (1436)
- CMV IE Intron
- Hpa I (1755)
- Pst I (1865)
- Sal I (1875)
- Pml I (1882)
- Bcl I (1886)
- Eco RV (1894)
- Not I (1899)
- Xba I (1906)
- Sal I (2081)
- Eco RV (2597)
- Ebola GP Zaire(BstXI/BspMI)
- Bsp EI (3088)
- Bcl I (3414)
- Msc I (3623)
- BstXI/BspMI
- Bsp MI (3780)
- Kpn I (4048)
- Sph I (4267)
- Kpn I (4295)
- bovine growth hormone poly A
- Bst XI (4382)

pVRC 6006
7044 bp

FIG. 7 pVR1012-GP(Z) delta GP2 delta FUS pVRC 6007
7106 bp

- Dra III (6904)
- Xho I (6768)
- kanamycin resistance
- Pvu I (6372)
- Hind III (6248)
- Bst XI (4444)
- bovine growth hormone poly A
- Kpn I (4357)
- Sph I (4329)
- Kpn I (4110)
- Bsp MI (3842)
- Bst XI (3732)
- Msc I (3575)
- 3508/3555
- Nde I (185)
- Msc I (248)
- Nde I (571)
- CMV enhancer
- Sac II (992)
- CMV IE 5' UTR
- Sph I (1092)
- CMV IE Intron
- Hpa I (1755)
- Sal I (1875)
- Pml I (1882)
- Eco RV (1894)
- Not I (1899)
- Xba I (1906)
- Sal I (2081)
- Eco RV (2597)
- Ebola GP Zaire (3508/3555)

FIG. 8 pVR1012-GP(Z) delta TM

*Dra* III (6712)
*Xho* I (6576)
kanamycin resistance
*Pvu* I (6180)
*Hin*d III (6056)
*Nde* I (185)
*Msc* I (248)
*Nde* I (571)
CMV enhancer
*Sac* II (992)
CMV IE 5' UTR
*Sph* I (1092)
CMV IE Intron
*Hpa* I (1755)
*Sal* I (1875)
*Pml* I (1882)
*Eco* RV (1894)
*Not* I (1899)
*Xba* I (1906)
*Sal* I (2081)
*Eco* RV (2597)
Ebola Glycoprotein Zaire Subtype (U31033)
*Bst* XI (4252)
bovine growth hormone poly A
*Kpn* I (4165)
*Sph* I (4137)
*Bgl* II (3930)
*Bst* XI (3780)
*Msc* I (3623)

pVRC 6008
6914 bp

FIG. 9 pVR1012-GP(Z) delta SGP pVRC 6052
6467 bp

- Dra III (6265)
- Xho I (6129)
- kanamycin resistance
- Pvu I (5733)
- Hind III (5609)
- Nde I (185)
- Msc I (248)
- Nde I (571)
- CMV enhancer
- Sac II (992)
- CMV IE 5' UTR
- Sph I (1092)
- CMV IE Intron
- Pvu II (1701)
- Hpa I (1755)
- Sal I (1875)
- Pml I (1882)
- Eco RV (1894)
- Not I (1899)
- Xba I (1906)
- Ebola GP (delta SGP)
- Pvu II (2932)
- Msc I (2936)
- Bst XI (3093)
- Bsp MI (3203)
- Kpn I (3471)
- Sph I (3690)
- Kpn I (3718)
- bovine growth hormone poly A
- Bst XI (3805)

FIG. 10

*Dra* III (6711)   pVR1012x/s Ebola GP(R)(dTM)
*Xho* I (6575)
*Cla* I (6484)
Kan
*Pvu* I (6179)
*Hin* d III (6055)

CMV enhancer
*Sac* II (992)
CMV IE 5' UTR
*Sph* I (1092)
CMV IE Intron
*Pvu* II (1701)
*Hpa* I (1755)
*Sal* I (1875)
*Pml* I (1882)
*Bcl* I (1886)
*Eco* RV (1927)
*Xmn* I (1955)
*Bcl* I (2061)
*Xmn* I (2693)
Ebola GP (Reston)(dTM)
*Sal* I (3002)
*Pvu* I (3420)
*Pvu* II (3474)
*Bgl* II (3455)
*Kpn* I (3715)
*Xba* I (3874)
*Bgl* II (3895)
*Sph* I (4102)
*Kpn* I (4130)
bovine growth hormone poly A
*Sfi* I (4472)

VRC6101
6913 bp

FIG. 11 pAdApt Ebola GP(R) (dTM)

VRC6110
8131 bp

- Ad5(bp1-454)
- Nde I (843)
- CMV enhancer
- Pml I (1279)
- Bcl I (1283)
- Eco RV (1291)
- Bcl I (1425)
- Nde I (2001)
- Ebola GP(Reston)(dTM)
- Pvu I (2784)
- Kpn I (3079)
- Xba I (3238)
- Bovine Growth Hormone Poly A
- Kpn I (3494)
- LoxP
- Ad5(bp3511-6093)
- Kas I (5553)
- Nar I (5554)
- Xho I (5823)
- Pml I (6026)
- Amp
- Pvu I (7502)

FIG. 12 pVR1012-GP(S)

- Dra III (6880)
- Nde I (185)
- Cla I (6653)
- Msc I (248)
- kanamycin resistance
- Nde I (571)
- Pvu I (6348)
- CMV enhancer
- Hind III (6224)
- Sac II (992)
- CMV IE 5' UTR
- Bsp EI (1436)
- CMV IE Intron
- Hpa I (1755)
- Sal I (1875)
- pVRC 6200
- 7082 bp
- Pml I (1882)
- Bcl I (1886)
- Not I (1899)
- Not I (1928)
- Xmn I (4650)
- bovine growth hormone poly A
- Kpn I (4333)
- Xba I (4077)
- Ebola Glycoprotein Sudan subtype (#U28134)
- Hpa I (3491)

FIG. 13 pVR1012x/s Ebola GP(S)

Dra III (6885)
Xho I (6749)
Cla I (6658)
Xma I (6475)
Kan r
Pvu I (6353)
Hin d III (6229)
Nde I (185)
Nde I (571)
CMV enhancer
Sac II (992)
CMV IE 5' UTR
Sph I (1092)
CMV IE Intron
Hpa I (1755)
Sal I (1875)
Pml I (1882)
Bcl I (1886)
Not I (1899)
Xho I (2161)
Xma I (2394)

VRC6201
7087 bp

Sfi I (4646)
TbGH
Sph I (4276)
Xba I (4048)
Hpa I (3462)
Ebola GP(S)

FIG. 14 pVR1012-GP(S) delta TM

- Dra III (6738)
- Cla I (6511)
- kanamycin resistance
- Pvu I (6206)
- Hind III (6082)
- Nde I (185)
- Msc I (248)
- Nde I (571)
- CMV enhancer
- Sac II (992)
- CMV IE 5' UTR
- Bsp EI (1436)
- CMV IE Intron
- Hpa I (1755)
- Sal I (1875)
- Not I (1903)
- Eco RV (1922)
- Eco RV (2191)
- Ebola Glycoprotein Sudan Subtype (#U28134)
- Hpa I (3466)
- Kpn I (4191)
- bovine growth hormone poly A
- Xmn I (4508)

pVRC 6202
6940 bp

FIG. 15 pVR1012-GP(IC)

pVRC 6300
7002 bp

- Dra III (6800)
- Xho I (6664)
- Cla I (6573)
- kanamycin resistance
- Pvu I (6268)
- Hind III (6144)
- Nde I (185)
- Msc I (248)
- Nde I (571)
- CMV enhancer
- Sac II (992)
- CMV IE 5' UTR
- Sph I (1092)
- Bsp EI (1436)
- CMV IE Intron
- Hpa I (1755)
- Pst I (1865)
- Sal I (1875)
- Pml I (1882)
- Eco RV (1894)
- Not I (1899)
- Xba I (1906)
- Xho I (2665)
- Ebola Glycoprotein Ivory Coast subtype (#U28006)
- Bst XI (2982)
- Bsp MI (3485)
- Msc I (3619)
- Xba I (3997)
- Bgl II (4018)
- Sph I (4225)
- Kpn I (4253)
- bovine growth hormone poly A
- Bst XI (4340)
- Xmn I (4570)

FIG. 16 pVR1012x/s Ebola GP(IC)

Dra III (6834)
Xho I (6698)
Cla I (6607)
Xma I (6424)
Kan r
Pvu I (6302)
Hin d III (6178)

Nde I (185)
Nde I (571)
CMV enhancer
Sac II (992)
CMV IE 5' UTR
Sph I (1092)
CMV IE Intron VRC6301
7036 bp Hpa I (1755)
Pst I (1865)
Sal I (1875)
Pml I (1882)
Eco RV (1894)
Not I (1899)
Xba I (1906)
Eco RI (1910)

Sfi I (4595)
TbGH
Sph I (4225)
Bgl II (4018)
Xba I (3997)
Eco RI (3993)

Xho I (2665)
Ebola GP(IC)

FIG. 17 pVR1012-GP(IC) delta TM

- Dra III (6683)
- Xho I (6547)
- Cla I (6456)
- kanamycin resistance
- Pvu I (6151)
- Hind III (6027)
- Nde I (185)
- Msc I (248)
- Nde I (571)
- CMV enhancer
- Sac II (992)
- CMV IE 5' UTR
- Sph I (1092)
- Bsp EI (1436)
- CMV IE Intron
- Hpa I (1755)
- Pst I (1865)
- Sal I (1875)
- Pml I (1882)
- Eco RV (1894)
- Not I (1899)
- Xba I (1906)
- Xho I (2665)
- Ebola Glycoprotein Ivory Coast subtype (#U28006)
- Bst XI (2982)
- Bsp MI (3485)
- Msc I (3619)
- Bgl II (3901)
- Sph I (4108)
- Kpn I (4136)
- bovine growth hormone poly A
- Bst XI (4223)
- Xmn I (4453)

pVRC 6302
6885 bp

FIG. 18 pVR1012x/s Ebola GP(IC)(dTM)

VRC6303
6889 bp

- Dra III (6687)
- Xho I (6551)
- Cla I (6460)
- Kan
- Pvu I (6155)
- Hin d III (6031)
- Sfi I (4448)
- Bovine Growth Hormone Poly A
- Kpn I (4106)
- Sph I (4078)
- Bgl II (3871)
- Bam HI (3397)
- Nde I (185)
- Nde I (571)
- CMV Enhancer
- Sac II (992)
- CMV IE 5' UTR
- Sph I (1092)
- CMV IE Intron
- Hpa I (1755)
- Pst I (1865)
- Sal I (1875)
- Pml I (1882)
- Bam HI (2536)
- Xho I (2645)
- Ebola GP(Ivory Coast)(dTM)

FIG. 19 pAdApt Ebola GP(IC)(dTM)

Xmn I (7746)
Pvu I (7517)
Amp
Ad5(bp1-454)
Nde I (843)
CMV Enhancer
Sal I (1272)
Pml I (1279)

Sal I (6144)
Pml I (6041)
Xho I (5838)
Nar I (5569)
Kas I (5568)

VRC6310
8146 bp

Bam HI (1933)
Xho I (2042)

Ebola GP(Ivory Coast)(dTM)
Bam HI (2794)
Bgl II (3274)

Ad5(bp3511-6093)
Bovine Growth Hormone Poly A
Kpn I (3509)
LoxP
Bgl II (3555)

FIG. 20 pVR1012x/s Ebola-NP

*Dra* III (7127)
*Xho* I (6991)
*Cla* I (6900)
*Xma* I (6717)
Kan r
*Pvu* I (6595)
*Hin* d III (6471)

CMV enhancer

*Sac* II (992)

CMV IE 5' UTR

CMV IE Intron

*Pvu* II (1701)
*Hpa* I (1755)
*Pst* I (1865)
MCS
*Sal* I (1875)
*Pml* I (1882)
*Eco* RV (1894)
*Not* I (1899)
*Xba* I (1906)
*Bam* H I (1921)
*Cla* I (1930)
*Bgl* II (2008)

VRC6401
7329 bp

*Sfi* I (4888)

TbGH

Untranslated NP

Ebola NP

*Xba* I (3401)

FIG. 23 pAdApt Ebola GP(S)

VRC6601
8338 bp

- Xmn I (7938)
- Pvu I (7709)
- Amp
- Ad5(1-454)
- Nde I (843)
- CMV Enhancer
- Sal I (1272)
- Pml I (1279)
- Bcl I (1283)
- Not I (1296)
- Xho I (1558)
- Ebola GP(Sudan)
- Hpa I (2859)
- Xba I (3445)
- TbGH
- Kpn I (3701)
- LoxP
- Ad5(3511-6093)
- Kas I (5760)
- Nar I (5761)
- Xho I (6030)
- Pml I (6233)
- Sal I (6336)

FIG. 26 pAdApt Ebola GP(S)(dTM)

Ad5(1-454)

Xmn I (7821)

Pvu I (7592)

Nde I (843)

CMV Enhancer
Sal I (1272)
Pml I (1279)
Bcl I (1283)
Not I (1296)
Eco RI (1323)
Xho I (1558)

Amp

Sal I (6219)
Pml I (6116)
Xho I (5913)
Nar I (5644)
Kas I (5643)

VRC6602
8221 bp

Ebola GP(Sudan)(dTM)
Eco RI (2445)
Hpa I (2859)

TbGH
LoxP
Kpn I (3584)

FIG. 28 pAdApt Ebola GP(Z)(dTM)

VRC6604
8199 bp

- Pvu I (7570)
- Amp
- Ad5(1-454)
- Nde I (843)
- CMV enhancer
- Pml I (1279)
- Eco RV (1291)
- Not I (1296)
- Xba I (1303)
- Cla I (1321)
- Cla I (1372)
- Eco RV (1994)
- Ebola GP(Zaire)(dTM)
- Bgl II (3327)
- TbGH
- Kpn I (3562)
- LoxP
- Bgl II (3608)
- Ad5(3511-6093)
- Kas I (5621)
- Nar I (5622)
- Xho I (5891)
- Pml I (6094)

FIG. 29 pVR1012 Marburg

VRC6701
7778 bp

- Dra III (7576)
- Xho I (7440)
- Cla I (7349)
- kanamycin resistance
- Pvu I (7044)
- Hin d III (6920)
- CMV enhancer
- Sac II (992)
- CMV IE 5' UTR
- CMV IE Intron
- Pvu II (1701)
- Hpa I (1755)
- Sal I (1875)
- Pml I (1882)
- Bcl I (1886)
- Eco RV (1894)
- Not I (1899)
- Xba I (1906)
- Xmn I (1992)
- Dra III (2197)
- Bam H I (2328)
- Kpn I (2592)
- Marburg
- Cla I (4207)
- Bgl I (4653)
- Hin d III (4779)
- Bam H I (4787)
- Bgl II (4793)
- Kpn I (5028)
- bovine growth hormone poly A
- Xmn I (5345)

FIG. 30 pVR1012x/s Marburg GP(dTM)

Dra III (6803)
Xho I (6667)
Cla I (6576)
Kan
Pvu I (6271)
Hin d III (6147)

CMV Enhancer
Sac II (992)
CMV IE 5' UTR
Sph I (1092)
CMV IE/Intron
Pvu II (1701)
Hpa I (1755)
Pst I (1865)
Sal I (1875)
Pml I (1882)
Bcl I (1886)
Eco RV (1894)
Not I (1899)
Xba I (1906)
Xmn I (1992)
Dra III (2197)
Bam H I (2328)
Kpn I (2592)

VRC6702
7005 bp

Sfi I (4564)
Bovine Growth Hormone Poly A
Kpn I (4222)
Sph I (4194)
Bgl II (3987)
Pst I (3706)
Marburg GP(dTM)

FIG. 31 pAdApt Marburg GP (dTM)

- Xmn I (7856)
- Pvu I (7627)
- Amp
- Ad5(bp1-454)
- Nde I (843)
- CMV Enhancer
- Sal I (1272)
- Pml I (1279)
- Bcl I (1283)
- Eco RV (1291)
- Not I (1296)
- Xba I (1303)
- Xmn I (1389)
- Dra III (1594)
- Bam H I (1725)
- Kpn I (1989)
- Nde I (1994)
- Sal I (6254)
- Pml I (6151)
- Xho I (5948)
- Nar I (5679)
- Kas I (5678)
- VRC6710 8256 bp
- GP(Marburg)(dTM)
- Ad5(bp3511-6093)
- Bgl II (3384)
- Bovine Growth Hormone Poly A
- Kpn I (3619)
- Bgl II (3665)
- LoxP

FIG. 32

*Dra* III (6245)
*Xho* I (6109)
*Cla* I (6018)
Kan
*Pvu* I (5713)
*Hin* d III (5589)

pVR1012x/s Lassa GP
*Nde* I (185)
*Nde* I (571)
CMV Enhancer
*Sac* II (992)
CMV IE 5' UTR
*Sph* I (1092)
CMV IE/Intron
*Pvu* II (1701)
*Hpa* I (1755)
*Pst* I (1865)
*Sal* I (1875)
*Pml* I (1882)
*Eco* RV (1894)
*Not* I (1899)
*Xba* I (1906)
*Eco* RI (1950)

VRC6800
6447 bp

*Sfi* I (4006)
Bovine Growth Poly A
*Sph* I (3649)
*Bgl* II (3442)
*Bam* H I (3436)
*Hin* d III (3273)
Lassa GP(Strain LP)
*Dra* III (2785)
*Pvu* II (2848)

FIG. 33 pVR1012x/s Lassa GP(dTM)

*Dra* III (6056)
*Xho* I (5920)
*Cla* I (5829)
Kan
*Pvu* I (5524)
*Hin* d III (5400)
*Nde* I (185)
*Nde* I (571)
CMV Enhancer
*Sac* II (992)
CMV IE 5' UTR
*Sph* I (1092)
CMV IE/Intron
*Pvu* II (1701)
*Hpa* I (1755)
*Pst* I (1865)
*Sal* I (1875)
*Pml* I (1882)
*Eco* RV (1894)
*Not* I (1899)
*Xba* I (1906)
*Eco* RI (1950)

VRC6801
6258 bp

*Sfi* I (3817)
Bovine Growth Poly A
*Sph* I (3460)
*Bgl* II (3253)
*Bam* H I (3247)
*Dra* III (2785)
*Pvu* II (2848)
Lassa GP(dTM)(Strain LP)

*PaeR7I* (6530)
*Xho*I (6530)
*Nru*I (6475)
*Bsp*DI (6439)
*Cla*I (6439)
*Sma*I (6258)
*Xma*I (6256)
kanamycin resistance
*Ssp*I (6207)
*Pvu*I (6134)
*Hind*III (6010)

*Stu*I (5508)
*Aat*I (5508)

pVR1012x/s
*Spe*I (336)
CMV enhancer
*Sna*BI (677)
*Ecl*136II (903)
*Sac*I (905)
*Sac*II (992)
*Eag*I (992)
*Ecl*XI (992)
*Ksp*I (992)
*Xma*III (992)
CMV IE 5' UTR
*Acc*III (1436)
*Bse*AI (1436)
*Bsp*EI (1436)
*Mro*I (1436)
*Sap*I (1454)
CMV IE intron
*Afl*II (1670)
*Bfr*I (1670)
*Hpa*I (1755)
multiple cloning site
*Sal*I (1875)
*Acc*I (1876)
*Eco*RV (1883)

pVR1012x/s Ebola GP(Z) delta TM/h (P87666)
6868 bp

*Sfi*I (4427)
bovine growth hormone poly A
*Bgl*II (3850)
*Eco*RI (3844)
*Pma*CI (3840)
*Bbr*PI (3840)
*Pml*I (3840)
*Apa*I (3708)
*Bsp*120I (3704)

*Bcg*I (2399)
*Asp*700 (2466)
*Xmn*I (2466)
*Xba*I (2628)
Ebola GP(Z) (P87666)/h
*Bam*H I (3224)

DraIII (6122)
PaeR7I (5986)
XhoI (5986)
NruI (5931)
BspDI (5895)
ClaI (5895)
SmaI (5714)
XmaI (5712)
Kan.
EcoNI (5675)
SspI (5663)
PvuI (5590)
HindIII (5466)

BsrGI (280)
SspBI (280)
SpeI (336)
CMV Enhancer/Promoter
SnaBI (677)
HTLV-1R Region
HpaI (1224)
CMV IE Splicing Acceptor
SalI (1344)
AccI (1345)
EcoRV (1352)
BcgI (1400)
Asp700 (1449)
XmnI (1449)
XcmI (1484)
XbaI (2012)

CMV/R-GP(S,Q66798)(dTM)/h
6324 bp

SfiI (3883)
BstXI (3641)
Tbgh
KpnI (3554)
Asp718 (3550)
Acc65I (3550)
BglII (3319)
EcoRI (3313)
PpuMI (3100)
BamHI (2709)
SexAI (2383)
Ebola GP(S,Q66798)(delta TM)/h

FIG. 40 pVR1012x/s Lassa(codon optimized)

- Dra III (6034)
- Xho I (5898)
- Cla I (5807)
- Xma I (5624)
- kanamycin resistance
- Pvu I (5502)
- Hin d III (5378)
- Nde I (185)
- Nde I (571)
- CMV enhancer
- Sac II (992)
- CMV IE 5' UTR
- Sph I (1092)
- CMV IE Intron
- Hpa I (1755)
- Sal I (1875)
- Pml I (1882)
- Eco RV (1894)
- Not I (1899)
- Xba I (1906)
- Eco RV (1914)
- Sfi I (2054)
- Lassa (codon optimized)
- Sfi I (3795)
- bovine growth hormone poly A
- Sph I (3425)
- Bgl II (3218)
- Bam HI (3212)
- Pml I (3208)

VRC6802
6236 bp

FIG. 41 pVR1012x/s Marburg (codon optimized)

Dra III (6700)
Xho I (6564)
Cla I (6473)
Xma I (6290)
kanamycin resistance
Pvu I (6168)
Hin d III (6044)

Nde I (185)
Nde I (571)
CMV enhancer
Nco I (697)
Sac II (992)
CMV IE 5' UTR
CMV IE Intron
Pvu II (1701)
Hpa I (1755)
Nco I (1848)
Sal I (1875)
Pml I (1882)
Eco RV (1894)
Not I (1899)
Xba I (1906)
Eco RV (1914)
Hpa I (2433)
Marburg (codon optimized)

VRC6703
6902 bp

Sfi I (4461)
bovine growth hormone poly A
Bgl II (3884)
Bam HI (3878)
Pml I (3874)
Dra III (3207)

Domain: GP — GP/sGP Identity, Mucin-like, Fusion, Trimerization, TM; Furin Cleavage Site

FIG. 46

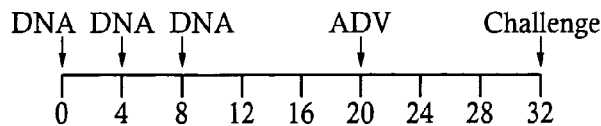
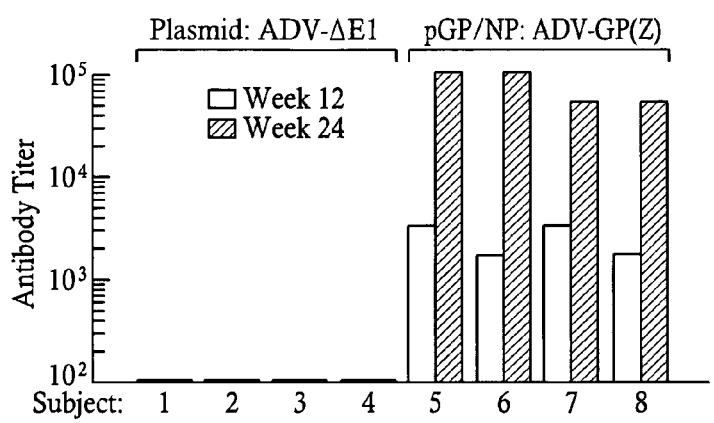
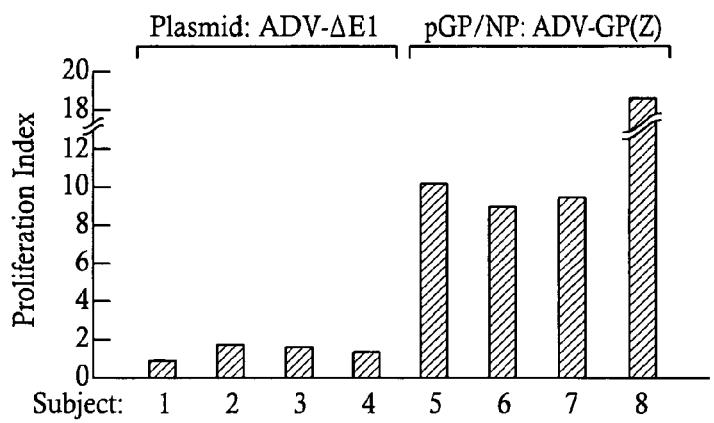
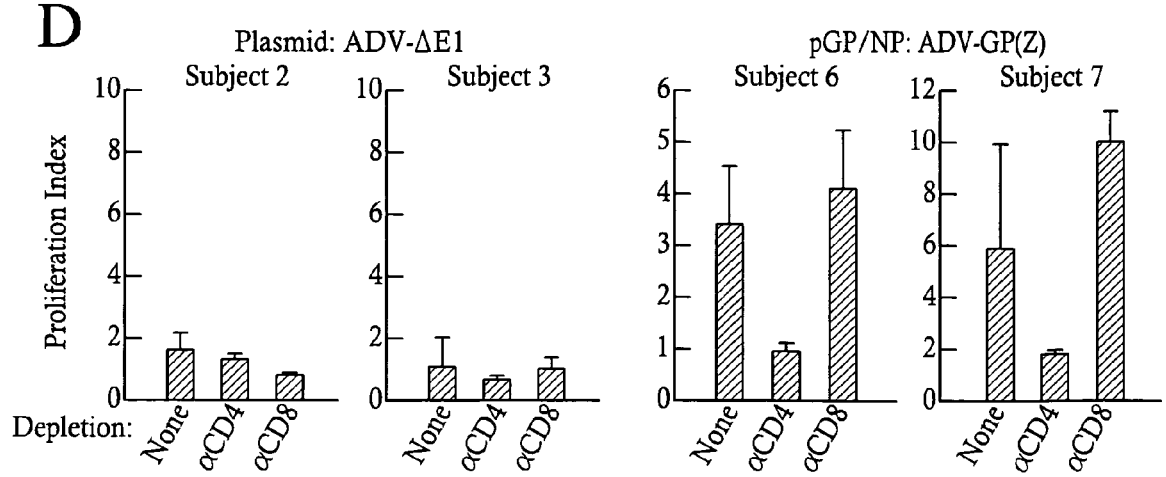
FIG. 48

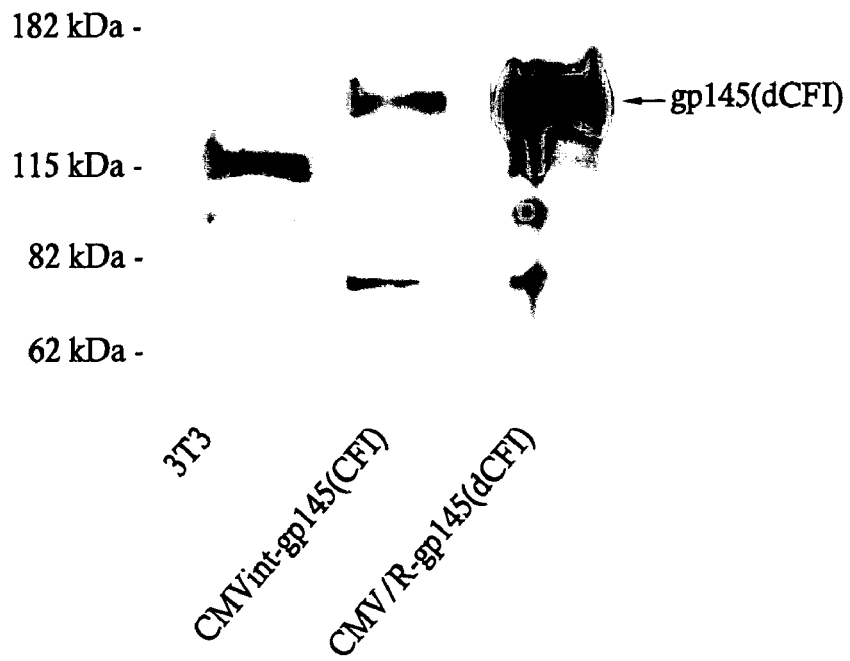
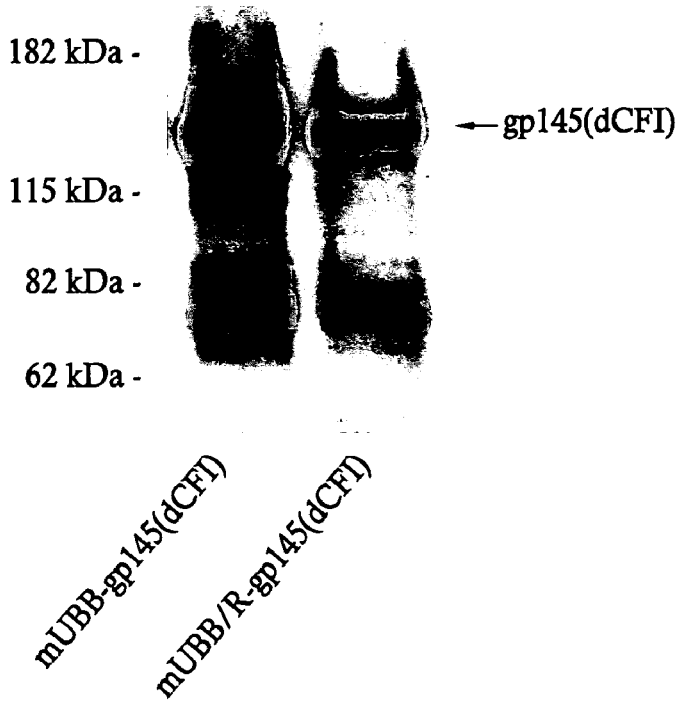
FIG. 50

SEQUENCE LISTING

<160> NUMBER OF SEQ ID NOS: 52

<210> SEQ ID NO 1
<211> LENGTH: 7154
<212> TYPE: DNA
<213> ORGANISM: Artificial Sequence
<220> FEATURE:
<223> OTHER INFORMATION: Synthetic Construct pVR1012 -GP(Z)

<400> SEQUENCE: 1

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgaccccg cccattgacg tcaataatga cgtatgttcc      480
catagtaacg ccaataggga ctttccattg acgtcaatgg gtggagtatt tacggtaaac     540
tgcccacttg gcagtacatc aagtgtatca tatgccaagt acgccccta ttgacgtcaa      600 tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag     900
agctcgttta gtgaaccgtc agatcgcctg gagacgccat ccacgctgtt ttgacctcca     960
tagaagacac cgggaccgat ccagcctccg cggccgggaa cggtgcattg gaacgcggat    1020
tccccgtgcc aagagtgacg taagtaccgc ctatagactc tataggcaca ccctttggc    1080 tcttatgcat gctatactgt ttttggcttg gggcctatac accccgctt ccttatgcta    1140 taggtgatgg tatagcttag cctataggtg tgggttattg accattattg accactcccc    1200
tattggtgac gatactttcc attactaatc cataacatgg ctctttgcca caactatctc    1260
tattggctat atgccaatac tctgtccttc agagactgac acggactctg tatttttaca    1320
ggatggggtc ccatttatta tttacaaatt cacatataca acaacgccgt cccccgtgcc    1380
cgcagttttt attaaacata gcgtgggatc tccacgcgaa tctcgggtac gtgttccgga    1440
```

```
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgaca cgtgtgatca gatatcgcgg ccgctctaga ccaggccctg   1920
gatcgatcca acaacacaat gggcgttaca ggaatattgc agttacctcg tgatcgattc   1980
aagaggacat cattctttct ttgggtaatt atccttttcc aaagaacatt ttccatccca   2040
cttggagtca tccacaatag cacattacag gttagtgatg tcgacaaact agtttgtcgt   2100
gacaaactgt catccacaaa tcaattgaga tcagttggac tgaatctcga agggaatgga   2160
gtggcaactg acgtgccatc tgcaactaaa agatggggct tcaggtccgg tgtcccacca   2220
aaggtggtca attatgaagc tggtgaatgg gctgaaaact gctacaatct tgaaatcaaa   2280
aaacctgacg ggagtgagtg tctaccagca gcgccagacg ggattcgggg cttccccgg   2340 tgccggtatg tgcacaaagt atcaggaacg ggaccgtgtg ccggagactt tgccttccat   2400
aaagagggtg ctttcttcct gtatgatcga cttgcttcca cagttatcta ccgaggaacg   2460
actttcgctg aaggtgtcgt tgcatttctg atactgcccc aagctaagaa ggacttcttc   2520
agctcacacc ccttgagaga gccggtcaat gcaacggagg accgtctag tggctactat   2580 tctaccacaa ttagatatca ggctaccggt tttggaacca atgagacaga gtacttgttc   2640
gaggttgaca atttgaccta cgtccaactt gaatcaagat tcacaccaca gtttctgctc   2700
cagctgaatg agacaatata tacaagtggg aaaaggagca ataccacggg aaaactaatt   2760
tggaaggtca accccgaaat tgatacaaca atcggggagt gggccttctg ggaaactaaa   2820
aaaaacctca ctagaaaaat tcgcagtgaa gagttgtctt tcacagttgt atcaaacgga   2880
gccaaaaaca tcagtggtca gagtccggcg cgaacttctt ccgacccagg gaccaacaca   2940
acaactgaag accacaaaat catggcttca gaaaattcct ctgcaatggt tcaagtgcac   3000
agtcaaggaa gggaagctgc agtgtcgcat ctaacaaccc ttgccacaat ctccacgagt   3060
ccccaatccc tcacaaccaa accaggtccg gacaacagca cccataatac acccgtgtat   3120
aaacttgaca tctctgaggc aactcaagtt gaacaacatc accgcagaac agacaacgac   3180
agcacagcct ccgacactcc ctctgccacg accgcagccg gacccccaaa agcagagaac   3240
accaacacga gcaagagcac tgacttcctg gaccccgcca ccacaacaag tccccaaaac   3300
cacagcgaga ccgctggcaa caacaacact catcaccaag ataccggaga agagagtgcc   3360
agcagcggga agctaggctt aattaccaat actattgctg gagtcgcagg actgatcaca   3420
ggcgggagaa gaactcgaag agaagcaatt gtcaatgctc aacccaaatg caacccctaat   3480 ttacattact ggactactca ggatgaaggt gctgcaatcg gactggcctg gataccatat   3540
ttcgggccag cagccgaggg aatttacata gaggggctaa tgcacaatca agatggttta   3600
atctgtgggt tgagacagct ggccaacgag acgactcaag ctcttcaact gttcctgaga   3660
gccacaactg agctacgcac cttttcaatc ctcaaccgta aggcaattga tttcttgctg   3720
cagcgatggg gcggcacatg ccacattctg ggaccggact gctgtatcga accacatgat   3780
tggaccaaga acataacaga caaaattgat cagattattc atgattttgt tgataaaacc   3840
```

```
cttccggacc aggggacaa tgacaattgg tggacaggat ggagacaatg gataccggca    3900
ggtattggag ttacaggcgt tgtaattgca gttatcgctt tattctgtat atgcaaattt    3960
gtcttttagt ttttcttcag attgcttcat ggaaaagctc agcctcaaat caatgaaacc    4020
aggatttaat tatatggatt acttgaatct aagattactt gacaaatgat aatataatac    4080
actggagctt taaacatagc caatgtgatt ctaactcctt taaactcaca gttaatcata    4140
aacaaggttt gaggtaccga gctcgaattg atctgctgtg ccttctagtt gccagccatc    4200
tgttgtttgc ccctcccccg tgccttcctt gaccctggaa ggtgccactc ccactgtcct    4260
ttcctaataa aatgaggaaa ttgcatcgca ttgtctgagt aggtgtcatt ctattctggg    4320
gggtggggtg gggcaggaca gcaaggggga ggattgggaa gacaatagca ggcatgctgg    4380
ggatgcggtg ggctctatgg gtacccaggt gctgaagaat tgacccggtt cctcctgggc    4440
cagaaagaag caggcacatc cccttctctg tgacacaccc tgtccacgcc cctggttctt    4500
agttccagcc ccactcatag gacactcata gctcaggagg gctccgcctt caatcccacc    4560
cgctaaagta cttggagcgg tctctccctc cctcatcagc ccaccaaacc aaacctagcc    4620
tccaagagtg ggaagaaatt aaagcaagat aggctattaa gtgcagaggg agagaaaatg    4680
cctccaacat gtgaggaagt aatgagagaa atcatagaat tcttccgct tcctcgctca    4740
ctgactcgct gcgctcggtc gttcggctgc ggcgagcggt atcagctcac tcaaaggcgg    4800
taatacggtt atccacagaa tcaggggata acgcaggaaa gaacatgtga gcaaaaggcc    4860
agcaaaaggc caggaaccgt aaaaaggccg cgttgctggc gttttccat aggctccgcc    4920
cccctgacga gcatcacaaa aatcgacgct caagtcagag gtggcgaaac ccgacaggac    4980
tataaagata ccaggcgttt ccccctggaa gctccctcgt gcgctctcct gttccgaccc    5040
tgccgcttac cggatacctg tccgcctttc tcccttcggg aagcgtggcg ctttctcata    5100
gctcacgctg taggtatctc agttcggtgt aggtcgttcg ctccaagctg ggctgtgtgc    5160
acgaaccccc cgttcagccc gaccgctgcg ccttatccgg taactatcgt cttgagtcca    5220
acccggtaag acacgactta tcgccactgg cagcagccac tggtaacagg attagcagag    5280
cgaggtatgt aggcggtgct acagagttct tgaagtggtg gcctaactac ggctacacta    5340
gaagaacagt atttggtatc tgcgctctgc tgaagccagt taccttcgga aaaagagttg    5400
gtagctcttg atccggcaaa caaaccaccg ctggtagcgg tggtttttt gtttgcaagc    5460
agcagattac gcgcagaaaa aaaggatctc aagaagatcc tttgatcttt tctacggggt    5520
ctgacgctca gtggaacgaa aactcacgtt aagggatttt ggtcatgaga ttatcaaaaa    5580
ggatcttcac ctagatcctt ttaaattaaa aatgaagttt taaatcaatc taagtatat    5640
atgagtaaac ttggtctgac agttaccaat gcttaatcag tgaggcacct atctcagcga    5700
tctgtctatt tcgttcatcc atagttgcct gactcggggg ggggggcgc tgaggtctgc    5760
ctcgtgaaga aggtgttgct gactcatacc aggcctgaat cgccccatca tccagccaga    5820
aagtgaggga gccacggttg atgagagctt tgttgtaggt ggaccagttg gtgattttga    5880
acttttgctt tgccacggaa cggtctgcgt tgtcgggaag atgcgtgatc tgatccttca    5940
actcagcaaa agttcgattt attcaacaaa gccgccgtcc cgtcaagtca gcgtaatgct    6000
ctgccagtgt tacaaccaat taaccaattc tgattagaaa aactcatcga gcatcaaatg    6060
aaactgcaat ttattcatat caggattatc aataccatat ttttgaaaaa gccgtttctg    6120
taatgaagga gaaaactcac cgaggcagtt ccataggatg caagatcct ggtatcggtc    6180
```

-continued

| | |
|---|---|
| tgcgattccg actcgtccaa catcaataca acctattaat ttccccctcgt caaaaataag | 6240 |
| gttatcaagt gagaaatcac catgagtgac gactgaatcc ggtgagaatg caaaagctt | 6300 |
| atgcatttct ttccagactt gttcaacagg ccagccatta cgctcgtcat caaaatcact | 6360 |
| cgcatcaacc aaaccgttat tcattcgtga ttgcgcctga gcgagacgaa atacgcgatc | 6420 |
| gctgttaaaa ggacaattac aaacaggaat cgaatgcaac cggcgcagga acactgccag | 6480 |
| cgcatcaaca atattttcac ctgaatcagg atattcttct aatacctgga atgctgtttt | 6540 |
| cccggggatc gcagtggtga gtaaccatgc atcatcagga gtacggataa aatgcttgat | 6600 |
| ggtcggaaga ggcataaatt ccgtcagcca gtttagtctg accatctcat ctgtaacatc | 6660 |
| attggcaacg ctacctttgc catgtttcag aaacaactct ggcgcatcgg gcttcccata | 6720 |
| caatcgatag attgtcgcac ctgattgccc gacattatcg cgagcccatt tatacccata | 6780 |
| taaatcagca tccatgttgg aatttaatcg cggcctcgag caagacgttt cccgttgaat | 6840 |
| atggctcata caccccttg tattactgtt tatgtaagca gacagtttta ttgttcatga | 6900 |
| tgatatattt ttatcttgtg caatgtaaca tcagagattt tgagacacaa cgtggctttc | 6960 |
| cccccccccc cattattgaa gcattatca gggttattgt ctcatgagcg gatacatatt | 7020 |
| tgaatgtatt tagaaaaata aacaaatagg ggttccgcgc acatttcccc gaaaagtgcc | 7080 |
| acctgacgtc taagaaacca ttattatcat gacattaacc tataaaaata ggcgtatcac | 7140 |
| gaggcccttt cgtc | 7154 |

<210> SEQ ID NO 2
<211> LENGTH: 7188
<212> TYPE: DNA
<213> ORGANISM: Artificial Sequence
<220> FEATURE:
<223> OTHER INFORMATION: Synthetic Construct pVR1012x/s Ebola GP(Z)

<400> SEQUENCE: 2

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcagattgg | 240 |
| ctattggcca ttgcatacgt tgtatccata tcataatatg tacatttata ttggctcatg | 300 |
| tccaacatta ccgccatgtt gacattgatt attgactagt tattaatagt aatcaattac | 360 |
| ggggtcatta gttcatagcc catatatgga gttccgcgtt acataactta cggtaaatgg | 420 |
| cccgcctggc tgaccgccca acgacccccg cccattgacg tcaataatga cgtatgttcc | 480 |
| catagtaacg ccaataggga cttccattg acgtcaatgg gtggagtatt tacggtaaac | 540 |
| tgcccacttg gcagtacatc aagtgtatca tatgccaagt acgccccta ttgacgtcaa | 600 |
| tgacggtaaa tggcccgcct ggcattatgc ccagtacatg accttatggg actttcctac | 660 |
| ttggcagtac atctacgtat tagtcatcgc tattaccatg gtgatgcggt tttggcagta | 720 |
| catcaatggg cgtggatagc ggtttgactc acggggattt ccaagtctcc accccattga | 780 |
| cgtcaatggg agtttgtttt ggcaccaaaa tcaacgggac tttccaaaat gtcgtaacaa | 840 |
| ctccgcccca ttgacgcaaa tgggcggtag gcgtgtacgg tggaggtct atataagcag | 900 |
| agctcgttta gtgaaccgtc agatcgcctg gagacgccat ccacgctgtt ttgacctcca | 960 |
| tagaagacac cgggaccgat ccagcctccg cggccgggaa cggtgcattg gaacgcggat | 1020 |
| tccccgtgcc aagagtgacg taagtaccgc ctatagactc tataggcaca ccctttggc | 1080 |

```
tcttatgcat gctatactgt ttttggcttg gggcctatac accccgctt ccttatgcta    1140 taggtgatgg tatagcttag cctataggtg tgggttattg accattattg accactcccc    1200
tattggtgac gatactttcc attactaatc cataacatgg ctctttgcca caactatctc    1260
tattggctat atgccaatac tctgtccttc agagactgac acggactctg tatttttaca    1320
ggatggggtc ccatttatta tttacaaatt cacatataca acaacgccgt cccccgtgcc    1380
cgcagttttt attaaacata gcgtgggatc tccacgcgaa tctcgggtac gtgttccgga    1440
catgggctct tctccggtag cggcggagct tccacatccg agccctggtc ccatgcctcc    1500
agcggctcat ggtcgctcgg cagctccttg ctcctaacag tggaggccag acttaggcac    1560
agcacaatgc ccaccaccac cagtgtgccg cacaaggccg tggcggtagg gtatgtgtct    1620
gaaaatgagc gtggagattg ggctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tcctttccat gggtcttttc    1860
tgcagtcacc gtcgtcgaca cgtgtgatca gatatcgcgg ccgctctaga ccaggccctg    1920
gatcgatcca acaacacaat gggcgttaca ggaatattgc agttacctcg tgatcgattc    1980
aagaggacat cattctttct tgggtaatt atccttttcc aaagaacatt ttccatccca    2040
cttggagtca tccacaatag cacattacag gttagtgatg tcgacaaact agtttgtcgt    2100
gacaaactgt catccacaaa tcaattgaga tcagttggac tgaatctcga agggaatgga    2160
gtggcaactg acgtgccatc tgcaactaaa agatggggct tcaggtccgg tgtcccacca    2220
aaggtggtca attatgaagc tggtgaatgg gctgaaaact gctacaatct tgaaatcaaa    2280
aaacctgacg ggagtgagtg tctaccagca gcgccagacg ggattcgggg cttccccgg    2340 tgccggtatg tgcacaaagt atcaggaacg ggaccgtgtg ccggagactt tgccttccat    2400
aaagagggtg ctttcttcct gtatgatcga cttgcttcca cagttatcta ccgaggaacg    2460
actttcgctg aaggtgtcgt tgcatttctg tatactgcccc aagctaagaa ggacttcttc    2520
agctcacacc ccttgagaga gccggtcaat gcaacggagg accgtctag tggctactat    2580 tctaccacaa ttagatatca ggctaccggt tttggaacca atgagacaga gtacttgttc    2640
gaggttgaca atttgaccta cgtccaactt gaatcaagat tcacaccaca gtttctgctc    2700
cagctgaatg agacaatata tacaagtggg aaaaggagca ataccacggg aaaactaatt    2760
tggaaggtca accccgaaat tgatacaaca atcggggagt gggccttctg ggaaactaaa    2820
aaaaacctca ctagaaaaat tcgcagtgaa gagttgtctt tcacagttgt atcaaacgga    2880
gccaaaaaca tcagtggtca gagtccggcg cgaacttctt ccgacccagg gaccaacaca    2940
acaactgaag accacaaaat catggcttca gaaaattcct ctgcaatggt tcaagtgcac    3000
agtcaaggaa gggaagctgc agtgtcgcat ctaacaaccc ttgccacaat ctccacgagt    3060
ccccaatccc tcacaaccaa accaggtccg gacaacagca cccataatac acccgtgtat    3120
aaacttgaca tctctgaggc aactcaagtt gaacaacatc accgcagaac agacaacgac    3180
agcacagcct ccgacactcc ctctgccacg accgcagccg gaccccaaaa gcagagaac    3240 accaacacga gcaagagcac tgacttcctg gaccccgcca ccaacaacaag tccccaaaac    3300 cacagcgaga ccgctggcaa caacaacact catcaccaag ataccggaga agagagtgcc    3360
agcagcggga agctaggctt aattaccaat actattgctg gagtcgcagg actgatcaca    3420
```

```
ggcgggagaa gaactcgaag agaagcaatt gtcaatgctc aacccaaatg caaccctaat    3480
ttacattact ggactactca ggatgaaggt gctgcaatcg gactggcctg gataccatat    3540
ttcgggccag cagccgaggg aatttacata gagggctaa tgcacaatca agatggttta    3600
atctgtgggt tgagacagct ggccaacgag acgactcaag ctcttcaact gttcctgaga    3660
gccacaactg agctacgcac cttttcaatc ctcaaccgta aggcaattga tttcttgctg    3720
cagcgatggg gcggcacatg ccacattctg ggaccggact gctgtatcga accacatgat    3780
tggaccaaga acataacaga caaaattgat cagattattc atgattttgt tgataaaacc    3840
cttccggacc aggggacaa tgacaattgg tggacaggat ggagacaatg gataccggca    3900
ggtattggag ttacaggcgt tgtaattgca gttatcgctt tattctgtat atgcaaattt    3960
gtcttttagt ttttcttcag attgcttcat ggaaaagctc agcctcaaat caatgaaacc    4020
aggatttaat tatatggatt acttgaatct aagattactt gacaaatgat aatataatac    4080
actggagctt taaacatagc caatgtgatt ctaactcctt taaactcaca gttaatcata    4140
aacaaggttt gaggtaccga gctcgaattg atctgctgtg ccttctagtt gccagccatc    4200
tgttgtttgc ccctcccccg tgccttcctt gaccctggaa ggtgccactc ccactgtcct    4260
ttcctaataa aatgaggaaa ttgcatcgca ttgtctgagt aggtgtcatt ctattctggg    4320
gggtggggtg gggcaggaca gcaagggggga ggattgggaa gacaatagca ggcatgctgg    4380
ggatgcggtg ggctctatgg gtacccaggt gctgaagaat tgacccggtt cctcctgggc    4440
cagaaagaag caggcacatc cccttctctg tgacacaccc tgtccacgcc cctggttctt    4500
agttccagcc ccactcatag gacactcata gctcaggagg gctccgcctt caatcccacc    4560
cgctaaagta cttggagcgg tctctccctc cctcatcagc ccaccaaacc aaacctagcc    4620
tccaagagtg ggaagaaatt aaagcaagat aggctattaa gtgcagaggg agagaaaatg    4680
cctccaacat gtgaggaagt aatgagagaa atcatagaat tttaaggcca tgatttaagg    4740
ccatcatggc cttaatcttc cgcttcctcg ctcactgact cgctgcgctc ggtcgttcgg    4800
ctgcggcgag cggtatcagc tcactcaaag gcggtaatac ggttatccac agaatcaggg    4860
gataacgcag gaaagaacat gtgagcaaaa ggccagcaaa aggccaggaa ccgtaaaaag    4920
gccgcgttgc tggcgttttt ccataggctc cgcccccctg acgagcatca aaaaatcga    4980 cgctcaagtc agaggtggcg aaacccgaca ggactataaa gataccaggc gtttccccct    5040
ggaagctccc tcgtgcgctc tcctgttccg accctgccgc ttaccggata cctgtccgcc    5100
tttctccctt cgggaagcgt ggcgctttct catagctcac gctgtaggta tctcagttcg    5160
gtgtaggtcg ttcgctccaa gctgggctgt gtgcacgaac cccccgttca gcccgaccgc    5220
tgcgccttat ccggtaacta tcgtcttgag tccaacccgg taagcacga cttatcgcca    5280 ctggcagcag ccactggtaa caggattagc agagcgaggt atgtaggcgg tgctacagag    5340
ttcttgaagt ggtggcctaa ctacggctac actagaagaa cagtatttgg tatctgcgct    5400
ctgctgaagc cagttacctt cggaaaaaga gttggtagct cttgatccgg caaacaaacc    5460
accgctggta gcggtggttt ttttgtttgc aagcagcaga ttacgcgcag aaaaaaagga    5520
tctcaagaag atcctttgat cttttctacg gggtctgacg ctcagtggaa cgaaaactca    5580
cgttaaggga ttttggtcat gagattatca aaaaggatct tcacctagat ccttttaaat    5640
taaaaatgaa gttttaaatc aatctaaagt atatatgagt aaacttggtc tgacagttac    5700
caatgcttaa tcagtgaggc acctatctca gcgatctgtc tatttcgttc atccatagtt    5760
gcctgactcg gggggggggg gcgctgaggt ctgcctcgtg aagaaggtgt tgctgactca    5820
```

```
taccaggcct gaatcgcccc atcatccagc cagaaagtga gggagccacg gttgatgaga      5880
gctttgttgt aggtggacca gttggtgatt ttgaacttt gctttgccac ggaacggtct       5940
gcgttgtcgg gaagatgcgt gatctgatcc ttcaactcag caaagttcg atttattcaa       6000 caaagccgcc gtcccgtcaa gtcagcgtaa tgctctgcca gtgttacaac caattaacca      6060
attctgatta gaaaaactca tcgagcatca aatgaaactg caattattc atatcaggat       6120 tatcaatacc atattttga aaaagccgtt tctgtaatga aggagaaaac tcaccgaggc       6180
agttccatag gatggcaaga tcctggtatc ggtctgcgat tccgactcgt ccaacatcaa      6240
tacaacctat taatttcccc tcgtcaaaaa taaggttatc aagtgagaaa tcaccatgag      6300
tgacgactga atccggtgag aatggcaaaa gctttatgcat ttctttccag acttgttcaa     6360
caggccagcc attacgctcg tcatcaaaat cactcgcatc aaccaaaccg ttattcattc      6420
gtgattgcgc ctgagcgaga cgaaatacgc gatcgctgtt aaaaggacaa ttacaaacag      6480
gaatcgaatg caaccggcgc aggaacactg ccagcgcatc aacaatattt tcacctgaat      6540
caggatattc ttctaatacc tggaatgctg tttcccggg gatcgcagtg gtgagtaacc       6600
atgcatcatc aggagtacgg ataaaatgct tgatggtcgg aagaggcata aattccgtca      6660
gccagtttag tctgaccatc tcatctgtaa catcattggc aacgctacct ttgccatgtt      6720
tcagaaacaa ctctggcgca tcgggcttcc catacaatcg atagattgtc gcacctgatt      6780
gcccgacatt atcgcgagcc catttatacc catataaatc agcatccatg ttggaattta     6840
atcgcggcct cgagcaagac gtttcccgtt gaatatggct cataacaccc cttgtattac     6900
tgtttatgta agcagacagt tttattgttc atgatgatat attttatct tgtgcaatgt      6960 aacatcagag attttgagac acaacgtggc tttccccccc ccccattat tgaagctttt       7020 atcagggtta ttgtctcatg agcggataca tatttgaatg tatttagaaa aataaacaaa      7080
taggggttcc gcgcacattt ccccgaaaag tgccacctga cgtctaagaa accattatta      7140
tcatgacatt aacctataaa aataggcgta tcacgaggcc ctttcgtc                   7188
```

<210> SEQ ID NO 3
<211> LENGTH: 6624
<212> TYPE: DNA
<213> ORGANISM: Artificial Sequence
<220> FEATURE:
<223> OTHER INFORMATION: Synthetic Construct pVR1012-GP(Z) delta MUC

<400> SEQUENCE: 3

```
tcgcgcgttt cggtgatgac ggtgaaaacc tctgacacat gcagctcccg gagacggtca       60
cagcttgtct gtaagcggat gccgggagca gacaagcccg tcaggcgcg tcagcgggtg       120 ttggcgggtg tcgggctgg cttaactatg cggcatcaga gcagattgta ctgagagtgc       180
accatatgcg gtgtgaaata ccgcacagat gcgtaaggag aaaataccgc atcagattgg       240
ctattggcca ttgcatacgt tgtatccata tcataatatg tacatttata ttggctcatg      300
tccaacatta ccgccatgtt gacattgatt attgactagt tattaatagt aatcaattac      360
ggggtcatta gttcatagcc catatatgga gttccgcgtt acataactta cggtaaatgg      420
cccgcctggc tgaccgccca acgacccccg cccattgacg tcaataatga cgtatgttcc      480
catagtaacg ccaataggga ctttccattg acgtcaatgg gtggagtatt tacggtaaac      540
tgcccacttg gcagtacatc aagtgtatca tatgccaagt acgccccta ttgacgtcaa       600 tgacggtaaa tggcccgcct ggcattatgc ccagtacatg accttatggg actttcctac      660
```

```
ttggcagtac atctacgtat tagtcatcgc tattaccatg gtgatgcggt tttggcagta      720
catcaatggg cgtggatagc ggtttgactc acggggattt ccaagtctcc accccattga      780
cgtcaatggg agtttgtttt ggcaccaaaa tcaacgggac tttccaaaat gtcgtaacaa      840
ctccgcccca ttgacgcaaa tgggcggtag gcgtgtacgg tgggaggtct atataagcag      900
agctcgttta gtgaaccgtc agatcgcctg gagacgccat ccacgctgtt ttgacctcca      960
tagaagacac cgggaccgat ccagcctccg cggccgggaa cggtgcattg gaacgcggat     1020
tccccgtgcc aagagtgacg taagtaccgc ctatagactc tataggcaca ccccttttggc    1080 tcttatgcat gctatactgt ttttggcttg gggcctatac cccccgctt ccttatgcta      1140 taggtgatgg tatagcttag cctataggtg tgggttattg accattattg accactcccc     1200
tattggtgac gatactttcc attactaatc cataacatgg ctctttgcca caactatctc     1260
tattggctat atgccaatac tctgtccttc agagactgac acggactctg tatttttaca     1320
ggatggggtc ccatttatta tttacaaatt cacatataca acaacgccgt cccccgtgcc    1380
cgcagttttt attaaacata gcgtgggatc tccacgcgaa tctcgggtac gtgttccgga     1440
catgggctct tctccggtag cggcggagct tccacatccg agccctggtc ccatgcctcc     1500
agcggctcat ggtcgctcgg cagctccttg ctcctaacag tggaggccag acttaggcac     1560
agcacaatgc ccaccaccac cagtgtgccg cacaaggccg tggcggtagg gtatgtgtct    1620
gaaaatgagc gtggagattg ggctcgcacg gctgacgcag atggaagact taaggcagcg     1680
gcagaagaag atgcaggcag ctgagttgtt gtattctgat aagagtcaga ggtaactccc     1740
gttgcggtgc tgttaacggt ggagggcagt gtagtctgag cagtactcgt tgctgccgcg     1800
cgcgccacca gacataatag ctgacagact aacagactgt tcctttccat gggtcttttc     1860
tgcagtcacc gtcgtcgaca cgtgtgatca gatatcgcgg ccgctctaga ccaggccctg     1920
gatcgatcca acaacacaat gggcgttaca ggaatattgc agttacctcg tgatcgattc     1980
aagaggacat cattctttct ttgggtaatt atccttttcc aaagaacatt ttccatccca    2040
cttggagtca tccacaatag cacattacag gttagtgatg tcgacaaaact agtttgtcgt   2100 gacaaactgt catccacaaa tcaattgaga tcagttggac tgaatctcga agggaatgga    2160
gtggcaactg acgtgccatc tgcaactaaa agatggggct tcaggtccgg tgtcccacca    2220
aaggtggtca attatgaagc tggtgaatgg gctgaaaact gctacaatct tgaaatcaaa    2280
aaacctgacg ggagtgagtg tctaccagca gcgccagacg ggattcgggg cttccccgg    2340 tgccggtatg tgcacaaagt atcaggaacg ggaccgtgtg ccggagactt tgccttccat    2400
aaagagggtg ctttcttcct gtatgatcga cttgcttcca cagttatcta ccgaggaacg    2460
actttcgctg aaggtgtcgt tgcatttctg atactgcccc aagctaagaa ggacttcttc    2520
agctcacacc ccttgagaga gccggtcaat gcaacggagg accgtctag tggctactat    2580 tctaccacaa ttagatatca ggctaccggt tttgaaccca atgagacaga gtacttgttc    2640
gaggttgaca atttgaccta cgtccaactt gaatcaagat tcacaccaca gtttctgctc   2700
cagctgaatg agacaatata tacaagtggg aaaaggagca ataccacggg aaaactaatt    2760
tggaaggtca accccgaaat tgatacaaca atcggggagt gggccttctg ggaaactaaa    2820
aaaaccctca ctagaaaaat tcgtaggctt aattaccaat actattgctg gagtcgcagg    2880
actgatcaca ggcgggagaa gaactcgaag agaagcaatt gtcaatgctc acccaaatg    2940 caaccctaat ttacattact ggactactca ggatgaaggt gctgcaatcg gactggcctg    3000
gataccatat ttcgggccag cagccgaggg aatttacata gaggggctaa tgcacaatca    3060
```

```
agatggttta atctgtgggt tgagacagct ggccaacgag acgactcaag ctcttcaact   3120
gttcctgaga gccacaactg agctacgcac cttttcaatc ctcaaccgta aggcaattga   3180
tttcttgctg cagcgatggg gcggcacatg ccacattctg ggaccggact gctgtatcga   3240
accacatgat tggaccaaga acataacaga caaaattgat cagattattc atgattttgt   3300
tgataaaacc cttccggacc aggggggacaa tgacaattgg tggacaggat ggagacaatg   3360
gataccggca ggtattggag ttacaggcgt tgtaattgca gttatcgctt tattctgtat   3420
atgcaaattt gtcttttagt ttttcttcag attgcttcat ggaaaagctc agcctcaaat   3480
caatgaaacc aggatttaat tatatggatt acttgaatct aagattactt gacaaatgat   3540
aatataatac actggagctt taaacatagc caatgtgatt ctaactcctt aaaactcaca   3600
gttaatcata aacaaggttt gaggtaccga gctcgaattg atctgctgtg ccttctagtt   3660
gccagccatc tgttgtttgc ccctcccccg tgccttcctt gaccctggaa ggtgccactc   3720
ccactgtcct ttcctaataa aatgaggaaa ttgcatcgca ttgtctgagt aggtgtcatt   3780
ctattctggg gggtgggtg gggcaggaca gcaaggggga ggattgggaa gacaatagca   3840
ggcatgctgg ggatgcggtg ggctctatgg gtacccaggt gctgaagaat tgacccggtt   3900
cctcctgggc cagaaagaag caggcacatc cccttctctg tgacacaccc tgtccacgcc   3960
cctggttctt agttccagcc ccactcatag gacactcata gctcaggagg gctccgcctt   4020
caatcccacc cgctaaagta cttggagcgg tctctcctc cctcatcagc ccaccaaacc   4080
aaacctagcc tccaagagtg ggaagaaatt aaagcaagat aggctattaa gtgcagaggg   4140
agagaaaatg cctccaacat gtgaggaagt aatgagagaa atcatagaat ttcttccgct   4200
tcctcgctca ctgactcgct gcgctcggtc gttcggctgc ggcgagcggt atcagctcac   4260
tcaaaggcgg taatacggtt atccacagaa tcaggggata acgcaggaaa gaacatgtga   4320
gcaaaaggcc agcaaaaggc caggaaccgt aaaaaggccg cgttgctggc gtttttccat   4380
aggctccgcc cccctgacga gcatcacaaa aatcgacgct caagtcagag gtggcgaaac   4440
ccgacaggac tataaagata ccaggcgttt ccccctggaa gctccctcgt gcgctctcct   4500
gttccgaccc tgccgcttac cggatacctg tccgcctttc tcccttcggg aagcgtggcg   4560
ctttctcata gctcacgctg taggtatctc agttcggtgt aggtcgttcg ctccaagctg   4620
ggctgtgtgc acgaaccccc cgttcagccc gaccgctgcg ccttatccgg taactatcgt   4680
cttgagtcca acccggtaag acacgactta tcgccactgg cagcagccac tggtaacagg   4740
attagcagag cgaggtatgt aggcggtgct acagagttct tgaagtggtg cctaactac   4800 ggctacacta gaagaacagt atttggtatc tgcgctctgc tgaagccagt taccttcgga   4860
aaaagagttg gtagctcttg atccggcaaa caaaccaccg ctggtagcgg tggttttttt   4920
gtttgcaagc agcagattac gcgcagaaaa aaaggatctc aagaagatcc tttgatcttt   4980
tctacggggt ctgacgctca gtggaacgaa aactcacgtt aagggatttt ggtcatgaga   5040
ttatcaaaaa ggatcttcac ctagatcctt taaattaaa aatgaagttt taaatcaatc   5100
taaagtatat atgagtaaac ttggtctgac agttaccaat gcttaatcag tgaggcacct   5160
atctcagcga tctgtctatt tcgttcatcc atagttgcct gactcggggg gggggggcgc   5220
tgaggtctgc ctcgtgaaga aggtgttgct gactcatacc aggcctgaat cgccccatca   5280
tccagccaga aagtgaggga gccacggttg atgagagctt tgttgtaggt ggaccagttg   5340
gtgattttga acttttgctt tgccacggaa cggtctgcgt tgtcgggaag atgcgtgatc   5400
```

```
tgatccttca actcagcaaa agttcgattt attcaacaaa gccgccgtcc cgtcaagtca    5460
gcgtaatgct ctgccagtgt tacaaccaat taaccaattc tgattagaaa aactcatcga    5520
gcatcaaatg aaactgcaat ttattcatat caggattatc aataccatat ttttgaaaaa    5580
gccgtttctg taatgaagga gaaaactcac cgaggcagtt ccataggatg gcaagatcct    5640
ggtatcggtc tgcgattccg actcgtccaa catcaataca acctattaat ttcccctcgt    5700
caaaaataag gttatcaagt gagaaatcac catgagtgac gactgaatcc ggtgagaatg    5760
gcaaaagctt atgcatttct ttccagactt gttcaacagg ccagccatta cgctcgtcat    5820
caaaatcact cgcatcaacc aaaccgttat tcattcgtga ttgcgcctga gcgagacgaa    5880
atacgcgatc gctgttaaaa ggacaattac aaacaggaat cgaatgcaac ggcgcagga    5940 acactgccag cgcatcaaca atattttcac ctgaatcagg atattcttct aatacctgga    6000
atgctgtttt cccggggatc gcagtggtga gtaaccatgc atcatcagga gtacggataa    6060
aatgcttgat ggtcggaaga ggcataaatt ccgtcagcca gtttagtctg accatctcat    6120
ctgtaacatc attggcaacg ctacctttgc catgtttcag aaacaactct ggcgcatcgg    6180
gcttcccata caatcgatag attgtcgcac ctgattgccc gacattatcg cgagcccatt    6240
tatacccata taaatcagca tccatgttgg aatttaatcg cggcctcgag caagacgttt    6300
cccgttgaat atggctcata caccccttg tattactgtt tatgtaagca gacagtttta    6360
ttgttcatga tgatatattt ttatcttgtg caatgtaaca tcagagattt tgagacacaa    6420
cgtggctttc cccccccccc cattattgaa gcatttatca gggttattgt ctcatgagcg    6480
gatacatatt tgaatgtatt tagaaaaata aacaaatagg ggttccgcgc acatttcccc    6540
gaaaagtgcc acctgacgtc taagaaacca ttattatcat gacattaacc tataaaaata    6600
ggcgtatcac gaggcccttt cgtc                                          6624
```

<210> SEQ ID NO 4
<211> LENGTH: 6561
<212> TYPE: DNA
<213> ORGANISM: Artificial Sequence
<220> FEATURE:
<223> OTHER INFORMATION: Synthetic Construct pVR1012-GP(Z) deltaMUC
      delta FUR

<400> SEQUENCE: 4

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
```

-continued

```
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctccg cggccgggaa cggtgcattg gaacgcggat   1020
tccccgtgcc aagagtgacg taagtaccgc ctatagactc tataggcaca cccctttggc   1080
tcttatgcat gctatactgt ttttggcttg gggcctatac accccgctt ccttatgcta    1140 taggtgatgg tatagcttag cctataggtg tgggttattg accattattg accactcccc   1200
tattggtgac gatactttcc attactaatc cataacatgg ctctttgcca caactatctc   1260
tattggctat atgccaatac tctgtccttc agagactgac acggactctg tattttttaca  1320 ggatggggtc ccatttatta tttacaaatt cacatataca acaacgccgt cccccgtgcc   1380
cgcagttttt attaaacata gcgtgggatc tccacgcgaa tctcgggtac gtgttccgga   1440
catgggctct ctccggtag cggcggagct tccacatccg agccctggtc ccatgcctcc    1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgaca cgtgtgatca gatatcgcgg ccgctctaga ccaggccctg   1920
gatcgatcca acaacacaat gggcgttaca ggaatattgc agttacctcg tgatcgattc   1980
aagaggacat cattctttct tgggtaatt atccttttcc aaagaacatt ttccatccca    2040
cttggagtca tccacaatag cacattacag gttagtgatg tcgacaaact agtttgtcgt   2100
gacaaactgt catccacaaa tcaattgaga tcagttggac tgaatctcga agggaatgga   2160
gtggcaactg acgtgccatc tgcaactaaa agatggggct tcaggtccgg tgtcccacca   2220
aaggtggtca attatgaagc tggtgaatgg gctgaaaact gctacaatct tgaaatcaaa   2280
aaacctgacg ggagtgagtg tctaccagca gcgccagacg ggattcgggg cttccccgg    2340 tgccggtatg tgcacaaagt atcaggaacg ggaccgtgtg ccggagactt tgccttccat   2400
aaagagggtg ctttcttcct gtatgatcga cttgcttcca cagttatcta ccgaggaacg   2460
actttcgctg aaggtgtcgt tgcatttctg atactgcccc aagctaagaa ggacttcttc   2520
agctcacacc ccttgagaga gccggtcaat gcaacggagg accgtctag tggctactat    2580 tctaccacaa ttagatatca ggctaccggt tttggaacca atgagacaga gtacttgttc   2640
gaggttgaca atttgaccta cgtccaactt gaatcaagat tcacaccaca gtttctgctc   2700
cagctgaatg agacaatata caagtgggaa aaaggagca ataccacggg aaaactaatt    2760
tggaaggtca accccgaaat tgatacaaca atcggggagt gggccttctg ggaaactaaa   2820
aaaaacctca ctagaaaaat tcggaagaga agcaattgtc aatgctcaac ccaaatgcaa   2880
ccctaattta cattactgga ctactcagga tgaaggtgct gcaatcggac tggcctggat   2940
accatatttc gggccagcag ccgagggaat ttacatagag gggctaatgc acaatcaaga   3000
tggtttaatc tgtgggttga gacagctggc caacgagacg actcaagctc ttcaactgtt   3060
cctgagagcc acaactgagc tacgcacctt ttcaatcctc aaccgtaagg caattgattt   3120
cttgctgcag cgatggggcg gcacatgcca cattctggga ccggactgct gtatcgaacc   3180
```

-continued

```
acatgattgg accaagaaca taacagacaa aattgatcag attattcatg attttgttga   3240
taaaacccTT ccggaccagg gggacaatga caattggtgg acaggatgga gacaatggat   3300
accggcaggt attggagtta caggcgttgt aattgcagtt atcgctttat tctgtatatg   3360
caaatttgtc ttttagtttt tcttcagatt gcttcatgga aaagctcagc ctcaaatcaa   3420
tgaaaccagg atttaattat atggattact tgaatctaag attacttgac aaatgataat   3480
ataatacact ggagctttaa acatagccaa tgtgattcta actcctttaa actcacagtt   3540
aatcataaac aaggtttgag gtaccgagct cgaattgatc tgctgtgcct tctagttgcc   3600
agccatctgt tgtttgcccc tcccccgtgc cttccttgac cctggaaggt gccactccca   3660
ctgtcctttc ctaataaaat gaggaaattg catcgcattg tctgagtagg tgtcattcta   3720
ttctgggggg tggggtgggg caggacagca aggggggagga ttgggaagac aatagcaggc   3780
atgctgggga tgcggtgggc tctatgggta cccaggtgct gaagaattga cccggttcct   3840
cctgggccag aaagaagcag gcacatcccc ttctctgtga cacaccctgt ccacgcccct   3900
ggttcttagt tccagcccca ctcataggac actcatagct caggagggct ccgccttcaa   3960
tcccacccgc taaagtactt ggagcggtct ctccctccct catcagccca ccaaaccaaa   4020
cctagcctcc aagagtggga agaaattaaa gcaagatagg ctattaagtg cagagggaga   4080
gaaaatgcct ccaacatgtg aggaagtaat gagagaaatc atagaatttc ttccgcttcc   4140
tcgctcactg actcgctgcg ctcggtcgtt cggctgcggc gagcggtatc agctcactca   4200
aaggcggtaa tacggttatc cacagaatca ggggataacg caggaaagaa catgtgagca   4260
aaaggccagc aaaaggccag gaaccgtaaa aaggccgcgt tgctggcgtt tttccatagg   4320
ctccgccccc ctgacgagca tcacaaaaat cgacgctcaa gtcagaggtg gcgaaacccg   4380
acaggactat aaagatacca ggcgtttccc cctggaagct ccctcgtgcg ctctcctgtt   4440
ccgaccctgc cgcttaccgg atacctgtcc gcctttctcc cttcgggaag cgtggcgctt   4500
tctcatagct cacgctgtag gtatctcagt tcggtgtagg tcgttcgctc caagctgggc   4560
tgtgtgcacg aaccccccgt tcagcccgac cgctgcgcct tatccggtaa ctatcgtctt   4620
gagtccaacc cggtaagaca cgacttatcg ccactggcag cagccactgg taacaggatt   4680
agcagagcga ggtatgtagg cggtgctaca gagttcttga agtggtggcc taactacggc   4740
tacactagaa gaacagtatt tggtatctgc gctctgctga agccagttac cttcggaaaa   4800
agagttggta gctcttgatc cggcaaacaa accaccgctg gtagcggtgg tttttttgtt   4860
tgcaagcagc agattacgcg cagaaaaaaa ggatctcaag aagatccttt gatcttttct   4920
acggggtctg acgctcagtg gaacgaaaac tcacgttaag ggattttggt catgagatta   4980
tcaaaaagga tcttcaccta gatccttta aattaaaaat gaagttttaa atcaatctaa   5040
agtatatatg agtaaacttg gtctgacagt taccaatgct taatcagtga ggcacctatc   5100
tcagcgatct gtctatttcg ttcatccata gttgcctgac tcggggggg ggggcgctga   5160
ggtctgcctc gtgaagaagg tgttgctgac tcataccagg cctgaatcgc ccatcatcc   5220
agccagaaag tgagggagcc acggttgatg agagctttgt tgtaggtgga ccagttggtg   5280
attttgaact tttgctttgc cacggaacgg tctgcgttgt cgggaagatg cgtgatctga   5340
tccttcaact cagcaaaagt tcgatttatt caacaaagcc gccgtccgt caagtcagcg   5400
taatgctctg ccagtgttac aaccaattaa ccaattctga ttagaaaaac tcatcgagca   5460
tcaaatgaaa ctgcaattta ttcatatcag gattatcaat accatatttt tgaaaaagcc   5520
```

-continued

```
gtttctgtaa tgaaggagaa aactcaccga ggcagttcca taggatggca agatcctggt    5580
atcggtctgc gattccgact cgtccaacat caatacaacc tattaatttc ccctcgtcaa    5640
aaataaggtt atcaagtgag aaatcaccat gagtgacgac tgaatccggt gagaatggca    5700
aaagcttatg catttctttc cagacttgtt caacaggcca gccattacgc tcgtcatcaa    5760
aatcactcgc atcaaccaaa ccgttattca ttcgtgattg cgcctgagcg agacgaaata    5820
cgcgatcgct gttaaaagga caattacaaa caggaatcga atgcaaccgg cgcaggaaca    5880
ctgccagcgc atcaacaata ttttcacctg aatcaggata ttcttctaat acctggaatg    5940
ctgtttccc ggggatcgca gtggtgagta accatgcatc atcaggagta cggataaaat    6000
gcttgatggt cggaagaggc ataaattccg tcagccagtt tagtctgacc atctcatctg    6060
taacatcatt ggcaacgcta cctttgccat gtttcagaaa caactctggc gcatcgggct    6120
tcccatacaa tcgatagatt gtcgcacctg attgcccgac attatcgcga gcccatttat    6180
acccatataa atcagcatcc atgttggaat ttaatcgcgg cctcgagcaa gacgtttccc    6240
gttgaatatg gctcataaca ccccttgtat tactgtttat gtaagcagac agttttattg    6300
ttcatgatga tatatttta tcttgtgcaa tgtaacatca gagattttga cacaacgt    6360
ggctttcccc cccccccat tattgaagca tttatcaggg ttattgtctc atgagcggat    6420
acatatttga atgtatttag aaaaataaac aaataggggt tccgcgcaca tttccccgaa    6480
aagtgccacc tgacgtctaa gaaaccatta ttatcatgac attaacctat aaaaataggc    6540
gtatcacgag gccctttcgt c                                             6561
```

<210> SEQ ID NO 5
<211> LENGTH: 6724
<212> TYPE: DNA
<213> ORGANISM: Artificial Sequence
<220> FEATURE:
<223> OTHER INFORMATION: Synthetic Construct pVR1012-GP(Z) delta GP2

<400> SEQUENCE: 5

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgacccccg cccattgacg tcaataatga cgtatgttcc     480
catagtaacg ccaatagga ctttccattg acgtcaatgg gtggagtatt tacggtaaac     540
tgcccacttg gcagtacatc aagtgtatca tatgccaagt acgcccccta ttgacgtcaa     600
tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag     900
agctcgttta gtgaaccgtc agatcgcctg gagacgccat ccacgctgtt ttgacctcca     960
tagaagacac cgggaccgat ccagcctccg cggccgggaa cggtgcattg gaacgcggat    1020
```

-continued

```
tccccgtgcc aagagtgacg taagtaccgc ctatagactc tataggcaca ccccttttggc    1080
tcttatgcat gctatactgt ttttggcttg gggcctatac accccgctt ccttatgcta     1140
taggtgatgg tatagcttag cctataggtg tgggttattg accattattg accactcccc    1200
tattggtgac gatactttcc attactaatc cataacatgg ctcttgccat caactatctc    1260
tattggctat atgccaatac tctgtccttc agagactgac acggactctg tattttaca     1320
ggatggggtc ccatttatta tttacaaatt cacatataca caacgccgt ccccgtgcc      1380
cgcagttttt attaaacata gcgtgggatc tccacgcgaa tctcgggtac gtgttccgga    1440
catgggctct ctccggtag cggcggagct tccacatccg agccctggtc ccatgcctcc     1500
agcggctcat ggtcgctcgg cagctccttg ctcctaacag tggaggccag acttaggcac    1560
agcacaatgc ccaccaccac cagtgtgccg cacaaggccg tgcggtagg gtatgtgtct     1620
gaaaatgagc gtggagattg ggctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tcctttccat gggtctttttc   1860
tgcagtcacc gtcgtcgaca cgtgtgatca gatatcgcgg ccgctctaga ccaggccctg    1920
gatcgatcca acaacacaat gggcgttaca ggaatattgc agttacctcg tgatcgattc    1980
aagaggacat cattctttct ttgggtaatt atccttttcc aaagaacatt ttccatccca    2040
cttggagtca tccacaatag cacattacag gttagtgatg tcgacaaact agtttgtcgt    2100
gacaaactgt catccacaaa tcaattgaga tcagttggac tgaatctcga agggaatgga    2160
gtggcaactg acgtgccatc tgcaactaaa agatggggct tcaggtccgg tgtcccacca    2220
aaggtggtca attatgaagc tggtgaatgg gctgaaaact gctacaatct tgaaatcaaa    2280
aaacctgacg ggagtgagtg tctaccagca gcgccagacg ggattcgggg cttccccgg     2340
tgccggtatg tgcacaaagt atcaggaacg ggaccgtgtg ccggagactt tgccttccat    2400
aaagagggtg ctttcttcct gtatgatcga cttgcttcca cagttatcta ccgaggaacg    2460
actttcgctg aaggtgtcgt tgcatttctg atactgcccc aagctaagaa ggacttcttc    2520
agctcacacc ccttgagaga gccggtcaat gcaacggagg acccgtctag tggctactat    2580
tctaccacaa ttagatatca ggctaccggt tttggaacca atgagacaga gtacttgttc    2640
gaggttgaca atttgaccta cgtccaactt gaatcaagat tcacaccaca gtttctgctc    2700
cagctgaatg agacaatata tacaagtggg aaaaggagca ataccacggg aaaactaatt    2760
tggaaggtca accccgaaat tgatacaaca atcggggagt gggccttctg ggaaactaaa    2820
aaaaacctca ctagaaaaat tcgcagtgaa gagttgtctt tcacagttgt atcaaacgga    2880
gccaaaaaca tcagtggtca gagtccggcg cgaacttctt ccgacccagg accaacaca    2940
acaactgaag accacaaaat catggcttca gaaaattcct ctgcaatggt tcaagtgcac    3000
agtcaaggaa gggaagctgc agtgtcgcat ctaacaaccc ttgccacaat ctccacgagt    3060
ccccaatccc tcacaaccaa accaggtccg gacaacagca cccataatac acccgtgtat    3120
aaacttgaca tctctgaggc aactcaagtt gaacaacatc accgcagaac agacaacgac    3180
agcacagcct ccgacactcc ctctgccacg accgcagccg gacccccaaa gcagagaac    3240
accaacacga gcaagagcac tgacttcctg gaccccgcca ccacaacaag tcccaaaac    3300
cacagcgaga ccgctggcaa caacaacact catcaccaag ataccggaga agagagtgcc    3360
```

```
agcagcggga agctaggctt aattaccaat actattgctg gagtcgcagg actccggacc   3420 aggggggacaa tgacaattgg tggacaggat ggagacaatg gataccggca ggtattggag   3480
ttacaggcgt tgtaattgca gttatcgctt tattctgtat atgcaaattt gtcttttagt   3540
ttttcttcag attgcttcat ggaaaagctc agcctcaaat caatgaaacc aggatttaat   3600
tatatggatt acttgaatct aagattactt gacaaatgat aatataatac actggagctt   3660
taaacatagc caatgtgatt ctaactcctt taaactcaca gttaatcata aacaaggttt   3720
gaggtaccga gctcgaattg atctgctgtg ccttctagtt gccagccatc tgttgtttgc   3780
ccctcccccg tgccttcctt gaccctggaa ggtgccactc ccactgtcct ttcctaataa   3840
aatgaggaaa ttgcatcgca ttgtctgagt aggtgtcatt ctattctggg gggtggggtg   3900
gggcaggaca gcaaggggga ggattgggaa gacaatagca ggcatgctgg ggatgcggtg   3960
ggctctatgg gtacccaggt gctgaagaat tgacccggtt cctcctgggc cagaaagaag   4020
caggcacatc cccttctctg tgacacaccc tgtccacgcc cctggttctt agttccagcc   4080
ccactcatag gacactcata gctcaggagg gctccgcctt caatcccacc cgctaaagta   4140
cttggagcgg tctctccctc cctcatcagc ccaccaaacc aaacctagcc tccaagagtg   4200
ggaagaaatt aaagcaagat aggctattaa gtgcagaggg agagaaaatg cctccaacat   4260
gtgaggaagt aatgagagaa atcatagaat ttcttccgct tcctcgctca ctgactcgct   4320
gcgctcggtc gttcggctgc ggcgagcggt atcagctcac tcaaaggcgg taatacggtt   4380
atccacagaa tcaggggata acgcaggaaa gaacatgtga gcaaaaggcc agcaaaaggc   4440
caggaaccgt aaaaaggccg cgttgctggc gttttcccat aggctccgcc ccctgacga   4500 gcatcacaaa aatcgacgct caagtcagag gtggcgaaac ccgacaggac tataaagata   4560
ccaggcgttt ccccctggaa gctccctcgt gcgctctcct gttccgaccc tgccgcttac   4620
cggatacctg tccgcctttc tcccttcggg aagcgtggcg ctttctcata gctcacgctg   4680
taggtatctc agttcggtgt aggtcgttcg ctccaagctg ggctgtgtgc acgaaccccc   4740
cgttcagccc gaccgctgcg ccttatccgg taactatcgt cttgagtcca acccggtaag   4800
acacgactta tcgccactgg cagcagccac tggtaacagg attagcagag cgaggtatgt   4860
aggcggtgct acagagttct tgaagtggtg gcctaactac ggctacacta agaacagt   4920 atttggtatc tgcgctctgc tgaagccagt taccttcgga aaaagagttg gtagctcttg   4980
atccggcaaa caaaccaccg ctggtagcgg tggtttttttt gtttgcaagc agcagattac   5040
gcgcagaaaa aaggatctc aagaagatcc tttgatcttt tctacgggt ctgacgctca   5100 gtggaacgaa aactcacgtt aagggatttt ggtcatgaga ttatcaaaaa ggatcttcac   5160
ctagatcctt ttaaattaaa aatgaagttt taaatcaatc taaagtatat atgagtaaac   5220
ttggtctgac agttaccaat gcttaatcag tgaggcacct atctcagcga tctgtctatt   5280
tcgttcatcc atagttgcct gactcggggg ggggggggcgc tgaggtctgc ctcgtgaaga   5340
aggtgttgct gactcatacc aggcctgaat cgccccatca tccagccaga aagtgaggga   5400
gccacggttg atgagagctt tgttgtaggt ggaccagttg gtgattttga acttttgctt   5460
tgccacggaa cggtctgcgt tgtcgggaag atgcgtgatc tgatccttca actcagcaaa   5520
agttcgattt attcaacaaa gccgccgtcc cgtcaagtca gcgtaatgct ctgccagtgt   5580
tacaaccaat taaccaattc tgattagaaa aactcatcga gcatcaaatg aaactgcaat   5640
ttattcatat caggattatc aataccatat ttttgaaaaa gccgtttctg taatgaagga   5700
gaaaactcac cgaggcagtt ccataggatg gcaagatcct ggtatcggtc tgcgattccg   5760
```

```
actcgtccaa catcaataca acctattaat ttcccctcgt caaaaataag gttatcaagt    5820
gagaaatcac catgagtgac gactgaatcc ggtgagaatg gcaaaagctt atgcatttct    5880
ttccagactt gttcaacagg ccagccatta cgctcgtcat caaaatcact cgcatcaacc    5940
aaaccgttat tcattcgtga ttgcgcctga gcgagacgaa atacgcgatc gctgttaaaa    6000
ggacaattac aaacaggaat cgaatgcaac cggcgcagga acactgccag cgcatcaaca    6060
atattttcac ctgaatcagg atattcttct aatacctgga atgctgtttt cccggggatc    6120
gcagtggtga gtaaccatgc atcatcagga gtacggataa aatgcttgat ggtcggaaga    6180
ggcataaatt ccgtcagcca gtttagtctg accatctcat ctgtaacatc attggcaacg    6240
ctacctttgc catgtttcag aaacaactct ggcgcatcgg gcttcccata caatcgatag    6300
attgtcgcac ctgattgccc gacattatcg cgagcccatt tatacccata taaatcagca    6360
tccatgttgg aatttaatcg cggcctcgag caagacgttt cccgttgaat atggctcata    6420 acacccctttg tattactgtt tatgtaagca gacagttttaa ttgttcatga tgatatattt    6480
```

```
actcgtccaa catcaataca acctattaat ttcccctcgt caaaaataag gttatcaagt    5820
gagaaatcac catgagtgac gactgaatcc ggtgagaatg gcaaaagctt atgcatttct    5880
ttccagactt gttcaacagg ccagccatta cgctcgtcat caaaatcact cgcatcaacc    5940
aaaccgttat tcattcgtga ttgcgcctga gcgagacgaa atacgcgatc gctgttaaaa    6000
ggacaattac aaacaggaat cgaatgcaac cggcgcagga acactgccag cgcatcaaca    6060
atattttcac ctgaatcagg atattcttct aatacctgga atgctgtttt cccggggatc    6120
gcagtggtga gtaaccatgc atcatcagga gtacggataa aatgcttgat ggtcggaaga    6180
ggcataaatt ccgtcagcca gtttagtctg accatctcat ctgtaacatc attggcaacg    6240
ctacctttgc catgtttcag aaacaactct ggcgcatcgg gcttcccata caatcgatag    6300
attgtcgcac ctgattgccc gacattatcg cgagcccatt tatacccata taaatcagca    6360
tccatgttgg aatttaatcg cggcctcgag caagacgttt cccgttgaat atggctcata    6420 acacccctttg tattactgtt tatgtaagca gacagttttaa ttgttcatga tgatatattt    6480
ttatcttgtg caatgtaaca tcagagattt tgagacacaa cgtggctttc ccccccccc    6540 cattattgaa gcatttatca gggttattgt ctcatgagcg gatacatatt tgaatgtatt    6600
tagaaaaata aacaaatagg ggttccgcgc acatttcccc gaaagtgcc acctgacgtc    6660 taagaaacca ttattatcat gacattaacc tataaaaata ggcgtatcac gaggcccttt    6720
cgtc                                                                  6724
```

<210> SEQ ID NO 6
<211> LENGTH: 6887
<212> TYPE: DNA
<213> ORGANISM: Artificial Sequence
<220> FEATURE:
<223> OTHER INFORMATION: Synthetic Construct pVR1012-GP(Z) delta GP2
      delta C-term A

<400> SEQUENCE: 6

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgacccccg cccattgacg tcaataatga cgtatgttcc     480
catagtaacg ccaatagggα ctttccattg acgtcaatgg gtggagtatt tacggtaaac     540
tgcccacttg gcagtacatc aagtgtatca tatgccaagt acgccccta ttgacgtcaa     600 tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag     900
agctcgttta gtgaaccgtc agatcgcctg gagacgccat ccacgctgtt tgacctccα     960 tagaagacac cgggaccgat ccagcctccg cggccgggaa cggtgcattg gaacgcggat    1020
```

```
tcccegtgcc aagagtgacg taagtaccgc ctatagactc tataggcaca cccctttggc    1080
tcttatgcat gctatactgt ttttggcttg gggcctatac accccegctt ccttatgcta    1140 taggtgatgg tatagcttag cctataggtg tgggttattg accattattg accactcccc    1200
tattggtgac gatactttcc attactaatc cataacatgg ctcttttgcca caactatctc    1260 tattggctat atgccaatac tctgtccttc agagactgac acggactctg tatttttaca    1320
ggatggggtc ccatttatta tttacaaatt cacatataca acaacgccgt ccccegtgcc    1380 cgcagttttt attaaacata gcgtgggatc tccacgcgaa tctcgggtac gtgttccgga    1440
catgggctct tctccggtag cggcggagct tccacatccg agccctggtc ccatgcctcc    1500
agcggctcat ggtcgctcgg cagctccttg ctcctaacag tggaggccag acttaggcac    1560
agcacaatgc ccaccaccac cagtgtgccg cacaaggccg tggcggtagg gtatgtgtct    1620
gaaaatgagc gtggagattg ggctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tcctttccat gggtcttttc    1860
tgcagtcacc gtcgtcgaca cgtgtgatca gatatcgcgg ccgctctaga ccaggccctg    1920
gatcgatcca acaacacaat gggcgttaca ggaatattgc agttacctcg tgatcgattc    1980
aagaggacat cattctttct ttgggtaatt atccttttcc aaagaacatt ttccatccca    2040
cttggagtca tccacaatag cacattacag gttagtgatg tcgacaaact agtttgtcgt    2100
gacaaactgt catccacaaa tcaattgaga tcagttggac tgaatctcga agggaatgga    2160
gtggcaactg acgtgccatc tgcaactaaa agatggggct tcaggtccgg tgtcccacca    2220
aaggtggtca attatgaagc tggtgaatgg gctgaaaact gctacaatct tgaaatcaaa    2280
aaacctgacg ggagtgagtg tctaccagca gcgccagacg ggattcgggg cttccccggg    2340
tgccggtatg tgcacaaagt atcaggaacg ggaccgtgtg ccggagactt gccttccat    2400 aaagagggtg ctttcttcct gtatgatcga cttgcttcca cagttatcta ccgaggaacg    2460
actttcgctg aaggtgtcgt tgcatttctg atactgcccc aagctaagaa ggacttcttc    2520
agctcacacc ccttgagaga gccggtcaat gcaacggagg acccgtctag tggctactat    2580
tctaccacaa ttagatatca ggctaccggt tttggaacca atgagacaga gtacttgttc    2640
gaggttgaca atttgaccta cgtccaactt gaatcaagat tcacaccaca gtttctgctc    2700
cagctgaatg agacaatata tacaagtggg aaaaggagca ataccacggg aaaactaatt    2760
tggaaggtca accccgaaat tgatacaaca atcggggagt gggcccttctg ggaaactaaa    2820 aaaaacctca ctagaaaaat tcgcagtgaa gagttgtctt tcacagttgt atcaaacgga    2880
gccaaaaaca tcagtggtca gagtccggcg cgaacttctt ccgacccagg gaccaacaca    2940
acaactgaag accacaaaat catggcttca gaaaattcct ctgcaatggt tcaagtgcac    3000
agtcaaggaa gggaagctgc agtgtcgcat ctaacaaccc ttgccacaat ctccacgagt    3060
ccccaatccc tcacaaccaa accaggtccg gacaacagca cccataatac acccgtgtat    3120
aaacttgaca tctctgaggc aactcaagtt gaacaacatc accgcagaac agacaacgac    3180
agcacagcct ccgacactcc ctctgccacg accgcagccg gaccccccaaa agcagagaac    3240 accaacacga gcaagagcac tgacttcctg gaccccgcca ccacaacaag tccccaaaac    3300
cacagcgaga ccgctggcaa caacaacact catcaccaag ataccggaga agagagtgcc    3360
```

```
agcagcggga agctaggctt aattaccaat actattgctg gagtcgcagg actgatcaca    3420
ggcgggagaa gaactcgaag agaagcaatt gtcaatgctc aacccaaatg caaccctaat    3480
ttacattact ggactactca ggatgaaggt gctgcaatcg gactggcctg gataccatat    3540
ttcgggccag cagccgaggg aatttacata gaggggctaa tgcacaatca agatggttta    3600
atctgtgggt tgagacagct ggggataccg gcaggtattg gagttacagg cgttgtaatt    3660
gcagttatcg ctttattctg tatatgcaaa tttgtctttt agttttctt cagattgctt    3720
catggaaaag ctcagcctca aatcaatgaa accaggattt aattatatgg attacttgaa    3780
tctaagatta cttgacaaat gataatataa tacactggag ctttaaacat agccaatgtg    3840
attctaactc ctttaaactc acagttaatc ataaacaagg tttgaggtac cgagctcgaa    3900
ttgatctgct gtgccttcta gttgccagcc atctgttgtt tgcccctccc ccgtgccttc    3960
cttgaccctg gaaggtgcca ctcccactgt cctttcctaa taaaatgagg aaattgcatc    4020
gcattgtctg agtaggtgtc attctattct ggggggtggg gtgggcagg acagcaaggg    4080
ggaggattgg gaagacaata gcaggcatgc tggggatgcg gtgggctcta tgggtaccca    4140
ggtgctgaag aattgacccg gttcctcctg ggccagaaag aagcaggcac atcccttct    4200
ctgtgacaca ccctgtccac gccctggtt cttagttcca gccccactca taggacactc    4260
atagctcagg agggctccgc cttcaatccc acccgctaaa gtacttggag cggtctctcc    4320
ctccctcatc agcccaccaa accaaaccta gcctccaaga gtgggaagaa attaaagcaa    4380
gataggctat taagtgcaga gggagagaaa atgcctccaa catgtgagga agtaatgaga    4440
gaaatcatag aatttcttcc gcttcctcgc tcactgactc gctgcgctcg gtcgttcggc    4500
tgcggcgagc ggtatcagct cactcaaagg cggtaatacg gttatccaca gaatcagggg    4560
ataacgcagg aaagaacatg tgagcaaaag gccagcaaaa ggccaggaac cgtaaaaagg    4620
ccgcgttgct ggcgttttc cataggctcc gcccccctga cgagcatcac aaaaatcgac    4680
gctcaagtca gaggtggcga aacccgacag gactataaag ataccaggcg tttccccctg    4740
gaagctccct cgtgcgctct cctgttccga cctgccgct taccggatac ctgtccgcct    4800
ttctcccttc gggaagcgtg gcgctttctc atagctcacg ctgtaggtat ctcagttcgg    4860
tgtaggtcgt tcgctccaag ctgggctgtg tgcacgaacc ccccgttcag cccgaccgct    4920
gcgccttatc cggtaactat cgtcttgagt ccaacccggt aagacacgac ttatcgccac    4980
tggcagcagc cactggtaac aggattagca gagcgaggta tgtaggcggt gctacagagt    5040
tcttgaagtg gtgcctaac tacggctaca ctagaagaac agtatttggt atctgcgctc    5100
tgctgaagcc agttaccttc ggaaaaagag ttggtagctc ttgatccggc aaacaaacca    5160
ccgctggtag cggtggtttt tttgtttgca agcagcagat tacgcgcaga aaaaaggat    5220
ctcaagaaga tcctttgatc ttttctacgg ggtctgacgc tcagtggaac gaaaactcac    5280
gttaagggat tttggtcatg agattatcaa aaaggatctt cacctagatc ctttaaatt    5340
aaaaatgaag ttttaaatca atctaaagta tatatgagta aacttggtct gacagttacc    5400
aatgcttaat cagtgaggca cctatctcag cgatctgtct atttcgttca tccatagttg    5460
cctgactcgg ggggggggg cgctgaggtc tgcctcgtga agaaggtgtt gctgactcat    5520
accaggcct aatcgcccca tcatccagcc agaaagtgag ggagccacgg ttgatgagag    5580
ctttgttgta ggtggaccag ttggtgattt tgaactttg ctttgccacg gaacggtctg    5640
cgttgtcgga aagatgcgtg atctgatcct tcaactcagc aaaagttcga tttattcaac    5700
aaagccgccg tcccgtcaag tcagcgtaat gctctgccag tgttacaacc aattaaccaa    5760
```

```
ttctgattag aaaaactcat cgagcatcaa atgaaactgc aatttattca tatcaggatt      5820
atcaatacca tattttgaa aaagccgttt ctgtaatgaa ggagaaaact caccgaggca       5880
gttccatagg atggcaagat cctggtatcg gtctgcgatt ccgactcgtc aacatcaat       5940 acaacctatt aatttcccct cgtcaaaaat aaggttatca agtgagaaat caccatgagt     6000
gacgactgaa tccggtgaga atggcaaaag cttatgcatt tctttccaga cttgttcaac     6060
aggccagcca ttacgctcgt catcaaaatc actcgcatca accaaaccgt tattcattcg     6120
tgattgcgcc tgagcgagac gaaatacgcg atcgctgtta aaaggacaat acaaacagg      6180 aatcgaatgc aaccggcgca ggaacactgc cagcgcatca acaatatttt cacctgaatc     6240
aggatattct tctaatacct ggaatgctgt tttcccgggg atcgcagtgg tgagtaacca     6300
tgcatcatca ggagtacgga taaaatgctt gatggtcgga agaggcataa attccgtcag     6360
ccagtttagt ctgaccatct catctgtaac atcattggca acgctacctt tgccatgttt     6420
cagaaacaac tctggcgcat cgggcttccc atacaatcga tagattgtcg cacctgattg     6480
cccgacatta tcgcgagccc atttataccc atataaatca gcatccatgt tggaatttaa     6540
tcgcggcctc gagcaagacg tttcccgttg aatatggctc ataacacccc ttgtattact     6600
gtttatgtaa gcagacagtt ttattgttca tgatgatata tttttatctt gtgcaatgta     6660
acatcagaga ttttgagaca acgtggct tccccccccc cccattatt gaagcattta        6720 tcagggttat tgtctcatga gcggatacat atttgaatgt atttagaaaa ataaacaaat     6780
aggggttccg cgcacatttc cccgaaaagt gccacctgac gtctaagaaa ccattattat     6840
catgacatta acctataaaa ataggcgtat cacgaggccc tttcgtc                   6887
```

<210> SEQ ID NO 7
<211> LENGTH: 7044
<212> TYPE: DNA
<213> ORGANISM: Artificial Sequence
<220> FEATURE:
<223> OTHER INFORMATION: Synthetic Construct pVR1012-GP(Z) delta GP2
      Delta C-term B

<400> SEQUENCE: 7

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgacccccg cccattgacg tcaataatga cgtatgttcc     480
catagtaacg ccaataggga ctttccattg acgtcaatgg gtggagtatt tacggtaaac     540
tgcccacttg gcagtacatc aagtgtatca tatgccaagt acgcccccta ttgacgtcaa     600
tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag     900
```

```
agctcgttta gtgaaccgtc agatcgcctg gagacgccat ccacgctgtt ttgacctcca    960
tagaagacac cgggaccgat ccagcctccg cggccgggaa cggtgcattg gaacgcggat   1020
tccccgtgcc aagagtgacg taagtaccgc ctatagactc tataggcaca cccctttggc   1080
tcttatgcat gctatactgt ttttggcttg gggcctatac accccgctt ccttatgcta    1140 taggtgatgg tatagcttag cctataggtg tgggttattg accattattg accactcccc   1200
tattggtgac gatactttcc attactaatc cataacatgg ctctttgcca caactatctc   1260
tattggctat atgccaatac tctgtccttc agagactgac acggactctg tattttaca    1320 ggatggggtc ccatttatta tttacaaatt cacatataca acaacgccgt ccccgtgcc    1380 cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgaca cgtgtgatca gatatcgcgg ccgctctaga ccaggccctg   1920
gatcgatcca acaacacaat gggcgttaca ggaatattgc agttacctcg tgatcgattc   1980
aagaggacat cattctttct ttgggtaatt atccttttcc aaagaacatt ttccatccca   2040
cttggagtca tccacaatag cacattacag gttagtgatg tcgacaaact agtttgtcgt   2100
gacaaactgt catccacaaa tcaattgaga tcagttggac tgaatctcga agggaatgga   2160
gtggcaactg acgtgccatc tgcaactaaa agatggggct tcaggtccgg tgtcccacca   2220
aaggtggtca attatgaagc tggtgaatgg gctgaaaact gctacaatct tgaaatcaaa   2280
aaacctgacg ggagtgagtg tctaccagca gcgccagacg ggattcgggg cttccccgg    2340 tgccggtatg tgcacaaagt atcaggaacg ggaccgtgtg ccggagactt tgccttccat   2400
aaagagggtg ctttcttcct gtatgatcga cttgcttcca cagttatcta ccgaggaacg   2460
actttcgctg aaggtgtcgt tgcatttctg atactgcccc aagctaagaa ggacttcttc   2520
agctcacacc ccttgagaga gccggtcaat gcaacggagg accgtctag tggctactat    2580 tctaccacaa ttagatatca ggctaccggt tttggaacca atgagacaga gtacttgttc   2640
gaggttgaca atttgaccta cgtccaactt gaatcaagat tcacaccaca gtttctgctc   2700
cagctgaatg agacaatata tacaagtggg aaaaggagca ataccacggg aaaactaatt   2760
tggaaggtca accccgaaat tgatacaaca atcggggagt gggcccttctg ggaaactaaa   2820 aaaaacctca ctagaaaaat tcgcagtgaa gagttgtctt tcacagttgt atcaaacgga   2880
gccaaaaaca tcagtggtca gagtccggcg cgaacttctt ccgacccagg gaccaacaca   2940
acaactgaag accacaaaat catggcttca gaaaattcct ctgcaatggt tcaagtgcac   3000
agtcaaggaa gggaagctgc agtgtcgcat ctaacaaccc ttgccacaat ctccacgagt   3060
ccccaatccc tcacaaccaa accaggtccg gacaacagca cccataatac acccgtgtat   3120
aaacttgaca tctctgaggc aactcaagtt gaacaacatc accgcagaac agacaacgac   3180
agcacagcct ccgacactcc ctctgccacg accgcagccg gacccccaaa agcagagaac   3240
```

```
accaacacga gcaagagcac tgacttcctg gaccccgcca ccacaacaag tccccaaaac   3300
cacagcgaga ccgctggcaa caacaacact catcaccaag ataccggaga agagagtgcc   3360
agcagcggga agctaggctt aattaccaat actattgctg gagtcgcagg actgatcaca   3420
ggcgggagaa gaactcgaag agaagcaatt gtcaatgctc aacccaaatg caaccctaat   3480
ttacattact ggactactca ggatgaaggt gctgcaatcg gactggcctg gataccatat   3540
ttcgggccag cagccgaggg aatttacata gaggggctaa tgcacaatca agatggttta   3600
atctgtgggt tgagacagct ggccaacgag acgactcaag ctcttcaact gttcctgaga   3660
gccacaactg agctacgcac cttttcaatc ctcaaccgta aggcaattga tttcttgctg   3720
cagcgatggg gcggcacatg ccacattctg ggaccggact gctgtatcga accacatgag   3780
gataccggca ggtattggag ttacaggcgt tgtaattgca gttatcgctt tattctgtat   3840
atgcaaattt gtcttttagt ttttcttcag attgcttcat ggaaaagctc agcctcaaat   3900
caatgaaacc aggatttaat tatatggatt acttgaatct aagattactt gacaaatgat   3960
aatataatac actggagctt aaacatagc caatgtgatt ctaactcctt taaactcaca   4020
gttaatcata aacaaggttt gaggtaccga gctcgaattg atctgctgtg ccttctagtt   4080
gccagccatc tgttgtttgc ccctcccccg tgccttcctt gaccctggaa ggtgccactc   4140
ccactgtcct ttcctaataa aatgaggaaa ttgcatcgca ttgtctgagt aggtgtcatt   4200
ctattctggg gggtggggtg gggcaggaca gcaaggggga ggattgggaa gacaatagca   4260
ggcatgctgg ggatgcggtg ggctctatgg gtacccaggt gctgaagaat tgacccggtt   4320
cctcctgggc cagaaagaag caggcacatc cccttctctg tgacacaccc tgtccacgcc   4380
cctggttctt agttccagcc ccactcatag gacactcata gctcaggagg gctccgcctt   4440
caatcccacc cgctaaagta cttggagcgg tctctccctc cctcatcagc ccaccaaacc   4500
aaacctagcc tccaagagtg ggaagaaatt aaagcaagat aggctattaa gtgcagaggg   4560
agagaaaatg cctccaacat gtgaggaagt aatgagagaa atcatagaat tcttccgct   4620 tcctcgctca ctgactcgct gcgctcggtc gttcggctgc ggcgagcggt atcagctcac   4680
tcaaaggcgg taatacggtt atccacagaa tcagggggata acgcaggaaa gaacatgtga   4740
gcaaaaggcc agcaaaaggc caggaaccgt aaaaaggccg cgttgctggc gttttccat   4800 aggctccgcc cccctgacga gcatcacaaa aatcgacgct caagtcagag gtggcgaaac   4860
ccgacaggac tataaagata ccaggcgttt ccccctggaa gctccctcgt gcgctctcct   4920
gttccgaccc tgccgcttac cggatacctg tccgcctttc tcccttcggg aagcgtggcg   4980
ctttctcata gctcacgctg taggtatctc agttcggtgt aggtcgttcg ctccaagctg   5040
ggctgtgtgc acgaaccccc cgttcagccc gaccgctgcg ccttatccgg taactatcgt   5100
cttgagtcca acccggtaag acacgactta tcgccactgg cagcagccac tggtaacagg   5160
attagcagag cgaggtatgt aggcggtgct acagagttct tgaagtggtg gcctaactac   5220
ggctacacta gaagaacagt atttggtatc tgcgctctgc tgaagccagt taccttcgga   5280
aaaagagttg gtagctcttg atccggcaaa caaaccaccg ctggtagcgg tggtttttt   5340 gtttgcaagc agcagattac gcgcagaaaa aaggatctc aagaagatcc tttgatcttt   5400
tctacggggt ctgacgctca gtggaacgaa aactcacgtt aagggatttt ggtcatgaga   5460
ttatcaaaaa ggatcttcac ctagatcctt ttaaattaaa aatgaagttt taaatcaatc   5520
taaagtatat atgagtaaac ttggtctgac agttaccaat gcttaatcag tgaggcacct   5580
atctcagcga tctgtctatt tcgttcatcc atagttgcct gactcggggg ggggggggcgc   5640
```

-continued

```
tgaggtctgc tcgtgaagaa aggtgttgct gactcatacc aggcctgaat cgccccatca    5700
tccagccaga aagtgaggga gccacggttg atgagagctt tgttgtaggt ggaccagttg    5760
gtgattttga acttttgctt tgccacggaa cggtctgcgt tgtcgggaag atgcgtgatc    5820
tgatccttca actcagcaaa agttcgattt attcaacaaa gccgccgtcc cgtcaagtca    5880
gcgtaatgct ctgccagtgt tacaaccaat taaccaattc tgattagaaa aactcatcga    5940
gcatcaaatg aaactgcaat ttattcatat caggattatc aataccatat ttttgaaaaa    6000
gccgtttctg taatgaagga gaaaactcac cgaggcagtt ccataggatg caagatcct    6060
ggtatcggtc tgcgattccg actcgtccaa catcaataca acctattaat ttcccctcgt    6120
caaaaataag gttatcaagt gagaaatcac catgagtgac gactgaatcc ggtgagaatg    6180
gcaaaagctt atgcatttct ttccagactt gttcaacagg ccagccatta cgctcgtcat    6240
caaaatcact cgcatcaacc aaaccgttat tcattcgtga ttgcgcctga gcagacgaa     6300
atacgcgatc gctgttaaaa ggacaattac aaacaggaat cgaatgcaac cggcgcagga    6360
acactgccag cgcatcaaca atattttcac ctgaatcagg atattcttct aatacctgga    6420
atgctgtttt cccggggatc gcagtggtga gtaaccatgc atcatcagga gtacggataa    6480
aatgcttgat ggtcggaaga ggcataaatt ccgtcagcca gtttagtctg accatctcat    6540
ctgtaacatc attggcaacg ctacctttgc catgtttcag aaacaactct ggcgcatcgg    6600
gcttcccata caatcgatag attgtcgcac ctgattgccc gacattatcg cgagcccatt    6660
tatacccata taaatcagca tccatgttgg aatttaatcg cggcctcgag caagacgttt    6720
cccgttgaat atggctcata acaccccttg tattactgtt tatgtaagca gacagtttta    6780
ttgttcatga tgatatattt ttatcttgtg caatgtaaca tcagagattt tgagacacaa    6840
cgtggctttc cccccccccc cattattgaa gcatttatca gggttattgt ctcatgagcg    6900
gatacatatt tgaatgtatt tagaaaaata acaaataggg gttccgcgc acatttcccc     6960
gaaaagtgcc acctgacgtc taagaaacca ttattatcat gacattaacc tataaaaata    7020
ggcgtatcac gaggcccttt cgtc                                           7044
```

<210> SEQ ID NO 8
<211> LENGTH: 7106
<212> TYPE: DNA
<213> ORGANISM: Artificial Sequence
<220> FEATURE:
<223> OTHER INFORMATION: Synthetic Construct pVR1012-GP(Z) delta GP2 delta FUS

<400> SEQUENCE: 8

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc     180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaatagggga ctttccattg acgtcaatgg gtggagtatt tacggtaaac    540
tgcccacttg gcagtacatc aagtgtatca tatgccaagt acgccccta ttgacgtcaa     600
```

```
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctccg cggccgggaa cggtgcattg gaacgcggat   1020
tccccgtgcc aagagtgacg taagtaccgc ctatagactc tataggcaca ccccctttggc   1080 tcttatgcat gctatactgt ttttggcttg gggcctatac accccgctt ccttatgcta    1140 taggtgatgg tatagcttag cctataggtg tgggttattg accattattg accactcccc   1200
tattggtgac gatactttcc attactaatc cataacatgg ctctttgcca caactatctc   1260
tattggctat atgccaatac tctgtccttc agagactgac acggactctg tatttttaca    1320
ggatggggtc ccatttatta tttacaaatt cacatataca acaacgccgt cccccgtgcc   1380
cgcagttttt attaaacata gcgtgggatc tccacgcgaa tctcgggtac gtgttccgga    1440
catgggctct tctccggtag cggcggagct tccacatccg agccctggtc ccatgcctcc    1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg   1800
cgcgccacca gacataatag ctgacagact aacagactgt tcctttccat gggtcttttc    1860
tgcagtcacc gtcgtcgaca cgtgtgatca gatatcgcgg ccgctctaga ccaggccctg   1920
gatcgatcca acaacacaat gggcgttaca ggaatattgc agttacctcg tgatcgattc   1980
aagaggacat cattctttct ttgggtaatt atccttttcc aaagaacatt ttccatccca    2040
cttggagtca tccacaatag cacattacag gttagtgatg tcgacaaact agtttgtcgt   2100
gacaaactgt catccacaaa tcaattgaga tcagttggac tgaatctcga agggaatgga    2160
gtggcaactg acgtgccatc tgcaactaaa agatggggct tcaggtccgg tgtcccacca    2220
aaggtggtca attatgaagc tggtgaatgg gctgaaaact gctacaatct tgaaatcaaa    2280
aaacctgacg ggagtgagtg tctaccagca gcgccagacg ggattcgggg cttccccgg    2340 tgccggtatg tgcacaaagt atcaggaacg ggaccgtgtg ccggagactt tgccttccat    2400
aaagagggtg ctttcttcct gtatgatcga cttgcttcca cagttatcta ccgaggaacg    2460
actttcgctg aaggtgtcgt tgcatttctg tatactgcccc aagctaagaa ggacttcttc    2520
agctcacacc ccttgagaga gccggtcaat gcaacggagg accccgtctag tggctactat   2580 tctaccacaa ttagatatca ggctaccggt tttggaacca atgagacaga gtacttgttc   2640
gaggttgaca atttgaccta cgtccaactt gaatcaagat tcacaccaca gtttctgctc   2700
cagctgaatg agacaatata tacaagtggg aaaaggagca ataccacggg aaaactaatt   2760
tggaaggtca accccgaaat tgatacaaca atcggggagt gggccttctg ggaaactaaa    2820
aaaaacctca ctagaaaaat tcgcagtgaa gagttgtctt tcacagttgt atcaaacgga   2880
gccaaaaaca tcagtggtca gagtccggcg cgaacttctt ccgacccagg gaccaacaca   2940
```

```
acaactgaag accacaaaat catggcttca gaaaattcct ctgcaatggt tcaagtgcac   3000
agtcaaggaa gggaagctgc agtgtcgcat ctaacaaccc ttgccacaat ctccacgagt   3060
ccccaatccc tcacaaccaa accaggtccg dacaacagca cccataatac acccgtgtat   3120
aaacttgaca tctctgaggc aactcaagtt gaacaacatc accgcagaac agacaacgac   3180
agcacagcct ccgacactcc ctctgccacg accgcagccg dacccccaaa agcagagaac   3240
accaacacga gcaagagcac tgacttcctg dacccccgcca ccacaacaag tccccaaaac   3300
cacagcgaga ccgctggcaa caacaacact catcaccaag ataccggaga agagagtgcc   3360
agcagcggga agctaggctt aattaccaat actattgctg gagtcgcagg actgatcaca   3420
ggcgggagaa gaactcgaag agaagcaatt gtcaatgctc aacccaaatg caacccctaat   3480 ttacattact ggactactca ggatgaagag ggaatttaca tagaggggct aatgcacaat   3540
caagatggtt taatctgtgg gttgagacag ctggccaacg agacgactca agctcttcaa   3600
ctgttcctga gagccacaac tgagctacgc acctttcaa tcctcaaccg taaggcaatt   3660
gatttcttgc tgcagcgatg gggcggcaca tgccacattc tgggaccgga ctgctgtatc   3720
gaaccacatg attggaccaa gaacataaca gacaaaattg atcagattat tcatgatttt   3780
gttgataaaa cccttccgga ccaggggdac aatgacaatt ggtggacagg atggagacaa   3840
tggataccgg caggtattgg agttacaggc gttgtaattg cagttatcgc tttattctgt   3900
atatgcaaat ttgtctttta gtttttcttc agattgcttc atggaaaagc tcagcctcaa   3960
atcaatgaaa ccaggattta attatatgga ttacttgaat ctaagattac ttgacaaatg   4020
ataatataat acactggagc tttaaacata gccaatgtga ttctaactcc tttaaactca   4080
cagttaatca taaacaaggt ttgaggtacc gagctcgaat tgatctgctg tgccttctag   4140
ttgccagcca tctgttgttt gcccctcccc cgtgccttcc ttgaccctgg aaggtgccac   4200
tcccactgtc ctttcctaat aaaatgagga aattgcatcg cattgtctga gtaggtgtca   4260
ttctattctg gggggtgggg tggggcagga cagcaagggg gaggattggg aagacaatag   4320
caggcatgct ggggatgcgg tgggctctat gggtacccag gtgctgaaga attgacccgg   4380
ttcctcctgg gccagaaaga agcaggcaca tccccttctc tgtgacacac cctgtccacg   4440
cccctggttc ttagttccag ccccactcat aggacactca tagctcagga gggctccgcc   4500
ttcaatccca cccgctaaag tacttggagc ggtctctccc tccctcatca gcccaccaaa   4560
ccaaacctag cctccaagag tgggaagaaa ttaaagcaag ataggctatt aagtgcagag   4620
ggagagaaaa tgcctccaac atgtgaggaa gtaatgagag aaatcataga atttcttccg   4680
cttcctcgct cactgactcg ctgcgctcgg tcgttcggct gcggcgagcg gtatcagctc   4740
actcaaaggc ggtaatacgg ttatccacag aatcagggga taacgcagga agaacatgt   4800 gagcaaaagg ccagcaaaag gccaggaacc gtaaaaaggc cgcgttgctg gcgttttccc   4860
ataggctccg ccccccctgac gagcatcaca aaaatcgacg ctcaagtcag aggtggcgaa   4920
acccgacagg actataaaga taccaggcgt ttccccctgg aagctccctc gtgcgctctc   4980
ctgttccgac cctgccgctt accggatacc tgtccgcctt tctcccttcg ggaagcgtgg   5040
cgctttctca tagctcacgc tgtaggtatc tcagttcggt gtaggtcgtt cgctccaagc   5100
tgggctgtgt gcacgaaccc cccgttcagc ccgaccgctg cgccttatcc ggtaactatc   5160
gtcttgagtc caacccggta agacacgact tatcgccact ggcagcagcc actggtaaca   5220
ggattagcag agcgaggtat gtaggcggtg ctacagagtt cttgaagtgg tggcctaact   5280
acggctacac tagaagaaca gtatttggta tctgcgctct gctgaagcca gttaccttcg   5340
```

-continued

```
gaaaaagagt tggtagctct tgatccggca aacaaaccac cgctggtagc ggtggttttt      5400
ttgtttgcaa gcagcagatt acgcgcagaa aaaaggatc tcaagaagat cctttgatct       5460
tttctacggg gtctgacgct cagtggaacg aaaactcacg ttaagggatt ttggtcatga      5520
gattatcaaa aaggatcttc acctagatcc ttttaaatta aaaatgaagt tttaaatcaa      5580
tctaaagtat atatgagtaa acttggtctg acagttacca atgcttaatc agtgaggcac      5640
ctatctcagc gatctgtcta tttcgttcat ccatagttgc ctgactcggg ggggggggc       5700 gctgaggtct gcctcgtgaa gaaggtgttg ctgactcata ccaggcctga atcgccccat      5760
catccagcca gaaagtgagg gagccacggt tgatgagagc tttgttgtag gtggaccagt      5820
tggtgatttt gaacttttgc tttgccacgg aacggtctgc gttgtcggga agatgcgtga      5880
tctgatcctt caactcagca aaagttcgat ttattcaaca aagccgccgt cccgtcaagt      5940
cagcgtaatg ctctgccagt gttacaacca attaaccaat tctgattaga aaaactcatc      6000
gagcatcaaa tgaaactgca atttattcat atcaggatta tcaataccat atttttgaaa      6060
aagccgtttc tgtaatgaag gagaaaactc accgaggcag ttccatagga tggcaagatc      6120
ctggtatcgg tctgcgattc cgactcgtcc aacatcaata acctatta atttcccctc        6180 gtcaaaaata aggttatcaa gtgagaaatc accatgagtg acgactgaat ccggtgagaa      6240
tggcaaaagc ttatgcattt ctttccagac ttgttcaaca ggccagccat tacgctcgtc      6300
atcaaaatca ctcgcatcaa ccaaaccgtt attcattcgt gattgcgcct gagcgagacg      6360
aaatacgcga tcgctgttaa aaggacaatt acaaacagga tcgaatgca accggcgcag       6420 gaacactgcc agcgcatcaa caatattttc acctgaatca ggatattctt ctaatacctg      6480
gaatgctgtt ttcccgggga tcgcagtggt gagtaaccat gcatcatcag gagtacggat      6540
aaaatgcttg atggtcggaa gaggcataaa ttccgtcagc cagtttagtc tgaccatctc      6600
atctgtaaca tcattggcaa cgctacctt gccatgtttc agaaacaact ctggcgcatc        6660
gggcttccca tacaatcgat agattgtcgc acctgattgc ccgacattat cgcgagccca      6720
tttataccca tataaatcag catccatgtt ggaatttaat cgcggcctcg agcaagacgt      6780
ttcccgttga atatggctca taacaccct tgtattactg tttatgtaag cagacagttt        6840
tattgttcat gatgatatat ttttatcttg tgcaatgtaa catcagagat tttgagacac       6900
aacgtggctt tccccccccc cccattattg aagcatttat cagggttatt gtctcatgag      6960
cggatacata tttgaatgta tttagaaaaa taaacaaata ggggttccgc gcacatttcc      7020
ccgaaaagtg ccacctgacg tctaagaaac cattattatc atgacattaa cctataaaaa      7080
taggcgtatc acgaggccct ttcgtc                                            7106
```

<210> SEQ ID NO 9
<211> LENGTH: 6914
<212> TYPE: DNA
<213> ORGANISM: Artificial Sequence
<220> FEATURE:
<223> OTHER INFORMATION: Synthetic Construct pVR1012-GP(Z) delta TM

<400> SEQUENCE: 9

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc      180
accatatgcg gtgtgaaata ccgcacagat gcgtaaggag aaaataccgc atcagattgg     240
```

-continued

```
ctattggcca ttgcatacgt tgtatccata tcataatatg tacatttata ttggctcatg   300
tccaacatta ccgccatgtt gacattgatt attgactagt tattaatagt aatcaattac   360
ggggtcatta gttcatagcc catatatgga gttccgcgtt acataactta cggtaaatgg   420
cccgcctggc tgaccgccca acgaccccg cccattgacg tcaataatga cgtatgttcc    480
catagtaacg ccaataggga ctttccattg acgtcaatgg gtggagtatt tacggtaaac   540
tgcccacttg gcagtacatc aagtgtatca tatgccaagt acgccccta ttgacgtcaa    600 tgacggtaaa tggcccgcct ggcattatgc ccagtacatg accttatggg actttcctac   660
ttggcagtac atctacgtat tagtcatcgc tattaccatg gtgatgcggt tttggcagta   720
catcaatggg cgtggatagc ggtttgactc acggggattt ccaagtctcc accccattga   780
cgtcaatggg agtttgtttt ggcaccaaaa tcaacgggac tttccaaaat gtcgtaacaa   840
ctccgcccca ttgacgcaaa tgggcggtag gcgtgtacgg tgggaggtct atataagcag   900
agctcgttta gtgaaccgtc agatcgcctg gagacgccat ccacgctgtt ttgacctcca   960
tagaagacac cgggaccgat ccagcctccg cggccgggaa cggtgcattg aacgcggat   1020 tccccgtgcc aagagtgacg taagtaccgc ctatagactc tataggcaca cccctttggc  1080
tcttatgcat gctatactgt ttttggcttg ggcctatac accccgctt ccttatgcta    1140 taggtgatgg tatagcttag cctataggtg tgggttattg accattattg accactcccc  1200
tattggtgac gatactttcc attactaatc cataacatgg ctctttgcca caactatctc  1260
tattggctat atgccaatac tctgtccttc agagactgac acggactctg tattttaca   1320 ggatggggtc ccatttatta tttacaaatt cacatataca acaacgccgt ccccgtgcc   1380 cgcagttttt attaaacata gcgtgggatc tccacgcgaa tctcgggtac gtgttccgga  1440
catgggctct tctccggtag cggcggagct tccacatccg agccctggtc ccatgcctcc  1500
agcggctcat ggtcgctcgg cagctccttg ctcctaacag tggaggccag acttaggcac  1560
agcacaatgc ccaccaccac cagtgtgccg cacaaggccg tggcggtagg gtatgtgtct  1620
gaaaatgagc gtggagattg gctcgcacg gctgacgcag atggaagact taaggcagcg   1680
gcagaagaag atgcaggcag ctgagttgtt gtattctgat aagagtcaga ggtaactccc  1740
gttgcggtgc tgttaacggt ggagggcagt gtagtctgag cagtactcgt tgctgccgcg  1800
cgcgccacca gacataatag ctgacagact aacagactgt tcctttccat gggtctttc   1860 tgcagtcacc gtcgtcgaca cgtgtgatca gatatcgcgg ccgctctaga ccaggccctg  1920
gatcgatcca acaacacaat gggcgttaca ggaatattgc agttacctcg tgatcgattc  1980
aagaggacat cattctttct ttgggtaatt atccttttcc aaagaacatt ttccatccca  2040
cttggagtca tccacaatag cacattacag gttagtgatg tcgacaaact agtttgtcgt  2100
gacaaactgt catccacaaa tcaattgaga tcagttggac tgaatctcga agggaatgga  2160
gtggcaactg acgtgccatc tgcaactaaa agatggggct tcaggtccgg tgtcccacca  2220
aaggtggtca attatgaagc tggtgaatgg gctgaaaact gctacaatct tgaaatcaaa  2280
aaacctgacg ggagtgagtg tctaccagca gcgccagacg ggattcgggg cttccccgg   2340 tgccggtatg tgcacaaagt atcaggaacg ggaccgtgtg ccggagactt tgccttccat  2400
aaagagggtc ctttcttcct gtatgatcga cttgcttcca cagttatcta ccgaggaacg  2460
actttcgctg aagtgtcgt tgcatttctg atactgcccc aagctaagaa ggacttcttc   2520
agctcacacc ccttgagaga gccggtcaat gcaacggagg acccgtctag tggctactat  2580
tctaccacaa ttagatatca ggctaccggt tttggaacca atgagacaga gtacttgttc  2640
```

-continued

```
gaggttgaca atttgaccta cgtccaactt gaatcaagat tcacaccaca gtttctgctc    2700
cagctgaatg agacaatata tacaagtggg aaaaggagca ataccacggg aaaactaatt    2760
tggaaggtca accccgaaat tgatacaaca atcggggagt gggccttctg ggaaactaaa    2820
aaaaacctca ctagaaaaat tcgcagtgaa gagttgtctt tcacagttgt atcaaacgga    2880
gccaaaaaca tcagtggtca gagtccggcg cgaacttctt ccgacccagg gaccaacaca    2940
acaactgaag accacaaaat catggcttca gaaaattcct ctgcaatggt tcaagtgcac    3000
agtcaaggaa gggaagctgc agtgtcgcat ctaacaaccc ttgccacaat ctccacgagt    3060
ccccaatccc tcacaaccaa accaggtccg dacaacagca cccataatac acccgtgtat    3120
aaacttgaca tctctgaggc aactcaagtt gaacaacatc accgcagaac agacaacgac    3180
agcacagcct ccgacactcc ctctgccacg accgcagccg acccccaaa agcagagaac     3240 accaacacga gcaagagcac tgacttcctg daccccgcca ccacaacaag tccccaaaac    3300
cacagcgaga ccgctggcaa caacaacact catcaccaag ataccggaga agagagtgcc    3360
agcagcggga agctaggctt aattaccaat actattgctg gagtcgcagg actgatcaca    3420
ggcgggagaa gaactcgaag agaagcaatt gtcaatgctc aacccaaatg caaccctaat    3480
ttacattact ggactactca ggatgaaggt gctgcaatcg gactggcctg gataccatat    3540
ttcgggccag cagccgaggg aatttacata gaggggctaa tgcacaatca agatggttta    3600
atctgtgggt tgagacagct ggccaacgag acgactcaag ctcttcaact gttcctgaga    3660
gccacaactg agctacgcac cttttcaatc ctcaaccgta aggcaattga tttcttgctg    3720
cagcgatggg gcggcacatg ccacattctg ggaccggact gctgtatcga accacatgat    3780
tggaccaaga acataacaga caaaattgat cagattattc atgattttgt tgataaaacc    3840
cttccggacc aggggacaa tgacaattgg tggacaggat ggagacaatg gatggccgca    3900
tcgtgactga ctgacgatct gcctcgcgag atctgctgtg ccttctagtt gccagccatc    3960
tgttgtttgc ccctcccccg tgccttcctt gaccctggaa ggtgccactc ccactgtcct    4020
ttcctaataa aatgaggaaa ttgcatcgca ttgtctgagt aggtgtcatt ctattctggg    4080
gggtggggtg gggcaggaca gcaaggggga ggattgggaa gacaatagca ggcatgctgg    4140
ggatgcggtg ggctctatgg gtacccaggt gctgaagaat tgacccggtt cctcctgggc    4200
cagaaagaag caggcacatc cccttctctg tgacacaccc tgtccacgcc cctggttctt    4260
agttccagcc ccactcatag dacactcata gctcaggagg ctccgcctt caatcccacc     4320 cgctaaagta cttggagcgg tctctcgctc cctcatcagc ccaccaaacc aaacctagcc    4380
tccaagagtg gaagaaatt aaagcaagat aggctattaa gtgcagaggg agagaaaatg      4440
cctccaacat gtgaggaagt aatgagagaa atcatagaat ttcttccgct tcctcgctca    4500
ctgactcgct cgctcggtc gttcggctgc ggcgagcggg atcagctcac tcaaaggcgg    4560
taatacggtt atccacagaa tcaggggata acgcaggaaa gaacatgtga gcaaaaggcc    4620
agcaaaaggc caggaaccgt aaaaaggccg cgttgctggc gttttttccat aggctccgcc    4680 cccctgacga gcatcacaaa aatcgacgct caagtcagag gtggcgaaac ccgacaggac    4740
tataaagata ccaggcgttt ccccctggaa gctccctcgt gcgctctcct gttccgaccc    4800
tgccgcttac cggatacctg tccgcctttc tcccttcggg aagcgtggcg ctttctcata    4860
gctcacgctg taggtatctc agttcggtgt aggtcgttcg ctccaagctg ggctgtgtgc    4920
acgaaccccc cgttcagccc gaccgctgcg ccttatccgg taactatcgt cttgagtcca    4980
```

-continued

```
acccggtaag acacgactta tcgccactgg cagcagccac tggtaacagg attagcagag    5040
cgaggtatgt aggcggtgct acagagttct tgaagtggtg gcctaactac ggctacacta    5100
gaagaacagt atttggtatc tgcgctctgc tgaagccagt taccttcgga aaaagagttg    5160
gtagctcttg atccggcaaa caaaccaccg ctggtagcgg tggttttttt gtttgcaagc    5220
agcagattac gcgcagaaaa aaggatctc aagaagatcc tttgatcttt tctacggggt     5280
ctgacgctca gtggaacgaa aactcacgtt aagggatttt ggtcatgaga ttatcaaaaa    5340
ggatcttcac ctagatcctt ttaaattaaa aatgaagttt taaatcaatc taaagtatat    5400
atgagtaaac ttggtctgac agttaccaat gcttaatcag tgaggcacct atctcagcga    5460
tctgtctatt tcgttcatcc atagttgcct gactcggggg ggggggcgc tgaggtctgc     5520 ctcgtgaaga aggtgttgct gactcatacc aggcctgaat cgccccatca tccagccaga    5580
aagtgaggga gccacggttg atgagagctt tgttgtaggt ggaccagttg gtgattttga    5640
acttttgctt tgccacggaa cggtctgcgt tgtcggaag atgcgtgatc tgatccttca     5700
actcagcaaa agttcgattt attcaacaaa gccgccgtcc cgtcaagtca gcgtaatgct    5760
ctgccagtgt tacaaccaat taaccaattc tgattagaaa aactcatcga gcatcaaatg    5820
aaactgcaat ttattcatat caggattatc aataccatat ttttgaaaaa gccgtttctg    5880
taatgaagga gaaaactcac cgaggcagtt ccataggatg gcaagatcct ggtatcggtc    5940
tgcgattccg actcgtccaa catcaataca acctattaat ttcccctcgt caaaaataag    6000
gttatcaagt gagaaatcac catgagtgac gactgaatcc ggtgagaatg gcaaaagctt    6060
atgcatttct ttccagactt gttcaacagg ccagccatta cgctcgtcat caaaatcact    6120
cgcatcaacc aaaccgttat tcattcgtga ttgcgcctga gcgagacgaa atacgcgatc    6180
gctgttaaaa ggacaattac aaacaggaat cgaatgcaac cggcgcagga acactgccag    6240
cgcatcaaca atattttcac ctgaatcagg atattcttct aatacctgga atgctgtttt    6300 cccgggatc gcagtggtga gtaaccatgc atcatcagga gtacggataa aatgcttgat     6360
ggtcggaaga ggcataaatt ccgtcagcca gtttagtctg accatctcat ctgtaacatc    6420
attggcaacg ctacctttgc catgtttcag aaacaactct ggcgcatcgg gcttcccata    6480
caatcgatag attgtcgcac ctgattgccc gacattatcg cgagcccatt tatacccata    6540
taaatcagca tccatgttgg aatttaatcg cggcctcgag caagacgttt cccgttgaat    6600
atggctcata acaccccttg tattactgtt tatgtaagca gacagtttta ttgttcatga    6660
tgatatattt ttatcttgtg caatgtaaca tcagagattt tgagacacaa cgtggctttc    6720 ccccccccc cattattgaa gcatttatca gggttattgt ctcatgagcg gatacatatt     6780
tgaatgtatt tagaaaaata acaaataggg gttccgcgc acatttcccc gaaaagtgcc     6840
acctgacgtc taagaaacca ttattatcat gacattaacc tataaaaata ggcgtatcac    6900
gaggcccttt cgtc                                                      6914
```

<210> SEQ ID NO 10
<211> LENGTH: 6467
<212> TYPE: DNA
<213> ORGANISM: Artificial Sequence
<220> FEATURE:
<223> OTHER INFORMATION: Synthetic Construct pVR1012-GP(Z) delta SGP

<400> SEQUENCE: 10

```
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg    120
```

-continued

```
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgaccccg cccattgacg tcaataatga cgtatgttcc    480
catagtaacg ccaatagggda cttccattg acgtcaatgg gtggagtatt tacggtaaac    540
tgcccacttg gcagtacatc aagtgtatca tatgccaagt acgccccta ttgacgtcaa    600 tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt tgacctcca    960 tagaagacac cgggaccgat ccagcctccg cggccgggaa cggtgcattg gaacgcggat   1020
tccccgtgcc aagagtgacg taagtaccgc ctatagactc tataggcaca cccctttggc   1080
tcttatgcat gctatactgt ttttggcttg gggcctatac accccgctt ccttatgcta   1140 taggtgatgg tatagcttag cctataggtg tgggttattg accattattg accactcccc   1200
tattggtgac gatactttcc attactaatc ataacatgg ctctttgcca caactatctc   1260
tattggctat atgccaatac tctgtccttc agagactgac acggactctg tattttaca    1320 ggatggggtc ccatttatta tttacaaatt cacatataca acaacgccgt cccccgtgcc   1380
cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgaca cgtgtgatca gatatcgcgg ccgctctaga ccaggccctg   1920
gatcgatcca acaacacaat gggcgttaca ggaatattgc agttacctcg tgatcgattc   1980
aagaggacat cattctttct ttgggtaatt atccttttcc aaagaacatt ttccatccca   2040
cttggagtca tccacaatag cacattacag gttagtgatg tcaaccccga aattgataca   2100
acaatcgggg agtgggcctt ctgggaaact aaaaaaaacc tcactagaaa aattcgcagt   2160
gaagagttgt cttcacagt tgtatcaaac ggagccaaaa acatcagtgg tcagagtccg   2220
gcgcgaactt cttccgaccc agggaccaac acaacaactg aagaccacaa aatcatggct   2280
tcagaaaatt cctctgcaat ggttcaagtg cacagtcaag gaagggaagc tgcagtgtcg   2340
catctaacaa cccttgccac aatctccacg agtccccaat ccctcacaac caaaccaggt   2400
ccggacaaca gcacccataa tacacccgtg tataaacttg acatctctga ggcaactcaa   2460
```

-continued

```
gttgaacaac atcaccgcag aacagacaac gacagcacag cctccgacac tccctctgcc    2520
acgaccgcag ccggaccccc aaaagcagag aacaccaaca cgagcaagag cactgacttc    2580
ctggaccccg ccaccacaac aagtcccaa aaccacagcg agaccgctgg caacaacaac     2640
actcatcacc aagataccgg agaagagagt gccagcagcg ggaagctagg cttaattacc    2700
aatactattg ctggagtcgc aggactgatc acaggcggga gaagaactcg aagagaagca    2760
attgtcaatg ctcaacccaa atgcaaccct aatttacatt actggactac tcaggatgaa    2820
ggtgctgcaa tcggactggc ctggatacca tatttcgggc cagcagccga gggaatttac    2880
atagaggggc taatgcacaa tcaagatggt ttaatctgtg ggttgagaca gctggccaac    2940
gagacgactc aagctcttca actgttcctg agagccacaa ctgagctacg cacctttca    3000 atcctcaacc gtaaggcaat tgatttcttg ctgcagcgat ggggcggcac atgccacatt    3060
ctgggaccgg actgctgtat cgaaccacat gattggacca agaacataac agacaaaatt    3120
gatcagatta ttcatgattt tgttgataaa acccttccgg accaggggga caatgacaat    3180
tggtggacag gatggagaca atggataccg gcaggtattg gagttacagg cgttgtaatt    3240
gcagttatcg ctttattctg tatatgcaaa tttgtctttt agttttctt cagattgctt     3300 catggaaaag ctcagcctca aatcaatgaa accaggattt aattatatgg attacttgaa    3360
tctaagatta cttgacaaat gataatataa tacactggag cttaaacat agccaatgtg     3420 attctaactc ctttaaactc acagttaatc ataaacaagg tttgaggtac cgagctcgaa    3480
ttgatctgct gtgccttcta gttgccagcc atctgttgtt tgcccctccc ccgtgccttc    3540
cttgaccctg gaaggtgcca ctcccactgt cctttcctaa taaaatgagg aaattgcatc    3600
gcattgtctg agtaggtgtc attctattct gggggggtggg gtgggcagg acagcaaggg    3660 ggaggattgg gaagacaata gcaggcatgc tggggatgcg gtgggctcta tgggtaccca   3720
ggtgctgaag aattgacccg gttcctcctg ggccagaaag aagcaggcac atcccttct    3780 ctgtgacaca ccctgtccac gcccctggtt cttagttcca gccccactca taggacactc    3840
atagctcagg agggctccgc cttcaatccc acccgctaaa gtacttggag cggtctctcc    3900
ctccctcatc agcccaccaa accaaaccta gcctccaaga gtgggaagaa attaaagcaa    3960
gataggctat taagtgcaga gggagagaaa atgcctccaa catgtgagga agtaatgaga    4020
gaaatcatag aatttcttcc gcttcctcgc tcactgactc gctgcgctcg gtcgttcggc    4080
tgcggcgagc ggtatcagct cactcaaagg cggtaatacg gttatccaca gaatcagggg    4140
ataacgcagg aaagaacatg tgagcaaaag gccagcaaaa ggccaggaac cgtaaaaagg    4200
ccgcgttgct ggcgtttttc cataggctcc gcccccctga cgagcatcac aaaaatcgac    4260
gctcaagtca gaggtggcga aacccgacag gactataaag ataccaggcg tttccccctg    4320
gaagctccct cgtgcgctct cctgttccga ccctgccgct taccggatac ctgtccgcct    4380
ttctcccttc gggaagcgtg gcgctttctc atagctcacg ctgtaggtat ctcagttcgg    4440
tgtaggtcgt tcgctccaag ctgggctgtg tgcacgaacc cccgttcag cccgaccgct     4500 gcgccttatc cggtaactat cgtcttgagt ccaacccgt aagacacgac ttatcgccac     4560
tggcagcagc cactggtaac aggattagca gagcgaggta tgtaggcggt gctacagagt    4620
tcttgaagtg gtggcctaac tacgctacac tagaagaac agtatttggt atctgcgctc    4680
tgctgaagcc agttaccttc ggaaaaagag ttggtagctc ttgatccggc aaacaaacca    4740
ccgctggtag cggtggtttt tttgtttgca agcagcagat tacgcgcaga aaaaaggat    4800 ctcaagaaga tcctttgatc ttttctacgg ggtctgacgc tcagtggaac gaaaactcac    4860
```

-continued

```
gttaagggat tttggtcatg agattatcaa aaaggatctt cacctagatc cttttaaatt    4920
aaaaatgaag ttttaaatca atctaaagta tatatgagta aacttggtct gacagttacc    4980
aatgcttaat cagtgaggca cctatctcag cgatctgtct atttcgttca tccatagttg    5040
cctgactcgg ggggggggg cgctgaggtc tgcctcgtga agaaggtgtt gctgactcat     5100
accaggcctg aatcgcccca tcatccagcc agaaagtgag ggagccacgg ttgatgagag    5160 cttttgttgta ggtggaccag ttggtgattt tgaacttttg ctttgccacg gaacggtctg   5220
cgttgtcggg aagatgcgtg atctgatcct tcaactcagc aaaagttcga tttattcaac    5280
aaagccgccg tcccgtcaag tcagcgtaat gctctgccag tgttacaacc aattaaccaa    5340
ttctgattag aaaaactcat cgagcatcaa atgaaactgc aatttattca tatcaggatt    5400
atcaatacca tattttgaa aaagccgttt ctgtaatgaa ggagaaaact caccgaggca     5460
gttccatagg atggcaagat cctggtatcg gtctgcgatt ccgactcgtc caacatcaat    5520
acaacctatt aatttcccct cgtcaaaaat aaggttatca agtgagaaat caccatgagt    5580
gacgactgaa tccggtgaga atggcaaaag cttatgcatt tctttccaga cttgttcaac    5640
aggccagcca ttacgctcgt catcaaaatc actcgcatca accaaaccgt tattcattcg    5700
tgattgcgcc tgagcgagac gaaatacgcg atcgctgtta aaaggacaat acaaacagg     5760 aatcgaatgc aaccggcgca ggaacactgc cagcgcatca acaatatttt cacctgaatc    5820
aggatattct tctaatacct ggaatgctgt tttcccgggg atcgcagtgg tgagtaacca    5880
tgcatcatca ggagtacgga taaaatgctt gatggtcgga agaggcataa attccgtcag    5940
ccagtttagt ctgaccatct catctgtaac atcattggca acgctacctt tgccatgttt    6000
cagaaacaac tctggcgcat cgggcttccc atacaatcga tagattgtcg cacctgattg    6060
cccgacatta tcgcgagccc atttataccc atataaatca gcatccatgt tggaatttaa    6120
tcgcggcctc gagcaagacg tttcccgttg aatatggctc ataacacccc ttgtattact    6180
gtttatgtaa gcagacagtt ttattgttca tgatgatata ttttatctt gtgcaatgta    6240 acatcagaga ttttgagaca caacgtggct ttcccccccc cccattatt gaagcattta    6300 tcagggttat tgtctcatga gcggatacat atttgaatgt atttagaaaa ataaacaaat    6360
aggggttccg cgcacatttc cccgaaaagt gccacctgac gtctaagaaa ccattattat    6420
catgacatta acctataaaa ataggcgtat cacgaggccc tttcgtc                  6467
```

<210> SEQ ID NO 11
<211> LENGTH: 6913
<212> TYPE: DNA
<213> ORGANISM: Artificial Sequence
<220> FEATURE:
<223> OTHER INFORMATION: Synthetic Construct pVR1012x/s Ebola GP(R)(dTM)

<400> SEQUENCE: 11

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
```

```
cccgcctggc tgaccgccca acgaccccg cccattgacg tcaataatga cgtatgttcc    480
catagtaacg ccaataggga cttccattg acgtcaatgg gtggagtatt tacggtaaac    540
tgcccacttg gcagtacatc aagtgtatca tatgccaagt acgccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctccg cggccgggaa cggtgcattg gaacgcggat   1020
tccccgtgcc aagagtgacg taagtaccgc ctatagactc tataggcaca ccctttggc    1080
tcttatgcat gctatactgt ttttggcttg gggcctatac accccgctt ccttatgcta    1140
taggtgatgg tatagcttag cctataggtg tgggttattg accattattg accactcccc    1200
tattggtgac gatactttcc attactaatc cataacatgg ctctttgcca caactatctc    1260
tattggctat atgccaatac tctgtccttc agagactgac acggactctg tatttttaca    1320
ggatggggtc ccatttatta tttacaaatt cacatataca acaacgccgt cccccgtgcc    1380
cgcagttttt attaaacata gcgtgggatc tccacgcgaa tctcgggtac gtgttccgga    1440
catgggctct tctccggtag cggcggagct tccacatccg agccctggtc ccatgcctcc    1500
agcggctcat ggtcgctcgg cagctccttg ctcctaacag tggaggccag acttaggcac    1560
agcacaatgc ccaccaccac cagtgtgccg cacaaggccg tggcggtagg gtatgtgtct    1620
gaaaatgagc gtggagattg ggctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tcctttccat gggtcttttc    1860
tgcagtcacc gtcgtcgaca cgtgtgatca gatccccaaa ttacctatac aacatggggt    1920
caggatatca acttctccaa ttgcctcggg aacgttttcg taaaacttcg ttcttagtat    1980
gggtaatcat cctcttccag cgagcaatct ccatgccgct tggtatagtg acaaatagca    2040
ctctcaaagc aacagaaatt gatcaattgg tttgtcggga caaactgtca tcaaccagtc    2100
agctcaagtc tgtggggctg aatctggaag gaaatggaat tgcaaccgat gtcccatcag    2160
caacaaaacg ctggggattt cgttcaggtg tgcctcccaa ggtggtcagc tatgaagccg    2220
gagaatgggc agaaaattgc tacaatctgg agatcaaaaa gtcagacgga agtgaatgcc    2280
tccctctccc tcccgacggt gtacgaggat tccctagatg tcgctatgtc cacaaagttc    2340
aaggaacagg tccttgtccc ggtgacttag cttccaataa aaatgggct ttttcttgt    2400
atgatagatt ggcctcaact gtcatctacc gagggacaac ttttgctgaa ggtgtcgtag    2460
cttttttaat tctgtcagag cccaagaagc attttggaa ggctacacca gctcatgaac    2520
cggtgaacac aacagatgat tccacaagct actacatgac cctgacactc agctacgaga    2580
tgtcaaattt tgggggcaat gaaagtaaca ccctttttaa ggtagacaac cacacatatg    2640
tgcaactaga tcgtccacac actccgcagt tccttgttca gctcaatgaa acacttcgaa    2700
gaaataatcg cctagcaac agtacaggga gattgacttg acattggat cctaaaattg    2760
aaccagatgt tggtgagtgg gccttctggg aaactaaaaa aacttttccc aacaacttca    2820
```

```
tggagaaaac ttgcatttcc aaattctatc aacccacacc aacaactcct cagatcagag   2880
cccggcggga actgtccaag gaaaaattag ctaccaccca cccgccaaca actccgagct   2940
ggttccaacg gattcccctc cagtggtttc agtgctcact gcaggacgga cagaggaaat   3000
gtcgacccaa ggtctaacca acggagagac aatcacaggt ttcaccgcga acccaatgac   3060
aaccaccatt gccccaagtc caaccatgac aagcgaggtt gataacaatg taccaagtga   3120
acaaccgaac aacacagcat ccattgaaga ctcccccca tcggcaagca acgagacaat    3180
ttaccactcc gagatggatc cgatccaagg ctcgaacaac tccgcccaga gcccacagac   3240
caagaccacg ccagcaccca aacatcccc gatgacccag acccgcaag agacggccaa     3300 cagcagcaaa ccaggaacca gcccaggaag cgcagccgga ccaagtcagc ccggactcac   3360
tataaataca gtaagtaagg tagctgattc actgagtccc accaggaaac aaaagcgatc   3420
ggttcgacaa acaccgcta ataaatgtaa cccagatctt tactattgga cagctgttga    3480
tgagggggca gcagtaggat tggcatggat tccatatttc ggacctgcag cagaaggcat   3540
ctacattgag ggtgtaatgc ataatcagaa tgggcttatt tgcgggctac gtcagctagc   3600
caatgaaact acccaggctc ttcaattatt tctgcgggcc acaacagaac tgaggactta   3660
ctcacttctt aacagaaaag ctattgattt tcttcttcaa cgatggggag gtacctgtcg   3720
aatcctagga ccatcttgtt gcattgagcc acatgattgg acaaaaaata ttactgatga   3780
aattaaccaa attaaacatg actttattga caatccccta ccagaccacg agatgatct    3840 taatctatgg acaggttgga gacaatggtg aatctagacc aggccctgga tccagatctg   3900
ctgtgccttc tagttgccag ccatctgttg tttgccccctc cccgtgcct tccttgaccc    3960 tggaaggtgc cactcccact gtccttttcct aataaaatga ggaaattgca tcgcattgtc   4020
tgagtaggtg tcattctatt ctgggggtg gggtgggca ggacagcaag ggggaggatt     4080
gggaagacaa tagcaggcat gctggggatg cggtgggctc tatgggtacc caggtgctga   4140
agaattgacc cggttcctcc tgggccagaa agaagcaggc catccccctt ctctgtgaca   4200
caccctgtcc acgccctgg ttcttagttc cagccccact cataggacac tcatagctca    4260
ggagggctcc gccttcaatc ccacccgcta aagtacttgg agcggtctct ccctccctca   4320
tcagcccacc aaaccaaacc tagcctccaa gagtgggaag aaattaaagc aagataggct   4380
attaagtgca gagggagaga aaatgcctcc aacatgtgag gaagtaatga gagaaatcat   4440 agaatttaa ggccatgatt taaggccatc atggccttaa tcttccgctt cctcgctcac    4500
tgactcgctg cgctcggtcg ttcggctgcg gcgagcggta tcagctcact caaaggcggt   4560
aatacggtta tccacagaat caggggataa cgcaggaaag aacatgtgag caaaaggcca   4620
gcaaaaggcc aggaaccgta aaaaggccgc gttgctggcg ttttccata ggctccgccc     4680 ccctgacgag catcacaaaa atcgacgctc aagtcagagg tggcgaaacc cgacaggact   4740
ataaagatac caggcgtttc ccctggaag ctccctcgtg cgctctcctg ttccgaccct     4800
gccgcttacc ggatacctgt ccgcctttct cccttcggga agcgtggcgc tttctcatag   4860
ctcacgctgt aggtatctca gttcggtgta ggtcgttcgc tccaagctgg gctgtgtgca   4920 cgaaccccc gttcagcccg accgctgcgc cttatccggt aactatcgtc ttgagtccaa     4980
cccggtaaga cacgacttat cgccactggc agcagccact ggtaacagga ttagcagagc   5040
gaggtatgta ggcggtgcta cagagttctt gaagtggtgg cctaactacg gctacactag   5100
aagaacagta tttggtatct gcgctctgct gaagccagtt accttcggaa aaagagttgg   5160
```

-continued

```
tagctcttga tccggcaaac aaaccaccgc tggtagcggt ggttttttg tttgcaagca    5220 gcagattacg cgcagaaaaa aaggatctca agaagatcct tgatctttt ctacggggtc    5280 tgacgctcag tggaacgaaa actcacgtta agggattttg gtcatgagat tatcaaaaag    5340
gatcttcacc tagatccttt taaattaaaa atgaagtttt aaatcaatct aaagtatata    5400
tgagtaaact tggtctgaca gttaccaatg cttaatcagt gaggcaccta tctcagcgat    5460
ctgtctattt cgttcatcca tagttgcctg actcgggggg ggggggcgct gaggtctgcc    5520
tcgtgaagaa ggtgttgctg actcatacca ggcctgaatc gccccatcat ccagccagaa    5580
agtgagggag ccacggttga tgagagcttt gttgtaggtg gaccagttgg tgattttgaa    5640
cttttgcttt gccacggaac ggtctgcgtt gtcgggaaga tgcgtgatct gatccttcaa    5700
ctcagcaaaa gttcgattta ttcaacaaag ccgccgtccc gtcaagtcag cgtaatgctc    5760
tgccagtgtt acaaccaatt aaccaattct gattagaaaa actcatcgag catcaaatga    5820
aactgcaatt tattcatatc aggattatca ataccatatt tttgaaaaag ccgtttctgt    5880
aatgaaggag aaaactcacc gaggcagttc cataggatgg caagatcctg gtatcggtct    5940
gcgattccga ctcgtccaac atcaatacaa cctattaatt tccctcgtc aaaaataagg    6000 ttatcaagtg agaaatcacc atgagtgacg actgaatccg gtgagaatgg caaaagctta    6060
tgcatttctt ccagacttg ttcaacaggc cagccattac gctcgtcatc aaaatcactc    6120
gcatcaacca accgttatt cattcgtgat tgcgcctgag cgagacgaaa tacgcgatcg    6180
ctgttaaaag gacaattaca acaggaatc gaatgcaacc ggcgcaggaa cactgccagc    6240
gcatcaacaa tattttcacc tgaatcagga tattcttcta atacctggaa tgctgttttc    6300
ccggggatcg cagtggtgag taaccatgca tcatcaggag tacggataaa atgcttgatg    6360
gtcggaagag gcataaattc cgtcagccag tttagtctga ccatctcatc tgtaacatca    6420
ttggcaacgc tacctttgcc atgtttcaga aacaactctg gcgcatcggg cttcccatac    6480
aatcgataga ttgtcgcacc tgattgcccg acattatcgc gagcccattt atacccatat    6540
aaatcagcat ccatgttgga atttaatcgc ggcctcgagc aagacgtttc ccgttgaata    6600
tggctcataa caccccttgt attactgttt atgtaagcag acagttttat tgttcatgat    6660
gatatatttt tatcttgtgc aatgtaacat cagagatttt gagacacaac gtggctttcc    6720 ccccccccc attattgaag catttatcag ggttattgtc tcatgagcgg atacatattt    6780
gaatgtattt agaaaaataa acaaataggg gttccgcgca catttccccg aaaagtgcca    6840
cctgacgtct aagaaaccat tattatcatg acattaacct ataaaaatag gcgtatcacg    6900 aggcccttc gtc                                                        6913
```

<210> SEQ ID NO 12
<211> LENGTH: 8131
<212> TYPE: DNA
<213> ORGANISM: Artificial Sequence
<220> FEATURE:
<223> OTHER INFORMATION: Synthetic Construct pAdApt Ebola GP(R)(dTM)

<400> SEQUENCE: 12

```
ttaattaacc gcaattctca tgtttgacag cttatcatca tcaataatat accttatttt     60
ggattgaagc caatatgata atgagggggt ggagtttgtg acgtggcgcg gggcgtggga    120
acggggcggg tgacgtagta gtgtggcgga agtgtgatgt tgcaagtgtg gcggaacaca    180
tgtaagcgac ggatgtggca aaagtgacgt ttttggtgtg cgccggtgta cacaggaagt    240 gacaatttc gcgcggtttt aggcggatgt tgtagtaaat ttgggcgtaa ccgagtaaga    300
```

-continued

```
tttggccatt ttcgcgggaa aactgaataa gaggaagtga aatctgaata attttgtgtt    360
actcatagcg cgtaatattt gtctagggcc gcggggactt tgaccgttta cgtggagact    420
cgcccaggtg tttttctcag gtgttttccg cgttccgggt caaagttggc gttttattat    480
tatagtcagt acgtaccagt gcactggcct agagcggccc cattgcatac gttgtatcca    540
tatcataata tgtacattta tattggctca tgtccaacat taccgccatg ttgacattga    600
ttattgacta gttattaata gtaatcaatt acggggtcat tagttcatag cccatatatg    660
gagttccgcg ttacataact tacgtaaat ggcccgcctg gctgaccgcc caacgacccc    720
cgcccattga cgtcaataat gacgtatgtt cccatagtaa cgccaatagg gactttccat    780
tgacgtcaat gggtggagta tttacggtaa actgcccact tggcagtaca tcaagtgtat    840
catatgccaa gtacgccccc tattgacgtc aatgacggta aatggcccgc ctggcattat    900
gcccagtaca tgaccttatg gactttcct acttggcagt acatctacgt attagtcatc    960
gctattacca tggtgatgcg gttttggcag tacatcaatg ggcgtggata gcggtttgac    1020
tcacggggat ttccaagtct ccaccccatt gacgtcaatg ggagtttgtt ttggcaccaa    1080
aatcaacggg actttccaaa atgtcgtaac aactccgccc cattgacgca aatgggcggt    1140
aggcgtgtac ggtgggaggt ctatataagc agagctcgtt tagtgaaccg tcagatcgcc    1200
tggagacgcc atccacgctg ttttgacctc catagaagac accggaccg atccagcctc     1260
cgtcaccgtc gtcgacacgt gtgatcagat atcaacttct ccaattgcct cgggaacgtt    1320
ttcgtaaaac ttcgttctta gtatgggtaa tcatcctctt ccagcgagca atctccatgc    1380
cgcttggtat agtgacaaat agcactctca aagcaacaga aattgatcaa ttggtttgtc    1440
gggacaaact gtcatcaacc agtcagctca agtctgtggg gctgaatctg aaggaaatg    1500
gaattgcaac cgatgtccca tcagcaacaa aacgctgggg atttcgttca ggtgtgcctc    1560
ccaaggtggt cagctatgaa gccggagaat gggcagaaaa ttgctacaat ctggagatca    1620
aaaagtcaga cggaagtgaa tgcctccctc tccctcccga cggtgtacga ggattcccta    1680
gatgtcgcta tgtccacaaa gttcaaggaa caggtccttg tcccggtgac ttagcttcc    1740
ataaaaatgg ggctttttc ttgtatgata gattggcctc aactgtcatc taccgaggga    1800
caactttgtc tgaaggtgtc gtagcttttt taattctgtc agagcccaag aagcattttt    1860
ggaaggctac accagctcat gaaccggtga acacaacaga tgattccaca agctactaca    1920
tgaccctgac actcagctac gagatgtcaa attttggggg caatgaaagt aacacccttt    1980
ttaaggtaga caaccacaca tatgtgcaac tagatcgtcc acacactccg cagttccttg    2040
ttcagctcaa tgaaacactt cgaagaaata atcgccttag caacagtaca gggagattga    2100
cttggacatt ggatcctaaa attgaaccag atgttggtga gtgggccttc tgggaaacta    2160
aaaaaacttt tcccaacaac ttcatggaga aacttgcat ttccaaattc tatcaaccca    2220
caccaacaac tcctcagatc agagcccggc gggaactgtc caaggaaaaa ttagctacca    2280
cccacccgcc aacaactccg agctggttcc aacggattcc cctccagtgg tttcagtgct    2340
cactgcagga cggacagagg aaatgtcgac ccaaggtcta accaacggag agacaatcac    2400
aggtttcacc gcgaacccaa tgacaaccac cattgcccca gtccaaccac tgacaagcga    2460
ggttgataac aatgtaccaa gtgaacaacc gaacaacaca gcatccattg aagactcccc    2520
cccatcggca agcaacgaga caatttacca ctccgagatg gatccgatcc aaggctcgaa    2580
caactccgcc cagagcccac agaccaagac cacgccagca cccacaacat ccccgatgac    2640
```

```
ccaggacccg caagagacgg ccaacagcag caaaccagga accagcccag gaagcgcagc    2700
cggaccaagt cagcccggac tcactataaa tacagtaagt aaggtagctg attcactgag    2760
tcccaccagg aaacaaaagc gatcggttcg acaaaacacc gctaataaat gtaacccaga    2820
tctttactat tggacagctg ttgatgaggg ggcagcagta ggattggcat ggattccata    2880
tttcggacct gcagcagaag gcatctacat tgagggtgta atgcataatc agaatgggct    2940
tatttgcggg ctacgtcagc tagccaatga aactacccag gctcttcaat tatttctgcg    3000
ggccacaaca gaactgagga cttactcact tcttaacaga aaagctattg attttcttct    3060
tcaacgatgg ggaggtacct gtcgaatcct aggaccatct tgttgcattg agccacatga    3120
ttggacaaaa aatattactg atgaaattaa ccaaattaaa catgacttta ttgacaatcc    3180
cctaccagac cacggagatg atcttaatct atggacaggt tggagacaat ggtgaatcta    3240
gaccaggccc tggatccaga tctgctgtgc cttctagttg ccagccatct gttgtttgcc    3300
cctcccccgt gccttccttg accctggaag gtgccactcc cactgtcctt tcctaataaa    3360
atgaggaaat tgcatcgcat tgtctgagta ggtgtcattc tattctgggg ggtggggtgg    3420
ggcagcacag caaggggggag gattgggaag acaatagcag gcatgctggg gatgcggtgg    3480
gctctatggg tacccagggc cgcataactt cgtataatgt atgctatacg aagttataag    3540
atctgtactg aaatgtgtgg gcgtggctta agggtgggaa agaatatata aggtgggggt    3600
cttatgtagt tttgtatctg ttttgcagca gccgccgccg ccatgagcac caactcgttt    3660
gatggaagca ttgtgagctc atatttgaca acgcgcatgc ccccatgggc cggggtgcgt    3720
cagaatgtga tgggctccag cattgatggt cgccccgtcc tgcccgcaaa ctctactacc    3780
ttgacctacg agaccgtgtc tggaacgccg ttggagactg cagcctccgc cgccgcttca    3840
gccgctgcag ccaccgcccg cgggattgtg actgactttg cttcctgag cccgcttgca    3900
agcagtgcag cttcccgttc atccgcccgc gatgacaagt tgacggctct tttggcacaa    3960
ttggattctt tgacccggga acttaatgtc gtttctcagc agctgttgga tctgcgccag    4020
caggtttctg ccctgaaggc ttcctcccct cccaatgcgg tttaaaacat aaataaaaaa    4080
ccagactctg tttggatttg gatcaagcaa gtgtcttgct gtctttattt aggggttttg    4140
cgcgcgcggt aggcccggga ccagcggtct cggtcgttga gggtcctgtg tattttttcc    4200
aggacgtggt aaaggtgact ctggatgttc agatacatgg gcataagccc gtctctgggg    4260
tggaggtagc accactgcag agcttcatgc tgcggggtgg tgttgtagat gatccagtcg    4320
tagcaggagc gctgggcgtg gtgcctaaaa atgtctttca gtagcaagct gattgccagg    4380
ggcaggccct tggtgtaagt gtttacaaag cggttaagct gggatgggtg catacgtggg    4440
gatatgagat gcatcttgga ctgtattttt aggttggcta tgttcccagc catatccctc    4500
cggggattca tgttgtgcag aaccaccagc acagtgtatc cggtgcactt gggaaatttg    4560
tcatgtagct tagaaggaaa tgcgtggaag aacttggaga cgcccttgtg acctccaaga    4620
ttttccatgc attcgtccat aatgatggca atgggcccac gggcggcggc ctgggcgaag    4680
atatttctgg gatcactaac gtcatagttg tgttccagga tgagatcgtc ataggccatt    4740
tttacaaagc gcgggcggag ggtgccagac tgcggtataa tggttccatc cggcccaggg    4800
gcgtagttac cctcacagat ttgcatttcc cacgctttga gttcagatgg ggggatcatg    4860
tctacctgcg gggcgatgaa gaaaacggtt ccggggtag gggagatcag ctgggaagaa    4920
agcaggttcc tgagcagctg cgacttaccg cagccggtgg gccgtaaat cacacctatt    4980
accggctgca actggtagtt aagagagctg cagctgccgt catccctgag cagggggcc    5040
```

-continued

```
acttcgttaa gcatgtccct gactcgcatg ttttccctga ccaaatccgc cagaaggcgc    5100
tcgccgccca gcgatagcag ttcttgcaag gaagcaaagt ttttcaacgg tttgagaccg    5160
tccgccgtag gcatgctttt gagcgtttga ccaagcagtt ccaggcggtc ccacagctcg    5220
gtcacctgct ctacggcatc tcgatccagc atatctcctc gtttcgcggg ttggggcggc    5280
tttcgctgta cggcagtagt cggtgctcgt ccagacgggc cagggtcatg tctttccacg    5340
ggcgcagggt cctcgtcagc gtagtctggg tcacggtgaa ggggtgcgct ccgggctgcg    5400
cgctggccag ggtgcgcttg aggctggtcc tgctggtgct gaagcgctgc cggtcttcgc    5460
cctgcgcgtc ggccaggtag catttgacca tggtgtcata gtccagcccc tccgcggcgt    5520
ggcccttggc gcgcagcttg cccttggagg aggcgccgca cgaggggcag tgcagacttt    5580
tgagggcgta gagcttgggc gcgagaaata ccgattccgg ggagtaggca tccgcgccgc    5640
aggccccgca gacggtctcg cattccacga gccaggtgag ctctggccgt tcggggtcaa    5700
aaaccaggtt tcccccatgc ttttttgatgc gtttcttacc tctggttttcc atgagccggt    5760
gtccacgctc ggtgacgaaa aggctgtccg tgtccccgta tacagacttg agaggcctgt    5820
cctcgagcgg tgttccgcgg tcctcctcgt atagaaactc ggaccactct gagacaaagg    5880
ctcgcgtcca ggccagcacg aaggaggcta agtgggaggg gtagcggtcg ttgtccacta    5940
gggggtccac tcgctccagg gtgtgaagac acatgtcgcc ctcttcggca tcaaggaagg    6000
tgattggttt gtaggtgtag ccacgtgac cgggtgttcc tgaaggggggg ctataaaagg    6060
gggtggggc gcgttcgtcc tcactctctt ccgcatcgct gtctgcgagg ccagctgtt    6120
ggggtgagtc gacgcgaggc tggatggcct tccccattat gattcttctc gcttccggcg    6180
gcatcgggat gcccgcgttg caggccatgc tgtccaggca ggtagatgac gaccatcagg    6240
gacagcttca aggccagcaa aaggccagga accgtaaaaa ggccgcgttg ctggcgtttt    6300
tccataggct ccgcccccct gacgagcatc acaaaaatcg acgctcaagt cagaggtggc    6360
gaaacccgac aggactataa agataccagg cgtttccccc tggaagctcc ctcgtgcgct    6420
ctcctgttcc gaccctgccg cttaccggat acctgtccgc ctttctccct cgggaagcg    6480
tggcgctttc tcatagctca cgctgtaggt atctcagttc ggtgtaggtc gttcgctcca    6540
agctgggctg tgtgcacgaa ccccccgttc agcccgaccg ctgcgcctta tccggtaact    6600
atcgtcttga gtccaacccg gtaagacacg acttatcgcc actggcagca gccactggta    6660
acaggattag cagagcgagg tatgtaggcg gtgctacaga gttcttgaag tggtggccta    6720
actacggcta cactagaagg acagtatttg gtatctgcgc tctgctgaag ccagttacct    6780
tcggaaaaag agttggtagc tcttgatccg gcaaacaaac caccgctggt agcggtggtt    6840
tttttgtttg caagcagcag attacgcgca gaaaaaaagg atctcaagaa gatcctttga    6900
tcttttctac ggggtctgac gctcagtgga acgaaaactc acgttaaggg attttggtca    6960
tgagattatc aaaaaggatc ttcacctaga tccttttaaa ttaaaaatga agttttaaat    7020
caatctaaag tatatatgag taaacttggt ctgacagtta ccaatgctta atcagtgagg    7080
cacctatctc agcgatctgt ctatttcgtt catccatagt tgcctgactc cccgtcgtgt    7140
agataactac gatacgggag ggcttaccat ctggccccag tgctgcaatg ataccgcgag    7200
acccacgctc accggctcca gatttatcag caataaacca gccagccgga agggccgagc    7260
gcagaagtgg tcctgcaact ttatccgcct ccatccagtc tattaattgt tgccgggaag    7320
ctagagtaag tagttcgcca gttaatagtt tgcgcaacgt tgttgccatt gctgcaggca    7380
```

-continued

```
tcgtggtgtc acgctcgtcg tttggtatgg cttcattcag ctccggttcc aacgatcaa    7440 ggcgagttac atgatccccc atgttgtgca aaaaagcggt tagctccttc ggtcctccga    7500
tcgttgtcag aagtaagttg gccgcagtgt tatcactcat ggttatggca gcactgcata    7560
attctcttac tgtcatgcca tccgtaagat gcttttctgt gactggtgag tactcaacca    7620
agtcattctg agaatagtgt atgcggcgac cgagttgctc ttgcccggcg tcaacacggg    7680
ataataccgc gccacatagc agaactttaa aagtgctcat cattggaaaa cgttcttcgg    7740
ggcgaaaact ctcaaggatc ttaccgctgt tgagatccag ttcgatgtaa cccactcgtg    7800
cacccaactg atcttcagca tcttttactt tcaccagcgt ttctgggtga gcaaaaacag    7860
gaaggcaaaa tgccgcaaaa aagggaataa gggcgacacg gaaatgttga atactcatac    7920
tcttcctttt tcaatattat tgaagcattt atcagggtta ttgtctcatg agcggataca    7980
tatttgaatg tatttagaaa aataaacaaa tagggggttcc gcgcacattt ccccgaaaag    8040
tgccacctga cgtctaagaa accattatta tcatgacatt aacctataaa aataggcgta    8100
tcacgaggcc ctttcgtctt caagaattgt t    8131
```

<210> SEQ ID NO 13
<211> LENGTH: 7082
<212> TYPE: DNA
<213> ORGANISM: Artificial Sequence
<220> FEATURE:
<223> OTHER INFORMATION: Synthetic Construct pVR1012-GP(S)

<400> SEQUENCE: 13

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgacccccg cccattgacg tcaataatga cgtatgttcc     480
catagtaacg ccaatagggga cttccattg acgtcaatgg gtggagtatt tacggtaaac     540
tgcccacttg gcagtacatc aagtgtatca tatgccaagt acgccccta ttgacgtcaa     600 tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag     900
agctcgttta gtgaaccgtc agatcgcctg gagacgccat ccacgctgtt tgacctccca     960
tagaagacac cgggaccgat ccagcctccg cggccgggaa cggtgcattg gaacgcggat    1020
tccccgtgcc aagagtgacg taagtaccgc ctatagactc tataggcaca ccctttggc    1080 tcttatgcat gctatactgt ttttggcttg ggcctatac accccgctt ccttatgcta    1140 taggtgatgg tatagcttag cctataggtg tgggttattg accattattg accactcccc    1200
tattggtgac gatactttcc attactaatc cataacatgg ctctttgcca caactatctc    1260
tattggctat atgccaatac tctgtccttc agagactgac acggactctg tattttttaca    1320
```

-continued

```
ggatggggtc ccatttatta tttacaaatt cacatataca acaacgccgt cccccgtgcc   1380
cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgaca cgtgtgatca gatatcgcgg ccgctctagc tagatgcatg   1920
ctcgagcggc cgccagtgtg atggatatct gcagaattcg gcttatcttc aggatctcgc   1980
catggagggt cttagcctac tccaattgcc cagagataaa tttcgaaaaa gctctttctt   2040
tgtttgggtc atcatcttat ttcaaaaggc ctttttccatg cctttgggtg ttgtgaccaa   2100
cagcacttta gaagtaacag agattgacca gctagtctgc aaggatcatc ttgcatccac   2160
tgaccagctg aaatcagttg gtctcaacct cgagggagc ggagtatcta ctgatatccc    2220
atctgcgaca aagcgttggg gcttcagatc tggtgtgcct cccaaggtgg tcagctatga   2280
agcaggagaa tgggctgaaa attgctacaa tcttgaaata aagaagccgg acgggagcga   2340
atgcttaccc ccaccgccgg atggtgtcag aggcttccca aggtgccgct atgttcacaa   2400
agcccaagga accgggccct gcccgggtga ctatgccttt cacaaggatg gagctttctt   2460
cctctatgac aggctggctt caactgtaat ttacagagga gtcaattttg ctgaggggt    2520
aattgcattc ttgatattgg ctaaaccaaa ggaaacgttc cttcaatcac cccccattcg   2580
agaggcagta aactacactg aaaatacatc aagttactat gccacatcct acttggagta   2640
cgaaatcgaa aattttggtg ctcaacactc cacgacccctt ttcaaaatta acaataatac   2700
ttttgttctt ctggacaggc cccacacgcc tcagttcctt ttccagctga atgataccat   2760
tcaccttcac caacagttga gcaacacaac tgggaaacta atttggacac tagatgctaa   2820
tatcaatgct gatattggtg aatgggcttt ttggaaaaat aaaaaaaatc tctccgaaca   2880
actacgtgga gaagagctgt ctttcgaaac tttatcgctc aacgagacag aagacgatga   2940
tgcgacatcg tcgagaacta caaagggaag aatctccgac cggccacca ggaagtattc    3000
ggacctggtt ccaaaggatt cccctgggat ggtttcattg cacgtaccag aaggggaaac   3060
aacattgccg tctcagaatt cgacagaagg tcgaagagta gatgtgaata tcaggaaac    3120
tatcacagag acaactgcaa caatcatagg cactaacggt aacaacatgc agatctccac   3180
catcgggaca ggactgagct ccagccaaat cctgagttcc tcaccgacca tggcaccaag   3240
ccctgagact cagacctcca caacctacac accaaaacta ccagtgatga ccaccgagga   3300
accaacaaca ccaccgagaa actctcctgg ctcaacaaca gaagcaccca ctctcaccac   3360
cccagagaat ataacaacag cggttaaaac tgttttgcca caagagtcca caagcaacgg   3420
tctaataact tcaacagtaa cagggattct tgggagcctt ggacttcgaa aacgcagcag   3480
aagacaagtt aacaccaggg ccacgggtaa atgcaatccc aacttacact actgactgc    3540
acaagaacaa cataatgctg ctgggattgc ctggatcccg tactttggac cgggtgcaga   3600
aggcatatac actgaaggcc ttatgcacaa ccaaaatgcc ttagtctgtg gactcagaca   3660
```

```
acttgcaaat gaaacaactc aagctctgca gcttttctta agggccacga cggagctgcg   3720
gacatatacc atactcaata ggaaggccat agatttcctt ctgcgacgat ggggcgggac   3780
atgtaggatc ctgggaccag attgttgcat tgagccacat gattggacca aaaacatcac   3840
tgataaaatc aaccaaatca tccatgattt catcgacaac cctttaccca atcaggataa   3900
tgatgataat tggtggacgg gctggagaca gtggatccct gcaggaatag cattactgg    3960 aattattatt gcaatcattg ctcttctttg cgtctgcaag ctgctttgtt gaatatcaag   4020
ccgaattcca gcacactggc ggccgttact agtggatccg agctcggatc caagctctag   4080
accaggccct ggatccagat ctgctgtgcc ttctagttgc cagccatctg ttgtttgccc   4140 ctccccgtg ccttccttga ccctggaagg tgccactccc actgtccttt cctaataaaa    4200
tgaggaaatt gcatcgcatt gtctgagtag gtgtcattct attctggggg gtggggtggg   4260
gcaggacagc aaggggagg attgggaaga caatagcagg catgctgggg atgcggtggg    4320
ctctatgggt acccaggtgc tgaagaattg acccggttcc tcctgggcca gaaagaagca   4380
ggcacatccc cttctctgtg acacaccctg tccacgcccc tggttcttag ttccagcccc   4440
actcatagga cactcatagc tcaggagggc tccgccttca atcccacccg ctaaagtact   4500
tggagcggtc tctccctccc tcatcagccc accaaaccaa acctagcctc caagagtggg   4560
aagaaattaa agcaagatag gctattaagt gcagagggag agaaaatgcc tccaacatgt   4620
gaggaagtaa tgagagaaat catagaattt cttccgcttc ctcgctcact gactcgctgc   4680
gctcggtcgt tcggctgcgg cgagcggtat cagctcactc aaaggcggta atacggttat   4740
ccacagaatc aggggataac gcaggaaaga acatgtgagc aaaaggccag caaaaggcca   4800
ggaaccgtaa aaaggccgcg ttgctggcgt ttttccatag gctccgcccc cctgacgagc   4860
atcacaaaaa tcgacgctca agtcagaggt ggcgaaaccc gacaggacta taaagatacc   4920
aggcgtttcc ccctggaagc tccctcgtgc gctctcctgt tccgaccctg ccgcttaccg   4980
gatacctgtc cgcctttctc ccttcgggaa gcgtggcgct ttctcatagc tcacgctgta   5040
ggtatctcag ttcggtgtag tcgttcgct ccaagctggg ctgtgtgcac gaaccccccg    5100
ttcagcccga ccgctgcgcc ttatccggta actatcgtct tgagtccaac ccggtaagac   5160
acgacttatc gccactggca gcagccactg gtaacaggat tagcagagcg aggtatgtag   5220
gcggtgctac agagttcttg aagtggtggc ctaactacgg ctacactaga agaacagtat   5280
ttggtatctg cgctctgctg aagccagtta ccttcggaaa aagagttggt agctcttgat   5340
ccggcaaaca aaccaccgct ggtagcggtg gttttttttgt ttgcaagcag cagattacgc   5400
gcagaaaaaa aggatctcaa gaagatcctt tgatcttttc tacggggtct gacgctcagt   5460
ggaacgaaaa ctcacgttaa gggattttgg tcatgagatt atcaaaaagg atcttcacct   5520
agatcctttt aaattaaaaa tgaagtttta atcaatcta aagtatatat gagtaaactt     5580
ggtctgacag ttaccaatgc ttaatcagtg aggcacctat ctcagcgatc tgtctatttc   5640
gttcatccat agttgcctga ctcgggggg ggggcgctg aggtctgcct cgtgaagaag      5700
gtgttgctga ctcataccag gcctgaatcg ccccatcatc cagccagaaa gtgagggagc   5760
cacggttgat gagagctttg ttgtaggtgg accagttggt gattttgaac ttttgctttg   5820
ccacggaacg gtctgcgttg tcgggaagat gcgtgatctg atccttcaac tcagcaaaag   5880
ttcgatttat tcaacaaagc cgccgtcccg tcaagtcagc gtaatgctct gccagtgtta   5940
caaccaatta accaattctg attagaaaaa ctcatcgagc atcaaatgaa actgcaattt   6000
attcatatca ggattatcaa taccatattt ttgaaaaagc cgtttctgta atgaaggaga   6060
```

| | |
|---|---|
| aaactcaccg aggcagttcc ataggatggc aagatcctgg tatcggtctg cgattccgac | 6120 |
| tcgtccaaca tcaatacaac ctattaattt ccctcgtca aaataaggt tatcaagtga | 6180 |
| gaaatcacca tgagtgacga ctgaatccgg tgagaatggc aaaagcttat gcatttcttt | 6240 |
| ccagacttgt tcaacaggcc agccattacg ctcgtcatca aaatcactcg catcaaccaa | 6300 |
| accgttattc attcgtgatt gcgcctgagc gagacgaaat acgcgatcgc tgttaaaagg | 6360 |
| acaattacaa acaggaatcg aatgcaaccg cgcaggaac actgccagcg catcaacaat | 6420 |
| attttcacct gaatcaggat attcttctaa tacctggaat gctgttttcc cggggatcgc | 6480 |
| agtggtgagt aaccatgcat catcaggagt acggataaaa tgcttgatgg tcggaagagg | 6540 |
| cataaattcc gtcagccagt ttagtctgac catctcatct gtaacatcat ggcaacgct | 6600 |
| acctttgcca tgtttcagaa caactctggg cgcatcgggc ttcccataca atcgatagat | 6660 |
| tgtcgcacct gattgcccga cattatcgcg agcccattta tacccatata atcagcatc | 6720 |
| catgttggaa tttaatcgcg gcctcgagca agacgtttcc cgttgaatat ggctcataac | 6780 |
| acccctgta ttactgttta tgtaagcaga cagtttatt gttcatgatg atatattttt | 6840 |
| atcttgtgca atgtaacatc agagattttg agacacaacg tggctttccc ccccccca | 6900 |
| ttattgaagc atttatcagg ttattgtct catgagcgga tacatatttg aatgtattta | 6960 |
| gaaaaataaa caaatagggg ttccgcgcac atttccccga aaagtgccac ctgacgtcta | 7020 |
| agaaaccatt attatcatga cattaaccta taaaaatagg cgtatcacga ggccctttcg | 7080 |
| tc | 7082 |

<210> SEQ ID NO 14
<211> LENGTH: 7087
<212> TYPE: DNA
<213> ORGANISM: Artificial Sequence
<220> FEATURE:
<223> OTHER INFORMATION: Synthetic Construct pVR1012x/s Ebola GP(S)

<400> SEQUENCE: 14

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcagattgg | 240 |
| ctattggcca ttgcatacgt tgtatccata tcataatatg tacatttata ttggctcatg | 300 |
| tccaacatta ccgccatgtt gacattgatt attgactagt tattaatagt aatcaattac | 360 |
| ggggtcatta gttcatagcc catatatgga gttccgcgtt acataactta cggtaaatgg | 420 |
| cccgcctggc tgaccgccca acgacccccg cccattgacg tcaataatga cgtatgttcc | 480 |
| catagtaacg ccaatagggA cttTccattg acgtcaatgg gtggagtatt tacggtaaac | 540 |
| tgcccacttg gcagtacatc aagtgtatca tatgccaagt acgccccta ttgacgtcaa | 600 |
| tgacggtaaa tggcccgcct ggcattatgc ccagtacatg accttatggg actttcctac | 660 |
| ttggcagtac atctacgtat tagtcatcgc tattaccatg gtgatgcggt tttggcagta | 720 |
| catcaatggg cgtggatagc ggtttgactc acggggattt ccaagtctcc accccattga | 780 |
| cgtcaatggg agtttgtttt ggcaccaaaa tcaacgggac tttccaaaat gtcgtaacaa | 840 |
| ctccgcccca ttgacgcaaa tgggcggtag gcgtgtacgg tgggaggtct atataagcag | 900 |
| agctcgttta gtgaaccgtc agatcgcctg gagacgccat ccacgctgtt ttgacctcca | 960 |

-continued

```
tagaagacac cgggaccgat ccagcctccg cggccgggaa cggtgcattg aacgcggat    1020 tccccgtgcc aagagtgacg taagtaccgc ctatagactc tataggcaca cccctttggc    1080
tcttatgcat gctatactgt ttttggcttg gggcctatac accccgctt ccttatgcta    1140 taggtgatgg tatagcttag cctataggtg tgggttattg accattattg accactcccc    1200
tattggtgac gatactttcc attactaatc cataacatgg ctctttgcca caactatctc    1260
tattggctat atgccaatac tctgtccttc agagactgac acggactctg tattttaca    1320 ggatggggtc ccatttatta tttacaaatt cacatataca acaacgccgt ccccgtgcc    1380 cgcagttttt attaaacata gcgtgggatc tccacgcgaa tctcgggtac gtgttccgga    1440
catgggctct tctccggtag cggcggagct tccacatccg agccctggtc ccatgcctcc    1500
agcggctcat ggtcgctcgg cagctccttg ctcctaacag tggaggccag acttaggcac    1560
agcacaatgc ccaccaccac cagtgtgccg cacaaggccg tggcggtagg gtatgtgtct    1620
gaaaatgagc gtggagattg ggctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tcctttccat gggtcttttc    1860
tgcagtcacc gtcgtcgaca cgtgtgatca gatatcgcgg ccgccagtgt gatggatatc    1920
tgcagaattc ggcttatctt caggatctcg ccatggaggg tcttagccta ctccaattgc    1980
ccagagataa atttcgaaaa agctcttttct ttgtttgggt catcatctta tttcaaaagg    2040
ccttttccat gcctttgggt gttgtgacca acagcacttt agaagtaaca gagattgacc    2100
agctagtctg caaggatcat cttgcatcca ctgaccagct gaaatcagtt ggtctcaacc    2160 tcgagggag cggagtatct actgatatcc catctgcgac aaagcgttgg ggcttcagat    2220
ctggtgtgcc tcccaaggtg gtcagctatg aagcaggaga atgggctgaa aattgctaca    2280
atcttgaaat aaagaagccg gacgggagcg aatgcttacc cccaccgccg gatggtgtca    2340
gaggctttcc aaggtgccgc tatgttcaca agcccaagg aacgggccc tgcccgggtg    2400 actatgcctt tcacaaggat ggagctttct tcctctatga caggctggct tcaactgtaa    2460
tttacagagg agtcaattt gctgaggggg taattgcatt cttgatattg ctaaaccaa    2520 aggaaacgtt ccttcaatca cccccattc gagaggcagt aaactacact gaaaatacat    2580
caagttacta tgccacatcc tacttggagt acgaaatcga aaattttggt gctcaacact    2640
ccacgaccct tttcaaaatt aacaataata cttttgttct tctggacagg ccccacacgc    2700
ctcagttcct tttccagctg aatgatacca ttcaccttca ccaacagttg agcaacacaa    2760
ctgggaaact aatttggaca ctagatgcta atatcaatgc tgatattggt gaatgggctt    2820
tttgggaaaa taaaaaaat ctctccgaac aactacgtgg agaagagctg tctttcgaaa    2880
ctttatcgct caacgagaca gaagacgatg atgcgcatc gtcgagaact acaaagggaa    2940
gaatctccga ccgggccacc aggaagtatt cggacctggt tccaaaggat tcccctggga    3000
tggtttcatt gcacgtacca gaagggggaa caacattgcc gtctcagaat cgacagaag    3060 gtcgaagagt agatgtgaat actcaggaaa ctatcacaga gacaactgca acaatcatag    3120
gcactaacgg taacaacatg cagatctcca ccatcgggac aggactgagc tccagccaaa    3180
tcctgagttc ctcaccgacc atggcaccaa gccctgagac tcagacctcc acaacctaca    3240
caccaaaact accagtgatg accaccgagg aatcaacaac accaccgaga aactctcctg    3300
gctcaacaac agaagcaccc actctcacca ccccagagaa tataacaaca gcggttaaaa    3360
```

```
ctgttttgcc acaagagtcc acaagcaacg gtctaataac ttcaacagta acagggattc    3420
ttgggagcct tggacttcga aaacgcagca gaagacaagt taacaccagg gccacgggta    3480
aatgcaatcc caacttacac tactggactg cacaagaaca acataatgct gctgggattg    3540
cctggatccc gtactttgga ccgggtgcag aaggcatata cactgaaggc cttatgcaca    3600
accaaaatgc cttagtctgt ggactcagac aacttgcaaa tgaaacaact caagctctgc    3660
agcttttctt aagggccacg acggagctgc ggacatatac catactcaat aggaaggcca    3720
tagatttcct tctgcgacga tggggcggga catgtaggat cctgggacca gattgttgca    3780
ttgagccaca tgattggacc aaaaacatca ctgataaaat caaccaaatc atccatgatt    3840
tcatcgacaa cccttaccc aatcaggata atgatgataa ttggtggacg ggctggagac    3900
agtggatccc tgcaggaata ggcattactg gaattattat tgcaatcatt gctcttcttt    3960
gcgtctgcaa gctgctttgt tgaatatcaa gccgaattcc agcacactgg cggccgttac    4020
tagtggatcc gagctcggta ccaagctcta gaccaggccc tggatccaga tctgctgtgc    4080
cttctagttg ccagccatct gttgtttgcc cctcccccgt gccttccttg acctggaag    4140
gtgccactcc cactgtcctt tcctaataaa atgaggaaat tgcatcgcat tgtctgagta    4200
ggtgtcattc tattctgggg ggtggggtgg ggcaggacag caaggggag gattgggaag    4260
acaatagcag gcatgctggg gatgcggtgg gctctatggg tacccaggtg ctgaagaatt    4320
gacccggttc ctcctgggcc agaaagaagc aggcacatcc ccttctctgt gacacaccct    4380
gtccacgccc ctggttctta gttccagccc cactcatagg acactcatag ctcaggaggg    4440
ctccgccttc aatcccaccc gctaaagtac ttggagcggt ctctccctcc ctcatcagcc    4500
caccaaacca aacctagcct ccaagagtgg aagaaatta aagcaagata ggctattaag    4560
tgcagggga gagaaaatgc ctccaacatg tgaggaagta atgagagaaa tcatagaatt    4620
ttaaggccat gatttaaggc catcatggcc ttaatcttcc gcttcctcgc tcactgactc    4680
gctgcgctcg gtcgttcggc tgcggcgagc ggtatcagct cactcaaagg cggtaatacg    4740
gttatccaca gaatcagggg ataacgcagg aaagaacatg tgagcaaaag gccagcaaaa    4800
ggccaggaac cgtaaaaagg ccgcgttgct ggcgtttttc cataggctcc gcccccctga    4860
cgagcatcac aaaaatcgac gctcaagtca gaggtggcga aacccgacag gactataaag    4920
ataccaggcg tttccccctg gaagctccct cgtgcgctct cctgttccga ccctgccgct    4980
taccggatac ctgtccgcct ttctcccttc gggaagcgtg gcgctttctc atagctcacg    5040
ctgtaggtat ctcagttcgg tgtaggtcgt tcgctccaag ctgggctgtg tgcacgaacc    5100
ccccgttcag cccgaccgct gcgccttatc cggtaactat cgtcttgagt ccaacccggt    5160
aagacacgac ttatcgccac tggcagcagc cactggtaac aggattagca gagcgaggta    5220
tgtaggcggt gctacagagt tcttgaagtg gtggcctaac tacggctaca ctagaagaac    5280
agtatttggt atctgcgctc tgctgaagcc agttaccttc ggaaaaagag ttggtagctc    5340
ttgatccggc aaacaaacca ccgctggtag cggtggtttt tttgtttgca agcagcagat    5400
tacgcgcaga aaaaaggat ctcaagaaga tcctttgatc ttttctacgg ggtctgacgc    5460
tcagtggaac gaaaactcac gttaagggat tttggtcatg agattatcaa aaaggatctt    5520
cacctagatc cttttaaatt aaaaatgaag ttttaaatca atctaaagta tatatgagta    5580
aacttggtct gacagttacc aatgcttaat cagtgaggca cctatctcag cgatctgtct    5640
atttcgttca tccatagttg cctgactcgg ggggggggg cgctgaggtc tgcctcgtga    5700
```

-continued

```
agaaggtgtt gctgactcat accaggcctg aatcgcccca tcatccagcc agaaagtgag    5760
ggagccacgg ttgatgagag ctttgttgta ggtggaccag ttggtgattt tgaacttttg    5820
ctttgccacg gaacggtctg cgttgtcggg aagatgcgtg atctgatcct tcaactcagc    5880
aaaagttcga tttattcaac aaagccgccg tcccgtcaag tcagcgtaat gctctgccag    5940
tgttacaacc aattaaccaa ttctgattag aaaaactcat cgagcatcaa atgaaactgc    6000
aatttattca tatcaggatt atcaatacca tatttttgaa aaagccgttt ctgtaatgaa    6060
ggagaaaact caccgaggca gttccatagg atggcaagat cctggtatcg gtctgcgatt    6120
ccgactcgtc caacatcaat acaacctatt aatttcccct cgtcaaaaat aaggttatca    6180
agtgagaaat caccatgagt gacgactgaa tccggtgaga atggcaaaag cttatgcatt    6240
tctttccaga cttgttcaac aggccagcca ttacgctcgt catcaaaatc actcgcatca    6300
accaaaccgt tattcattcg tgattgcgcc tgagcgagac gaaatacgcg atcgctgtta    6360
aaaggacaat tacaaacagg aatcgaatgc aaccggcgca ggaacactgc cagcgcatca    6420
acaatatttt cacctgaatc aggatattct tctaatacct ggaatgctgt ttcccgggg    6480
atcgcagtgg tgagtaacca tgcatcatca ggagtacgga taaaatgctt gatggtcgga    6540
agaggcataa attccgtcag ccagtttagt ctgaccatct catctgtaac atcattggca    6600
acgctacctt tgccatgttt cagaaacaac tctggcgcat cgggcttccc atacaatcga    6660
tagattgtcg cacctgattg cccgacatta tcgcgagccc atttataccc atataaatca    6720
gcatccatgt tggaatttaa tcgcggcctc gagcaagacg tttcccgttg aatatggctc    6780
ataacacccc ttgtattact gtttatgtaa gcagacagtt ttattgttca tgatgatata    6840
tttttatctt gtgcaatgta acatcagaga ttttgagaca caacgtggct ttccccccc    6900
ccccattatt gaagcattta tcagggttat tgtctcatga gcggatacat atttgaatgt    6960
atttagaaaa ataacaaat aggggttccg cgcacatttc cccgaaaagt gccacctgac    7020
gtctaagaaa ccattattat catgacatta acctataaaa ataggcgtat cacgaggccc    7080
tttcgtc                                                              7087
```

<210> SEQ ID NO 15
<211> LENGTH: 6940
<212> TYPE: DNA
<213> ORGANISM: Artificial Sequence
<220> FEATURE:
<223> OTHER INFORMATION: Synthetic Construct pVR1012-GP(S) delta TM

<400> SEQUENCE: 15

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgacccccg cccattgacg tcaataatga cgtatgttcc     480
catagtaacg ccaataggga ctttccattg acgtcaatgg gtggagtatt tacggtaaac     540
tgcccacttg gcagtacatc aagtgtatca tatgccaagt acgcccccta ttgacgtcaa     600
tgacggtaaa tggcccgcct ggcattatgc ccagtacatg accttatggg actttcctac     660
```

```
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctccg cggccgggaa cggtgcattg gaacgcggat   1020
tccccgtgcc aagagtgacg taagtaccgc ctatagactc tataggcaca ccccttbggc   1080
tcttatgcat gctatactgt ttttggcttg gggcctatac accccgctt ccttatgcta    1140 taggtgatgg tatagcttag cctataggtg tgggttattg accattattg accactcccc   1200
tattggtgac gatactttcc attactaatc cataacatgg ctctttgcca caactatctc   1260
tattggctat atgccaatac tctgtccttc agagactgac acggactctg tatttttaca   1320
ggatggggtc ccatttatta tttacaaatt cacatataca acaacgccgt cccccgtgcc   1380
cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgact ctagctagat gcatgctcga gcggccgcca gtgtgatgga   1920
tatctgcaga attcggctta tcttcaggat ctcgccatgg agggtcttag cctactccaa   1980
ttgcccagag ataaatttcg aaaaagctct tctttgttt gggtcatcat cttatttcaa    2040
aaggcctttt ccatgccttt gggtgttgtg accaacagca ctttagaagt aacagagatt   2100
gaccagctag tctgcaagga tcatcttgca tccactgacc agctgaaatc agttggtctc   2160
aacctcgagg ggagcggagt atctactgat atcccatctg cgacaaagcg ttggggcttc   2220
agatctggtg tgcctcccaa ggtggtcagc tatgaagcag agaatgggc tgaaaattgc     2280 tacaatcttg aaataaagaa gccggacggg agcgaatgct taccccccacc gccgatggt    2340 gtcagaggct ttccaaggtg ccgctatgtt cacaaagccc aaggaaccgg ccctgcccg     2400 ggtgactatg cctttcacaa ggatggagct ttcttcctct atgacaggct ggcttcaact    2460
gtaatttaca gaggagtcaa ttttgctgag ggggtaattg cattcttgat attggctaaa   2520
ccaaaggaaa cgttccttca atcaccccc attcgagagg cagtaaacta cactgaaaat    2580
acatcaagtt actatgccac atcctacttg gagtacgaaa tcgaaaattt tggtgctcaa   2640
cactccacga ccctttttcaa aattaacaat aatactttg ttcttctgga caggccccac   2700
acgcctcagt tccttttcca gctgaatgat accattcacc ttcaccaaca gttgagcaac   2760
acaactggga aactaatttg gacactagat gctaatatca atgctgatat tggtgaatgg   2820 gcttttttggg aaaataaaaa aaatctctcc gaacaactac gtggagaaga gctgtctttc   2880
gaaactttat cgctcaacga gacagaagac gatgatgcga catcgtcgag aactacaaag   2940
ggaagaatct ccgaccgggc caccaggaag tattcggacc tggttccaaa ggattccct    3000
```

```
gggatggttt cattgcacgt accagaaggg gaaacaacat tgccgtctca gaattcgaca    3060
gaaggtcgaa gagtagatgt gaatactcag gaaactatca cagagacaac tgcaacaatc    3120
ataggcacta acggtaacaa catgcagatc tccaccatcg ggacaggact gagctccagc    3180
caaatcctga gttcctcacc gaccatggca ccaagccctg agactcagac ctccacaacc    3240
tacacaccaa aactaccagt gatgaccacc gaggaaccaa caacaccacc gagaaactct    3300
cctggctcaa caacagaagc acccactctc accaccccag agaatataac aacagcggtt    3360
aaaactgttt tgccacaaga gtccacaagc aacggtctaa taacttcaac agtaacaggg    3420
attcttggga gccttggact tcgaaaacgc agcagaagac aagttaacac cagggccacg    3480
ggtaaatgca atcccaactt acactactgg actgcacaag aacaacataa tgctgctggg    3540
attgcctgga tcccgtactt tggaccgggt gcagaaggca tatacactga aggccttatg    3600
cacaaccaaa atgccttagt ctgtggactc agacaacttg caaatgaaac aactcaagct    3660
ctgcagcttt tcttaagggc cacgacggag ctgcggacat ataccatact caataggaag    3720
gccatagatt tccttctgcg acgatggggc gggacatgta ggatcctggg accagattgt    3780
tgcattgagc cacatgattg gaccaaaaac atcactgata aaatcaacca aatcatccat    3840
gatttcatcg acaacccttt acccaatcag gataatgatg ataattggtg gacgggctgg    3900
agacagtgga tccggccgc atcgtgactg actgacgatc tgcctcgcgg atccagatct    3960
gctgtgcctt ctagttgcca gccatctgtt gtttgcccct ccccgtgcc ttccttgacc    4020 ctggaaggtg ccactcccac tgtcctttcc taataaaatg aggaaattgc atcgcattgt    4080
ctgagtaggt gtcattctat tctgggggt ggggtgggc aggacagcaa gggggaggat    4140
tgggaagaca atagcaggca tgctggggat gcggtgggct ctatgggtac ccaggtgctg    4200
aagaattgac ccggttcctc ctgggccaga aagaagcagg cacatcccct tctctgtgac    4260 acacctgtc cacgccctg gttcttagtt ccagccccac tcataggaca ctcatagctc    4320
aggagggctc cgccttcaat cccacccgct aaagtacttg gagcggtctc tccctccctc    4380
atcagcccac caaaccaaac ctagcctcca agagtgggaa gaaattaaag caagataggc    4440
tattaagtgc agagggagag aaaatgcctc caacatgtga ggaagtaatg agagaaatca    4500
tagaatttct tccgcttcct cgctcactga ctcgctgcgc tcggtcgttc ggctgcggcg    4560
agcggtatca gctcactcaa aggcggtaat acggttatcc acagaatcag gggataacgc    4620
aggaaagaac atgtgagcaa aaggccagca aaaggccagg aaccgtaaaa aggccgcgtt    4680
gctggcgttt ttccataggc tccgcccccc tgacgagcat cacaaaaatc gacgctcaag    4740
tcagaggtgg cgaaacccga caggactata aagataccag gcgtttcccc ctggaagctc    4800
cctcgtgcgc tctcctgttc cgaccctgcc gcttaccgga tacctgtccg cctttctccc    4860
ttcgggaagc gtggcgcttt ctcatagctc acgctgtagg tatctcagtt cggtgtaggt    4920
cgttcgctcc aagctgggct gtgtgcacga accccccgtt cagcccgacc gctgcgcctt    4980
atccggtaac tatcgtcttg agtccaaccc ggtaagacac gacttatcgc cactggcagc    5040
agccactggt aacaggatta gcagagcgag gtatgtaggc ggtgctacag agttcttgaa    5100
gtggtggcct aactacggct acactagaag aacagtattt ggtatctgcg ctctgctgaa    5160
gccagttacc ttcggaaaaa gagttggtag ctcttgatcc ggcaaacaaa ccaccgctgg    5220
tagcggtggt ttttttgttt gcaagcagca gattacgcgc agaaaaaaag gatctcaaga    5280
agatcctttg atcttttcta cggggtctga cgctcagtgg aacgaaaact cacgttaagg    5340
gattttggtc atgagattat caaaaaggat cttcacctag atccttttaa attaaaaatg    5400
```

```
aagtttaaa tcaatctaaa gtatatatga gtaaacttgg tctgacagtt accaatgctt    5460
aatcagtgag gcacctatct cagcgatctg tctatttcgt tcatccatag ttgcctgact    5520
cggggggggg gggcgctgag gtctgcctcg tgaagaaggt gttgctgact cataccaggc    5580
ctgaatcgcc ccatcatcca gccagaaagt gagggagcca cggttgatga gagctttgtt    5640
gtaggtggac cagttggtga ttttgaactt ttgctttgcc acggaacggt ctgcgttgtc    5700
gggaagatgc gtgatctgat ccttcaactc agcaaaagtt cgatttattc aacaaagccg    5760
ccgtcccgtc aagtcagcgt aatgctctgc cagtgttaca accaattaac caattctgat    5820
tagaaaaact catcgagcat caaatgaaac tgcaatttat tcatatcagg attatcaata    5880
ccatattttt gaaaaagccg tttctgtaat gaaggagaaa actcaccgag gcagttccat    5940
aggatggcaa gatcctggta tcggtctgcg attccgactc gtccaacatc aatacaacct    6000
attaatttcc cctcgtcaaa aataaggtta tcaagtgaga atcaccatg agtgacgact    6060 gaatccggtg agaatggcaa aagcttatgc atttctttcc agacttgttc aacaggccag    6120
ccattacgct cgtcatcaaa atcactcgca tcaaccaaac cgttattcat cgtgattgc    6180 gcctgagcga gacgaaatac gcgatcgctg ttaaaaggac aattacaaac aggaatcgaa    6240
tgcaaccggc gcaggaacac tgccagcgca tcaacaatat tttcacctga atcaggatat    6300
tcttctaata cctggaatgc tgttttcccg gggatcgcag tggtgagtaa ccatgcatca    6360
tcaggagtac ggataaaatg cttgatggtc ggaagaggca taaattccgt cagccagttt    6420
agtctgacca tctcatctgt aacatcattg gcaacgctac ctttgccatg tttcagaaac    6480
aactctggcg catcgggctt cccatacaat cgatagattg tcgcacctga ttgcccgaca    6540
ttatcgcgag cccatttata cccatataaa tcagcatcca tgttggaatt taatcgcggc    6600
ctcgagcaag acgtttcccg ttgaatatgg ctcataacac cccttgtatt actgtttatg    6660
taagcagaca gttttattgt tcatgatgat atattttat cttgtgcaat gtaacatcag    6720
agattttgag acacaacgtg gctttccccc ccccccatt attgaagcat ttatcagggt    6780
tattgtctca tgagcggata catatttgaa tgtatttaga aaaataaaca aataggggtt    6840
ccgcgcacat ttccccgaaa agtgccacct gacgtctaag aaaccattat tatcatgaca    6900
ttaacctata aaaataggcg tatcacgagg ccctttcgtc                          6940
```

<210> SEQ ID NO 16
<211> LENGTH: 7002
<212> TYPE: DNA
<213> ORGANISM: Artificial Sequence
<220> FEATURE:
<223> OTHER INFORMATION: Synthetic Construct pVR1012-GP(IC)

<400> SEQUENCE: 16

```
tcgcgcgttt cggtgatgac ggtgaaaacc tctgacacat gcagctcccg gagacggtca     60
cagcttgtct gtaagcggat gccggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
```

```
catagtaacg ccaataggga ctttccattg acgtcaatgg gtggagtatt tacggtaaac    540
tgcccacttg gcagtacatc aagtgtatca tatgccaagt acgccccta ttgacgtcaa    600 tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctccg cggccgggaa cggtgcattg gaacgcggat   1020
tccccgtgcc aagagtgacg taagtaccgc ctatagactc tataggcaca ccccttggc    1080 tcttatgcat gctatactgt ttttggcttg ggccctatac accccgcctt ccttatgcta   1140
taggtgatgg tatagcttag cctataggtg tgggttattg accattattg ccactcccc    1200 tattggtgac gatactttcc attactaatc cataacatgg ctctttgcca caactatctc   1260
tattggctat atgccaatac tctgtccttc agagactgac acggactctg tatttttaca   1320
ggatggggtc ccatttatta tttacaaatt cacatataca acaacgccgt ccccgtgcc   1380 cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgaca cgtgtgatca gatatcgcgg ccgctctaga attcggcttc   1920
taatcacagt caccatggga gcgtcaggga ttctgcaatt gccccgtgag cgcttcagga   1980
aaacatcttt ctttgtttgg gtaataatcc tattccataa agtcttttca atcccgttgg   2040
gggttgtaca caacaatacc ctacaagtga gtgatattga caagtttgtg tgccgagaca   2100
aactctcttc aactagccaa ttgaagtcag tcgggttgaa cttggagggc aatggagtag   2160
caactgatgt accaacggca accaaaagat ggggttttcg agctggtgtt ccaccaaagg   2220
tggtaaattg cgaagctgga gaatgggctg agaactgtta taacctggct ataaagaaag   2280
ttgatggtag tgagtgccta ccagaagccc ctgagggagt gagggatttt ccccgttgcc   2340
gctatgtaca caaagtctca ggaactggac catgcccagg aggactcgcc tttcacaaag   2400
aaggagcctt cttcctgtat gaccgactcg catcaacaat catttatcgg ggtacaacct   2460
ttgccgaagg agttattgca tttctgatct tgcctaaggc gcgaaaggat ttttccagt    2520 ctcctccatt gcatgagcct gccaacatga ccacggatcc ctccagttac tatcacacga   2580
caacaataaa ctacgtggtt gataattttg gaaccaacac cacagagttt ctgttccaag   2640
tcgatcattt gacgtatgtg cagctcgagg caagattcac accacaattc cttgtcctcc   2700
taaatgaaac catctactct gataaccgca gaagtaacac aacaggaaaa ctaatctgga   2760
aaataaatcc cactgttgat accagcatgg gtgagtgggc tttctgggaa aataaaaaaa   2820
acttcacaaa aacccttca agtgaagagt tgtctttcgt acctgtacca gaaacccaga   2880
```

```
accaggtcct tgacacgaca gcgacggtct ctcctcccat ctccgcccac aaccacgcag  2940
ccgaagacca caaagaattg gtttcagagg attccactcc agtggttcag atgcaaaaca  3000
tcaagggaaa ggacacaatg ccaaccacag tgacgggtgt accaacaacc acaccctctc  3060
catttccaat caatgctcgc aacactgatc ataccaaatc atttatcggc ctggaggggc  3120
cccaagaaga ccacagcacc acacagcctg ccaagaccac cagccaacca accaacagca  3180
cagaatcgac gacactaaac ccaacatcag agccctccag tagaggcacg ggaccatcca  3240
gccccacggt ccccaacacc acagaaagcc acgccgaact tggcaagaca accccaacca  3300
cactcccaga acagcacact gccgccagtg ccattccaag agccgtgcac cccgacgaac  3360
tcagtggacc tggcttcctg acgaacacaa tacgggggt tacaaatctc ctgacaggat  3420
ccagaagaaa gcgaagggat gtcactccca atacacaacc caaatgcaac ccaaacctgc  3480
actattggac agccttggat gagggtgctg ccataggttt agcctggata ccatacttcg  3540
ggccagcagc tgagggaatt tacactgaag gcataatgga gaatcaaaat ggattgatct  3600
gtggattgag gcagctggcc aacgaaacga cacaagctct tcaattgttc ttaagggcaa  3660
ctactgagtt gcgtacattc tctatactaa atcggaaagc aatagacttc ttgctccaaa  3720 gatgggagg aacatgtcac attctagggc ctgattgttg cattgaaccc caagattgga  3780
ccaaaaatat cactgataaa attgatcaaa taatccatga ctttgtcgat aataatcttc  3840
caaatcagaa tgatggcagc aactggtgga ctggatggaa acaatgggtt cctgctggaa  3900
taggaatcac aggagtaatc attgctatta ttgctttgct gtgcatttgc aaattcatgc  3960
tttgaactaa tatagcatca tactttaagc cgaattctag accaggccct ggatccagat  4020
ctgctgtgcc ttctagttgc cagccatctg ttgtttgccc ctcccccgtg ccttccttga  4080
ccctggaagg tgccactccc actgtccttt cctaataaaa tgaggaaatt gcatcgcatt  4140
gtctgagtag gtgtcattct attctggggg gtggggtggg caggacagc aaggggggagg  4200 attgggaaga caatagcagg catgctgggg atgcggtggg ctctatgggt acccaggtgc  4260
tgaagaattg acccggttcc tcctgggcca gaaagaagca ggcacatccc cttctctgtg  4320
acacaccctg tccacgcccc tggttcttag ttccagcccc actcatagga cactcatagc  4380
tcaggagggc tccgccttca atcccacccg ctaaagtact tggagcggtc tctccctccc  4440
tcatcagccc accaaaccaa acctagcctc aagagtggg aagaaattaa agcaagatag  4500
gctattaagt gcagagggag agaaaatgcc tccaacatgt gaggaagtaa tgagagaaat  4560
catagaattt cttccgcttc ctcgctcact gactcgctgc gctcggtcgt tcggctgcgg  4620
cgagcggtat cagctcactc aaaggcggta atacggttat ccacagaatc agggggataac  4680 gcaggaaaga acatgtgagc aaaaggccag caaaaggcca ggaaccgtaa aaaggccgcg  4740
ttgctggcgt ttttccatag gctccgcccc cctgacgagc atcacaaaaa tcgacgctca  4800
agtcagaggt ggcgaaaccc gacaggacta taaagatacc aggcgtttcc ccctggaagc  4860
tccctcgtgc gctctcctgt tccgaccctg ccgcttaccg gatacctgtc cgcctttctc  4920
ccttcgggaa gcgtggcgct ttctcatagc tcacgctgta ggtatctcag ttcggtgtag  4980
gtcgttcgct ccaagctggg ctgtgtgcac gaaccccccg ttcagcccga ccgctgcgcc  5040
ttatccggta actatcgtct tgagtccaac ccggtaagac acgacttatc gccactggca  5100
gcagccactg gtaacaggat tagcagagcg aggtatgtag gcggtgctac agagttcttg  5160
aagtggtggc ctaactacgg ctacactaga agaacagtat ttggtatctg cgctctgctg  5220
```

```
aagccagtta ccttcggaaa aagagttggt agctcttgat ccggcaaaca aaccaccgct    5280
ggtagcggtg gttttttgt ttgcaagcag cagattacgc gcagaaaaaa aggatctcaa    5340
gaagatcctt tgatctttc tacggggtct gacgctcagt ggaacgaaaa ctcacgttaa    5400
gggattttgg tcatgagatt atcaaaaagg atcttcacct agatcctttt aaattaaaaa    5460
tgaagtttta aatcaatcta agtatatat gagtaaactt ggtctgacag ttaccaatgc    5520
ttaatcagtg aggcacctat ctcagcgatc tgtctatttc gttcatccat agttgcctga    5580
ctcggggggg ggggcgctg aggtctgcct cgtgaagaag gtgttgctga ctcataccag    5640
gcctgaatcg ccccatcatc cagccagaaa gtgagggagc cacggttgat gagagctttg    5700
ttgtaggtgg accagttggt gattttgaac ttttgctttg ccacggaacg gtctgcgttg    5760 tcggaagat gcgtgatctg atccttcaac tcagcaaaag ttcgatttat caacaaagc    5820 cgccgtcccg tcaagtcagc gtaatgctct gccagtgtta caaccaatta accaattctg    5880
attagaaaaa ctcatcgagc atcaaatgaa actgcaattt attcatatca ggattatcaa    5940
taccatattt ttgaaaaagc cgtttctgta atgaaggaga aaactcaccg aggcagttcc    6000
ataggatggc aagatcctgg tatcggtctg cgattccgac tcgtccaaca tcaatacaac    6060
ctattaattt ccctcgtca aaaataaggt tatcaagtga aaatcacca tgagtgacga    6120 ctgaatccgg tgagaatggc aaaagcttat gcatttcttt ccagacttgt tcaacaggcc    6180
agccattacg ctcgtcatca aaatcactcg catcaaccaa accgttattc attcgtgatt    6240
gcgcctgagc gagacgaaat acgcgatcgc tgttaaaagg acaattacaa acaggaatcg    6300
aatgcaaccg gcgcaggaac actgccagcg catcaacaat atttcaccct gaatcaggat    6360
attcttctaa tacctggaat gctgttttcc cggggatcgc agtggtgagt aaccatgcat    6420
catcaggagt acggataaaa tgcttgatgg tcggaagagg cataaattcc gtcagccagt    6480
ttagtctgac catctcatct gtaacatcat tggcaacgct accttttgcca tgtttcagaa    6540 acaactctgg cgcatcgggc ttcccataca atcgatagat tgtcgcacct gattgcccga    6600
cattatcgcg agcccattta tacccatata aatcagcatc catgttggaa tttaatcgcg    6660
gcctcgagca agacgtttcc cgttgaatat ggctcataac accccttgta ttactgttta    6720
tgtaagcaga cagttttatt gttcatgatg atatattttt atcttgtgca atgtaacatc    6780
agagattttg agacacaacg tggctttccc cccccccca ttattgaagc atttatcagg    6840
gttattgtct catgagcgga tacatatttg aatgtattta gaaaaataaa caaataggg    6900 ttccgcgcac atttccccga aaagtgccac ctgacgtcta agaaaccatt attatcatga    6960
cattaaccta taaaaatagg cgtatcacga ggccctttcg tc                       7002
```

<210> SEQ ID NO 17
<211> LENGTH: 7036
<212> TYPE: DNA
<213> ORGANISM: Artificial Sequence
<220> FEATURE:
<223> OTHER INFORMATION: Synthetic Construct pVR1012 x/s Ebola GP(IC)

<400> SEQUENCE: 17

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
```

-continued

| | |
|---|---|
| tccaacatta ccgccatgtt gacattgatt attgactagt tattaatagt aatcaattac | 360 |
| ggggtcatta gttcatagcc catatatgga gttccgcgtt acataactta cggtaaatgg | 420 |
| cccgcctggc tgaccgccca acgaccccg cccattgacg tcaataatga cgtatgttcc | 480 |
| catagtaacg ccaataggga ctttccattg acgtcaatgg gtggagtatt tacggtaaac | 540 |
| tgcccacttg gcagtacatc aagtgtatca tatgccaagt acgccccta ttgacgtcaa | 600 |
| tgacggtaaa tggcccgcct ggcattatgc ccagtacatg accttatggg actttcctac | 660 |
| ttggcagtac atctacgtat tagtcatcgc tattaccatg gtgatgcggt tttggcagta | 720 |
| catcaatggg cgtggatagc ggtttgactc acggggattt ccaagtctcc accccattga | 780 |
| cgtcaatggg agtttgtttt ggcaccaaaa tcaacgggac tttccaaaat gtcgtaacaa | 840 |
| ctccgcccca ttgacgcaaa tgggcggtag gcgtgtacgg tgggaggtct atataagcag | 900 |
| agctcgttta gtgaaccgtc agatcgcctg gagacgccat ccacgctgtt ttgacctcca | 960 |
| tagaagacac cgggaccgat ccagcctccg cggccgggaa cggtgcattg aacgcggat | 1020 |
| tccccgtgcc aagagtgacg taagtaccgc ctatagactc tataggcaca cccctttggc | 1080 |
| tcttatgcat gctatactgt ttttggcttg gggcctatac accccgctt ccttatgcta | 1140 |
| taggtgatgg tatagcttag cctataggtg tgggttattg accattattg accactcccc | 1200 |
| tattggtgac gatactttcc attactaatc cataacatgg ctctttgcca caactatctc | 1260 |
| tattggctat atgccaatac tctgtccttc agagactgac acggactctg tatttttaca | 1320 |
| ggatggggtc ccatttatta tttacaaatt cacatataca acaacgccgt cccccgtgcc | 1380 |
| cgcagttttt attaaacata gcgtgggatc tccacgcgaa tctcgggtac gtgttccgga | 1440 |
| catgggctct tctccggtag cggcggagct tccacatccg agcccggtc ccatgcctcc | 1500 |
| agcggctcat ggtcgctcgg cagctccttg ctcctaacag tggaggccag acttaggcac | 1560 |
| agcacaatgc ccaccaccac cagtgtgccg cacaaggccg tggcggtagg gtatgtgtct | 1620 |
| gaaaatgagc gtggagattg ggctcgcacg gctgacgcag atggaagact taaggcagcg | 1680 |
| gcagaagaag atgcaggcag ctgagttgtt gtattctgat aagagtcaga ggtaactccc | 1740 |
| gttgcggtgc tgttaacggt ggagggcagt gtagtctgag cagtactcgt tgctgccgcg | 1800 |
| cgcgccacca gacataatag ctgacagact aacagactgt tcctttccat gggtcttttc | 1860 |
| tgcagtcacc gtcgtcgaca cgtgtgatca gatatcgcgg ccgctctaga attcggcttc | 1920 |
| taatcacagt caccatggga gcgtcaggga ttctgcaatt gccccgtgag cgcttcagga | 1980 |
| aaacatcttt ctttgtttgg gtaataatcc tattccataa agtcttttca atcccgttgg | 2040 |
| gggttgtaca caacaatacc ctacaagtga gtgatattga caagtttgtg tgccgagaca | 2100 |
| aactctcttc aactagccaa ttgaagtcag tcgggttgaa cttggagggc aatggagtag | 2160 |
| caactgatgt accaacggca accaaaagat ggggttttcg agctggtgtt ccaccaaagg | 2220 |
| tggtaaattg cgaagctgga gaatgggctg agaactgtta taacctggct ataaagaaag | 2280 |
| ttgatggtag tgagtgccta ccagaagccc ctgagggagt gagggatttt ccccgttgcc | 2340 |
| gctatgtaca caaagtctca ggaactggac catgcccagg aggactcgcc tttcacaaag | 2400 |
| aaggagcctt cttcctgtat gaccgactcg catcaacaat catttatcgg ggtacaacct | 2460 |
| ttgccgaagg agttattgca tttctgatct tgcctaaggc gcgaaggat ttttccagt | 2520 |
| ctcctccatt gcatgagcct gccaacatga ccacggatcc ctccagttac tatcacacga | 2580 |
| caacaataaa ctacgtggtt gataaattttg gaaccaacac cacagagttt ctgttccaag | 2640 |

```
tcgatcattt gacgtatgtg cagctcgagg caagattcac accacaattc cttgtcctcc    2700
taaatgaaac catctactct gataaccgca gaagtaacac aacaggaaaa ctaatctgga    2760
aaataaatcc cactgttgat accagcatgg gtgagtgggc tttctgggaa aataaaaaaa    2820
acttcacaaa aacccttca agtgaagagt tgtctttcgt acctgtacca gaaacccaga    2880
accaggtcct tgacacgaca gcgacggtct ctcctcccat ctccgccac aaccacgcag    2940 ccgaagacca caaagaattg gtttcagagg attccactcc agtggttcag atgcaaaaca    3000
tcaagggaaa ggacacaatg ccaaccacag tgacgggtgt accaacaacc acaccctctc    3060
catttccaat caatgctcgc aacactgatc ataccaaatc atttatcggc ctggaggggc    3120
cccaagaaga ccacagcacc acacagcctg ccaagaccac cagccaacca accaacagca    3180
cagaatcgac gacactaaac ccaacatcag agccctccag tagaggcacg ggaccatcca    3240
gccccacggt ccccaacacc acagaaagcc acgccgaact tggcaagaca accccaacca    3300
cactcccaga acagcacact gccgccagtg ccattccaag agccgtgcac cccgacgaac    3360
tcagtggacc tggcttcctg acgaacacaa tacggggggt tacaaatctc ctgacaggat    3420
ccagaagaaa gcgaagggat gtcactccca atacacaacc caaatgcaac ccaaacctgc    3480
actattggac agccttggat gagggtgctg ccataggttt agcctggata ccatacttcg    3540
ggccagcagc tgagggaatt tacactgaag gcataatgga gaatcaaaat ggattgatct    3600
gtggattgag gcagctggcc aacgaaacga cacaagctct tcaattgttc ttaagggcaa    3660
ctactgagtt gcgtacattc tctatactaa atcggaaagc aatagacttc ttgctccaaa    3720 gatgggagg aacatgtcac attctagggc ctgattgttg cattgaaccc caagattgga    3780
ccaaaaatat cactgataaa attgatcaaa taatccatga ctttgtcgat aataatcttc    3840
caaatcagaa tgatggcagc aactggtgga ctggatggaa acaatgggtt cctgctggaa    3900
taggaatcac aggagtaatc attgctatta ttgctttgct gtgcatttgc aaattcatgc    3960
tttgaactaa tatagcatca tactttaagc cgaattctag accaggccct ggatccagat    4020
ctgctgtgcc ttctagttgc cagccatctg ttgtttgccc ctcccccgtg ccttccttga    4080
ccctggaagg tgccactccc actgtccttt cctaataaa tgaggaaatt gcatcgcatt    4140
gtctgagtag tgtcattct attctggggg gtggggtggg gcaggacagc aaggggggag    4200
attgggaaga caatagcagg catgctgggg atgcggtggg ctctatgggt acccaggtgc    4260
tgaagaattg acccggttcc tcctgggcca gaaagaagca ggcacatccc cttctctgtg    4320
acacaccctg tccacgcccc tggttcttag ttccagcccc actcatagga cactcatagc    4380
tcaggagggc tccgccttca atcccaccc ctaaagtact tggagcggtc tctccctccc    4440
tcatcagccc accaaaccaa acctagcctc caagagtggg aagaaattaa agcaagatag    4500
gctattaagt gcagagggag agaaaatgcc tccaacatgt gaggaagtaa tgagagaaat    4560
catagaattt taaggccatg atttaaggcc atcatggcct taatcttccg cttcctcgct    4620
cactgactcg ctgcgctcgg tcgttcggct gcggcgagcg gtatcagctc actcaaaggc    4680
ggtaatacgg ttatccacag aatcagggga taacgcagga agaacatgt gagcaaaagg    4740 ccagcaaaag gccaggaacc gtaaaaaggc cgcgttgctg gcgtttttcc ataggctccg    4800 ccccctgac gagcatcaca aaaatcgacg ctcaagtcag aggtggcgaa acccgacagg    4860
actataaaga taccaggcgt ttccccctgg aagctccctc gtgcgctctc ctgttccgac    4920
cctgccgctt accggatacc tgtccgcctt tctcccttcg ggaagcgtgg cgctttctca    4980
tagctcacgc tgtaggtatc tcagttcggt gtaggtcgtt cgctccaagc tgggctgtgt    5040
```

-continued

| | |
|---|---|
| gcacgaaccc cccgttcagc ccgaccgctg cgccttatcc ggtaactatc gtcttgagtc | 5100 |
| caacccggta agacacgact tatcgccact ggcagcagcc actggtaaca ggattagcag | 5160 |
| agcgaggtat gtaggcggtg ctacagagtt cttgaagtgg tggcctaact acggctacac | 5220 |
| tagaagaaca gtatttggta tctgcgctct gctgaagcca gttaccttcg gaaaaagagt | 5280 |
| tggtagctct tgatccggca aacaaaccac cgctggtagc ggtggttttt ttgtttgcaa | 5340 |
| gcagcagatt acgcgcagaa aaaaggatc tcaagaagat cctttgatct tttctacggg | 5400 |
| gtctgacgct cagtggaacg aaaactcacg ttaagggatt ttggtcatga gattatcaaa | 5460 |
| aaggatcttc acctagatcc ttttaaatta aaaatgaagt tttaaatcaa tctaaagtat | 5520 |
| atatgagtaa acttggtctg acagttacca atgcttaatc agtgaggcac ctatctcagc | 5580 |
| gatctgtcta tttcgttcat ccatagttgc ctgactcggg ggggggggc gctgaggtct | 5640 |
| gcctcgtgaa gaaggtgttg ctgactcata ccaggcctga atcgccccat catccagcca | 5700 |
| gaaagtgagg gagccacggt tgatgagagc tttgttgtag gtggaccagt tggtgatttt | 5760 |
| gaacttttgc tttgccacgg aacggtctgc gttgtcggga agatgcgtga tctgatcctt | 5820 |
| caactcagca aaagttcgat ttattcaaca aagccgccgt cccgtcaagt cagcgtaatg | 5880 |
| ctctgccagt gttacaacca attaaccaat tctgattaga aaaactcatc gagcatcaaa | 5940 |
| tgaaactgca atttattcat atcaggatta tcaataccat atttttgaaa aagccgtttc | 6000 |
| tgtaatgaag gagaaaactc accgaggcag ttccatagga tggcaagatc ctggtatcgg | 6060 |
| tctgcgattc cgactcgtcc aacatcaata caacctatta atttccctc gtcaaaaata | 6120 |
| aggttatcaa gtgagaaatc accatgagtg acgactgaat ccggtgagaa tggcaaaagc | 6180 |
| ttatgcattt ctttccagac ttgttcaaca ggccagccat tacgctcgtc atcaaaatca | 6240 |
| ctcgcatcaa ccaaaccgtt attcattcgt gattgcgcct gagcgagacg aaatacgcga | 6300 |
| tcgctgttaa aaggacaatt acaaacagga tcgaatgca accggcgcag gaacactgcc | 6360 |
| agcgcatcaa caatattttc acctgaatca ggatattctt ctaatacctg gaatgctgtt | 6420 |
| ttcccgggga tcgcagtggt gagtaaccat gcatcatcag gagtacggat aaaatgcttg | 6480 |
| atggtcggaa gaggcataaa ttccgtcagc cagtttagtc tgaccatctc atctgtaaca | 6540 |
| tcattggcaa cgctaccttt gccatgtttc agaaacaact ctggcgcatc gggcttccca | 6600 |
| tacaatcgat agattgtcgc acctgattgc ccgacattat cgcgagccca tttataccca | 6660 |
| tataaatcag catccatgtt ggaatttaat cgcggcctcg agcaagacgt ttcccgttga | 6720 |
| atatggctca taacacccct tgtattactg tttatgtaag cagacagttt tattgttcat | 6780 |
| gatgatatat ttttatcttg tgcaatgtaa catcagagat tttgagacac aacgtggctt | 6840 |
| tcccccccc cccattattg aagcatttat cagggttatt gtctcatgag cggatacata | 6900 |
| tttgaatgta tttagaaaaa taaacaaata ggggttccgc gcacatttcc ccgaaaagtg | 6960 |
| ccacctgacg tctaagaaac cattattatc atgacattaa cctataaaaa taggcgtatc | 7020 |
| acgaggccct ttcgtc | 7036 |

<210> SEQ ID NO 18
<211> LENGTH: 6885
<212> TYPE: DNA
<213> ORGANISM: Artificial Sequence
<220> FEATURE:
<223> OTHER INFORMATION: Synthetic Construct pVR1012-GP(IC) delta TM

<400> SEQUENCE: 18

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca cgacccccg cccattgacg tcaataatga cgtatgttcc     480
catagtaacg ccaataggga ctttccattg acgtcaatgg gtggagtatt tacggtaaac     540
tgcccacttg gcagtacatc aagtgtatca tatgccaagt acgcccccta ttgacgtcaa     600
tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag     900
agctcgttta gtgaaccgtc agatcgcctg gagacgccat ccacgctgtt ttgacctcca     960
tagaagacac cgggaccgat ccagcctccg cggccgggaa cggtgcattg gaacgcggat    1020
tccccgtgcc aagagtgacg taagtaccgc ctatagactc tataggcaca ccccttggc    1080 tcttatgcat gctatactgt ttttggcttg ggcctatac accccgctt ccttatgcta    1140 taggtgatgg tatagcttag cctataggtg tgggttattg accattattg accactcccc    1200
tattggtgac gatactttcc attactaatc cataacatgg ctctttgcca caactatctc    1260
tattggctat atgccaatac tctgtccttc agagactgac acggactctg tatttttaca    1320
ggatggggtc ccatttatta tttacaaatt cacatataca acaacgccgt cccccgtgcc    1380
cgcagttttt attaaacata gcgtgggatc tccacgcgaa tctcgggtac gtgttccgga    1440
catgggctct tctccggtag cggcggagct tccacatccg agccctggtc ccatgcctcc    1500
agcggctcat ggtcgctcgg cagctccttg ctcctaacag tggaggccag acttaggcac    1560
agcacaatgc ccaccaccac cagtgtgccg cacaaggccg tggcggtagg gtatgtgtct    1620
gaaaatgagc gtggagattg ggctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tcctttccat gggtcttttc    1860
tgcagtcacc gtcgtcgaca cgtgtgatca gatatcgcgg ccgctctaga attcggcttc    1920
taatcacagt caccatggga gcgtcaggga ttctgcaatt gccccgtgag cgcttcagga    1980
aaacatcttt ctttgtttgg gtaataatcc tattccataa agtcttttca atcccgttgg    2040
gggttgtaca caacaatacc ctacaagtga gtgatattga caagtttgtg tgccgagaca    2100
aactctcttc aactagccaa ttgaagtcag tcggttgaa cttggagggc aatggagtag    2160
caactgatgt accaacggca accaaaagat ggggttttcg agctggtgtt ccaccaaagg    2220
tggtaaattg cgaagctgga gaatgggctg agaactgtta taacctggct ataaagaaag    2280
ttgatggtag tgagtgccta ccagaagccc ctgagggagt gagggatttt ccccgttgcc    2340
gctatgtaca caaagtctca ggaactggac catgcccagg aggactcgcc tttcacaaag    2400
```

```
aaggagcctt cttcctgtat gaccgactcg catcaacaat catttatcgg ggtacaacct    2460
ttgccgaagg agttattgca tttctgatct tgcctaaggc gcgaaaggat ttttccagt     2520 ctcctccatt gcatgagcct gccaacatga ccacggatcc ctccagttac tatcacacga    2580
caacaataaa ctacgtggtt gataattttg gaaccaacac cacagagttt ctgttccaag    2640
tcgatcattt gacgtatgtg cagctcgagg caagattcac accacaattc cttgtcctcc    2700
taaatgaaac catctactct gataaccgca aagtaacac aacaggaaaa ctaatctgga     2760
aaataaatcc cactgttgat accagcatgg gtgagtgggc tttctgggaa aataaaaaaa    2820
acttcacaaa aacccttca agtgaagagt tgtctttcgt acctgtacca gaaacccaga    2880
accaggtcct tgacacgaca gcgacggtct ctcctcccat ctccgcccac aaccacgcag    2940
ccgaagacca caaagaattg gtttcagagg attccactcc agtggttcag atgcaaaaca    3000
tcaagggaaa ggacacaatg ccaaccacag tgacgggtgt accaacaacc acaccctctc    3060
catttccaat caatgctcgc aacactgatc ataccaaatc atttatcggc ctggagggc     3120 cccaagaaga ccacagcacc acacagcctg ccaagaccac cagccaacca accaacagca    3180
cagaatcgac gacactaaac ccaacatcag agccctccag tagaggcacg ggaccatcca    3240
gccccacggt ccccaacacc acagaaagcc acgccgaact tggcaagaca accccaacca    3300
cactcccaga acagcacact gccgccagtg ccattccaag agccgtgcac cccgacgaac    3360
tcagtggacc tggcttcctg acgaacacaa tacgggggt tacaaatctc ctgacaggat     3420
ccagaagaaa gcgaagggat gtcactccca atacacaacc caaatgcaac ccaaacctgc    3480
actattggac agccttggat gagggtgctg ccataggttt agcctggata ccatacttcg    3540
ggccagcagc tgagggaatt tacactgaag gcataatgga gaatcaaaat ggattgatct    3600
gtggattgag gcagctggcc aacgaaacga cacaagctct tcaattgttc ttaagggcaa    3660
ctactgagtt gcgtacattc tctatactaa atcggaaagc aatagacttc ttgctccaaa    3720 gatgggagg aacatgtcac attctagggc ctgattgttg cattgaaccc caagattgga     3780
ccaaaaatat cactgataaa attgatcaaa taatccatga ctttgtcgat aataatcttc    3840
caaatcagaa tgatggcagg gccgcatcgt gactgactga cgatctgcct cgcggatcca    3900
gatctgctgt gccttctagt tgccagccat ctgttgtttg cccctccccc gtgccttcct    3960
tgaccctgga aggtgccact cccactgtcc tttcctaata aaatgaggaa attgcatcgc    4020
attgtctgag taggtgtcat tctattctgg ggggtgggt gggcaggac agcaaggggg      4080 aggattggga agacaatagc aggcatgctg gggatgcggt gggctctatg ggtacccagg    4140
tgctgaagaa ttgaccccggt tcctcctggg ccagaaagaa gcaggcacat cccctttctct   4200 gtgacacacc ctgtccacgc ccctggttct tagttccagc cccactcata ggacactcat    4260
agctcaggag ggctccgcct tcaatcccac ccgctaaagt acttggagcg gtctctccct    4320
ccctcatcag cccaccaaac caaacctagc ctccaagagt gggaagaaat taaagcaaga    4380
taggctatta agtgcagagg gagagaaaat gcctccaaca tgtgaggaag taatgagaga    4440
aatcatagaa tttcttccgc ttcctcgctc actgactcgc tgcgctcggt cgttcggctg    4500
cggcgagcgg tatcagctca ctcaaaggcg gtaatacggt tatccacaga atcagggat    4560 aacgcaggaa agaacatgtg agcaaaaggc cagcaaaagg ccaggaaccg taaaaaggcc    4620
gcgttgctgg cgtttttcca taggctccgc cccctgacg agcatcacaa aaatcgacgc    4680
tcaagtcaga ggtggcgaaa cccgacagga ctataaagat accaggcgtt tccccctgga    4740
```

```
agctccctcg tgcgctctcc tgttccgacc ctgccgctta ccggatacct gtccgccttt   4800
ctcccttcgg gaagcgtggc gctttctcat agctcacgct gtaggtatct cagttcggtg   4860
taggtcgttc gctccaagct gggctgtgtg cacgaacccc ccgttcagcc cgaccgctgc   4920
gccttatccg gtaactatcg tcttgagtcc aacccggtaa gacacgactt atcgccactg   4980
gcagcagcca ctggtaacag gattagcaga gcgaggtatg taggcggtgc tacagagttc   5040
ttgaagtggt ggcctaacta cggctacact agaagaacag tatttggtat ctgcgctctg   5100
ctgaagccag ttaccttcgg aaaaagagtt ggtagctctt gatccggcaa acaaaccacc   5160
gctggtagcg gtggtttttt tgtttgcaag cagcagatta cgcgcagaaa aaaggatct   5220 caagaagatc ctttgatctt ttctacgggg tctgacgctc agtggaacga aaactcacgt   5280
taagggattt tggtcatgag attatcaaaa aggatcttca cctagatcct ttaaattaa   5340 aaatgaagtt ttaaatcaat ctaaagtata tatgagtaaa cttggtctga cagttaccaa   5400
tgcttaatca gtgaggcacc tatctcagcg atctgtctat ttcgttcatc catagttgcc   5460
tgactcgggg ggggggggcg ctgaggtctg cctcgtgaag aaggtgttgc tgactcatac   5520
caggcctgaa tcgccccatc atccagccag aaagtgaggg agccacggtt gatgagagct   5580
ttgttgtagg tggaccagtt ggtgattttg aacttttgct ttgccacgga acggtctgcg   5640
ttgtcgggaa gatgcgtgat ctgatccttc aactcagcaa aagttcgatt tattcaacaa   5700
agccgccgtc ccgtcaagtc agcgtaatgc tctgccagtg ttacaaccaa ttaaccaatt   5760
ctgattagaa aaactcatcg agcatcaaat gaaactgcaa tttattcata tcaggattat   5820
caataccata tttttgaaaa agccgtttct gtaatgaagg agaaaactca ccgaggcagt   5880
tccataggat ggcaagatcc tggtatcggt ctgcgattcc gactcgtcca acatcaatac   5940
aacctattaa tttcccctcg tcaaaaataa ggttatcaag tgagaaatca ccatgagtga   6000
cgactgaatc cggtgagaat ggcaaaagct tatgcatttc tttccagact tgttcaacag   6060
gccagccatt acgctcgtca tcaaaatcac tcgcatcaac caaaccgtta ttcattcgtg   6120
attgcgcctg agcgagacga atacgcgat cgctgttaaa aggacaatta caaacaggaa   6180
tcgaatgcaa ccggcgcagg aacactgcca gcgcatcaac aatattttca cctgaatcag   6240
gatattcttc taatacctgg aatgctgttt tcccggggat cgcagtggtg agtaaccatg   6300
catcatcagg agtacggata aaatgcttga tggtcggaag aggcataaat tccgtcagcc   6360
agtttagtct gaccatctca tctgtaacat cattggcaac gctacctttg ccatgtttca   6420
gaaacaactc tggcgcatcg gcttcccat acaatcgata gattgtcgca cctgattgcc   6480
cgacattatc gcgagcccat ttatacccat ataaatcagc atccatgttg gaatttaatc   6540
gcggcctcga gcaagacgtt tcccgttgaa tatggctcat aacacccctt gtattactgt   6600
ttatgtaagc agacagtttt attgttcatg atgatatatt tttatcttgt gcaatgtaac   6660
atcagagatt ttgagacaca acgtggcttt ccccccccc ccattattga agcatttatc   6720
agggttattg tctcatgagc ggatacatat ttgaatgtat ttagaaaaat aaacaaatag   6780
gggttccgcg cacatttccc cgaaaagtgc cacctgacgt ctaagaaacc attattatca   6840
tgacattaac ctataaaaat aggcgtatca cgaggccctt tcgtc                  6885
```

<210> SEQ ID NO 19
<211> LENGTH: 6889
<212> TYPE: DNA
<213> ORGANISM: Artificial Sequence
<220> FEATURE:
<223> OTHER INFORMATION: Synthetic Construct pVR1012x/s Ebola GP(IC)(dTM)

<400> SEQUENCE: 19

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgacccccg cccattgacg tcaataatga cgtatgttcc     480
catagtaacg ccaatagggg ctttccattg acgtcaatgg gtggagtatt tacggtaaac     540
tgcccacttg gcagtacatc aagtgtatca tatgccaagt acgcccccta ttgacgtcaa     600
tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag     900
agctcgttta gtgaaccgtc agatcgcctg gagacgccat ccacgctgtt ttgacctcca     960
tagaagacac cgggaccgat ccagcctccg cggccgggaa cggtgcattg gaacgcggat    1020
tccccgtgcc aagagtgacg taagtaccgc ctatagactc tataggcaca ccccttggc    1080
tcttatgcat gctatactgt ttttggcttg gggcctatac accccgctt ccttatgcta    1140
taggtgatgg tatagcttag cctataggtg tgggttattg accattattg accactcccc    1200
tattggtgac gatactttcc attactaatc cataacatgg ctctttgcca caactatctc    1260
tattggctat atgccaatac tctgtccttc agagactgac acggactctg tatttttaca    1320
ggatggggtc ccatttatta tttacaaatt cacatataca acaacgccgt ccccgtgcc    1380
cgcagttttt attaaacata gcgtgggatc tccacgcgaa tctcgggtac gtgttccgga    1440
catgggctct tctccggtag cggcggagct tccacatccg agccctggtc ccatgcctcc    1500
agcggctcat ggtcgctcgg cagctccttg ctcctaacag tggaggccag acttaggcac    1560
agcacaatgc ccaccaccac cagtgtgccg cacaaggccg tggcggtagg gtatgtgtct    1620
gaaaatgagc gtggagattg ggctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tcctttccat gggtcttttc    1860
tgcagtcacc gtcgtcgaca cgtgtgatca gataattctc taatcacagt catcatggga    1920
gcgtcaggga ttctgcaatt gccccgtgag cgcttcagga aaacatcttt ctttgtttgg    1980
gtaataatcc tattccataa agtctttttca atcccgttgg gggttgtaca caacaatacc    2040
ctacaagtga gtgatattga caagtttgtg tgccagacaa aactctcttc aactagccaa    2100
ttgaagtcag tcgggttgaa cttggagggc aatggagtag caactgatgt accaacggca    2160
accaaaagat ggggttttcg agctggtgtt ccaccaaagg tggtaaatta cgaagctgga    2220
gaatgggctg agaactgtta taacctggct ataaagaaag ttgatggtag tgagtgccta    2280
```

-continued

```
ccagaagccc ctgagggagt gagggatttt ccccgttgcc gctatgtaca caaagtctca      2340
ggaactggac catgcccagg aggactcgcc tttcacaaag aaggagcctt cttcctgtat      2400
gaccgactcg catcaacaat catttatcgg ggtacaacct ttgccgaagg agttattgca      2460
tttctgatct tgcctaaggc gcgaaaggat tttttccagt ctcctccatt gcatgagcct      2520
gccaacatga ccacggatcc ctccagttac tatcacacga caacaataaa ctacgtggtt      2580
gataattttg gaaccaacac cacagagttt ctgttccaag tcgatcattt gacgtatgtg      2640
cagctcgagg caagattcac accacaattc cttgtcctcc taaatgaaac catctactct      2700
gataaccgca gaagtaacac aacaggaaaa ctaatctgga aaataaatcc cactgttgat      2760
accagcatgg gtgagtgggc tttctgggaa aataaaaaaa cttcacaaaa acccttcaa      2820 gtgaagagtt gtctttcgta cctgtaccag aaacccagaa ccaggtcctt gacacgacag      2880
cgacggtctc tcctcccatc tccgcccaca accacgcagg cgaagaccac aaagaattgg      2940
tttcagagga ttccactcca gtggttcaga tgcaaaacat caagggaaag gacacaatgc      3000
caaccacagt gacgggtgta ccaacaacca caccctctcc atttccaatc aatgctcgca      3060
acactgatca taccaaatca tttatcggcc tggaggggcc ccaagaagac cacagcacca      3120
cacagcctgc caagaccacc agccaaccaa ccaacagcac agaatcgacg acactaaacc      3180
caacatcaga gccctccagt agaggcacgg gaccatccag ccccacggtc cccaacacca      3240
cagaaagcca cgccgaactt ggcaagacaa ccccaaccac actcccagaa cagcacactg      3300
ccgccagtgc cattccaaga gccgtgcacc ccgacgaact cagtggacct ggcttcctga      3360
cgaacacaat acggggggtg acaaatctcc tgacaggatc cagaagaaag cgaagggatg      3420
tcactcccaa tacacaaccc aaatgcaacc caaacctgca ctattggaca gccttggatg      3480
agggtgctgc cataggttta gcctggatac catacttcgg gccagcagct gagggaattt      3540
acactgaagg cataatggag aatcaaaatg gattgatctg tggattgagg cagctggcca      3600
acgaaacgac acaagctctt caattgttct aagggcaac tactgagttg cgtacattct      3660
ctatactaaa tcggaaagca atagacttct tgctccaaag atggggagga acatgtcaca      3720
ttctagggcc tgattgttgc attgaacccc aagattggac caaaatatc actgataaaa      3780 ttgatcaaat aatccatgac tttgtcgata ataatcttcc aaatcagaat gatggcagca      3840
actggtggac tggatggaaa caatggtgaa gatctgctgt gccttctagt tgccagccat      3900
ctgttgtttg cccctccccc gtgccttcct tgacccctgga aggtgccact cccactgtcc      3960
tttcctaata aaatgaggaa attgcatcgc attgtctgag taggtgtcat tctattctgg      4020
ggggtggggt gggcaggac agcaagggg aggattggga agacaatagc aggcatgctg      4080
gggatgcggt gggctctatg ggtacccagg tgctgaagaa ttgacccggt tcctcctggg      4140
ccagaaagaa gcaggcacat ccccttctct gtgacacacc ctgtccacgc ccctggttct      4200
tagttccagc cccactcata ggacactcat agctcaggag ggctccgcct tcaatcccac      4260
ccgctaaagt acttggagcg gtctctccct ccctcatcag cccaccaaac caaacctagc      4320
ctccaagagt gggaagaaat taaagcaaga taggctatta agtgcagagg gagagaaaat      4380
gcctccaaca tgtgaggaag taatgagaga aatcatagaa ttttaaggcc atgatttaag      4440
gccatcatgg ccttaatctt ccgcttcctc gctcactgac tcgctgcgct cggtcgttcg      4500
gctgcggcga gcggtatcag ctcactcaaa ggcggtaata cggttatcca cagaatcagg      4560
ggataacgca ggaaagaaca tgtgagcaaa aggccagcaa aaggccagga accgtaaaaa      4620
```

-continued

```
ggccgcgttg ctggcgtttt tccataggct ccgcccccct gacgagcatc acaaaaatcg   4680
acgctcaagt cagaggtggc gaaacccgac aggactataa agataccagg cgtttccccc   4740
tggaagctcc ctcgtgcgct ctcctgttcc gaccctgccg cttaccggat acctgtccgc   4800
ctttctccct tcgggaagcg tggcgctttc tcatagctca cgctgtaggt atctcagttc   4860
ggtgtaggtc gttcgctcca agctgggctg tgtgcacgaa ccccccgttc agcccgaccg   4920
ctgcgcctta tccggtaact atcgtcttga gtccaacccg gtaagacacg acttatcgcc   4980
actggcagca gccactggta acaggattag cagagcgagg tatgtaggcg gtgctacaga   5040
gttcttgaag tggtggccta actacggcta cactagaaga acagtatttg gtatctgcgc   5100
tctgctgaag ccagttacct tcggaaaaag agttggtagc tcttgatccg gcaaacaaac   5160
caccgctggt agcggtggtt ttttgtttg caagcagcag attacgcgca gaaaaaaagg   5220
atctcaagaa gatcctttga tcttttctac ggggtctgac gctcagtgga acgaaaactc   5280
acgttaaggg attttggtca tgagattatc aaaaaggatc ttcacctaga tccttttaaa   5340
ttaaaaatga agttttaaat caatctaaag tatatatgag taaacttggt ctgacagtta   5400
ccaatgctta atcagtgagg cacctatctc agcgatctgt ctatttcgtt catccatagt   5460
tgcctgactc ggggggggg ggcgctgagg tctgcctcgt gaagaaggtg ttgctgactc   5520
ataccaggcc tgaatcgccc catcatccag ccagaaagtg agggagccac ggttgatgag   5580
agctttgttg taggtggacc agttggtgat tttgaacttt tgctttgcca cggaacggtc   5640
tgcgttgtcg ggaagatgcg tgatctgatc cttcaactca gcaaaagttc gatttattca   5700
acaaagccgc cgtcccgtca gtcagcgta atgctctgcc agtgttacaa ccaattaacc   5760
aattctgatt agaaaaactc atcgagcatc aaatgaaact gcaatttatt catatcagga   5820
ttatcaatac catattttg aaaaagccgt ttctgtaatg aaggagaaaa ctcaccgagg   5880
cagttccata ggatggcaag atcctggtat cggtctgcga ttccgactcg tccaacatca   5940
atacaaccta ttaatttccc ctcgtcaaaa ataaggttat caagtgagaa atcaccatga   6000
gtgacgactg aatccggtga aatggcaaa agcttatgca tttctttcca gacttgttca   6060
acaggccagc cattacgctc gtcatcaaaa tcactcgcat caaccaaacc gttattcatt   6120
cgtgattgcg cctgagcgag acgaaatacg cgatcgctgt taaaaggaca attacaaaca   6180
ggaatcgaat gcaaccggcg caggaacact gccagcgcat caacaatatt ttcacctgaa   6240
tcaggatatt cttctaatac ctggaatgct gttttcccgg ggatcgcagt ggtgagtaac   6300
catgcatcat caggagtacg gataaaatgc ttgatggtcg gaagaggcat aaattccgtc   6360
agccagttta gtctgaccat ctcatctgta acatcattgg caacgctacc tttgccatgt   6420
ttcagaaaca actctggcgc atcgggcttc ccatacaatc gatagattgt cgcacctgat   6480
tgcccgacat tatcgcgagc ccatttatac ccatataaat cagcatccat gttggaattt   6540
aatcgcggcc tcgagcaaga cgtttcccgt tgaatatggc tcataacacc ccttgtatta   6600
ctgtttatgt aagcagacag ttttattgtt catgatgata tatttttatc ttgtgcaatg   6660
taacatcaga gattttgaga cacaacgtgg ctttccccc cccccatta ttgaagcatt   6720 tatcagggtt attgtctcat gagcggatac atatttgaat gtatttagaa aaataaacaa   6780
ataggggttc cgcgcacatt tccccgaaaa gtgccacctg acgtctaaga accattatt   6840 atcatgacat aacctataa aataggcgt atcacgaggc cctttcgtc   6889
```

<210> SEQ ID NO 20
<211> LENGTH: 8146

<212> TYPE: DNA
<213> ORGANISM: Artificial Sequence
<220> FEATURE:
<223> OTHER INFORMATION: Synthetic Construct pAdApt EbolaGP(IC)(dTM)

<400> SEQUENCE: 20

```
ttaattaacc gcaattctca tgtttgacag cttatcatca tcaataatat accttatttt      60
ggattgaagc caatatgata atgagggggt ggagtttgtg acgtggcgcg gggcgtggga     120
acggggcggg tgacgtagta gtgtggcgga agtgtgatgt tgcaagtgtg gcggaacaca     180
tgtaagcgac ggatgtggca aaagtgacgt ttttggtgtg cgccggtgta cacaggaagt     240
gacaattttc gcgcggtttt aggcggatgt tgtagtaaat ttgggcgtaa ccgagtaaga     300
tttggccatt ttcgcgggaa aactgaataa gaggaagtga aatctgaata attttgtgtt     360
actcatagcg cgtaatattt gtctagggcc gcggggactt tgaccgttta cgtggagact     420
cgcccaggtg ttttttctcag gtgttttccg cgttccgggt caaagttggc gttttattat     480
tatagtcagt acgtaccagt gcactggcct agagcggccc cattgcatac gttgtatcca     540
tatcataata tgtacattta tattggctca tgtccaacat taccgccatg ttgacattga     600
ttattgacta gttattaata gtaatcaatt acggggtcat tagttcatag cccatatatg     660
gagttccgcg ttacataact tacggtaaat ggcccgcctg gctgaccgcc caacgacccc     720
cgcccattga cgtcaataat gacgtatgtt cccatagtaa cgccaatagg gactttccat     780
tgacgtcaat gggtggagta tttacggtaa actgcccact tggcagtaca tcaagtgtat     840
catatgccaa gtacgccccc tattgacgtc aatgacggta aatggcccgc ctggcattat     900
gcccagtaca tgaccttatg ggactttcct acttggcagt acatctacgt attagtcatc     960
gctattacca tggtgatgcg gttttggcag tacatcaatg ggcgtggata gcggtttgac    1020
tcacggggat ttccaagtct ccaccccatt gacgtcaatg ggagtttgtt ttggcaccaa    1080
aatcaacggg actttccaaa atgtcgtaac aactccgccc cattgacgca atgggcggt     1140
aggcgtgtac ggtgggaggt ctatataagc agagctcgtt tagtgaaccg tcagatcgcc    1200
tggagacgcc atccacgctg ttttgacctc catagaagac accgggaccg atccagcctc    1260
cgtcaccgtc gtcgacacgt gtgatcagat aattctctaa tcacagtcat catgggagcg    1320
tcagggattc tgcaattgcc ccgtgagcgc ttcaggaaaa catctttctt tgtttgggta    1380
ataatcctat tccataaagt cttttcaatc ccgttggggg ttgtacacaa caataccta     1440
caagtgagtg atattgacaa gtttgtgtgc cgagacaaac tctcttcaac tagccaattg    1500
aagtcagtcg ggttgaactt ggagggcaat ggagtagcaa ctgatgtacc aacggcaacc    1560
aaaagatggg gttttcgagc tggtgttcca ccaaaggtgg taaattacga agctggagaa    1620
tgggctgaga actgttataa cctggctata aagaaagttg atggtagtga gtgcctacca    1680
gaagcccctg agggagtgag ggattttccc cgttgccgct atgtacacaa agtctcagga    1740
actggaccat gcccaggagg actcgccttt cacaaagaag gagccttctt cctgtatgac    1800
cgactcgcat caacaatcat ttatcgggggt acaaccttgg ccgaaggagt tattgcattt    1860
ctgatcttgc ctaaggcgcg aaaggatttt ttccagtctc ctccattgca tgagcctgcc    1920
aacatgacca cggatccctc cagttactat cacacgacaa caataaacta cgtggttgat    1980
aatttttggaa ccaacaccac agagtttctg ttccaagtcg atcatttgac gtatgtgcag    2040
ctcgaggcaa gattcacacc acaattcctt gtcctcctaa atgaaaccat ctactctgat    2100
aaccgcagaa gtaacacaac aggaaaacta atctggaaaa taaatcccac tgttgatacc    2160
```

-continued

```
agcatgggtg agtgggcttt ctgggaaaat aaaaaaactt cacaaaaacc ctttcaagtg    2220
aagagttgtc tttcgtacct gtaccagaaa cccagaacca ggtccttgac acgacagcga    2280
cggtctctcc tcccatctcc gcccacaacc acgcaggcga agaccacaaa gaattggttt    2340
cagaggattc cactccagtg gttcagatgc aaaacatcaa gggaaaggac acaatgccaa    2400
ccacagtgac gggtgtacca acaaccacac cctctccatt tccaatcaat gctcgcaaca    2460
ctgatcatac caaatcattt atcggcctgg aggggcccca agaagaccac agcaccacac    2520
agcctgccaa gaccaccagc caaccaacca acagcacaga atcgacgaca ctaaacccaa    2580
catcagagcc ctccagtaga ggcacgggac catccagccc cacggtcccc aacaccacag    2640
aaagccacgc cgaacttggc aagacaaccc caaccacact cccagaacag cacactgccg    2700
ccagtgccat tccaagagcc gtgcaccccg acgaactcag tggacctggc ttcctgacga    2760
acacaatacg gggggtgaca atctcctga caggatccag aagaaagcga agggatgtca    2820
ctcccaatac acaacccaaa tgcaacccaa acctgcacta ttggacagcc ttggatgagg    2880
gtgctgccat aggtttagcc tggataccat acttcgggcc agcagctgag ggaatttaca    2940
ctgaaggcat aatggagaat caaaatggat tgatctgtgg attgaggcag ctggccaacg    3000
aaacgacaca agctcttcaa ttgttcttaa gggcaactac tgagttgcgt acattctcta    3060
tactaaatcg gaaagcaata gacttcttgc tccaaagatg ggaggaaca tgtcacattc    3120 tagggcctga ttgttgcatt gaaccccaag attggaccaa aaatatcact gataaaattg    3180
atcaaataat ccatgacttt gtcgataata atcttccaaa tcagaatgat ggcagcaact    3240
ggtggactgg atggaaacaa tggtgaagat ccagatctgc tgtgccttct agttgccagc    3300
catctgttgt ttgcccctcc cccgtgcctt ccttgaccct ggaaggtgcc actcccactg    3360
tcctttccta ataaaatgag gaaattgcat cgcattgtct gagtaggtgt cattctattc    3420
tggggggtgg ggtggggcag cacagcaagg gggaggattg ggaagacaat agcaggcatg    3480
ctggggatgc ggtgggctct atgggtaccc agggccgcat aacttcgtat aatgtatgct    3540
atacgaagtt ataagatctg tactgaaatg tgtgggcgtg gcttaagggt gggaaagaat    3600
atataaggtg ggggtcttat gtagttttgt atctgttttg cagcagccgc cgccgccatg    3660
agcaccaact cgtttgatgg aagcattgtg agctcatatt tgacaacgcg catgcccca    3720 tgggccgggg tgcgtcagaa tgtgatgggc tccagcattg atggtcgccc cgtcctgccc    3780
gcaaactcta ctaccttgac ctacgagacc gtgtctggaa cgccgttgga gactgcagcc    3840
tccgccgccg cttcagccgc tgcagccacc gcccgcggga ttgtgactga ctttgctttc    3900
ctgagcccgc ttgcaagcag tgcagcttcc cgttcatccg cccgcgatga caagttgacg    3960
gctcttttgg cacaattgga ttctttgacc cgggaactta atgtcgtttc tcagcagctg    4020
ttggatctgc gccagcaggt ttctgccctg aaggcttcct cccctcccaa tgcggtttaa    4080
aacataaata aaaaaccaga ctctgtttgg atttggatca agcaagtgtc ttgctgtctt    4140
tatttagggg ttttgcgcgc gcggtaggcc cgggaccagc ggtctcggtc gttgagggtc    4200
ctgtgtattt tttccaggac gtggtaaagg tgactctgga tgttcagata catgggcata    4260
agcccgtctc tggggtggag gtagcaccac tgcagagctt catgctgcgg ggtggtgttg    4320
tagatgatcc agtcgtagca ggagcgctgg gcgtggtgcc taaaaatgtc tttcagtagc    4380
aagctgattg ccaggggcag gcccttggtg taagtgttta caaagcggtt aagctgggat    4440
gggtgcatac gtgggatat gagatgcatc ttggactgta ttttaggtt ggctatgttc    4500 ccagccatat ccctccgggg attcatgttg tgcagaacca ccagcacagt gtatccggtg    4560
```

```
cacttgggaa atttgtcatg tagcttagaa ggaaatgcgt ggaagaactt ggagacgccc    4620
ttgtgacctc caagattttc catgcattcg tccataatga tggcaatggg cccacgggcg    4680
gcggcctggg cgaagatatt tctgggatca ctaacgtcat agttgtgttc caggatgaga    4740
tcgtcatagg ccattttac aaagcgcggg cggagggtgc cagactgcgg tataatggtt     4800
ccatccggcc caggggcgta gttaccctca cagatttgca tttcccacgc tttgagttca    4860
gatgggggga tcatgtctac ctgcggggcg atgaagaaaa cggtttccgg ggtaggggag    4920
atcagctggg aagaaagcag gttcctgagc agctgcgact taccgcagcc ggtgggcccg    4980
taaatcacac ctattaccgg ctgcaactgg tagttaagag agctgcagct gccgtcatcc    5040
ctgagcaggg gggccacttc gttaagcatg tccctgactc gcatgttttc cctgaccaaa    5100
tccgccagaa ggcgctcgcc gcccagcgat agcagttctt gcaaggaagc aaagttttc    5160 aacggtttga gaccgtccgc cgtaggcatg cttttgagcg tttgaccaag cagttccagg    5220
cggtcccaca gctcggtcac ctgctctacg gcatctcgat ccagcatatc tcctcgtttc    5280
gcggggtggg gcggctttcg ctgtacggca gtagtcggtg ctcgtccaga cgggccaggg    5340
tcatgtcttt ccacgggcgc agggtcctcg tcagcgtagt ctgggtcacg gtgaaggggt    5400
gcgctccggg ctgcgcgctg gccagggtgc gcttgaggct ggtcctgctg gtgctgaagc    5460
gctgccggtc ttcgccctgc gcgtcggcca ggtagcattt gaccatggtg tcatagtcca    5520 gccctccgc ggcgtggccc ttggcgcgca gcttgccctt ggaggaggcg ccgcacgagg     5580
ggcagtgcag acttttgagg gcgtagagct tgggcgcgag aaataccgat tccggggagt    5640
aggcatccgc gccgcaggcc ccgcagacgg tctcgcattc cacgagccag gtgagctctg    5700
gccgttcggg gtcaaaaacc aggtttcccc catgcttttt gatgcgtttc ttacctctgg    5760
tttccatgag ccggtgtcca cgctcggtga cgaaaaggct gtccgtgtcc ccgtatacag    5820
acttgagagg cctgtcctcg agcggtgttc cgcggtcctc ctcgtataga aactcggacc    5880
actctgagac aaaggctcgc gtccaggcca gcacgaagga ggctaagtgg gagggtagc    5940 ggtcgttgtc cactagggg tccactcgct ccagggtgtg aagacacatg tcgccctctt     6000
cggcatcaag gaaggtgatt ggtttgtagg tgtaggccac gtgaccgggt gttcctgaag    6060
gggggctata aaaggggtg ggggcgcgtt cgtcctcact ctcttccgca tcgctgtctg     6120
cgagggccag ctgttggggt gagtcgacgc gaggctggat ggccttcccc attatgattc    6180
ttctcgcttc cggcggcatc gggatgcccg cgttgcaggc catgctgtcc aggcaggtag    6240
atgacgacca tcagggacag cttcaaggcc agcaaaaggc caggaaccgt aaaaaggccg    6300
cgttgctggc gttttccat aggctccgcc cccctgacga gcatcacaaa aatcgacgct     6360
caagtcagag gtggcgaaac ccgacaggac tataaagata ccaggcgttt ccccctggaa    6420
gctccctcgt gcgctctcct gttccgaccc tgccgcttac cggatacctg tccgcctttc    6480
tcccttcggg aagcgtggcg ctttctcata gctcacgctg taggtatctc agttcggtgt    6540
aggtcgttcg ctccaagctg ggctgtgtgc acgaacccc cgttcagccc gaccgctgcg     6600
ccttatccgg taactatcgt cttgagtcca acccggtaag acacgactta tcgccactgg    6660
cagcagccac tggtaacagg attagcagag cgaggtatgt aggcggtgct acagagttct    6720
tgaagtggtg gcctaactac ggctacacta aggacagt atttggtatc tgcgctctgc      6780
tgaagccagt taccttcgga aaagagttg gtagctcttg atccggcaaa caaaccaccg     6840
ctggtagcgg tggttttttt gtttgcaagc agcagattac gcgcagaaaa aaaggatctc    6900
```

| | |
|---|---|
| aagaagatcc tttgatctttt tctacggggt ctgacgctca gtggaacgaa aactcacgtt | 6960 |
| aagggatttt ggtcatgaga ttatcaaaaa ggatcttcac ctagatcctt ttaaattaaa | 7020 |
| aatgaagttt taaatcaatc taaagtatat atgagtaaac ttggtctgac agttaccaat | 7080 |
| gcttaatcag tgaggcacct atctcagcga tctgtctatt tcgttcatcc atagttgcct | 7140 |
| gactccccgt cgtgtagata actacgatac gggagggctt accatctggc cccagtgctg | 7200 |
| caatgatacc gcgagaccca cgctcaccgg ctccagattt atcagcaata aaccagccag | 7260 |
| ccggaagggc cgagcgcaga agtggtcctg caactttatc cgcctccatc cagtctatta | 7320 |
| attgttgccg ggaagctaga gtaagtagtt cgccagttaa tagtttgcgc aacgttgttg | 7380 |
| ccattgctgc aggcatcgtg gtgtcacgct cgtcgtttgg tatggcttca ttcagctccg | 7440 |
| gttcccaacg atcaaggcga gttacatgat cccccatgtt gtgcaaaaaa gcggttagct | 7500 |
| ccttcggtcc tccgatcgtt gtcagaagta agttggccgc agtgttatca ctcatggtta | 7560 |
| tggcagcact gcataattct cttactgtca tgccatccgt aagatgcttt tctgtgactg | 7620 |
| gtgagtactc aaccaagtca ttctgagaat agtgtatgcg gcgaccgagt tgctcttgcc | 7680 |
| cggcgtcaac acgggataat accgcgccac atagcagaac tttaaaagtg ctcatcattg | 7740 |
| gaaaacgttc ttcggggcga aaactctcaa ggatcttacc gctgttgaga tccagttcga | 7800 |
| tgtaacccac tcgtgcaccc aactgatctt cagcatcttt tactttcacc agcgtttctg | 7860 |
| ggtgagcaaa aacaggaagg caaaatgccg caaaaaaggg aataagggcg acacggaaat | 7920 |
| gttgaatact catactcttc ctttttcaat attattgaag catttatcag ggttattgtc | 7980 |
| tcatgagcgg atacatattt gaatgtattt agaaaaataa acaaataggg gttccgcgca | 8040 |
| catttccccg aaaagtgcca cctgacgtct aagaaaccat tattatcatg acattaacct | 8100 |
| ataaaaatag gcgtatcacg aggccctttc gtcttcaaga attgtt | 8146 |

<210> SEQ ID NO 21
<211> LENGTH: 7023
<212> TYPE: DNA
<213> ORGANISM: Artificial Sequence
<220> FEATURE:
<223> OTHER INFORMATION: Synthetic Construct pVR1012x/s-SGP(IC)

<400> SEQUENCE: 21

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcagattgg | 240 |
| ctattggcca ttgcatacgt tgtatccata tcataatatg tacatttata ttggctcatg | 300 |
| tccaacatta ccgccatgtt gacattgatt attgactagt tattaatagt aatcaattac | 360 |
| ggggtcatta gttcatagcc catatatgga gttccgcgtt acataactta cggtaaatgg | 420 |
| cccgcctggc tgaccgccca acgacccccg cccattgacg tcaataatga cgtatgttcc | 480 |
| catagtaacg ccaatagggA ctttccattg acgtcaatgg gtggagtatt tacggtaaac | 540 |
| tgcccacttg gcagtacatc aagtgtatca tatgccaagt acgccccctA ttgacgtcaa | 600 |
| tgacggtaaa tggcccgcct ggcattatgc ccagtacatg accttatggg actttcctac | 660 |
| ttggcagtac atctacgtat tagtcatcgc tattaccatg gtgatgcggt tttggcagta | 720 |
| catcaatggg cgtggatagc ggtttgactc acggggattt ccaagtctcc accccattga | 780 |
| cgtcaatggg agtttgtttt ggcaccaaaa tcaacgggac tttccaaaat gtcgtaacaa | 840 |

```
ctccgcccca ttgacgcaaa tgggcggtag gcgtgtacgg tgggaggtct atataagcag      900
agctcgttta gtgaaccgtc agatcgcctg gagacgccat ccacgctgtt ttgacctcca      960
tagaagacac cgggaccgat ccagcctccg cggccgggaa cggtgcattg aacgcggat      1020
tccccgtgcc aagagtgacg taagtaccgc ctatagactc tataggcaca ccccctttggc    1080
tcttatgcat gctatactgt ttttggcttg gggcctatac accccgctt ccttatgcta      1140
taggtgatgg tatagcttag cctataggtg tgggttattg accattattg accactcccc    1200
tattggtgac gatactttcc attactaatc cataacatgg ctctttgcca caactatctc    1260
tattggctat atgccaatac tctgtccttc agagactgac acggactctg tatttttaca    1320
ggatggggtc ccatttatta tttacaaatt cacatataca acaacgccgt cccccgtgcc    1380
cgcagttttt attaaacata gcgtgggatc tccacgcgaa tctcgggtac gtgttccgga    1440
catgggctct tctccggtag cggcggagct tccacatccg agccctggtc ccatgcctcc    1500
agcggctcat ggtcgctcgg cagctccttg ctcctaacag tggaggccag acttaggcac    1560
agcacaatgc ccaccaccac cagtgtgccg cacaaggccg tggcggtagg gtatgtgtct    1620
gaaaatgagc gtggagattg ggctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tcctttccat gggtcttttc    1860
tgcagtcacc gtcgtcgaca cgtgtgatca gatatcgcgg ccgctctaga attcggcttc    1920
taatcacagt caccatggga gcgtcaggga ttctgcaatt gccccgtgag cgcttcagga    1980
aaacatcttt ctttgtttgg gtaataatcc tattccataa agtctttttca atcccgttgg    2040
gggttgtaca caacaatacc ctacaagtga gtgatattga caagtttgtg tgccgagaca    2100
aactctcttc aactagccaa ttgaagtcag tcgggttgaa cttggagggc aatggagtag    2160
caactgatgt accaacggca accaaaagat ggggttttcg agctggtgtt ccaccaaagg    2220
tggtaaattg cgaagctgga gaatgggctg agaactgtta taacctggct ataaagaaag    2280
ttgatggtag tgagtgccta ccagaagccc ctgagggagt gagggatttt ccccgttgcc    2340
gctatgtaca caaagtctca ggaactggac catgcccagg aggactcgcc tttcacaaag    2400
aaggagcctt cttcctgtat gaccgactcg catcaacaat catttatcgg ggtacaacct    2460
ttgccgaagt agttattgca tttctgatct tgcctaaggc gcgaaaggat tttttccagt    2520
ctcctccatt gcatgagcct gccaacatga ccacggatcc ctccagttac tatcacacga    2580
caacaataaa ctacgtggtt gataattttg gaaccaacac cacagagttt ctgttccaag    2640
tcgatcattt gacgtatgtg cagctcgagg caagattcac accacaattc cttgtcctcc    2700
taaatgaaac catctactct gataaccgca gaagtaacac aacaggaaaa ctaatctgga    2760
aaataaatcc cactgttgat accagcatgg gtgagtgggc tttctgggaa aataaaaaaa    2820
acttcacaaa aacccttca agtgaagagt tgtctttcgt acctgtacca gaaacccaga    2880
accaggtcct tgacacgaca gcgacggtct tcctcccat ctccgcccac aaccacgcag    2940
ccgaagacca caagaattg gtttcagagg attccactcc agtggttcag atgcaaaaca    3000
tcaagggaaa ggacacaatg ccaaccacag tgacgggtgt accaacaacc acaccctctc    3060
catttccaat caatgctcgc aacactgatc ataccaaatc attatcggc ctggaggggc    3120
cccaagaaga ccacagcacc acacagcctg ccaagaccac cagccaacca accaacagca    3180
```

-continued

```
cagaatcgac gacactaaac ccaacatcag agccctccag tagaggcacg ggaccatcca    3240
gccccacggt ccccaacacc acagaaagcc acgccgaact tggcaagaca accccaacca    3300
cactcccaga acagcacact gccgccagtg ccattccaag agccgtgcac cccgacgaac    3360
tcagtggacc tggcttcctg acgaacacaa tacgggggt tacaaatctc ctgacaggat     3420
ccagaagaaa gcgaagggat gtcactccca atacacaacc caaatgcaac ccaaacctgc    3480
actattggac agccttggat gagggtgctg ccataggttt agcctggata ccatacttcg    3540
ggccagcagc tgagggaatt tacactgaag gcataatgga gaatcaaaat ggattgatct    3600
gtggattgag gcagctggcc aacgaaacga cacaagctct tcaattgttc ttaagggcaa    3660
ctactgagtt gcgtacattc tctatactaa atcggaaagc aatagacttc ttgctccaaa    3720
gatggggagg aacatgtcac attctagggc ctgattgttg cattgaaccc caagattgga    3780
ccaaaaatat cactgataaa attgatcaaa taatccatga ctttgtcgat aataatcttc    3840
caaatcagaa tgatggcagc aactggtgga ctggatggaa acaatgggtt cctgctggaa    3900
taggaatcac aggagtaatc attgctatta ttgctttgct gtgcatttgc aaattcatgc    3960
tttgaactaa tatagcatca tactttaagc cgaattctag accaggccct ggatccagat    4020
ctgctgtgcc ttctagttgc cagccatctg ttgtttgccc ctcccccgtg ccttccttga    4080
ccctggaagg tgccactccc actgtccttt cctaataaaa tgaggaaatt gcatcgcatt    4140
gtctgagtag gtgtcattct attctggggg gtggggtggg gcaggacagc aaggggagg     4200 attgggaaga caatagcagg catgctgggg atgcggtggg ctctatgggt acccaggtgc    4260
tgaagaattg acccggttcc tcctgggcca gaaagaagca ggcacatccc cttctctgtg    4320
acacaccctg tccacgcccc tggttcttag ttccagcccc actcatagga cactcatagc    4380
tcaggagggc tccgccttca atcccacccg ctaaagtact tggagcggtc tctccctccc    4440
tcatcagccc accaaaccaa acctagcctc aagagtgggg aagaaattaa agcaagatag    4500
gctattaagt gcagagggag agaaaatgcc tccaacatgt gaggaagtaa tgagagaaat    4560
catagaattt taaggccatc atggccttaa tcttccgctt cctcgctcac tgactcgctg    4620
cgctcggtcg ttcggctgcg gcgagcggta tcagctcact caaaggcggt aatacggtta    4680
tccacagaat caggggataa cgcaggaaag aacatgtgag caaaaggcca gcaaaaggcc    4740
aggaaccgta aaaaggccgc gttgctggcg ttttttccata ggctccgccc ccctgacgag    4800
catcacaaaa atcgacgctc aagtcagagg tggcgaaacc cgacaggact ataaagatac    4860
caggcgtttc ccccctggaag ctccctcgtg cgctctcctg ttccgaccct gccgcttacc    4920
ggatacctgt ccgcctttct cccttcggga agcgtggcgc tttctcatag ctcacgctgt    4980
aggtatctca gttcggtgta ggtcgttcgc tccaagctgg gctgtgtgca cgaacccccc    5040
gttcagcccg accgctgcgc cttatccggt aactatcgtc ttgagtccaa cccggtaaga    5100
cacgacttat cgccactggc agcagccact ggtaacagga ttagcagagc gaggtatgta    5160
ggcggtgcta cagagttctt gaagtggtgg cctaactacg gctacactag aagaacagta    5220
tttggtatct gcgctctgct gaagccagtt accttcggaa aaagagttgg tagctcttga    5280
tccggcaaac aaaccaccgc tggtagcggt ggtttttttg tttgcaagca gcagattacg    5340
cgcagaaaaa aaggatctca agaagatcct ttgatctttt ctacggggtc tgacgctcag    5400
tggaacgaaa actcacgtta agggattttg gtcatgagat tatcaaaaag gatcttcacc    5460
tagatccttt taaattaaaa atgaagtttt aaatcaatct aaagtatata tgagtaaact    5520
tggtctgaca gttaccaatg cttaatcagt gaggcaccta tctcagcgat ctgtctattt    5580
```

```
cgttcatcca tagttgcctg actcgggggg ggggggcgct gaggtctgcc tcgtgaagaa    5640
ggtgttgctg actcatacca ggcctgaatc gccccatcat ccagccagaa agtgagggag    5700
ccacggttga tgagagcttt gttgtaggtg gaccagttgg tgattttgaa cttttgcttt    5760
gccacggaac ggtctgcgtt gtcgggaaga tgcgtgatct gatccttcaa ctcagcaaaa    5820
gttcgattta ttcaacaaag ccgccgtccc gtcaagtcag cgtaatgctc tgccagtgtt    5880
acaaccaatt aaccaattct gattagaaaa actcatcgag catcaaatga aactgcaatt    5940
tattcatatc aggattatca ataccatatt tttgaaaaag ccgtttctgt aatgaaggag    6000
aaaactcacc gaggcagttc cataggatgg caagatcctg gtatcggtct gcgattccga    6060
ctcgtccaac atcaatacaa cctattaatt cccctcgtc aaaataagg ttatcaagtg    6120 agaaatcacc atgagtgacg actgaatccg gtgagaatgg caaaagctta tgcatttctt    6180
tccagacttg ttcaacaggc cagccattac gctcgtcatc aaaatcactc gcatcaacca    6240
aaccgttatt cattcgtgat tgcgcctgag cgagacgaaa tacgcgatcg ctgttaaaag    6300
gacaattaca acaggaatc gaatgcaacc ggcgcaggaa cactgccagc gcatcaacaa    6360
tattttcacc tgaatcagga tattcttcta atacctggaa tgctgttttc ccggggatcg    6420
cagtggtgag taaccatgca tcatcaggag tacggataaa atgcttgatg gtcggaagag    6480
gcataaattc cgtcagccag tttagtctga ccatctcatc tgtaacatca ttggcaacgc    6540
tacctttgcc atgtttcaga aacaactctg gcgcatcggg cttcccatac aatcgataga    6600
ttgtcgcacc tgattgcccg acattatcgc gagcccattt atacccatat aaatcagcat    6660
ccatgttgga atttaatcgc ggcctcgagc aagacgtttc ccgttgaata tggctcataa    6720
cacccctggt attactgtt atgtaagcag acagttttat tgttcatgat gatatatttt    6780
tatcttgtgc aatgtaacat cagagatttt gagacacaac gtggctttcc cccccccccc    6840
attattgaag catttatcag ggttattgtc tcatgagcgg atacatattt gaatgtattt    6900
agaaaaataa acaaataggg gttccgcgca catttccccg aaaagtgcca cctgacgtct    6960
aagaaaccat tattatcatg acattaacct ataaaaatag gcgtatcacg aggccctttc    7020
gtc                                                                  7023
```

<210> SEQ ID NO 22
<211> LENGTH: 7295
<212> TYPE: DNA
<213> ORGANISM: Artificial Sequence
<220> FEATURE:
<223> OTHER INFORMATION: Synthetic Construct pVR1012-NP

<400> SEQUENCE: 22

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgacccccg cccattgacg tcaataatga cgtatgttcc     480
catagtaacg ccaataggga ctttccattg acgtcaatgg gtggagtatt tacggtaaac     540
```

```
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctccg cggccgggaa cggtgcattg gaacgcggat   1020
tccccgtgcc aagagtgacg taagtaccgc ctatagactc tataggcaca ccccttggc    1080 tcttatgcat gctatactgt ttttggcttg ggcctatac accccgctt ccttatgcta    1140 taggtgatgg tatagcttag cctataggtg tgggttattg accattattg accactcccc   1200
tattggtgac gatactttcc attactaatc cataacatgg ctctttgcca caactatctc   1260
tattggctat atgccaatac tctgtccttc agagactgac acggactctg tattttaca    1320 ggatggggtc ccatttatta tttacaaatt cacatataca acaacgccgt ccccgtgcc    1380 cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgaca cgtgtgatca gatatcgcgg ccgctctaga ccaggccctg   1920
gatccagatc gatccgagta tggattctcg tcctcagaaa atctggatgg cgccgagtct   1980
cactgaatct gacatggatt accacaagat cttgacagca ggtctgtccg ttcaacaggg   2040
gattgttcgg caaagagtca tcccagtgta tcaagtaaac aatcttgaag aaatttgcca   2100
acttatcata caggcctttg aagcaggtgt tgattttcaa gagagtgcgg acagtttcct   2160
tctcatgctt tgtcttcatc atgcgtacca gggagattac aaactttct tggaaagtgg    2220 cgcagtcaag tatttggaag ggcacgggtt ccgttttgaa gtcaagaagc gtgatggagt   2280
gaagcgcctt gaggaattgc tgccagcagt atctagtgga aaaaacatta agagaacact   2340
tgctgccatg ccggaagagg agacaactga agctaatgcc ggtcagtttc tctcctttgc   2400
aagtctattc cttccgaaat tggtagtagg agaaaaggct tgccttgaga aggttcaaag   2460
gcaaattcaa gtacatgcag agcaaggact gatacaatat ccaacagctt ggcaatcagt   2520
aggacacatg atggtgattt ccgtttgat gcgaacaaat tttctgatca aatttctcct    2580
aatacaccaa gggatgcaca tggttgccgg gcatgatgcc aacgatgctg tgatttcaaa   2640
ttcagtggct caagctcgtt tttcaggctt attgattgtc aaaacagtac ttgatcatat   2700
cctacaaaag acagaacgag gagttcgtct ccatcctctt gcaaggaccg ccaaggtaaa   2760
aaatgaggtg aactcctta aggctgcact cagctccctg gccaagcatg gagagtatgc    2820 tccttcgcc cgacttttga accttctctgg agtaaataat cttgagcatg gtcttttccc    2880
tcaactatcg gcaattgcac tcggagtcgc cacagcacac gggagtaccc tcgcaggagt   2940
```

-continued

```
aaatgttgga gaacagtatc aacaactcag agaggctgcc actgaggctg agaagcaact   3000
ccaacaatat gcagagtctc gcgaacttga ccatcttgga cttgatgatc aggaaaagaa   3060
aattcttatg aacttccatc agaaaaagaa cgaaatcagc ttccagcaaa caaacgctat   3120
ggtaactcta agaaaagagc gcctggccaa gctgacagaa gctatcactg ctgcgtcact   3180
gcccaaaaca gtggacatt acgatgatga tgacgacatt cccttccag gacccatcaa     3240 tgatgacgac aatcctggcc atcaagatga tgatccgact gactcacagg atacgaccat   3300
tcccgatgtg gtggttgatc ccgatgatgg aagctacggc gaataccaga gttactcgga   3360
aaacggcatg aatgcaccag atgacttggt cctattcgat ctagacgagg acgacgagga   3420
cactaagcca gtgcctaata gatcgaccaa gggtggacaa cagaagaaca gtcaaaaggg   3480
ccagcatata gagggcagac agacacaatc caggccaatt caaaatgtcc caggccctca   3540
cagaacaatc caccacgcca gtgcgccact cacggacaat gacagaagaa atgaaccctc   3600
cggctcaacc agccctcgca tgctgacacc aattaacgaa gaggcagacc cactggacga   3660
tgccgacgac gagacgtcta gccttccgcc cttggagtca gatgatgaag agcaggacag   3720
ggacggaact tccaaccgca cacccactgt cgccccaccg gctcccgtat acagagatca   3780
ctctgaaaag aaagaactcc cgcaagacga gcaacaagat caggaccaca ctcaagaggc   3840
caggaaccag gacagtgaca cacccagtc agaacactct tttgaggaga tgtatcgcca    3900
cattctaaga tcacagggg catttgatgc tgttttgtat tatcatatga tgaaggatga    3960
gcctgtagtt ttcagtacca gtgatggcaa agagtacacg tatccagact cccttgaaga   4020
ggaatatcca ccatggctca ctgaaaaaga ggctatgaat gaagagaata gatttgttac   4080
attggatggt caacaatttt attggccggt gatgaatcac aagaataaat tcatggcaat   4140
cctgcaacat catcagtgaa tgagcatgga acaatgggat gattcaaccg acaaatagct   4200
aacattaagt agtcaaggaa cgaaaacagg aagaattttt gatgtctaag gtgtgaatta   4260
ttatcacaat aaaagtgatt cttattttg aatttgggcg agctcgaatt gatctgctgt     4320
gccttctagt tgccagccat ctgttgtttg cccctccccc gtgccttcct tgaccctgga   4380
aggtgccact cccactgtcc tttcctaata aaatgaggaa attgcatcgc attgtctgag   4440
taggtgtcat tctattctgg ggggtgggt ggggcaggac agcaagggg aggattggga     4500 agacaatagc aggcatgctg gggatgcggt gggctctatg ggtacccagg tgctgaagaa   4560
ttgacccggt tcctcctggg ccagaaagaa gcaggcacat cccttctct gtgacacacc     4620 ctgtccacgc ccctggttct tagttccagc cccactcata ggacactcat agctcaggag   4680
ggctccgcct tcaatcccac ccgctaaagt acttggagcg gtctctccct ccctcatcag   4740
cccaccaaac caaacctagc ctccaagagt gggaagaaat taaagcaaga taggctatta   4800
agtgcagagg gagagaaaat gcctccaaca tgtgaggaag taatgagaga aatcatagaa   4860
tttcttccgc ttcctcgctc actgactcgc tgcgctcggt cgttcggctg cggcgagcgg   4920
tatcagctca ctcaaaggcg gtaatacggt tatccacaga atcaggggat aacgcaggaa   4980
agaacatgtg agcaaaaggc cagcaaaagg ccaggaaccg taaaaaggcc gcgttgctgg   5040 cgttttttcca taggctccgc cccctgacg agcatcacaa aaatcgacgc tcaagtcaga    5100
ggtggcgaaa cccgacagga ctataaagat accaggcgtt tccccctgga agctccctcg   5160
tgcgctctcc tgttccgacc ctgccgctta ccggatacct gtccgccttt ctcccttcgg   5220
gaagcgtggc gctttctcat agctcacgct gtaggtatct cagttcggtg taggtcgttc   5280
```

```
gctccaagct gggctgtgtg cacgaacccc ccgttcagcc cgaccgctgc gccttatccg    5340
gtaactatcg tcttgagtcc aacccggtaa gacacgactt atcgccactg gcagcagcca    5400
ctggtaacag gattagcaga gcgaggtatg taggcggtgc tacagagttc ttgaagtggt    5460
ggcctaacta cggctacact agaagaacag tatttggtat ctgcgctctg ctgaagccag    5520
ttaccttcgg aaaaagagtt ggtagctctt gatccggcaa acaaaccacc gctggtagcg    5580
gtggtttttt tgtttgcaag cagcagatta cgcgcagaaa aaaaggatct caagaagatc    5640
ctttgatctt ttctacgggg tctgacgctc agtggaacga aaactcacgt taagggattt    5700
tggtcatgag attatcaaaa aggatcttca cctagatcct tttaaattaa aaatgaagtt    5760
ttaaatcaat ctaaagtata tatgagtaaa cttggtctga cagttaccaa tgcttaatca    5820
gtgaggcacc tatctcagcg atctgtctat ttcgttcatc catagttgcc tgactcgggg    5880
ggggggggcg ctgaggtctg cctcgtgaag aaggtgttgc tgactcatac caggcctgaa    5940
tcgccccatc atccagccag aaagtgaggg agccacggtt gatgagagct tgttgtagg    6000 tggaccagtt ggtgattttg aacttttgct ttgccacgga acggtctgcg ttgtcgggaa    6060
gatgcgtgat ctgatccttc aactcagcaa aagttcgatt tattcaacaa agccgccgtc    6120
ccgtcaagtc agcgtaatgc tctgccagtg ttacaaccaa ttaaccaatt ctgattagaa    6180
aaactcatcg agcatcaaat gaaactgcaa tttattcata tcaggattat caataccata    6240
tttttgaaaa agccgtttct gtaatgaagg agaaaactca ccgaggcagt tccataggat    6300
ggcaagatcc tggtatcggt ctgcgattcc gactcgtcca acatcaatac aacctattaa    6360
tttcccctcg tcaaaaataa ggttatcaag tgagaaatca ccatgagtga cgactgaatc    6420
cggtgagaat ggcaaaagct tatgcatttc tttccagact tgttcaacag gccagccatt    6480
acgctcgtca tcaaaatcac tcgcatcaac caaaccgtta ttcattcgtg attgcgcctg    6540
agcgagacga atacgcgat cgctgttaaa aggacaatta caaacaggaa tcgaatgcaa    6600
ccggcgcagg aacactgcca gcgcatcaac aatattttca cctgaatcag gatattcttc    6660
taatacctgg aatgctgttt tcccggggat cgcagtggtg agtaaccatg catcatcagg    6720
agtacggata aaatgcttga tggtcggaag aggcataaat tccgtcagcc agtttagtct    6780
gaccatctca tctgtaacat cattggcaac gctacctttg ccatgtttca gaaacaactc    6840
tggcgcatcg ggcttcccat acaatcgata gattgtcgca cctgattgcc cgacattatc    6900
gcgagcccat ttatacccat ataaatcagc atccatgttg gaatttaatc gcggcctcga    6960
gcaagacgtt tcccgttgaa tatggctcat aacacccctt gtattactgt ttatgtaagc    7020
agacagtttt attgttcatg atgatatatt tttatcttgt gcaatgtaac atcagagatt    7080
ttgagacaca acgtggcttt cccccccccc ccattattga agcatttatc agggttattg    7140
tctcatgagc ggatacatat ttgaatgtat ttagaaaaat aaacaaatag gggttccgcg    7200
cacatttccc cgaaaagtgc cacctgacgt ctaagaaacc attattatca tgacattaac    7260
ctataaaaat aggcgtatca cgaggccctt tcgtc                               7295
```

<210> SEQ ID NO 23
<211> LENGTH: 7329
<212> TYPE: DNA
<213> ORGANISM: Artificial Sequence
<220> FEATURE:
<223> OTHER INFORMATION: Synthetic Construct pVR1012x/s Ebola-NP

<400> SEQUENCE: 23

```
tcgcgcgttt cggtgatgac ggtgaaaacc tctgacacat gcagctcccg gagacggtca    60
```

-continued

```
cagcttgtct gtaagcggat gccgggagca gacaagcccg tcagggcgcg tcagcgggtg      120
ttggcgggtg tcgggctgg cttaactatg cggcatcaga gcagattgta ctgagagtgc       180
accatatgcg gtgtgaaata ccgcacagat gcgtaaggag aaaataccgc atcagattgg      240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag   900
agctcgttta gtgaaccgtc agatcgcctg gagacgccat ccacgctgtt ttgacctcca   960
tagaagacac cgggaccgat ccagcctccg cggccgggaa cggtgcattg aacgcggat    1020
tccccgtgcc aagagtgacg taagtaccgc ctatagactc tataggcaca cccctttggc   1080
tcttatgcat gctatactgt ttttggcttg gggcctatac cccccgctt ccttatgcta    1140
taggtgatgg tatagcttag cctataggtg tgggttattg accattattg accactcccc   1200
tattggtgac gatactttcc attactaatc cataacatgg ctctttgcca caactatctc   1260
tattggctat atgccaatac tctgtccttc agagactgac acggactctg tatttttaca   1320
ggatggggtc ccatttatta tttacaaatt cacatataca acaacgccgt cccccgtgcc   1380
cgcagttttt attaaacata gcgtgggatc tccacgcgaa tctcgggtac gtgttccgga   1440
catgggctct ctccggtag cggcggagct tccacatccg agccctggtc ccatgcctcc    1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgaca cgtgtgatca gatatcgcgg ccgctctaga ccaggccctg   1920
gatccagatc gatccgagta tggattctcg tcctcagaaa atctggatgg cgccgagtct   1980
cactgaatct gacatggatt accacaagat cttgacagca ggtctgtccg ttcaacaggg   2040
gattgttcgg caaagagtca tcccagtgta tcaagtaaac aatcttgaag aaatttgcca   2100
acttatcata caggcctttg aagcaggtgt tgattttcaa gagagtgcgg acagtttcct   2160
tctcatgctt tgtcttcatc atgcgtacca gggagattac aaactttcct tggaaagtgg   2220
cgcagtcaag tatttggaag gcacggggtt ccgttttgaa gtcaagaagc gtgatggagt   2280
gaagcgcctt gaggaattgc tgccagcagt atctagtgga aaaaacatta agagaacact   2340
tgctgccatg ccggaagagg agacaactga agctaatgcc ggtcagtttc tctcctttgc   2400
```

```
aagtctattc cttccgaaat tggtagtagg agaaaaggct tgccttgaga aggttcaaag   2460
gcaaattcaa gtacatgcag agcaaggact gatacaatat ccaacagctt ggcaatcagt   2520
aggacacatg atggtgattt tccgtttgat gcgaacaaat tttctgatca aatttctcct   2580
aatacaccaa gggatgcaca tggttgccgg gcatgatgcc aacgatgctg tgatttcaaa   2640
ttcagtggct caagctcgtt tttcaggctt attgattgtc aaaacagtac ttgatcatat   2700
cctacaaaag acagaacgag gagttcgtct ccatcctctt gcaaggaccg ccaaggtaaa   2760
aaatgaggtg aactccttta aggctgcact cagctccctg ccaagcatg gagagtatgc    2820 tcctttcgcc cgacttttga acctttctgg agtaaataat cttgagcatg gtcttttccc   2880
tcaactatcg gcaattgcac tcggagtcgc cacagcacac gggagtaccc tcgcaggagt   2940
aaatgttgga gaacagtatc aacaactcag agaggctgcc actgaggctg agaagcaact   3000
ccaacaatat gcagagtctc gcgaacttga ccatcttgga cttgatgatc aggaaaagaa   3060
aattcttatg aacttccatc agaaaaagaa cgaaatcagc ttccagcaaa caacgctat    3120 ggtaactcta agaaaagagc gcctggccaa gctgacagaa gctatcactg ctgcgtcact   3180
gcccaaaaca gtggacatt acgatgatga tgacgacatt ccctttccag acccatcaa     3240 tgatgacgac aatcctggcc atcaagatga tgatccgact gactcacagg atacgaccat   3300
tcccgatgtg gtggttgatc ccgatgatgg aagctacggc gaataccaga gttactcgga   3360
aaacggcatg aatgcaccag atgacttggt cctattcgat ctagacgagg acgacgagga   3420
cactaagcca gtgcctaata gatcgaccaa gggtggacaa cagaagaaca gtcaaaaggg   3480
ccagcatata gagggcagac agacacaatc caggccaatt caaaatgtcc caggccctca   3540
cagaacaatc caccacgcca gtgcgccact cacggacaat gacagaagaa atgaaccctc   3600
cggctcaacc agccctcgca tgctgacacc aattaacgaa gaggcagacc cactggacga   3660
tgccgacgac gagacgtcta gccttccgcc cttggagtca gatgatgaag agcaggacag   3720
ggacggaact tccaaccgca cacccactgt cgccccaccg gctcccgtat acagagatca   3780
ctctgaaaag aaagaactcc cgcaagacga gcaacaagat caggaccaca ctcaagaggc   3840
caggaaccag gacagtgaca cacccagtc agaacactct tttgaggaga tgtatcgcca    3900
cattctaaga tcacagggc catttgatgc tgtttgtat tatcatatga tgaaggatga     3960
gcctgtagtt ttcagtacca gtgatggcaa agagtacacg tatccagact cccttgaaga   4020
ggaatatcca ccatggctca ctgaaaaaga ggctatgaat gaagagaata gatttgttac   4080
attggatggt caacaatttt attggccggt gatgaatcac aagaataaat tcatggcaat   4140
cctgcaacat catcagtgaa tgagcatgga acaatgggat gattcaaccg acaaatagct   4200
aacattaagt agtcaaggaa cgaaaacagg aagaattttt gatgtctaag gtgtgaatta   4260
ttatcacaat aaaagtgatt cttattttg aatttgggcg agctcgaatt gatctgctgt     4320
gccttctagt tgccagccat ctgttgtttg cccctccccc gtgccttcct tgaccctgga   4380
aggtgccact cccactgtcc tttcctaata aaatgaggaa attgcatcgc attgtctgag   4440
taggtgtcat tctattctgg ggggtgggt ggggcaggac agcaagggg aggattggga     4500 agacaatagc aggcatgctg gggatgcggt gggctctatg ggtacccagg tgctgaagaa   4560
ttgacccggt tcctcctggg ccagaaagaa gcaggcacat ccccttctct gtgacacacc   4620
ctgtccacgc cctggttct tagttccagc cccactcata ggacactcat agctcaggag    4680
ggctccgcct tcaatcccac ccgctaaagt acttggagcg gtctctccct ccctcatcag   4740
cccaccaaac caaacctagc ctccaagagt gggaagaaat taaagcaaga taggctatta   4800
```

```
agtgcagagg gagagaaaat gcctccaaca tgtgaggaag taatgagaga aatcatagaa    4860
ttttaaggcc atgatttaag gccatcatgg ccttaatctt ccgcttcctc gctcactgac    4920
tcgctgcgct cggtcgttcg gctgcggcga gcggtatcag ctcactcaaa ggcggtaata    4980
cggttatcca cagaatcagg ggataacgca ggaaagaaca tgtgagcaaa aggccagcaa    5040
aaggccagga accgtaaaaa ggccgcgttg ctggcgtttt tccataggct ccgcccccct    5100
gacgagcatc acaaaaatcg acgctcaagt cagaggtggc gaaacccgac aggactataa    5160
agataccagg cgtttccccc tggaagctcc ctcgtgcgct ctcctgttcc gaccctgccg    5220
cttaccggat acctgtccgc ctttctccct tcgggaagcg tggcgctttc tcatagctca    5280
cgctgtaggt atctcagttc ggtgtaggtc gttcgctcca agctgggctg tgtgcacgaa    5340
ccccccgttc agcccgaccg ctgcgcctta tccggtaact atcgtcttga gtccaacccg    5400
gtaagacacg acttatcgcc actggcagca gccactggta acaggattag cagagcgagg    5460
tatgtaggcg gtgctacaga gttcttgaag tggtggccta actacggcta cactagaaga    5520
acagtatttg gtatctgcgc tctgctgaag ccagttacct tcggaaaaag agttggtagc    5580
tcttgatccg gcaaacaaac caccgctggt agcggtggtt ttttttgttg caagcagcag    5640
attacgcgca gaaaaaaagg atctcaagaa gatcctttga tcttttctac ggggtctgac    5700
gctcagtgga acgaaaactc acgttaaggg attttggtca tgagattatc aaaaaggatc    5760
ttcacctaga tccttttaaa ttaaaaatga agttttaaat caatctaaag tatatatgag    5820
taaacttggt ctgacagtta ccaatgctta atcagtgagg cacctatctc agcgatctgt    5880
ctatttcgtt catccatagt tgcctgactc ccccgggggg ggcgctgagg tctgcctcgt    5940
gaagaaggtg ttgctgactc ataccaggcc tgaatcgccc catcatccag ccagaaagtg    6000
agggagccac ggttgatgag agctttgttg taggtggacc agttggtgat tttgaacttt    6060
tgctttgcca cggaacggtc tgcgttgtcg ggaagatgcg tgatctgatc cttcaactca    6120 gcaaagttc gatttattca acaaagccgc cgtcccgtca agtcagcgta atgctctgcc    6180
agtgttacaa ccaattaacc aattctgatt agaaaaactc atcgagcatc aaatgaaact    6240
gcaatttatt catatcagga ttatcaatac catattttg aaaagccgt ttctgtaatg    6300 aaggagaaaa ctcaccgagg cagttccata ggatggcaag atcctggtat cggtctgcga    6360
ttccgactcg tccaacatca atacaaccta ttaatttccc ctcgtcaaaa ataaggttat    6420
caagtgagaa atcaccatga gtgacgactg aatccggtga gaatggcaaa agcttatgca    6480
tttctttcca gacttgttca acaggccagc cattacgctc gtcatcaaaa tcactcgcat    6540
caaccaaacc gttattcatt cgtgattgcg cctgagcgag acgaaatacg cgatcgctgt    6600
taaaaggaca attacaaaca ggaatcgaat gcaaccggcg caggaacact gccagcgcat    6660
caacaatatt ttcacctgaa tcaggatatt cttctaatac ctggaatgct gttttcccgg    6720
ggatcgcagt ggtgagtaac catgcatcat caggagtacg gataaaatgc ttgatggtcg    6780
gaagaggcat aaattccgtc agccagttta gtctgaccat ctcatctgta acatcattgg    6840
caacgctacc tttgccatgt ttcagaaaca actctggcgc atcgggcttc ccatacaatc    6900
gatagattgt cgcacctgat tgcccgacat tatcgcgagc ccatttatac ccatataaat    6960
cagcatccat gttggaattt aatcgcggcc tcgagcaaga cgtttcccgt tgaatatggc    7020
tcataacacc ccttgtatta ctgtttatgt aagcagacag ttttattgtt catgatgata    7080
tatttttatc ttgtgcaatg taacatcaga gattttgaga cacaacgtgg ctttcccccc    7140
```

```
cccccccatta ttgaagcatt tatcagggtt attgtctcat gagcggatac atatttgaat   7200
gtatttagaa aaataaacaa ataggggttc cgcgcacatt tccccgaaaa gtgccacctg   7260
acgtctaaga aaccattatt atcatgacat taacctataa aaataggcgt atcacgaggc   7320
cctttcgtc                                                           7329

<210> SEQ ID NO 24
<211> LENGTH: 6148
<212> TYPE: DNA
<213> ORGANISM: Artificial Sequence
<220> FEATURE:
<223> OTHER INFORMATION: Synthetic Construct pVR1012-VP35

<400> SEQUENCE: 24
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc     180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaatagggga ctttccattg acgtcaatgg gtggagtatt tacggtaaac    540
tgcccacttg gcagtacatc aagtgtatca tatgccaagt acgccccta ttgacgtcaa    600 tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctccg cggccgggaa cggtgcattg gaacgcggat   1020
tccccgtgcc aagagtgacg taagtaccgc ctatagactc tataggcaca ccctttggc    1080 tcttatgcat gctatactgt ttttggcttg gggcctatac accccgctt ccttatgcta    1140 taggtgatgg tatagcttag cctataggtg tgggttattg accattattg accactcccc    1200
tattggtgac gatactttcc attactaatc cataacatgg ctctttgcca caactatctc    1260
tattggctat atgccaatac tctgtccttc agagactgac acggactctg tatttttaca    1320
ggatggggtc ccatttatta tttacaaatt cacatataca acaacgccgt ccccgtgcc    1380 cgcagttttt attaaacata gcgtgggatc tccacgcgaa tctcgggtac gtgttccgga   1440
catgggctct ctccggtag cggcggagct tccacatccg agccctggtc ccatgcctcc    1500
agcggctcat ggtcgctcgg cagctccttg ctcctaacag tggaggccag acttaggcac    1560
agcacaatgc ccaccaccac cagtgtgccg cacaaggccg tggcggtagg gtatgtgtct    1620
gaaaatgagc gtggagattg gctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tcctttccat gggtcttttc    1860
```

-continued

```
tgcagtcacc gtcgaattct ctagcactcg aagcttattg tcttcaatgt aaaagaaaag    1920
ctggtctaac aagatgacaa ctagaacaaa gggcaggggc catactgcgg ccacgactca    1980
aaacgacaga atgccaggcc ctgagctttc gggctggatc tctgagcagc taatgaccgg    2040
aagaattcct gtaagcgaca tcttctgtga tattgagaac aatccaggat tatgctacgc    2100
atcccaaatg caacaaacga agccaaaccc gaagacgcgc aacagtcaaa cccaaacgga    2160
cccaatttgc aatcatagtt ttgaggaggt agtacaaaca ttggcttcat tggctactgt    2220
tgtgcaacaa caaaccatcg catcagaatc attagaacaa cgcattacga gtcttgagaa    2280
tggtctaaag ccagtttatg atatggcaaa aacaatctcc tcattgaaca gggtttgtgc    2340
tgagatggtt gcaaaatatg atcttctggt gatgacaacc ggtcgggcaa cagcaaccgc    2400
tgcggcaact gaggcttatt gggccgaaca tggtcaacca ccacctggac catcacttta    2460
tgaagaaagt gcgattcggg gtaagattga atctagagat gagaccgtcc ctcaaagtgt    2520
tagggaggca ttcaacaatc taaacagtac cacttcacta actgaggaaa attttgggaa    2580
acctgacatt tcggcaaagg atttgagaaa cattatgtat gatcacttgc ctggttttgg    2640
aactgctttc caccaattag tacaagtgat ttgtaaattg ggaaaagata gcaactcatt    2700
ggacatcatt catgctgagt tccaggccag cctggctgaa ggagactctc tcaatgtgc     2760 cctaattcaa attacaaaaa gagttccaat cttccaagat gctgctccat ctgtcatcca    2820
catccgcttt cgaggtgaca ttccccgagc ttgccagaaa agcttgcgtc cagtcccacc    2880
atcgcccaag attgatcgag gttgggatgt gttttttcagc ttcaagatgg taaaacactt    2940
ggactcaaaa tttgagccaa tctcccttcc ctccgaaaga ggcgaataat agcagaggct    3000
tcaactgctg aactataggg tacgttacat taatgataca cttgtgagta tcagccctgg    3060
ataaataagg tcaattaaac gaccaagata aaattgttca tatctcgcta gcagcttaaa    3120
atataaatgt aataggagct atatctctga caggggatc cagatctgct gtgccttcta    3180
gttgccagcc atctgttgtt tgcccctccc ccgtgccttc cttgaccctg aaggtgcca    3240 ctcccactgt cctttcctaa taaaatgagg aaattgcatc gcattgtctg agtaggtgtc    3300
attctattct gggggtggg gtggggcagc acagcaaggg ggaggattgg gaagacaata    3360
gcaggcatgc tggggatgcg gtgggctcta tgggtaccca ggtgctgaag aattgacccg    3420
gttcctcctg ggccagaaag aagcaggcac atcccttct ctgtgacaca ccctgtccac    3480
gcccctggtt cttagttcca gccccactca taggacactc atagctcagg agggctccgc    3540
cttcaatccc acccgctaaa gtacttggag cggtctctcc ctccctcatc agcccaccaa    3600
accaaaccta gcctccaaga gtgggaagaa attaaagcaa gataggctat taagtgcaga    3660
gggagagaaa atgcctccaa catgtgagga agtaatgaga gaaatcatag aatttcttcc    3720
gcttcctcgc tcactgactc gctgcgctcg gtcgttcggc tgcggcgagc ggtatcagct    3780
cactcaaagg cggtaatacg gttatccaca gaatcagggg ataacgcagg aaagaacatg    3840
tgagcaaaag gccagcaaaa ggccaggaac cgtaaaaagg ccgcgttgct ggcgtttttc    3900
cataggctcc gcccccctga cgagcatcac aaaaatcgac gctcaagtca gaggtggcga    3960
aacccgacag gactataaag ataccaggcg tttccccctg gaagctccct cgtgcgctct    4020
cctgttccga ccctgccgct taccggatac ctgtccgcct ttctcccttc gggaagcgtg    4080
gcgctttctc aatgctcacg ctgtaggtat ctcagttcgg tgtaggtcgt tcgctccaag    4140
ctgggctgtg tgcacgaacc cccgttcag cccgaccgct gcgccttatc cggtaactat    4200
```

```
cgtcttgagt ccaacccggt aagacacgac ttatcgccac tggcagcagc cactggtaac    4260
aggattagca gagcgaggta tgtaggcggt gctacagagt tcttgaagtg gtggcctaac    4320
tacggctaca ctagaaggac agtatttggt atctgcgctc tgctgaagcc agttaccttc    4380
ggaaaaagag ttggtagctc ttgatccggc aaacaaacca ccgctggtag cggtggtttt    4440
tttgtttgca agcagcagat tacgcgcaga aaaaaaggat ctcaagaaga tcctttgatc    4500
ttttctacgg ggtctgacgc tcagtggaac gaaaactcac gttaagggat tttggtcatg    4560
agattatcaa aaaggatctt cacctagatc cttttaaatt aaaaatgaag ttttaaatca    4620
atctaaagta tatatgagta aacttggtct gacagttacc aatgcttaat cagtgaggca    4680
cctatctcag cgatctgtct atttcgttca tccatagttg cctgactccg gggggggggg    4740
gcgctgaggt ctgcctcgtg aagaaggtgt tgctgactca taccaggcct gaatcgcccc    4800
atcatccagc cagaaagtga gggagccacg gttgatgaga gctttgttgt aggtggacca    4860
gttggtgatt ttgaactttt gctttgccac ggaacggtct gcgttgtcgg aagatgcgt    4920 gatctgatcc ttcaactcag caaaagttcg atttattcaa caaagccgcc gtcccgtcaa    4980
gtcagcgtaa tgctctgcca gtgttacaac caattaacca attctgatta gaaaaactca    5040
tcgagcatca aatgaaactg caatttattc atatcaggat tatcaatacc atattttga    5100 aaaagccgtt tctgtaatga aggagaaaac tcaccgaggc agttccatag gatggcaaga    5160
tcctggtatc ggtctgcgat tccgactcgt ccaacatcaa taacctat taatttcccc    5220 tcgtcaaaaa taaggttatc aagtgagaaa tcaccatgag tgacgactga atccggtgag    5280
aatggcaaaa gcttatgcat ttctttccag acttgttcaa caggccagcc attacgctcg    5340
tcatcaaaat cactcgcatc aaccaaaccg ttattcattc gtgattgcgc ctgagcgaga    5400
cgaaatacgc gatcgctgtt aaaaggacaa ttacaaacag gaatcgaatg caaccggcgc    5460
aggaacactg ccagcgcatc aacaatattt tcacctgaat caggatattc ttctaatacc    5520
tggaatgctg ttttcccggg gatcgcagtg gtgagtaacc atgcatcatc aggagtacgg    5580
ataaaatgct tgatggtcgg aagaggcata aattccgtca gccagtttag tctgaccatc    5640
tcatctgtaa catcattggc aacgctacct ttgccatgtt tcagaaacaa ctctggcgca    5700
tcgggcttcc catacaatcg atagattgtc gcacctgatt gcccgacatt atcgcgagcc    5760
catttatacc catataaatc agcatccatg ttggaattta atcgcggcct cgagcaagac    5820
gtttcccgtt gaatatggct cataacaccc cttgtattac tgtttatgta agcagacagt    5880
tttattgttc atgatgatat atttttatct tgtgcaatgt aacatcagag attttgagac    5940
acaacgtggc tttccccccc ccccattat tgaagcattt atcagggtta ttgtctcatg    6000
agcggataca tatttgaatg tatttagaaa aataaacaaa taggggttcc gcgcacattt    6060
ccccgaaaag tgccacctga cgtctaagaa accattatta tcatgacatt aacctataaa    6120
aataggcgta tcacgaggcc ctttcgtc                                        6148

<210> SEQ ID NO 25
<211> LENGTH: 10783
<212> TYPE: DNA
<213> ORGANISM: Artificial Sequence
<220> FEATURE:
<223> OTHER INFORMATION: Synthetic Construct pAD/CMV-GP(dTM)(Z-CITE-S)

<400> SEQUENCE: 25
ttaattaacc gcaattctca tgtttgacag cttatcatca tcaataatat accttatttt      60
ggattgaagc caatatgata atgaggggt ggagtttgtg acgtggcgcg gggcgtggga     120
```

```
acggggcggg tgacgtagta gtgtggcgga agtgtgatgt tgcaagtgtg gcggaacaca      180
tgtaagcgac ggatgtggca aaagtgacgt ttttggtgtg cgccggtgta cacaggaagt      240
gacaattttc gcgcggtttt aggcggatgt tgtagtaaat ttgggcgtaa ccgagtaaga      300
tttggccatt ttcgcgggaa aactgaataa gaggaagtga aatctgaata attttgtgtt      360
actcatagcg cgtaatattt gtctagggcc gcggggactt tgaccgttta cgtggagact      420
cgcccaggtg ttttttctcag gtgttttccg cgttccgggt caaagttggc gttttattat      480
tatagtcagt acgtaccagt gcactggcct agagcggccc cattgcatac gttgtatcca      540
tatcataata tgtacattta tattggctca tgtccaacat taccgccatg ttgacattga      600
ttattgacta gttattaata gtaatcaatt acggggtcat tagttcatag cccatatatg      660
gagttccgcg ttacataact tacggtaaat ggcccgcctg gctgaccgcc caacgacccc      720
cgcccattga cgtcaataat gacgtatgtt cccatagtaa cgccaatagg gactttccat      780
tgacgtcaat gggtggagta tttacggtaa actgcccact tggcagtaca tcaagtgtat      840
catatgccaa gtacgccccc tattgacgtc aatgacggta atggcccgc ctggcattat       900
gcccagtaca tgaccttatg gactttcct acttggcagt acatctacgt attagtcatc       960
gctattacca tggtgatgcg gttttggcag tacatcaatg ggcgtggata gcggtttgac     1020
tcacggggat ttccaagtct ccaccccatt gacgtcaatg ggagtttgtt ttggcaccaa     1080
aatcaacggg actttccaaa atgtcgtaac aactccgccc cattgacgca aatgggcggt     1140
aggcgtgtac ggtgggaggt ctatataagc agagctcgtt tagtgaaccg tcagatcgcc     1200
tggagacgcc atccacgctg ttttgacctc catagaagac accgggaccg atccagcctc     1260
cgtcaccgtc gtcgacacgt gtgatcagat ctagaccagg ccctggatcg atccaacaac     1320
acaatgggcg ttacaggaat attgcagtta cctcgtgatc gattcaagag gacatcattc     1380
tttctttggg taattatcct tttccaaaga acattttcca tcccacttgg agtcatccac     1440
aatagcacat tacaggttag tgatgtcgac aaactagttt gtcgtgacaa actgtcatcc     1500
acaaatcaat tgagatcagt tggactgaat ctcgaaggga atggagtggc aactgacgtg     1560
ccatctgcaa ctaaaagatg gggcttcagg tccggtgtcc caccaaaggt ggtcaattat     1620
gaagctggtg aatgggctga aaactgctac aatcttgaaa tcaaaaaacc tgacgggagt     1680
gagtgtctac cagcagcgcc agacgggatt cggggcttcc cccggtgccg gtatgtgcac     1740
aaagtatcag gaacgggacc gtgtgccgga gactttgcct tccataaaga gggtgctttc     1800
ttcctgtatg atcgacttgc ttccacagtt atctaccgag gaacgacttt cgctgaaggt     1860
gtcgttgcat ttctgatact gccccaagct aagaaggact tcttcagctc cacccccttg     1920
agagagccgg tcaatgcaac ggaggacccg tctagtggct actattctac cacaattaga     1980
tatcaggcta ccggttttgg aaccaatgag acagagtact tgttcgaggt tgacaatttg     2040
acctacgtcc aacttgaatc aagattcaca ccacagtttc tgctccagct gaatgagaca     2100
atatatacaa gtgggaaaag gagcaatacc acgggaaaac taatttggaa ggtcaacccc     2160
gaaattgata caacaatcgg ggagtgggcc ttctgggaaa ctaaaaaaaa cctcactaga     2220
aaaattcgca gtgaagagtt gtcttttcaca gttgtatcaa acggagccaa aaacatcagt     2280
ggtcagagtc cggcgcgaac ttcttccgac ccagggacca acacaacaac tgaagaccac     2340
aaaatcatgg cttcagaaaa ttcctctgca atggttcaag tgcacagtca aggaagggaa     2400
gctgcagtgt cgcatctaac aacccttgcc acaatctcca cgagtcccca atccctcaca     2460
```

```
accaaaccag gtccggacaa cagcacccat aatacacccg tgtataaact tgacatctct  2520
gaggcaactc aagttgaaca acatcaccgc agaacagaca acgacagcac agcctccgac  2580
actccctctg ccacgaccgc agccggaccc ccaaaagcag agaacaccaa cacgagcaag  2640
agcactgact tcctggaccc cgccaccaca acaagtcccc aaaaccacag cgagaccgct  2700
ggcaacaaca acactcatca ccaagatacc ggagaagaga gtgccagcag cgggaagcta  2760
ggcttaatta ccaatactat tgctggagtc gcaggactga tcacaggcgg agaagaact  2820 cgaagagaag caattgtcaa tgctcaaccc aaatgcaacc ctaatttaca ttactggact  2880
actcaggatg aaggtgctgc aatcggactg gcctggatac catatttcgg gccagcagcc  2940
gagggaattt acatagaggg gctaatgcac aatcaagatg gtttaatctg tgggttgaga  3000
cagctggcca acgagacgac tcaagctctt caactgttcc tgagagccac aactgagcta  3060 cgcaccttt caatcctcaa ccgtaaggca attgatttct tgctgcagcg atggggcggc  3120
acatgccaca ttctgggacc ggactgctgt atcgaaccac atgattggac caagaacata  3180
acagacaaaa ttgatcagat tattcatgat tttgttgata aaacccttcc ggaccagggg  3240
gacaatgaca attggtggac aggatggaga caatggatgg ccgcatcgtg actgactgac  3300
gatctgcctc gcgagatcaa ttccgcccct ctccctcccc ccccctaac gttactggcc  3360 gaagccgctt ggaataaggc cggtgtgcgt ttgtctatat gttattttcc accatattgc  3420
cgtcttttgg caatgtgagg gcccggaaac ctggccctgt cttcttgacg agcattccta  3480
ggggtctttc ccctctcgcc aaaggaatgc aaggtctgtt gaatgtcgtg aaggaagcag  3540
ttcctctgga agcttcttga agacaaacaa cgtctgtagc gaccctttgc aggcagcgga  3600 acccccacc tggcgacagg tgcctctgcg gccaaaagcc acgtgtataa gatacacctg  3660
caaaggcggc acaaccccag tgccacgttg tgagttggat agttgtggaa agagtcaaat  3720
ggctctcctc aagcgtattc aacaagggc tgaaggatgc ccagaaggta ccccattgta  3780
tgggatctga tctggggcct cggtgcacat gctttacatg tgtttagtcg aggttaaaaa  3840
acgtctaggc cccccgaacc acggggacgt ggttttcctt tgaaaaacac gatgataata  3900
tggccacaac catggagggt cttagcctac tccaattgcc cagagataaa tttcgaaaaa  3960
gctctttctt tgtttgggtc atcatcttat ttcaaaaggc cttttccatg cctttgggtg  4020
ttgtgaccaa cagcactttta gaagtaacag agattgacca gctagtctgc aaggatcatc  4080
ttgcatccac tgaccagctg aaatcagttg gtctcaacct cgaggggagc ggagtatcta  4140
ctgatatccc atctgcgaca aagcgttggg gcttcagatc tggtgtgcct cccaaggtgg  4200
tcagctatga agcaggagaa tgggctgaaa attgctacaa tcttgaaata aagaagccgg  4260
acgggagcga atgcttaccc ccaccgccgg atggtgtcag aggctttcca aggtgccgct  4320
atgttcacaa agcccaagga accgggcct gcccgggtga ctatgccttt cacaaggatg  4380
gagctttctt cctctatgac aggctggctt caactgtaat ttacagagga gtcaattttg  4440 ctgaggggt aattgcattc ttgatattgg ctaaaccaaa ggaaacgttc cttcaatcac  4500
cccccattcg agaggcagta aactacactg aaaatacatc aagttactat gccacatcct  4560
acttggagta cgaaatcgaa attttggtg ctcaacactc cacgacccctt ttcaaaatta  4620 acaataatac ttttgttctt ctggacaggc cccacacgcc tcagttcctt ttccagctga  4680
atgataccat tcaccttcac caacagttga gcaacacaac tgggaaacta atttggacac  4740
tagatgctaa tatcaatgct gatattgtg aatgggcttt ttgggaaaat aaaaaaaatc  4800
tctccgaaca actacgtgga gaagagctgt cttttcgaaac tttatcgctc aacgagacag  4860
```

```
aagacgatga tgcgacatcg tcgagaacta caaagggaag aatctccgac cgggccacca    4920
ggaagtattc ggacctggtt ccaaaggatt cccctgggat ggtttcattg cacgtaccag    4980
aaggggaaac aacattgccg tctcagaatt cgacagaagg tcgaagagta gatgtgaata    5040
ctcaggaaac tatcacagag acaactgcaa caatcatagg cactaacggt aacaacatgc    5100
agatctccac catcgggaca ggactgagct ccagccaaat cctgagttcc tcaccgacca    5160
tggcaccaag ccctgagact cagacctcca aacctacac accaaaacta ccagtgatga     5220
ccaccgagga accaacaaca ccaccgagaa actctcctgg ctcaacaaca gaagcaccca    5280
ctctcaccac cccagagaat ataacaacag cggttaaaac tgttttgcca caagagtcca    5340
caagcaacgt tctaataact tcaacagtaa cagggattct tgggagcctt ggacttcgaa    5400
aacgcagcag aagacaagtt aacaccaggg ccacgggtaa atgcaatccc aacttacact    5460
actggactgc acaagaacaa cataatgctg ctgggattgc ctggatcccg tactttggac    5520
cgggtgcaga aggcatatac actgaaggcc ttatgcacaa ccaaaatgcc ttagtctgtg    5580
gactcagaca acttgcaaat gaaacaactc aagctctgca gcttttctta agggccacga    5640
cggagctgcg gacatatacc atactcaata ggaaggccat agatttcctt ctgcgacgat    5700
ggggcgggac atgtaggatc ctgggaccag attgttgcat tgagccacat gattggacca    5760
aaaacatcac tgataaaatc aaccaaatca tccatgattt catcgacaac cctttaccca    5820
atcaggataa tgatgataat tggtggacgg gctggagaca gtggatcccg gccgcatcgt    5880
gactgactga cgatctgcct cgcggatcca gatctgctgt gccttctagt tgccagccat    5940
ctgttgtttg cccctccccc gtgccttcct tgaccctgga aggtgccact cccactgtcc    6000
tttcctaata aaatgaggaa attgcatcgc attgtctgag taggtgtcat tctattctgg    6060
ggggtggggt ggggcagcac agcaaggggg aggattggga agacaatagc aggcatgctg    6120
gggatgcggt gggctctatg gtacccagg gccgcataac ttcgtataat gtatgctata     6180
cgaagttata agatctgtac tgaaatgtgt gggcgtggct taagggtggg aaagaatata    6240
taaggtgggg gtcttatgta gttttgtatc tgttttgcag cagccgccgc cgccatgagc    6300
accaactcgt ttgatggaag cattgtgagc tcatatttga caacgcgcat gccccatgg     6360
gccggggtgc gtcagaatgt gatgggctcc agcattgatg gtcgccccgt cctgcccgca    6420
aactctacta ccttgaccta cgagaccgtg tctggaacgc cgttggagac tgcagcctcc    6480
gccgccgctt cagccgctgc agccaccgcc cgcgggattg tgactgactt tgctttcctg    6540
agcccgcttg caagcagtgc agcttcccgt tcatccgccc gcgatgacaa gttgacggct    6600
cttttggcac aattggattc tttgacccgg gaacttaatg tcgtttctca gcagctgttg    6660
gatctgcgcc agcaggtttc tgccctgaag gcttcctccc ctcccaatgc ggtttaaaac    6720
ataaataaaa aaccagactc tgtttggatt tggatcaagc aagtgtcttg ctgtctttat    6780
ttaggggttt tgcgcgcgcg gtaggcccgg gaccagcggt ctcggtcgtt gagggtcctg    6840
tgtattttt ccaggacgtg gtaaaggtga ctctggatgt tcagatacat gggcataagc     6900
ccgtctctgg ggtggaggta gcaccactgc agagcttcat gctgcggggt ggtgttgtag    6960
atgatccagt cgtagcagga gcgctgggcg tggtgcctaa aaatgtcttt cagtagcaag    7020
ctgattgcca ggggcaggcc cttggtgtaa gtgtttacaa agcggttaag ctgggatggg    7080
tgcatacgtg gggatatgag atgcatcttg gactgtattt ttaggttggc tatgttccca    7140
gccatatccc tccggggatt catgttgtgc agaaccacca gcacagtgta tccggtgcac    7200
```

```
ttgggaaatt tgtcatgtag cttagaagga aatgcgtgga agaacttgga gacgcccttg   7260
tgacctccaa gattttccat gcattcgtcc ataatgatgg caatgggccc acgggcggcg   7320
gcctgggcga agatatttct gggatcacta acgtcatagt tgtgttccag gatgagatcg   7380
tcataggcca ttttttacaaa gcgcgggcgg agggtgccag actgcggtat aatggttcca   7440
tccggcccag gggcgtagtt accctcacag atttgcattt cccacgcttt gagttcagat   7500
gggggggatca tgtctacctg cggggcgatg aagaaaacgg tttccggggt aggggagatc   7560
agctgggaag aaagcaggtt cctgagcagc tgcgacttac cgcagccggt gggcccgtaa   7620
atcacaccta ttaccggctg caactggtag ttaagagagc tgcagctgcc gtcatccctg   7680
agcagggggg ccacttcgtt aagcatgtcc ctgactcgca tgttttccct gaccaaatcc   7740
gccagaaggc gctcgccgcc cagcgatagc agttcttgca aggaagcaaa gtttttcaac   7800
ggtttgagac cgtccgccgt aggcatgctt ttgagcgttt gaccaagcag ttccaggcgg   7860
tcccacagct cggtcacctg ctctacggca tctcgatcca gcatatctcc tcgtttcgcg   7920
ggttggggcg gctttcgctg tacggcagta gtcggtgctc gtccagacgg ccagggtca    7980
tgtctttcca cgggcgcagg gtcctcgtca gcgtagtctg ggtcacggtg aaggggtgcg   8040
ctccgggctg cgcgctggcc agggtgcgct tgaggctggt cctgctggtg ctgaagcgct   8100
gccggtcttc gccctgcgcg tcggccaggt agcatttgac catggtgtca tagtccagcc   8160
cctccgcggc gtggcccttg gcgcgcagct tgcccttgga ggaggcgccg cacgaggggc   8220
agtgcagact tttgagggcg tagagcttgg gcgcgagaaa taccgattcc ggggagtagg   8280
catccgcgcc gcaggccccg cagacggtct cgcattccac gagccaggtg agctctggcc   8340
gttcggggtc aaaaaccagg tttcccccat gcttttttgat gcgtttctta cctctggttt   8400
ccatgagccg gtgtccacgc tcggtgacga aaaggctgtc cgtgtccccg tatacagact   8460
tgagaggcct gtcctcgagc ggtgttccgc ggtcctcctc gtatagaaac tcggaccact   8520
ctgagacaaa ggctcgcgtc caggccagca cgaaggaggc taagtgggag gggtagcggt   8580
cgttgtccac taggggggtcc actcgctcca gggtgtgaag acacatgtcg ccctcttcgg   8640
catcaaggaa ggtgattggt ttgtaggtgt aggccacgtg accgggtgtt cctgaagggg   8700
ggctataaaa gggggtgggg gcgcgttcgt cctcactctc ttccgcatcg ctgtctgcga   8760
gggccagctg ttggggtgag tcgacgcgag gctggatggc cttccccatt atgattcttc   8820
tcgcttccgg cggcatcggg atgcccgcgt tgcaggccat gctgtccagg caggtagatg   8880
acgaccatca gggacagctt caaggccagc aaaaggccag gaaccgtaaa aaggccgcgt   8940
tgctggcgtt tttccatagg ctccgccccc ctgacgagca tcacaaaaat cgacgctcaa   9000
gtcagaggtg gcgaaacccg acaggactat aaagatacca ggcgtttccc cctggaagct   9060
ccctcgtgcg ctctcctgtt ccgaccctgc cgcttaccgg atacctgtcc gcctttctcc   9120
cttcgggaag cgtggcgctt tctcatagct cacgctgtag gtatctcagt tcggtgtagg   9180
tcgttcgctc caagctgggc tgtgtgcacg aaccccccgt tcagcccgac cgctgcgcct   9240
tatccggtaa ctatcgtctt gagtccaacc cggtaagaca cgacttatcg ccactggcag   9300
cagccactgg taacaggatt agcagagcga ggtatgtagg cggtgctaca gagttcttga   9360
agtggtggcc taactacggc tacactagaa ggacagtatt tggtatctgc gctctgctga   9420
agccagttac cttcggaaaa agagttggta gctcttgatc cggcaaacaa accaccgctg   9480
gtagcggtgg tttttttgtt tgcaagcagc agattacgcg cagaaaaaaa ggatctcaag   9540
aagatccttt gatcttttct acggggtctg acgctcagtg gaacgaaaac tcacgttaag   9600
```

-continued

```
ggattttggt catgagatta tcaaaaagga tcttcaccta gatccttta aattaaaaat    9660 gaagttttaa atcaatctaa agtatatatg agtaaacttg gtctgacagt taccaatgct    9720
taatcagtga ggcacctatc tcagcgatct gtctatttcg ttcatccata gttgcctgac    9780
tccccgtcgt gtagataact acgatacggg agggcttacc atctggcccc agtgctgcaa    9840
tgataccgcg agacccacgc tcaccggctc cagatttatc agcaataaac cagccagccg    9900
gaagggccga gcgcagaagt ggtcctgcaa ctttatccgc ctccatccag tctattaatt    9960
gttgccggga agctagagta agtagttcgc cagttaatag tttgcgcaac gttgttgcca    10020
ttgctgcagg catcgtggtg tcacgctcgt cgtttggtat ggcttcattc agctccggtt    10080
cccaacgatc aaggcgagtt acatgatccc ccatgttgtg caaaaaagcg gttagctcct    10140
tcggtcctcc gatcgttgtc agaagtaagt tggccgcagt gttatcactc atggttatgg    10200
cagcactgca taattctctt actgtcatgc catccgtaag atgcttttct gtgactggtg    10260
agtactcaac caagtcattc tgagaatagt gtatgcggcg accgagttgc tcttgcccgg    10320
cgtcaacacg ggataatacc gcgccacata gcagaacttt aaaagtgctc atcattggaa    10380
aacgttcttc ggggcgaaaa ctctcaagga tcttaccgct gttgagatcc agttcgatgt    10440
aacccactcg tgcacccaac tgatcttcag catcttttac tttcaccagc gtttctgggt    10500
gagcaaaaac aggaaggcaa aatgccgcaa aaaagggaat aagggcgaca cggaaatgtt    10560
gaatactcat actcttcctt tttcaatatt attgaagcat ttatcagggt tattgtctca    10620
tgagcggata catatttgaa tgtatttaga aaaataaaca ataggggtt ccgcgcacat    10680 ttccccgaaa agtgccacct gacgtctaag aaaccattat tatcatgaca ttaacctata    10740
aaaataggcg tatcacgagg cccttcgtc ttcaagaatt gtt                       10783
```

<210> SEQ ID NO 26
<211> LENGTH: 8338
<212> TYPE: DNA
<213> ORGANISM: Artificial Sequence
<220> FEATURE:
<223> OTHER INFORMATION: Synthetic Construct pAdApt Ebola GP(S)

<400> SEQUENCE: 26

```
ttaattaacc gcaattctca tgtttgacag cttatcatca tcaataatat accttatttt      60
ggattgaagc caatatgata atgaggggt ggagtttgtg acgtggcgcg gggcgtggga     120
acggggcggg tgacgtagta gtgtggcgga agtgtgatgt tgcaagtgtg gcggaacaca     180
tgtaagcgac ggatgtggca aaagtgacgt ttttggtgtg cgccggtgta cacaggaagt     240
gacaattttc gcgcggtttt aggcggatgt tgtagtaaat ttgggcgtaa ccgagtaaga     300
tttggccatt ttcgcgggaa aactgaataa gaggaagtga atctgaata attttgtgtt     360 actcatagcg cgtaatattt gtctagggcc gcggggactt tgaccgttta cgtggagact     420
cgcccaggtg ttttttctcag gtgttttccg cgttccgggt caaagttggc gttttattat     480
tatagtcagt acgtaccagt gcactggcct agagcggccc cattgcatac gttgtatcca     540
tatcataata tgtacatta tattggctca tgtccaacat taccgccatg ttgacattga     600
ttattgacta gttattaata gtaatcaatt acggggtcat tagttcatag cccatatatg     660
gagttccgcg ttacataact tacggtaaat ggcccgcctg gctgaccgcc caacgacccc     720
cgcccattga cgtcaataat gacgtatgtt cccatagtaa cgccaatagg gactttccat     780
tgacgtcaat gggtggagta tttacggtaa actgcccact tggcagtaca tcaagtgtat     840
```

```
catatgccaa gtacgccccc tattgacgtc aatgacggta aatggcccgc ctggcattat    900
gcccagtaca tgaccttatg ggactttcct acttggcagt acatctacgt attagtcatc    960
gctattacca tggtgatgcg gttttggcag tacatcaatg ggcgtggata gcggtttgac   1020
tcacggggat ttccaagtct ccaccccatt gacgtcaatg ggagtttgtt ttggcaccaa   1080
aatcaacggg actttccaaa atgtcgtaac aactccgccc cattgacgca aatgggcggt   1140
aggcgtgtac ggtgggaggt ctatataagc agagctcgtt tagtgaaccg tcagatcgcc   1200
tggagacgcc atccacgctg ttttgacctc catagaagac accgggaccg atccagcctc   1260
cgtcaccgtc gtcgacacgt gtgatcagat atcgcggccg ccagtgtgat ggatatctgc   1320
agaattcggc ttatcttcag gatctcgcca tggagggtct tagcctactc caattgccca   1380
gagataaatt tcgaaaaagc tctttctttg tttgggtcat catcttattt caaaggcct    1440
tttccatgcc tttgggtgtt gtgaccaaca gcactttaga agtaacagag attgaccagc   1500
tagtctgcaa ggatcatctt gcatccactg accagctgaa atcagttggt ctcaacctcg   1560
aggggagcgg agtatctact gatatcccat ctgcgacaaa gcgttgggc ttcagatctg    1620
gtgtgcctcc caaggtggtc agctatgaag caggagaatg ggctgaaaat tgctacaatc   1680
ttgaaataaa gaagccggac gggagcgaat gcttaccccc accgccggat ggtgtcagag   1740
gctttccaag gtgccgctat gttcacaaag cccaaggaac cgggccctgc ccgggtgact   1800
atgcctttca caaggatgga gctttcttcc tctatgacag gctggcttca actgtaattt   1860
acagaggagt caattttgct gagggggtaa ttgcattctt gatattggct aaaccaaagg   1920
aaacgttcct tcaatcaccc cccattcgag aggcagtaaa ctacactgaa aatacatcaa   1980
gttactatgc cacatcctac ttggagtacg aaatcgaaaa ttttggtgct caacactcca   2040
cgaccctttt caaaattaac aataatactt ttgttcttct ggacaggccc cacacgcctc   2100
agttcctttt ccagctgaat gataccattc accttcacca acagttgagc aacacaactg   2160
ggaaactaat ttggacacta gatgctaata tcaatgctga tattggtgaa tgggcttttt   2220
gggaaaataa aaaaaatctc tccgaacaac tacgtggaga agagctgtct ttcgaaactt   2280
tatcgctcaa cgagacagaa gacgatgatg cgacatcgtc gagaactaca aagggaagaa   2340
tctccgaccg ggccaccagg aagtattcgg acctggttcc aaaggattcc cctgggatgg   2400
tttcattgca cgtaccagaa ggggaaacaa cattgccgtc tcagaattcg acagaaggtc   2460
gaagagtaga tgtgaatact caggaaacta tcacagagac aactgcaaca atcataggca   2520
ctaacggtaa caacatgcag atctccacca tcgggacagg actgagctcc agccaaatcc   2580
tgagttcctc accgaccatg gcaccaagcc ctgagactca gacctccaca acctacacac   2640
caaaactacc agtgatgacc accgaggaac caacaacacc accgagaaac tctcctggct   2700
caacaacaga agcacccact ctcaccaccc cagagaatat aacaacagcg gttaaaactg   2760
ttttgccaca agagtccaca agcaacggtc taataacttc aacagtaaca gggattcttg   2820
ggagccttgg acttcgaaaa cgcagcagaa gacaagttaa caccagggcc acgggtaaat   2880
gcaatcccaa cttacactac tggactgcac aagaacaaca taatgctgct gggattgcct   2940
ggatcccgta cttttggacc ggtgcagaag gcatatacac tgaaggcctt atgcacaacc   3000
aaaatgcctt agtctgtgga ctcagacaac ttgcaaatga acaactcaa gctctgcagc    3060
ttttcttaag ggccacgacg gagctgcgga catataccat actcaatagg aaggccatag   3120
atttccttct gcgacgatgg ggcgggacat gtaggatcct gggaccagat tgttgcattg   3180
agccacatga ttggaccaaa aacatcactg ataaaatcaa ccaaatcatc catgatttca   3240
```

```
tcgacaaccc tttacccaat caggataatg atgataattg gtggacgggc tggagacagt    3300
ggatccctgc aggaataggc attactggaa ttattattgc aatcattgct cttctttgcg    3360
tctgcaagct gctttgttga atatcaagcc gaattccagc acactggcgg ccgttactag    3420
tggatccgag ctcggatcca agctctagac caggccctgg atccagatct gctgtgcctt    3480
ctagttgcca gccatctgtt gtttgcccct ccccgtgcc ttccttgacc ctggaaggtg      3540
ccactcccac tgtcctttcc taataaaatg aggaaattgc atcgcattgt ctgagtaggt    3600
gtcattctat tctgggggt ggggtggggc aggacagcaa gggggaggat tgggaagaca      3660
atagcaggca tgctggggat gcggtgggct ctatgggtac ccagggccgc ataacttcgt    3720
ataatgtatg ctatacgaag ttataagatc tgtactgaaa tgtgtgggcg tggcttaagg    3780
gtgggaaaga atatataagg tgggggtctt atgtagtttt gtatctgttt tgcagcagcc    3840
gccgccgcca tgagcaccaa ctcgtttgat ggaagcattg tgagctcata tttgacaacg    3900
cgcatgcccc catgggccgg ggtgcgtcag aatgtgatgg gctccagcat tgatggtcgc    3960
cccgtcctgc ccgcaaactc tactaccttg acctacgaga ccgtgtctgg aacgccgttg    4020
gagactgcag cctccgccgc cgcttcagcc gctgcagcca ccgcccgcgg gattgtgact    4080
gactttgctt tcctgagccc gcttgcaagc agtgcagctt cccgttcatc cgcccgcgat    4140
gacaagttga cggctctttt ggcacaattg gattctttga cccgggaact taatgtcgtt    4200
tctcagcagc tgttggatct cgccagcag gtttctgccc tgaaggcttc ctcccctccc      4260
aatgcggttt aaaacataaa taaaaaacca gactctgttt ggatttggat caagcaagtg    4320
tcttgctgtc tttatttagg ggttttgcgc gcgcggtagg cccgggacca gcggtctcgg    4380
tcgttgaggg tcctgtgtat tttttccagg acgtggtaaa ggtgactctg gatgttcaga    4440
tacatgggca taagcccgtc tctggggtgg aggtagcacc actgcagagc ttcatgctgc    4500
ggggtggtgt tgtagatgat ccagtcgtag caggagcgct gggcgtggtg cctaaaaatg    4560
tctttcagta gcaagctgat tgccaggggc aggcccttgg tgtaagtgtt tacaaagcgg    4620
ttaagctggg atgggtgcat acgtggggat atgagatgca tcttggactg tattttttagg   4680
ttggctatgt tcccagccat atccctccgg ggattcatgt tgtgcagaac caccagcaca    4740
gtgtatccgg tgcacttggg aaatttgtca tgtagcttag aaggaaatgc gtggaagaac    4800
ttggagacgc ccttgtgacc tccaagattt tccatgcatt cgtccataat gatggcaatg    4860
ggcccacggg cggcggcctg ggcgaagata tttctgggat cactaacgtc atagttgtgt    4920
tccaggatga gatcgtcata ggccattttt acaaagcgcg ggcggagggt gccagactgc    4980
ggtataatgt ttccatccgg cccaggggcg tagttaccct cacagatttg catttcccac    5040
gctttgagtt cagatggggg gatcatgtct acctgcgggg cgatgaagaa aacggtttcc    5100
ggggtagggg agatcagctg gaagaaagc aggttcctga gcagctgcga cttaccgcag     5160
ccggtgggcc cgtaaatcac acctattacc ggctgcaact ggtagttaag agagctgcag    5220
ctgccgtcat ccctgagcag gggggccact tcgttaagca tgtccctgac tcgcatgttt    5280
tccctgacca aatccgccag aaggcgctcg ccgcccagcg atagcagttc ttgcaaggaa    5340
gcaaagtttt tcaacggttt gagaccgtcc gccgtaggca tgcttttgag cgtttgacca    5400
agcagttcca ggcggtccca cagctcggtc acctgctcta cggcatctcg atccagcata    5460
tctcctcgtt tcgcggggttg gggcggcttt cgctgtacgg cagtagtcgg tgctcgtcca    5520
gacgggccag ggtcatgtct ttccacgggc gcagggtcct cgtcagcgta gtctgggtca    5580
```

```
cggtgaaggg gtgcgctccg ggctgcgcgc tggccagggt gcgcttgagg ctggtcctgc    5640
tggtgctgaa gcgctgccgg tcttcgccct gcgcgtcggc caggtagcat ttgaccatgg    5700
tgtcatagtc cagcccctcc gcggcgtggc ccttggcgcg cagcttgccc ttggaggagg    5760
cgccgcacga ggggcagtgc agacttttga gggcgtagag cttgggcgcg agaaataccg    5820
attccgggga gtaggcatcc gcgccgcagg ccccgcagac ggtctcgcat tccacgagcc    5880
aggtgagctc tggccgttcg gggtcaaaaa ccaggtttcc cccatgcttt ttgatgcgtt    5940
tcttacctct ggtttccatg agccggtgtc cacgctcggt gacgaaaagg ctgtccgtgt    6000
ccccgtatac agacttgaga ggcctgtcct cgagcggtgt tccgcggtcc tcctcgtata    6060
gaaactcgga ccactctgag acaaaggctc gcgtccaggc cagcacgaag gaggctaagt    6120
gggaggggta gcggtcgttg tccactaggg ggtccactcg ctccagggtg tgaagacaca    6180
tgtcgccctc ttcggcatca aggaaggtga ttggtttgta ggtgtaggcc acgtgaccgg    6240
gtgttcctga aggggggcta taaaaggggg tgggggcgcg ttcgtcctca ctctcttccg    6300
catcgctgtc tgcgagggcc agctgttggg gtgagtcgac gcgaggctgg atggccttcc    6360
ccattatgat tcttctcgct tccgcgggca tcgggatgcc cgcgttgcag gccatgctgt    6420
ccaggcaggt agatgacgac catcagggac agcttcaagg ccagcaaaag gccaggaacc    6480
gtaaaaaggc cgcgttgctg gcgttttttcc ataggctccg ccccccctgac gagcatcaca    6540 aaaatcgacg ctcaagtcag aggtggcgaa acccgacagg actataaaga taccaggcgt    6600
ttccccctgg aagctccctc gtgcgctctc ctgttccgac cctgccgctt accggatacc    6660
tgtccgcctt tctcccttcg ggaagcgtgg cgctttctca tagctcacgc tgtaggtatc    6720
tcagttcggt gtaggtcgtt cgctccaagc tgggctgtgt gcacgaaccc cccgttcagc    6780
ccgaccgctg cgccttatcc ggtaactatc gtcttgagtc aacccggta agacacgact    6840 tatcgccact ggcagcagcc actggtaaca ggattagcag agcgaggtat gtaggcggtg    6900
ctacagagtt cttgaagtgg tggcctaact acggctacac tagaaggaca gtatttggta    6960
tctgcgctct gctgaagcca gttaccttcg gaaaaagagt tggtagctct tgatccggca    7020
aacaaaccac cgctggtagc ggtggttttt tgtttgcaa gcagcagatt acgcgcagaa    7080
aaaaaggatc tcaagaagat cctttgatct tttctacggg gtctgacgct cagtggaacg    7140
aaaactcacg ttaagggatt ttggtcatga gattatcaaa aaggatcttc acctagatcc    7200
ttttaaatta aaaatgaagt tttaaatcaa tctaaagtat atatgagtaa acttggtctg    7260
acagttacca atgcttaatc agtgaggcac ctatctcagc gatctgtcta tttcgttcat    7320
ccatagttgc ctgactcccc gtcgtgtaga taactacgat acgggagggc ttaccatctg    7380
gccccagtgc tgcaatgata ccgcgagacc cacgctcacc ggctccagat ttatcagcaa    7440
taaaccagcc agccggaagg gccgagcgca gaagtggtcc tgcaacttta tccgcctcca    7500
tccagtctat taattgttgc cgggaagcta gagtaagtag ttcgccagtt aatagtttgc    7560
gcaacgttgt tgccattgct gcaggcatcg tggtgtcacg ctcgtcgttt ggtatggctt    7620
cattcagctc cggttcccaa cgatcaaggc gagttacatg atcccccatg ttgtgcaaaa    7680
aagcggttag ctccttcggt cctccgatcg ttgtcagaag taagttggcc gcagtgttat    7740
cactcatggt tatggcagca ctgcataatt ctcttactgt catgccatcc gtaagatgct    7800
tttctgtgac tggtgagtac tcaaccaagt cattctgaga atagtgtatg cggcgaccga    7860
gttgctcttg cccggcgtca acacgggata ataccgcgcc acatagcaga actttaaaag    7920
tgctcatcat tggaaaacgt tcttcggggc gaaaactctc aaggatctta ccgctgttga    7980
```

| | |
|---|---|
| gatccagttc gatgtaaccc actcgtgcac ccaactgatc ttcagcatct tttactttca | 8040 |
| ccagcgtttc tgggtgagca aaaacaggaa ggcaaaatgc cgcaaaaaag ggaataaggg | 8100 |
| cgacacggaa atgttgaata ctcatactct tccttttca atattattga agcatttatc | 8160 |
| agggttattg tctcatgagc ggatacatat ttgaatgtat ttagaaaaat aaacaaatag | 8220 |
| gggttccgcg cacatttccc cgaaaagtgc cacctgacgt ctaagaaacc attattatca | 8280 |
| tgacattaac ctataaaaat aggcgtatca cgaggccctt tcgtcttcaa gaattgtt | 8338 |

<210> SEQ ID NO 27
<211> LENGTH: 8221
<212> TYPE: DNA
<213> ORGANISM: Artificial Sequence
<220> FEATURE:
<223> OTHER INFORMATION: Synthetic Construct pAdApt Ebola GP(S)(dTM)

<400> SEQUENCE: 27

| | |
|---|---|
| ttaattaacc gcaattctca tgtttgacag cttatcatca tcaataatat accttatttt | 60 |
| ggattgaagc caatatgata atgaggggt ggagtttgtg acgtggcgcg gggcgtggga | 120 |
| acggggcggg tgacgtagta gtgtggcgga agtgtgatgt tgcaagtgtg gcggaacaca | 180 |
| tgtaagcgac ggatgtggca aaagtgacgt ttttggtgtg cgccggtgta cacaggaagt | 240 |
| gacaattttc gcgcggtttt aggcggatgt tgtagtaaat ttgggcgtaa ccgagtaaga | 300 |
| tttggccatt ttcgcgggaa aactgaataa gaggaagtga atctgaata attttgtgtt | 360 |
| actcatagcg cgtaatattt gtctagggcc gcggggactt tgaccgttta cgtggagact | 420 |
| cgcccaggtg ttttctcag gtgttttccg cgttccgggt caaagttggc gttttattat | 480 |
| tatagtcagt acgtaccagt gcactggcct agagcggccc cattgcatac gttgtatcca | 540 |
| tatcataata tgtacattta tattggctca tgtccaacat taccgccatg ttgacattga | 600 |
| ttattgacta gttattaata gtaatcaatt acggggtcat tagttcatag cccatatatg | 660 |
| gagttccgcg ttacataact tacggtaaat ggcccgcctg gctgaccgcc caacgacccc | 720 |
| cgcccattga cgtcaataat gacgtatgtt cccatagtaa cgccaatagg gactttccat | 780 |
| tgacgtcaat gggtggagta tttacggtaa actgcccact tggcagtaca tcaagtgtat | 840 |
| catatgccaa gtacgccccc tattgacgtc aatgacggta aatggcccgc ctggcattat | 900 |
| gcccagtaca tgaccttatg ggactttcct acttggcagt acatctacgt attagtcatc | 960 |
| gctattacca tggtgatgcg gttttggcag tacatcaatg ggcgtggata gcggtttgac | 1020 |
| tcacggggat ttccaagtct ccaccccatt gacgtcaatg ggagtttgtt ttggcaccaa | 1080 |
| aatcaacggg actttccaaa atgtcgtaac aactccgccc cattgacgca atgggcggt | 1140 |
| aggcgtgtac ggtgggaggt ctatataagc agagctcgtt tagtgaaccg tcagatcgcc | 1200 |
| tggagacgcc atccacgctg ttttgacctc catagaagac accgggaccg atccagcctc | 1260 |
| cgtcaccgtc gtcgacacgt gtgatcagat atcgcggccg ccagtgtgat ggatatctgc | 1320 |
| agaattcggc ttatcttcag gatctcgcca tggagggtct tagcctactc caattgccca | 1380 |
| gagataaatt tcgaaaaagc tctttctttg tttgggtcat catcttattt caaaaggcct | 1440 |
| tttccatgcc tttgggtgtt gtgaccaaca gcactttaga agtaacagag attgaccagc | 1500 |
| tagtctgcaa ggatcatctt gcatccactg accagctgaa atcagttggt ctcaacctcg | 1560 |
| aggggagcgg agtatctact gatatcccat ctgcgacaaa gcgttgggc ttcagatctg | 1620 |
| gtgtgcctcc caaggtggtc agctatgaag caggagaatg ggctgaaaat tgctacaatc | 1680 |

```
ttgaaataaa gaagccggac gggagcgaat gcttaccccc accgccggat ggtgtcagag    1740
gctttccaag gtgccgctat gttcacaaag cccaaggaac cgggccctgc ccgggtgact    1800
atgcctttca caaggatgga gctttcttcc tctatgacag gctggcttca actgtaattt    1860
acagaggagt caattttgct gagggggtaa ttgcattctt gatattggct aaaccaaagg    1920
aaacgttcct tcaatcaccc cccattcgag aggcagtaaa ctacactgaa aatacatcaa    1980
gttactatgc cacatcctac ttggagtacg aaatcgaaaa ttttggtgct caacactcca    2040 cgacccttt  caaaattaac aataatactt ttgttcttct ggacaggccc cacacgcctc    2100
agttcctttt ccagctgaat gataccattc accttcacca acagttgagc aacacaactg    2160
ggaaactaat ttggacacta gatgctaata tcaatgctga tattggtgaa tgggcttttt    2220
gggaaaataa aaaaaatctc tccgaacaac tacgtggaga agagctgtct ttcgaaactt    2280
tatcgctcaa cgagacagaa gacgatgatg cgacatcgtc gagaactaca aagggaagaa    2340
tctccgaccg ggccaccagg aagtattcgg acctggttcc aaaggattcc cctgggatgg    2400
tttcattgca cgtaccagaa ggggaaacaa cattgccgtc tcagaattcg acagaaggtc    2460
gaagagtaga tgtgaatact caggaaacta tcacagagac aactgcaaca atcataggca    2520
ctaacggtaa caacatgcag atctccacca tcgggacagg actgagctcc agccaaatcc    2580
tgagttcctc accgaccatg gcaccaagcc ctgagactca gacctccaca acctacacac    2640
caaaactacc agtgatgacc accgaggaac caacaacacc accgagaaac tctcctggct    2700
caacaacaga agcacccact ctcaccaccc cagagaatat aacaacagcg gttaaaactg    2760
ttttgccaca agagtccaca agcaacggtc taataacttc aacagtaaca gggattcttg    2820
ggagccttgg acttcgaaaa cgcagcagaa gacaagttaa caccagggcc acgggtaaat    2880
gcaatcccaa cttacactac tggactgcac aagaacaaca taatgctgct gggattgcct    2940
ggatcccgta ctttggaccg ggtgcagaag gcatatacac tgaaggcctt atgcacaacc    3000
aaaatgcctt agtctgtgga ctcagacaac ttgcaaatga acaactcaa  gctctgcagc    3060 ttttcttaag ggccacgacg gagctgcgga catataccat actcaatagg aaggccatag    3120
atttccttct gcgacgatgg ggcgggacat gtaggatcct gggaccagat tgttgcattg    3180
agccacatga ttggaccaaa aacatcactg ataaaatcaa ccaaatcatc catgatttca    3240
tcgacaaccc tttacccaat caggataatg atgataattg gtggacgggc tggagacagt    3300
ggatcccggc cgcatcgtga ctgactacg  atctgcctcg cggatccaga tctgctgtgc    3360
cttctagttg ccagccatct gttgtttgcc cctcccccgt gccttccttg accctggaag    3420
gtgccactcc cactgtcctt tcctaataaa atgaggaaat tgcatcgcat tgtctgagta    3480
ggtgtcattc tattctgggg ggtggggtgg ggcaggacag caaggggag  gattgggaag    3540 acaatagcag gcatgctggg gatgcggtgg gctctatggg tacccagggc cgcataactt    3600
cgtataatgt atgctatacg aagttataag atctgtactg aaatgtgtgg gcgtggctta    3660
agggtgggaa agaatatata aggtgggggt cttatgtagt tttgtatctg ttttgcagca    3720
gccgccgccg ccatgagcac caactcgttt gatggaagca ttgtgagctc atatttgaca    3780
acgcgcatgc ccccatgggc cggggtgcgt cagaatgtga tgggctccag cattgatggt    3840
cgccccgtcc tgcccgcaaa ctctactacc ttgacctacg agaccgtgtc tggaacgccg    3900
ttggagactg cagcctccgc cgccgcttca gccgctgcag ccaccgcccg cgggattgtg    3960
actgactttg ctttcctgag cccgcttgca agcagtgcag cttcccgttc atccgcccgc    4020
gatgacaagt tgacggctct ttttggcacaa ttggattctt tgacccggga acttaatgtc    4080
```

```
gtttctcagc agctgttgga tctgcgccag caggtttctg ccctgaaggc ttcctcccct    4140
cccaatgcgg tttaaaacat aaataaaaaa ccagactctg tttggatttg gatcaagcaa    4200
gtgtcttgct gtctttattt aggggttttg cgcgcgcggt aggcccggga ccagcggtct    4260
cggtcgttga gggtcctgtg tattttttcc aggacgtggt aaaggtgact ctggatgttc    4320
agatacatgg gcataagccc gtctctgggg tggaggtagc accactgcag agcttcatgc    4380
tgcggggtgg tgttgtagat gatccagtcg tagcaggagc gctgggcgtg gtgcctaaaa    4440
atgtctttca gtagcaagct gattgccagg ggcaggccct tggtgtaagt gtttacaaag    4500
cggttaagct gggatgggtg catacgtggg gatatgagat gcatcttgga ctgtattttt    4560
aggttggcta tgttcccagc catatccctc cggggattca tgttgtgcag aaccaccagc    4620
acagtgtatc cggtgcactt gggaaatttg tcatgtagct tagaaggaaa tgcgtggaag    4680
aacttggaga cgcccttgtg acctccaaga ttttccatgc attcgtccat aatgatggca    4740
atgggcccac gggcggcggc ctgggcgaag atatttctgg gatcactaac gtcatagttg    4800
tgttccagga tgagatcgtc ataggccatt tttacaaagc gcgggcggag ggtgccagac    4860
tgcggtataa tggttccatc cggcccaggg gcgtagttac cctcacagat ttgcatttcc    4920
cacgctttga gttcagatgg ggggatcatg tctacctgcg gggcgatgaa gaaaacggtt    4980
tccggggtag gggagatcag ctgggaagaa agcaggttcc tgagcagctg cgacttaccg    5040
cagccggtgg gcccgtaaat cacacctatt accggctgca actggtagtt aagagagctg    5100
cagctgccgt catccctgag caggggggcc acttcgttaa gcatgtccct gactcgcatg    5160
ttttccctga ccaaatccgc cagaaggcgc tcgccgccca gcgatagcag ttcttgcaag    5220
gaagcaaagt ttttcaacgg tttgagaccg tccgccgtag gcatgctttt gagcgtttga    5280
ccaagcagtt ccaggcggtc ccacagctcg gtcacctgct ctacggcatc tcgatccagc    5340
atatctcctc gtttcgcggg ttggggcggc tttcgctgta cggcagtagt cggtgctcgt    5400
ccagacgggc cagggtcatg tctttccacg ggcgcagggt cctcgtcagc gtagtctggg    5460
tcacggtgaa ggggtcgcgt ccgggctgcg cgctggccag ggtgcgcttg aggctggtcc    5520
tgctggtgct gaagcgctgc cggtcttcgc cctgcgcgtc ggccaggtag catttgacca    5580
tggtgtcata gtccagcccc tccgcggcgt ggcccttggc gcgcagcttg cccttggagg    5640
aggcgccgca cgaggggcag tgcagacttt tgagggcgta gagcttgggc gcgagaaata    5700
ccgattccgg ggagtaggca tccgcgccgc aggccccgca gacggtctcg cattccacga    5760
gccaggtgag ctctggccgt tcggggtcaa aaaccaggtt tcccccatgc tttttgatgc    5820
gtttcttacc tctggtttcc atgagccggt gtccacgctc ggtgacgaaa aggctgtccg    5880
tgtccccgta tacagacttg agaggcctgt cctcgagcgg tgttccgcgg tcctcctcgt    5940
atagaaactc ggaccactct gagacaaagg ctcgcgtcca ggccagcacg aaggaggcta    6000
agtgggaggg gtagcggtcg ttgtccacta gggggtccac tcgctccagg gtgtgaagac    6060
acatgtcgcc ctcttcggca tcaaggaagg tgattggttt gtaggtgtag gcacgtgac    6120
cgggtgttcc tgaaggggg ctataaaagg gggtggggc gcgttcgtcc tcactctctt    6180
ccgcatcgct gtctgcgagg ccagctgtt gggtgagtc gacgcgaggc tggatggcct    6240
tccccattat gattcttctc gcttccggcg gcatcgggat gcccgcgttg caggccatgc    6300
tgtccaggca ggtagatgac gaccatcagg gacagcttca aggccagcaa aaggccagga    6360
accgtaaaaa ggccgcgttg ctggcgtttt tccataggct ccgcccccct gacgagcatc    6420
```

```
acaaaaatcg acgctcaagt cagaggtggc gaaacccgac aggactataa agataccagg    6480
cgtttccccc tggaagctcc ctcgtgcgct ctcctgttcc gaccctgccg cttaccggat    6540
acctgtccgc ctttctccct tcgggaagcg tggcgctttc tcatagctca cgctgtaggt    6600
atctcagttc ggtgtaggtc gttcgctcca agctgggctg tgtgcacgaa ccccccgttc    6660
agcccgaccg ctgcgcctta tccggtaact atcgtcttga gtccaacccg gtaagcacg    6720 acttatcgcc actggcagca gccactggta acaggattag cagagcgagg tatgtaggcg    6780
gtgctacaga gttcttgaag tggtggccta actacggcta cactagaagg acagtatttg    6840
gtatctgcgc tctgctgaag ccagttacct tcggaaaaag agttggtagc tcttgatccg    6900
gcaaacaaac caccgctggt agcggtggtt ttttgtttg caagcagcag attacgcgca    6960 gaaaaaagg atctcaagaa gatcctttga tcttttctac ggggtctgac gctcagtgga    7020
acgaaaactc acgttaaggg attttggtca tgagattatc aaaaaggatc ttcacctaga    7080
tccttttaaa ttaaaaatga agttttaaat caatctaaag tatatatgag taaacttggt    7140
ctgacagtta ccaatgctta atcagtgagg cacctatctc agcgatctgt ctatttcgtt    7200
catccatagt tgcctgactc cccgtcgtgt agataactac gatacgggag gcttaccat     7260 ctggccccag tgctgcaatg ataccgcgag acccacgctc accggctcca gatttatcag    7320
caataaacca gccagccgga agggccgagc gcagaagtgg tcctgcaact ttatccgcct    7380
ccatccagtc tattaattgt tgccgggaag ctagagtaag tagttcgcca gttaatagtt    7440
tgcgcaacgt tgttgccatt gctgcaggca tcgtggtgtc acgctcgtcg tttggtatgg    7500
cttcattcag ctccggttcc caacgatcaa ggcgagttac atgatccccc atgttgtgca    7560
aaaaagcggt tagctccttc ggtcctccga tcgttgtcag aagtaagttg gccgcagtgt    7620
tatcactcat ggttatggca gcactgcata attctcttac tgtcatgcca tccgtaagat    7680
gcttttctgt gactggtgag tactcaacca agtcattctg agaatagtgt atgcggcgac    7740
cgagttgctc ttgcccggcg tcaacacggg ataataccgc gccacatagc agaactttaa    7800
aagtgctcat cattggaaaa cgttcttcgg ggcgaaaact ctcaaggatc ttaccgctgt    7860
tgagatccag ttcgatgtaa cccactcgtg cacccaactg atcttcagca tcttttactt    7920
tcaccagcgt ttctgggtga gcaaaaacag gaaggcaaaa tgccgcaaaa aagggaataa    7980
gggcgacacg gaaatgttga atactcatac tcttcctttt tcaatattat tgaagcattt    8040
atcagggtta ttgtctcatg agcggataca tatttgaatg tatttagaaa aataaacaaa    8100 tagggggttcc gcgcacattt ccccgaaaag tgccacctga cgtctaagaa accattatta    8160
tcatgacatt aacctataaa aataggcgta tcacgaggcc ctttcgtctt caagaattgt    8220
t                                                                    8221

<210> SEQ ID NO 28
<211> LENGTH: 8439
<212> TYPE: DNA
<213> ORGANISM: Artificial Sequence
<220> FEATURE:
<223> OTHER INFORMATION: Synthetic Construct pAdApt Ebola GP(Z)

<400> SEQUENCE: 28
ttaattaacc gcaattctca tgtttgacag cttatcatca tcaataatat accttatttt      60
ggattgaagc caatatgata atgagggggt ggagtttgtg acgtggcgcg ggcgtggga     120 acggggcggg tgacgtagta gtgtggcgga agtgtgatgt tgcaagtgtg gcggaacaca    180
tgtaagcgac ggatgtggca aaagtgacgt ttttggtgtg cgccggtgta cacaggaagt    240
```

-continued

```
gacaattttc gcgcggtttt aggcggatgt tgtagtaaat ttgggcgtaa ccgagtaaga    300
tttggccatt ttcgcgggaa aactgaataa gaggaagtga aatctgaata attttgtgtt    360
actcatagcg cgtaatattt gtctagggcc gcggggactt tgaccgttta cgtggagact    420
cgcccaggtg ttttttctcag gtgttttccg cgttccgggt caaagttggc gttttattat   480
tatagtcagt acgtaccagt gcactggcct agagcggccc cattgcatac gttgtatcca    540
tatcataata tgtacattta tattggctca tgtccaacat taccgccatg ttgacattga    600
ttattgacta gttattaata gtaatcaatt acggggtcat tagttcatag cccatatatg    660
gagttccgcg ttacataact tacggtaaat ggcccgcctg gctgaccgcc caacgacccc    720
cgcccattga cgtcaataat gacgtatgtt cccatagtaa cgccaatagg gactttccat    780
tgacgtcaat gggtggagta tttacggtaa actgcccact tggcagtaca tcaagtgtat    840
catatgccaa gtacgccccc tattgacgtc aatgacggta atggcccgc ctggcattat     900
gcccagtaca tgaccttatg ggactttcct acttggcagt acatctacgt attagtcatc    960
gctattacca tggtgatgcg gttttggcag tacatcaatg ggcgtggata gcggtttgac   1020
tcacggggat ttccaagtct ccaccccatt gacgtcaatg ggagtttgtt ttggcaccaa   1080
aatcaacggg actttccaaa atgtcgtaac aactccgccc cattgacgca atgggcggt    1140
aggcgtgtac ggtgggaggt ctatataagc agagctcgtt tagtgaaccg tcagatcgcc   1200
tggagacgcc atccacgctg ttttgacctc catagaagac accgggaccg atccagcctc   1260
cgtcaccgtc gtcgacacgt gtgatcagat atcgcggccg ctctagacca ggccctggat   1320
cgatccaaca acacaatggg cgttacagga atattgcagt tacctcgtga tcgattcaag   1380
aggacatcat tctttctttg ggtaattatc ctttttccaaa gaacattttc catcccactt   1440
ggagtcatcc acaatagcac attacaggtt agtgatgtcg acaaactagt ttgtcgtgac   1500
aaactgtcat ccacaaaatca attgagatca gttggactga atctcgaagg gaatggagtg   1560
gcaactgacg tgccatctgc aactaaaaga tggggcttca ggtccggtgt cccaccaaag   1620
gtggtcaatt atgaagctgg tgaatgggct gaaaactgct acaatcttga aatcaaaaaa   1680
cctgacggga gtgagtgtct accagcagcg ccagacggga ttcggggctt cccccggtgc   1740
cggtatgtgc acaaagtatc aggaacggga ccgtgtgccg gagactttgc cttccataaa   1800
gagggtgctt tcttcctgta tgatcgactt gcttccacag ttatctaccg aggaacgact   1860
ttcgctgaag gtgtcgttgc atttctgata ctgccccaag ctaagaagga cttcttcagc   1920
tcacaccccct tgagagagcc ggtcaatgca acggaggacc cgtctagtgg ctactattct   1980
accacaatta gatatcaggc taccggtttt ggaaccaatg agacagagta cttgttcgag   2040
gttgacaatt tgacctacgt ccaacttgaa tcaagattca caccacagtt tctgctccag   2100
ctgaatgaga caatatatac aagtgggaaa aggagcaata ccacgggaaa actaatttgg   2160
aaggtcaacc ccgaaattga tacaacaatc ggggagtggg ccttctggga aactaaaaaa   2220
aacctcacta gaaaaattcg cagtgaagag ttgtctttca cagttgtatc aaacggagcc   2280
aaaaacatca gtggtcagag tccggcgcga acttcttccg acccagggac caacacaaca   2340
actgaagacc acaaaatcat ggcttcagaa aattcctctg caatggttca agtgcacagt   2400
caaggaaggg aagctgcagt gtcgcatcta acaacccttg ccacaatctc cacgagtccc   2460
caatccctca caaccaaacc aggtccggac aacagcaccc ataatacacc cgtgtataaa   2520
cttgacatct ctgaggcaac tcaagttgaa caacatcacc gcagaacaga caacgacagc   2580
```

```
acagcctccg acactccctc tgccacgacc gcagccggac ccccaaaagc agagaacacc   2640
aacacgagca agagcactga cttcctggac cccgccacca caacaagtcc ccaaaaccac   2700
agcgagaccg ctggcaacaa caacactcat caccaagata ccggagaaga gagtgccagc   2760
agcgggaagc taggcttaat taccaatact attgctggag tcgcaggact gatcacaggc   2820
gggagaagaa ctcgaagaga agcaattgtc aatgctcaac ccaaatgcaa ccctaattta   2880
cattactgga ctactcagga tgaaggtgct gcaatcggac tggcctggat accatatttc   2940
gggccagcag ccgagggaat ttacatagag gggctaatgc acaatcaaga tggtttaatc   3000
tgtgggttga dacagctggc caacgagacg actcaagctc ttcaactgtt cctgagagcc   3060
acaactgagc tacgcacctt ttcaatcctc aaccgtaagg caattgattt cttgctgcag   3120
cgatggggcg gcacatgcca cattctggga ccggactgct gtatcgaacc acatgattgg   3180
accaagaaca taacagacaa aattgatcag attattcatg attttgttga taaaaccctt   3240
ccggaccagg gggacaatga caattggtgg acaggatgga dacaatggat accggcaggt   3300
attggagtta caggcgttgt aattgcagtt atcgctttat tctgtatatg caaatttgtc   3360
ttttagtttt tcttcagatt gcttcatgga aaagctcagc ctcaaatcaa tgaaaccagg   3420
atttaattat atggattact tgaatctaag attacttgac aaatgataat ataatacact   3480
ggagctttaa acatagccaa tgtgattcta actcctttaa actcacagtt aatcataaac   3540
aaggtttgag gtaccgagct cgaattgatc tgctgtgcct tctagttgcc agccatctgt   3600
tgtttgcccc tccccgtgc cttccttgac cctggaaggt gccactccca ctgtcctttc   3660
ctaataaaat gaggaaattg catcgcattg tctgagtagg tgtcattcta ttctggggg   3720 tggggtgggg caggacagca aggggagga ttgggaagac aatagcaggc atgctgggga   3780
tgcggtgggc tctatgggta cccagggccg cataacttcg tataatgtat gctatacgaa   3840
gttataagat ctgtactgaa atgtgtgggc gtggcttaag ggtgggaaag aatatataag   3900
gtgggggtct tatgtagttt tgtatctgtt ttgcagcagc cgccgccgcc atgagcacca   3960
actcgtttga tggaagcatt gtgagctcat atttgacaac gcgcatgccc ccatgggccg   4020
gggtgcgtca gaatgtgatg ggctccagca ttgatggtcg ccccgtcctg cccgcaaact   4080
ctactacctt gacctacgag accgtgtctg gaacgccgtt ggagactgca gcctccgccg   4140
ccgcttcagc cgctgcagcc accgcccgcg ggattgtgac tgactttgct ttcctgagcc   4200
cgcttgcaag cagtgcagct tcccgttcat ccgcccgcga tgacaagttg acggctcttt   4260
tggcacaatt ggattctttg acccgggaac ttaatgtcgt ttctcagcag ctgttggatc   4320
tgcgccagca ggtttctgcc ctgaaggctt cctcccctcc caatgcggtt taaaacataa   4380
ataaaaaacc agactctgtt tggatttgga tcaagcaagt gtcttgctgt ctttatttag   4440
gggttttgcg cgcgcggtag gcccgggacc agcggtctcg gtcgttgagg gtcctgtgta   4500
ttttttccag gacgtggtaa aggtgactct ggatgttcag atacatgggc ataagcccgt   4560
ctctggggtg gaggtagcac cactgcagag cttcatgctg cggggtggtg ttgtagatga   4620
tccagtcgta gcaggagcgc tgggcgtggt gcctaaaaat gtctttcagt agcaagctga   4680
ttgccagggg caggcccttg gtgtaagtgt ttacaaagcg gttaagctgg gatgggtgca   4740
tacgtgggga tatgagatgc atcttggact gtattttag gttggctatg ttcccagcca   4800
tatccctccg gggattcatg ttgtgcagaa ccaccagcac agtgtatccg gtgcacttgg   4860
gaaatttgtc atgtagctta gaaggaaatg cgtggaagaa cttggagacg cccttgtgac   4920
ctccaagatt ttccatgcat tcgtccataa tgatggcaat gggcccacgg gcggcggcct   4980
```

```
gggcgaagat atttctggga tcactaacgt catagttgtg ttccaggatg agatcgtcat   5040
aggccatttt tacaaagcgc gggcggaggg tgccagactg cggtataatg gttccatccg   5100
gcccaggggc gtagttaccc tcacagattt gcatttccca cgctttgagt tcagatgggg   5160
ggatcatgtc tacctgcggg gcgatgaaga aaacggtttc cggggtaggg gagatcagct   5220
gggaagaaag caggttcctg agcagctgcg acttaccgca gccggtgggc ccgtaaatca   5280
cacctattac cggctgcaac tggtagttaa gagagctgca gctgccgtca tccctgagca   5340
ggggggccac ttcgttaagc atgtccctga ctcgcatgtt ttccctgacc aaatccgcca   5400
gaaggcgctc gccgcccagc gatagcagtt cttgcaagga agcaaagttt ttcaacggtt   5460
tgagaccgtc cgccgtaggc atgcttttga gcgtttgacc aagcagttcc aggcggtccc   5520
acagctcggt cacctgctct acggcatctc gatccagcat atctcctcgt ttcgcgggtt   5580
ggggcggctt tcgctgtacg gcagtagtcg gtgctcgtcc agacgggcca gggtcatgtc   5640
tttccacggg cgcagggtcc tcgtcagcgt agtctgggtc acggtgaagg ggtgcgctcc   5700
gggctgcgcg ctggccaggg tgcgcttgag gctggtcctg ctggtgctga agcgctgccg   5760
gtcttcgccc tgcgcgtcgg ccaggtagca tttgaccatg gtgtcatagt ccagcccctc   5820
cgcggcgtgg cccttggcgc gcagcttgcc cttggaggag gcgccgcacg aggggcagtg   5880
cagactttg agggcgtaga gcttgggcgc gagaaatacc gattccgggg agtaggcatc   5940
cgcgccgcag gccccgcaga cggtctcgca ttccacgagc caggtgagct ctggccgttc   6000
ggggtcaaaa accaggtttc ccccatgctt tttgatgcgt ttcttacctc tggtttccat   6060
gagccggtgt ccacgctcgg tgacgaaaag gctgtccgtg tccccgtata cagacttgag   6120
aggcctgtcc tcgagcggtg ttccgcggtc ctcctcgtat agaaactcgg accactctga   6180
gacaaaggct cgcgtccagg ccagcacgaa ggaggctaag tgggaggggt agcggtcgtt   6240
gtccactagg gggtccactc gctccagggt gtgaagacac atgtcgccct cttcggcatc   6300
aaggaaggtg attggtttgt aggtgtaggc cacgtgaccg ggtgttcctg aagggggggct   6360
ataaaagggg gtggggcgc gttcgtcctc actctcttcc gcatcgctgt ctgcgagggc   6420
cagctgttgg ggtgagtcga cgcgaggctg gatggccttc cccattatga ttcttctcgc   6480
ttccggcggc atcgggatgc ccgcgttgca ggccatgctg tccaggcagg tagatgacga   6540
ccatcaggga cagcttcaag gccagcaaaa ggccaggaac cgtaaaaagg ccgcgttgct   6600
ggcgtttttc cataggctcc gcccccctga cgagcatcac aaaaatcgac gctcaagtca   6660
gaggtggcga acccgacag gactataaag ataccaggcg tttccccctg gaagctccct   6720
cgtgcgctct cctgttccga ccctgccgct taccggatac ctgtccgcct ttctcccttc   6780
gggaagcgtg gcgctttctc atagctcacg ctgtaggtat ctcagttcgg tgtaggtcgt   6840
tcgctccaag ctgggctgtg tgcacgaacc ccccgttcag cccgaccgct gcgccttatc   6900
cggtaactat cgtcttgagt ccaacccggt aagacacgac ttatcgccac tggcagcagc   6960
cactggtaac aggattagca gagcgaggta tgtaggcggt gctacagagt tcttgaagtg   7020
gtggcctaac tacggctaca ctagaaggac agtatttggt atctgcgctc tgctgaagcc   7080
agttaccttc ggaaaaagag ttggtagctc ttgatccggc aaacaaacca ccgctggtag   7140
cggtggtttt tttgtttgca agcagcagat tacgcgcaga aaaaaaggat ctcaagaaga   7200
tcctttgatc ttttctacgg ggtctgacgc tcagtggaac gaaaactcac gttaagggat   7260
tttggtcatg agattatcaa aaaggatctt cacctagatc cttttaaatt aaaaatgaag   7320
```

| | | |
|---|---|---|
| ttttaaatca atctaaagta tatatgagta aacttggtct gacagttacc aatgcttaat | 7380 |
| cagtgaggca cctatctcag cgatctgtct atttcgttca tccatagttg cctgactccc | 7440 |
| cgtcgtgtag ataactacga tacgggaggg cttaccatct ggccccagtg ctgcaatgat | 7500 |
| accgcgagac ccacgctcac cggctccaga tttatcagca ataaaccagc cagccggaag | 7560 |
| ggccgagcgc agaagtggtc ctgcaacttt atccgcctcc atccagtcta ttaattgttg | 7620 |
| ccgggaagct agagtaagta gttcgccagt taatagtttg cgcaacgttg ttgccattgc | 7680 |
| tgcaggcatc gtggtgtcac gctcgtcgtt tggtatggct tcattcagct ccggttccca | 7740 |
| acgatcaagg cgagttacat gatccccccat gttgtgcaaa aaagcggtta gctccttcgg | 7800 |
| tcctccgatc gttgtcagaa gtaagttggc cgcagtgtta tcactcatgg ttatggcagc | 7860 |
| actgcataat tctcttactg tcatgccatc cgtaagatgc ttttctgtga ctggtgagta | 7920 |
| ctcaaccaag tcattctgag aatagtgtat gcggcgaccg agttgctctt gcccggcgtc | 7980 |
| aacacgggat aataccgcgc cacatagcag aactttaaaa gtgctcatca ttggaaaacg | 8040 |
| ttcttcgggg cgaaaactct caaggatctt accgctgttg agatccagtt cgatgtaacc | 8100 |
| cactcgtgca cccaactgat cttcagcatc ttttactttc accagcgttt ctgggtgagc | 8160 |
| aaaaacagga aggcaaaatg ccgcaaaaaa gggaataagg gcgacacgga aatgttgaat | 8220 |
| actcatactc ttcctttttc aatattattg aagcatttat cagggttatt gtctcatgag | 8280 |
| cggatacata tttgaatgta tttagaaaaa taaacaaata ggggttccgc gcacatttcc | 8340 |
| ccgaaaagtg ccacctgacg tctaagaaac cattattatc atgacattaa cctataaaaa | 8400 |
| taggcgtatc acgaggccct ttcgtcttca agaattgtt | 8439 |

<210> SEQ ID NO 29
<211> LENGTH: 8199
<212> TYPE: DNA
<213> ORGANISM: Artificial Sequence
<220> FEATURE:
<223> OTHER INFORMATION: Synthetic Construct pAdApt Ebola GP(Z)(dTM)

<400> SEQUENCE: 29

| | | |
|---|---|---|
| ttaattaacc gcaattctca tgtttgacag cttatcatca tcaataatat accttatttt | 60 |
| ggattgaagc caatatgata atgagggggt ggagtttgtg acgtggcgcg ggcgtgggga | 120 |
| acggggcggg tgacgtagta gtgtggcgga agtgtgatgt tgcaagtgtg gcggaacaca | 180 |
| tgtaagcgac ggatgtggca aaagtgacgt ttttggtgtg cgccggtgta cacaggaagt | 240 |
| gacaattttc gcgcggtttt aggcggatgt tgtagtaaat ttgggcgtaa ccgagtaaga | 300 |
| tttggccatt ttcgcgggaa aactgaataa gaggaagtga aatctgaata attttgtgtt | 360 |
| actcatagcg cgtaatattt gtctagggcc gcggggactt tgaccgttta cgtggagact | 420 |
| cgcccaggtg ttttttctcag gtgttttccg cgttccgggt caaagttggc gttttattat | 480 |
| tatagtcagt acgtaccagt gcactggcct agagcggccc cattgcatac gttgtatcca | 540 |
| tatcataata tgtacattta tattggctca tgtccaacat taccgccatg ttgacattga | 600 |
| ttattgacta gttattaata gtaatcaatt acggggtcat tagttcatag cccatatatg | 660 |
| gagttccgcg ttacataact acggtaaat ggcccgcctg gctgaccgcc caacgacccc | 720 |
| cgcccattga cgtcaataat gacgtatgtt cccatagtaa cgccaatagg gactttccat | 780 |
| tgacgtcaat gggtggagta tttacggtaa actgcccact tggcagtaca tcaagtgtat | 840 |
| catatgccaa gtacgccccc tattgacgtc aatgacggta aatggcccgc ctggcattat | 900 |
| gcccagtaca tgaccttatg ggactttcct acttggcagt acatctacgt attagtcatc | 960 |

```
gctattacca tggtgatgcg gttttggcag tacatcaatg ggcgtggata gcggtttgac    1020
tcacggggat ttccaagtct ccaccccatt gacgtcaatg ggagtttgtt ttggcaccaa    1080
aatcaacggg actttccaaa atgtcgtaac aactccgccc cattgacgca aatgggcggt    1140
aggcgtgtac ggtgggaggt ctatataagc agagctcgtt tagtgaaccg tcagatcgcc    1200
tggagacgcc atccacgctg ttttgacctc catagaagac accggaccg  atccagcctc    1260 cgtcaccgtc gtcgacacgt gtgatcagat atcgcggccg ctctagacca ggccctggat    1320
cgatccaaca acacaatggg cgttacagga atattgcagt tacctcgtga tcgattcaag    1380
aggacatcat tctttctttg ggtaattatc cttttccaaa gaacattttc catcccactt    1440
ggagtcatcc acaatagcac attacaggtt agtgatgtcg acaaactagt ttgtcgtgac    1500
aaactgtcat ccacaaatca attgagatca gttggactga atctcgaagg gaatggagtg    1560
gcaactgacg tgccatctgc aactaaaaga tggggcttca ggtccggtgt cccaccaaag    1620
gtggtcaatt atgaagctgg tgaatgggct gaaaactgct acaatcttga aatcaaaaaa    1680
cctgacggga gtgagtgtct accagcagcg ccagacggga ttcggggctt ccccggtgc    1740 cggtatgtgc acaaagtatc aggaacggga ccgtgtgccg gagactttgc cttccataaa    1800
gagggtgctt tcttcctgta tgatcgactt gcttccacag ttatctaccg aggaacgact    1860
ttcgctgaag gtgtcgttgc atttctgata ctgccccaag ctaagaagga cttcttcagc    1920
tcacacccct tgagagagcc ggtcaatgca acgaggacc  cgtctagtgg ctactattct    1980
accacaatta gatatcaggc taccggtttt ggaaccaatg agacagagta cttgttcgag    2040
gttgacaatt tgacctacgt ccaacttgaa tcaagattca caccacagtt tctgctccag    2100
ctgaatgaga caatatatac aagtgggaaa aggagcaata ccacgggaaa actaatttgg    2160
aaggtcaacc ccgaaattga tacaacaatc ggggagtggg ccttctggga aactaaaaaa    2220
aacctcacta gaaaaattcg cagtgaagag ttgtctttca cagttgtatc aaacggagcc    2280
aaaaacatca gtggtcagag tccggcgcga acttcttccg acccagggac caacacaaca    2340
actgaagacc acaaaatcat ggcttcagaa aattcctctg caatggttca agtgcacagt    2400
caaggaaggg aagctgcagt gtcgcatcta caaccccttg ccacaatctc cacgagtccc    2460
caatccctca caaccaaacc aggtccggac aacagcaccc ataatacacc cgtgtataaa    2520
cttgacatct ctgaggcaac tcaagttgaa caacatcacc gcagaacaga caacgacagc    2580
acagcctccg acactccctc tgccacgacc gcagccggac ccccaaaagc agagaacacc    2640
aacacgagca agagcactga cttcctggac cccgccacca acaagtcc   ccaaaaccac    2700 agcgagaccg ctggcaacaa caacactcat caccaagata ccggagaaga gagtgccagc    2760
agcgggaagc taggcttaat taccaatact attgctggag tcgcaggact gatcacaggc    2820
gggagaagaa ctcgaagaga agcaattgtc aatgctcaac ccaaatgcaa ccctaattta    2880
cattactgga ctactcagga tgaaggtgct gcaatcggac tggcctggat accatatttc    2940
gggccagcag ccgagggaat ttacatagag gggctaatgc acaatcaaga tggtttaatc    3000
tgtgggttga gacagctggc caacgagacg actcaagctc ttcaactgtt cctgagagcc    3060
acaactgagc tacgcacctt ttcaatcctc aaccgtaagg caattgattt cttgctgcag    3120
cgatggggcg gcacatgcca cattctggga ccggactgct gtatcgaacc acatgattgg    3180
accaagaaca taacagacaa aattgatcag attattcatg attttgttga taaaaccctt    3240
ccggaccagg gggacaatga caattggtgg acaggatgga gacaatggat ggccgcatcg    3300
```

```
tgactgactg acgatctgcc tcgcgagatc tgctgtgcct tctagttgcc agccatctgt   3360
tgtttgcccc tcccccgtgc cttccttgac cctggaaggt gccactccca ctgtcctttc   3420
ctaataaaat gaggaaattg catcgcattg tctgagtagg tgtcattcta ttctgggggg   3480
tggggtgggg caggacagca agggggagga ttgggaagac aatagcaggc atgctgggga   3540
tgcggtgggc tctatgggta cccagggccg cataacttcg tataatgtat gctatacgaa   3600
gttataagat ctgtactgaa atgtgtgggc gtggcttaag ggtgggaaag aatatataag   3660
gtgggggtct tatgtagttt tgtatctgtt ttgcagcagc cgccgccgcc atgagcacca   3720
actcgtttga tggaagcatt gtgagctcat atttgacaac gcgcatgccc ccatgggccg   3780
gggtgcgtca gaatgtgatg ggctccagca ttgatggtcg ccccgtcctg cccgcaaact   3840
ctactacctt gacctacgag accgtgtctg gaacgccgtt ggagactgca gcctccgccg   3900
ccgcttcagc cgctgcagcc accgcccgcg ggattgtgac tgactttgct ttcctgagcc   3960
cgcttgcaag cagtgcagct tcccgttcat ccgcccgcga tgacaagttg acggctcttt   4020
tggcacaatt ggattctttg acccgggaac ttaatgtcgt ttctcagcag ctgttggatc   4080
tgcgccagca ggtttctgcc ctgaaggctt cctcccctcc caatgcggtt taaaacataa   4140
ataaaaaacc agactctgtt tggatttgga tcaagcaagt gtcttgctgt ctttatttag   4200
gggttttgcg cgcgcggtag gcccgggacc agcggtctcg gtcgttgagg gtcctgtgta   4260
ttttttccag gacgtggtaa aggtgactct ggatgttcag atacatgggc ataagcccgt   4320
ctctggggtg gaggtagcac cactgcagag cttcatgctg cggggtggtg ttgtagatga   4380
tccagtcgta gcaggagcgc tgggcgtggt gcctaaaaat gtctttcagt agcaagctga   4440
ttgccagggg caggcccttg gtgtaagtgt ttacaaagcg gttaagctgg gatgggtgca   4500
tacgtgggga tatgagatgc atcttggact gtattttag gttggctatg ttcccagcca   4560
tatccctccg gggattcatg ttgtgcagaa ccaccagcac agtgtatccg gtgcacttgg   4620
gaaatttgtc atgtagctta aaggaaatg cgtggaagaa cttggagacg cccttgtgac   4680
ctccaagatt ttccatgcat tcgtccataa tgatggcaat gggcccacgg gcggcggcct   4740
gggcgaagat atttctggga tcactaacgt catagttgtg ttccaggatg agatcgtcat   4800
aggccatttt tacaaagcgc gggcggaggg tgccagactg cggtataatg gttccatccg   4860
gcccagggc gtagttaccc tcacagattt gcatttccca cgctttgagt tcagatgggg   4920
ggatcatgtc tacctgcggg gcgatgaaga aaacggtttc cggggtaggg gagatcagct   4980
gggaagaaag caggttcctg agcagctgcg acttaccgca gccggtgggc ccgtaaatca   5040
cacctattac cggctgcaac tggtagttaa gagagctgca gctgccgtca tccctgagca   5100
ggggggccac ttcgttaagc atgtccctga ctcgcatgtt ttccctgacc aaatccgcca   5160
gaaggcgctc gccgcccagc gatagcagtt cttgcaagga agcaaagttt ttcaacggtt   5220
tgagaccgtc cgccgtaggc atgcttttga gcgtttgacc aagcagttcc aggcggtccc   5280
acagctcggt cacctgctct acggcatctc gatccagcat atctcctcgt ttcgcgggtt   5340
ggggcggctt tcgctgtacg gcagtagtcg gtgctcgtcc agacgggcca gggtcatgtc   5400
tttccacggg cgcagggtcc tcgtcagcgt agtctgggtc acggtgaagg ggtgcgctcc   5460
gggctgcgcg ctggccaggg tgcgcttgag gctggtcctg ctggtgctga gcgctgccg   5520
gtcttcgccc tgcgcgtcgg ccaggtagca tttgaccatg gtgtcatagt ccagccctc   5580
cgcggcgtgg cccttggcgc gcagcttgcc cttgaggag cgccgcacg aggggcagtg   5640
cagacttttg agggcgtaga gcttgggcgc gagaaatacc gattccgggg agtaggcatc   5700
```

```
cgcgccgcag gccccgcaga cggtctcgca ttccacgagc caggtgagct ctggccgttc    5760
ggggtcaaaa accaggtttc ccccatgctt tttgatgcgt ttcttacctc tggtttccat    5820
gagccggtgt ccacgctcgg tgacgaaaag gctgtccgtg tccccgtata cagacttgag    5880
aggcctgtcc tcgagcggtg ttccgcggtc ctcctcgtat agaaactcgg accactctga    5940
gacaaaggct cgcgtccagg ccagcacgaa ggaggctaag tgggagggt agcggtcgtt    6000
gtccactagg gggtccactc gctccagggt gtgaagacac atgtcgccct cttcggcatc    6060
aaggaaggta attggtttgt aggtgtaggc cacgtgaccg ggtgttcctg aaggggggct    6120
ataaaagggg gtggggcgc gttcgtcctc actctcttcc gcatcgctgt ctgcgagggc    6180
cagctgttgg ggtgagtcga cgcgaggctg gatggccttc cccattatga ttcttctcgc    6240
ttccggcggc atcgggatgc ccgcgttgca ggccatgctg tccaggcagg tagatgacga    6300
ccatcaggga cagcttcaag gccagcaaaa ggccaggaac cgtaaaaagg ccgcgttgct    6360
ggcgtttttc cataggctcc gccccctga cgagcatcac aaaaatcgac gctcaagtca    6420
gaggtggcga acccgacag gactataaag ataccaggcg tttccccctg gaagctccct    6480
cgtgcgctct cctgttccga ccctgccgct taccggatac ctgtccgcct ttctccttc    6540
gggaagcgtg gcgctttctc atagctcacg ctgtaggtat ctcagttcgg tgtaggtcgt    6600
tcgctccaag ctgggctgtg tgcacgaacc ccccgttcag cccgaccgct gcgccttatc    6660
cggtaactat cgtcttgagt ccaacccggt aagacacgac ttatcgccac tggcagcagc    6720
cactggtaac aggattagca gagcgaggta tgtaggcggt gctacagagt tcttgaagtg    6780
gtggcctaac tacggctaca ctagaaggac agtatttggt atctgcgctc tgctgaagcc    6840
agttaccttg gaaaaagag ttggtagctc ttgatccggc aaacaaacca ccgctggtag    6900
cggtggtttt tttgtttgca agcagcagat tacgcgcaga aaaaaggat ctcaagaaga    6960
tcctttgatc ttttctacgg ggtctgacgc tcagtggaac gaaaactcac gttaagggat    7020
tttggtcatg agattatcaa aaaggatctt cacctagatc cttttaaatt aaaaatgaag    7080
ttttaaatca atctaaagta tatatgagta aacttggtct gacagttacc aatgcttaat    7140
cagtgaggca cctatctcag cgatctgtct atttcgttca tccatagttg cctgactccc    7200
cgtcgtgtag ataactacga tacgggaggg cttaccatct ggccccagtg ctgcaatgat    7260
accgcgagac ccacgctcac cggctccaga tttatcagca ataaaccagc cagccggaag    7320
ggccgagcgc agaagtggtc ctgcaacttt atccgcctcc atccagtcta ttaattgttg    7380
ccgggaagct agagtaagta gttcgccagt taatagtttg cgcaacgttg ttgccattgc    7440
tgcaggcatc gtggtgtcac gctcgtcgtt tggtatggct tcattcagct ccggttccca    7500
acgatcaagg cgagttacat gatcccccat gttgtgcaaa aaagcggtta gctccttcgg    7560
tcctccgatc gttgtcagaa gtaagttggc cgcagtgtta tcactcatgg ttatggcagc    7620
actgcataat tctcttactg tcatgccatc cgtaagatgc ttttctgtga ctggtgagta    7680
ctcaaccaag tcattctgag aatagtgtat gcggcgaccg agttgctctt gcccggcgtc    7740
aacacgggat aataccgcgc cacatagcag aactttaaaa gtgctcatca ttggaaaacg    7800
ttcttcgggg cgaaaactct caaggatctt accgctgttg agatccagtt cgatgtaacc    7860
cactcgtgca cccaactgat cttcagcatc ttttactttc accagcgttt ctgggtgagc    7920
aaaaacagga aggcaaaatg ccgcaaaaaa gggaataagg gcgacacgga aatgttgaat    7980
actcatactc ttccttttc aatattattg aagcatttat cagggttatt gtctcatgag    8040
```

-continued

```
cggatacata tttgaatgta tttagaaaaa taaacaaata ggggttccgc gcacatttcc    8100
ccgaaaagtg ccacctgacg tctaagaaac cattattatc atgacattaa cctataaaaa    8160
taggcgtatc acgaggccct ttcgtcttca agaattgtt                           8199
```

<210> SEQ ID NO 30
<211> LENGTH: 7778
<212> TYPE: DNA
<213> ORGANISM: Artificial Sequence
<220> FEATURE:
<223> OTHER INFORMATION: Synthetic Construct pVR1012 Marburg

<400> SEQUENCE: 30

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgacccccg cccattgacg tcaataatga cgtatgttcc     480
catagtaacg ccaatagggac ttttccattg acgtcaatgg gtggagtatt tacggtaaac    540
tgcccacttg gcagtacatc aagtgtatca tatgccaagt acgccccta ttgacgtcaa      600 tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag     900
agctcgttta gtgaaccgtc agatcgcctg gagacgccat ccacgctgtt ttgacctcca     960
tagaagacac cgggaccgat ccagcctccg cggccgggaa cggtgcattg gaacgcggat    1020
tccccgtgcc aagagtgacg taagtaccgc ctatagactc tataggcaca ccctttggc     1080 tcttatgcat gctatactgt ttttggcttg ggcctatac accccgctt ccttatgcta      1140 taggtgatgg tatagcttag cctataggtg tgggttattg accattattg accactcccc    1200
tattggtgac gatactttcc attactaatc cataacatgc tctttgcca caactatctc     1260 tattggctat atgccaatac tctgtccttc agagactgac acggactctg tattttaca     1320 ggatgggtc ccatttatta tttacaaatt cacatataca acaacgccgt cccccgtgcc      1380
cgcagttttt attaaacata gcgtgggatc tccacgcgaa tctcgggtac gtgttccgga    1440
catgggctct tctccggtag cggcggagct tccacatccg agcccggtc ccatgcctcc     1500 agcggctcat ggtcgctcgg cagctccttg ctcctaacag tggaggccag acttaggcac    1560
agcacaatgc ccaccaccac cagtgtgccg cacaaggccg tggcggtagg gtatgtgtct    1620
gaaaatgagc gtggagattg ggctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tccttccat gggtcttttc     1860 tgcagtcacc gtcgtcgaca cgtgtgatca gatatcgcgg ccgctctaga gtcgaatgaa    1920
```

```
gaacattaat tgctgggtaa aagtgattaa tttctttaaa tttgaccaga ataatatttt    1980
gtcagtgaat atattctcat atcacttgat taaaaacaga aaattaccct aacatgaaga    2040
ccacatgttt ccttatcagt cttatcttaa ttcaagggac aaaaaatctc cccattttag    2100
agatagctag taataatcaa ccccaaaatg tggattcggt atgctccgga actctccaga    2160
agacagaaga cgtccatctg atgggattca cactgagtgg gcaaaaagtt gctgattccc    2220
ctttggaggc atccaagcga tgggctttca ggacaggtgt acctcccaag aatgttgagt    2280
acacagaggg ggaggaagcc aaaacatgct acaatataag tgtaacggat ccctctggaa    2340
aatccttgct gttagatcct cctaccaaca tccgtgacta tcctaaatgc aaaactatcc    2400
atcatattca aggtcaaaac cctcatgcac agggggatcgc ccttcattta tggggagcat    2460 ttttctgta tgatcgcatt gcctccacaa caatgtaccg aggcaaagtc ttcactgaag    2520
ggaacatagc agctatgatt gtcaataaga cagtgcacaa aatgattttc tcgcggcaag    2580
gacaagggta ccgtcatatg aatctgactt ctactaataa atattggaca agtagtaacg    2640
gaacgcaaac gaatgacact ggatgtttcg gcgctcttca agaatacaat tctacaaaga    2700
accaaacatg tgctccgtcc aaaataccte caccactgcc cacagcccgt ccggagatca    2760
aactcacaag cacccaact gatgccacca aactcaatac cacggaccca agcagtgatg    2820
atgaggacct cgcaacatcc ggctcagggt ccggagaacg agaaccccac acaacttctg    2880
atgcggtcac caagcaaggg ctttcatcaa caatgccacc cactccctca ccacaaccaa    2940
gcacgccaca gcaaggagga acaacacaa accattccca agatgctgtg actgaactag    3000
acaaaaataa cacaactgca caaccgtcca tgccccctca taacactacc acaatctcta    3060
ctaacaacac ctccaaacac aacttcagca ctctctctgc accattacaa acaccacca    3120 atgacaacac acagagcaca atcactgaaa atgagcaaac cagtgccccc tcgataacaa    3180
ccctgcctcc aacgggaaat cccaccacag caaagagcac cagcagcaaa aaaggccccg    3240
ccacaacggc accaaacacg acaaatgagc atttcaccag tcctcccccc accccagct    3300 cgactgcaca acatcttgta tatttcagaa gaaagcgaag tatcctctgg agggaaggcg    3360
acatgttccc ttttctggat gggttaataa atgctccaat tgattttgac ccagttccaa    3420
atacaaaaac aatctttgat gaatcctcta gttctggtgc ctcggctgag gaagatcaac    3480
atgcctcccc caatattagt ttaactttat cttatttcc taatataaat gagaacactg    3540
cctactctgg agaaaatgag aatgattgtg atgcagagtt aagaatttgg agcgttcagg    3600
aggatgacct ggccgcaggg ctcagttgga taccgttttt tggccctgga attgaaggac    3660
tttacactgc tgttttaatt aaaaatcaaa acaatttggt ctgcaggttg aggcgtctag    3720
ccaatcaaac tgccaaatcc ttggaactct tattgagagt cacaactgag gaaagaacat    3780
tctccttaat caatagacat gctattgact ttctactcac aagatgggga ggaacatgca    3840
aagtgcttgg acctgattgt tgcatcggga tagaagactt gtccaaaaat atttcagagc    3900
aaattgacca aattaaaaag gacgaacaaa aagaggggac tggttggggt ctgggtggta    3960
aatggtggac atccgactgg ggtgttctta ctaacttggg catttgcta ctattatcca    4020 tagctgtctt gattgctcta tcctgtattt gtcgtatctt tactaaatat atcgataac    4080 gttaaatgtg taatgattag gactttagga caattgctac tgagcccttt tctaatctac    4140
tgaaatcaac ttgggagatt tttaagaagc tgataactta atgtgaatca atagtttatg    4200
tattatcgat tattatggtt tgatattcaa ttgttattat tgtcaggagt gacctttct    4260
```

```
atttgatgca ttaatgtttt aaactacctc ttaagccttt gagggcgtcc caatatgtgc    4320
gtaggggtta atttaaaggg atttcttatt gtacagtttt ctgtattact tatttgggct    4380
tgaagacata gttaagattt gccgaaatgc tctccagtca attccatccc ctctcagaaa    4440
agacgtgctg ttcaaagagt cttaatttat aaccaactat tgcaagaatt aatttacttt    4500 ttccgtttata cttagttaca ttaatctttt gactgttcag cattattaac gacttgtctt    4560
aattcaatcg ttcggatgaa attcataagg aaaaatgagc ctccttcccc ctattctggg    4620
ctgagaaaat ttctcttatc cgcctaaaat cagatctgtt aggtcatggg tccttcataa    4680
tctgtttgag catgaatatt gatgaaatga ccaaatgata gtgcatttgt atagactcaa    4740 ttatcccttta ttaagaaaaa tcgacctgca ggcatgcaag cttcaggatc cagatctgct    4800
gtgccttcta gttgccagcc atctgttgtt tgcccctccc ccgtgccttc cttgaccctg    4860
gaaggtgcca ctcccactgt cctttcctaa taaaatgagg aaattgcatc gcattgtctg    4920
agtaggtgtc attctattct gggggtgggg gtggggcagc acagcaaggg ggaggattgg    4980
gaagacaata gcaggcatgc tggggatgcg gtgggctcta tgggtaccca ggtgctgaag    5040
aattgacccg gttcctcctg ggccagaaag aagcaggcac atccccttct ctgtgacaca    5100
ccctgtccac gcccctggtt cttagttcca gccccactca taggacactc atagctcagg    5160
agggctccgc cttcaatccc acccgctaaa gtacttggag cggtctctcc ctccctcatc    5220
agcccaccaa accaaaccta gcctccaaga gtgggaagaa attaaagcaa gataggctat    5280
taagtgcaga gggagagaaa atgcctccaa catgtgagga agtaatgaga gaaatcatag    5340
aatttcttcc gcttcctcgc tcactgactc gctgcgctcg gtcgttcggc tgcggcgagc    5400
ggtatcagct cactcaaagg cggtaatacg gttatccaca gaatcagggg ataacgcagg    5460
aaagaacatg tgagcaaaag gccagcaaaa ggccaggaac cgtaaaaagg ccgcgttgct    5520 ggcgttttc cataggctcc gcccccctga cgagcatcac aaaaatcgac gctcaagtca    5580
gaggtggcga aacccgacag gactataaag ataccaggcg tttccccctg gaagctccct    5640
cgtgcgctct cctgttccga ccctgccgct taccggatac ctgtccgcct ttctcccttc    5700
gggaagcgtg gcgctttctc aatgctcacg ctgtaggtat ctcagttcgg tgtaggtcgt    5760
tcgctccaag ctgggctgtg tgcacgaacc ccccgttcag cccgaccgct gcgccttatc    5820
cggtaactat cgtcttgagt ccaacccggt aagacacgac ttatcgccac tggcagcagc    5880
cactggtaac aggattagca gagcgaggta tgtaggcggt gctacagagt tcttgaagtg    5940
gtggcctaac tacggctaca ctagaaggac agtatttggt atctgcgctc tgctgaagcc    6000
agttaccttc ggaaaaagag ttggtagctc ttgatccggc aaacaaacca ccgctggtag    6060
cggtggtttt tttgtttgca agcagcagat tacgcgcaga aaaaaggat ctcaagaaga    6120 tcctttgatc ttttctacgg ggtctgacgc tcagtggaac gaaaactcac gttaagggat    6180
tttggtcatg agattatcaa aaaggatctt cacctagatc cttttaaatt aaaaatgaag    6240
ttttaaatca atctaaagta tatatgagta aacttggtct gacagttacc aatgcttaat    6300
cagtgaggca cctatctcag cgatctgtct atttcgttca tccatagttg cctgactccg    6360
gggggggggg gcgctgaggt ctgcctcgtg aagaaggtgt tgctgactca taccaggcct    6420
gaatcgcccc atcatccagc cagaaagtga gggagccacg gttgatgaga gctttgttgt    6480
aggtggacca gttggtgatt ttgaacttt gctttgccac ggaacggtct gcgttgtcgg    6540
gaagatgcgt gatctgatcc ttcaactcag caaaagttcg atttattcaa caaagccgcc    6600
gtcccgtcaa gtcagcgtaa tgctctgcca gtgttacaac caattaacca attctgatta    6660
```

-continued

| | |
|---|---|
| gaaaaactca tcgagcatca aatgaaactg caatttattc atatcaggat tatcaatacc | 6720 |
| atattttttga aaaagccgtt tctgtaatga aggagaaaac tcaccgaggc agttccatag | 6780 |
| gatggcaaga tcctggtatc ggtctgcgat tccgactcgt ccaacatcaa tacaacctat | 6840 |
| taatttcccc tcgtcaaaaa taaggttatc aagtgagaaa tcaccatgag tgacgactga | 6900 |
| atccggtgag aatggcaaaa gcttatgcat ttctttccag acttgttcaa caggccagcc | 6960 |
| attacgctcg tcatcaaaat cactcgcatc aaccaaaccg ttattcattc gtgattgcgc | 7020 |
| ctgagcgaga cgaaatacgc gatcgctgtt aaaaggacaa ttacaaacag gaatcgaatg | 7080 |
| caaccggcgc aggaacactg ccagcgcatc aacaatattt tcacctgaat caggatattc | 7140 |
| ttctaatacc tggaatgctg ttttcccggg gatcgcagtg gtgagtaacc atgcatcatc | 7200 |
| aggagtacgg ataaaatgct tgatggtcgg aagaggcata aattccgtca gccagtttag | 7260 |
| tctgaccatc tcatctgtaa catcattggc aacgctacct ttgccatgtt tcagaaacaa | 7320 |
| ctctggcgca tcgggcttcc catacaatcg atagattgtc gcacctgatt gcccgacatt | 7380 |
| atcgcgagcc catttatacc catataaatc agcatccatg ttggaattta atcgcggcct | 7440 |
| cgagcaagac gtttcccgtt gaatatggct cataacaccc cttgtattac tgtttatgta | 7500 |
| agcagacagt tttattgttc atgatgatat atttttatct tgtgcaatgt aacatcagag | 7560 |
| attttgagac acaacgtggc tttcccccccc ccccattat tgaagcattt atcagggtta | 7620 |
| ttgtctcatg agcggataca tatttgaatg tatttagaaa aataaacaaa taggggttcc | 7680 |
| gcgcacattt ccccgaaaag tgccacctga cgtctaagaa accattatta tcatgacatt | 7740 |
| aacctataaa aataggcgta tcacgaggcc ctttcgtc | 7778 |

<210> SEQ ID NO 31
<211> LENGTH: 7005
<212> TYPE: DNA
<213> ORGANISM: Artificial Sequence
<220> FEATURE:
<223> OTHER INFORMATION: Synthetic Construct pVR1012x/s Marburg GP(dTM)

<400> SEQUENCE: 31

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcagattgg | 240 |
| ctattggcca ttgcatacgt tgtatccata tcataatatg tacatttata ttggctcatg | 300 |
| tccaacatta ccgccatgtt gacattgatt attgactagt tattaatagt aatcaattac | 360 |
| ggggtcatta gttcatagcc catatatgga gttccgcgtt acataactta cggtaaatgg | 420 |
| cccgcctggc tgaccgccca acgaccccccg cccattgacg tcaataatga cgtatgttcc | 480 |
| catagtaacg ccaatagggga ctttccattg acgtcaatgg gtggagtatt tacggtaaac | 540 |
| tgcccacttg gcagtacatc aagtgtatca tatgccaagt acgccccccta ttgacgtcaa | 600 |
| tgacggtaaa tggcccgcct ggcattatgc ccagtacatg accttatggg actttcctac | 660 |
| ttggcagtac atctacgtat tagtcatcgc tattaccatg gtgatgcggt tttggcagta | 720 |
| catcaatggg cgtggatagc ggtttgactc acggggattt ccaagtctcc accccattga | 780 |
| cgtcaatggg agtttgtttt ggcaccaaaa tcaacgggac tttccaaaat gtcgtaacaa | 840 |
| ctccgcccca ttgacgcaaa tgggcggtag gcgtgtacgg tgggaggtct atataagcag | 900 |

```
agctcgttta gtgaaccgtc agatcgcctg gagacgccat ccacgctgtt ttgacctcca      960
tagaagacac cgggaccgat ccagcctccg cggccgggaa cggtgcattg gaacgcggat     1020
tccccgtgcc aagagtgacg taagtaccgc ctatagactc tataggcaca cccctttggc     1080
tcttatgcat gctatactgt ttttggcttg gggcctatac accccgctt ccttatgcta      1140
taggtgatgg tatagcttag cctataggtg tgggttattg accattattg accactcccc     1200
tattggtgac gatactttcc attactaatc cataacatgg ctctttgcca caactatctc     1260
tattggctat atgccaatac tctgtccttc agagactgac acggactctg tatttttaca     1320
ggatggggtc ccatttatta tttacaaatt cacatataca acaacgccgt cccccgtgcc     1380
cgcagttttt attaaacata gcgtgggatc tccacgcgaa tctcgggtac gtgttccgga     1440
catgggctct tctccggtag cggcggagct tccacatccg agccctggtc ccatgcctcc     1500
agcggctcat ggtcgctcgg cagctccttg ctcctaacag tggaggccag acttaggcac     1560
agcacaatgc ccaccaccac cagtgtgccg cacaaggccg tggcggtagg gtatgtgtct     1620
gaaaatgagc gtggagattg ggctcgcacg gctgacgcag atggaagact taaggcagcg     1680
gcagaagaag atgcaggcag ctgagttgtt gtattctgat aagagtcaga ggtaactccc     1740
gttgcggtgc tgttaacggt ggagggcagt gtagtctgag cagtactcgt tgctgccgcg     1800
cgcgccacca gacataatag ctgacagact aacagactgt tcctttccat gggtcttttc     1860
tgcagtcacc gtcgtcgaca cgtgtgatca gatatcgcgg ccgctctaga gtcgaatgaa     1920
gaacattaat tgctgggtaa aagtgattaa tttctttaaa tttgaccaga ataatatttt     1980
gtcagtgaat atattctcat atcacttgat taaaaacaga aaattaccct aacatgaaga     2040
ccacatgttt ccttatcagt cttatcttaa ttcaagggac aaaaaatctc cccattttag     2100
agatagctag taataatcaa ccccaaaatg tggattcggt atgctccgga actctccaga     2160
agacagaaga cgtccatctg atgggattca cactgagtgg gcaaaaagtt gctgattccc     2220
cttttggagg catccaagcga tgggctttca ggacaggtgt acctcccaag aatgttgagt     2280
acacagaggg ggaggaagcc aaaacatgct acaatataag tgtaacggat ccctctggaa     2340
aatccttgct gttagatcct cctaccaaca tccgtgacta tcctaaatgc aaaactatcc     2400
atcatattca aggtcaaaac cctcatgcac aggggatcgc ccttcattta tggggagcat     2460
ttttttctgta tgatcgcatt gcctccacaa caatgtaccg aggcaaagtc ttcactgaag     2520
ggaacatagc agctatgatt gtcaataaga cagtgcacaa aatgattttc tcgcggcaag     2580
gacaagggta ccgtcatatg aatctgactt ctactaataa atattggaca agtagtaacg     2640
gaacgcaaac gaatgacact ggatgtttcg gcgctcttca agaatacaat tctacaaaga     2700
accaaacatg tgctccgtcc aaaatacctc caccactgcc cacagccgt ccggagatca      2760
aactcacaag cacccaact gatgccacca aactcaatac cacggaccca agcagtgatg      2820
atgaggacct cgcaacatcc ggctcagggt ccggagaacg agaaccccac acaacttctg     2880
atgcggtcac caagcaaggg ctttcatcaa caatgccacc cactccctca ccacaaccaa     2940
gcacgccaca gcaaggagga acaacacaa accattccca agatgctgtg actgaactag       3000
acaaaaataa cacaactgca caaccgtcca tgcccctca taacactacc acaatctcta      3060
ctaacaaacac ctccaaacac aacttcagca ctctctctgc accattacaa acaccacca     3120
atgacaaca acagagcaca atcactgaaa atgagcaaac cagtgccccc tcgataacaa      3180
ccctgcctcc aacggaaat cccaccacag caaagagcac cagcagcaaa aaggccccg       3240
ccacaacggc accaaacacg acaaatgagc atttcaccag tcctcccccc accccagct     3300
```

```
cgactgcaca acatcttgta tatttcagaa gaaagcgaag tatcctctgg agggaaggcg   3360
acatgttccc ttttctggat gggttaataa atgctccaat tgattttgac ccagttccaa   3420
atacaaaaac aatctttgat gaatcctcta gttctggtgc ctcggctgag gaagatcaac   3480
atgcctcccc caatattagt ttaactttat cttattttcc taatataaat gagaacactg   3540
cctactctgg agaaaatgag aatgattgtg atgcagagtt aagaatttgg agcgttcagg   3600
aggatgacct ggccgcaggg ctcagttgga taccgttttt tggccctgga attgaaggac   3660
tttacactgc tgttttaatt aaaaatcaaa acaatttggt ctgcaggttg aggcgtctag   3720
ccaatcaaac tgccaaatcc ttggaactct tattgagagt cacaactgag gaaagaacat   3780
tctccttaat caatagacat gctattgact ttctactcac aagatgggga ggaacatgca   3840
aagtgcttgg acctgattgt tgcatcggga tagaagactt gtccaaaaat atttcagagc   3900
aaattgacca aattaaaaag gacgaacaaa aagaggggac tggttgggt ctgggtggta    3960
aatggtggac atccgactgg ggttaagatc tgctgtgcct tctagttgcc agccatctgt   4020
tgtttgcccc tccccgtgc cttccttgac cctggaaggt gccactccca ctgtcctttc    4080
ctaataaaat gaggaaattg catcgcattg tctgagtagg tgtcattcta ttctgggggg   4140
tggggtgggg caggacagca agggggagga ttgggaagac aatagcaggc atgctgggga   4200
tgcggtgggc tctatgggta cccaggtgct gaagaattga cccggttcct cctgggccag   4260
aaagaagcag gcacatcccc ttctctgtga cacaccctgt ccacgcccct ggttcttagt   4320
tccagcccca ctcataggac actcatagct caggagggct ccgccttcaa tcccaccgc    4380
taaagtactt ggagcggtct ctccctccct catcagccca ccaaaccaaa cctagcctcc   4440
aagagtggga agaaattaaa gcaagatagg ctattaagtg cagagggaga gaaaatgcct   4500
ccaacatgtg aggaagtaat gagagaaatc atagaatttt aaggccatga tttaaggcca   4560
tcatggcctt aatcttccgc ttcctcgctc actgactcgc tgcgctcggt cgttcggctg   4620
cggcgagcgg tatcagctca ctcaaaggcg gtaatacggt tatccacaga atcaggggat   4680
aacgcaggaa agaacatgtg agcaaaaggc cagcaaaagg ccaggaaccg taaaaaggcc   4740
gcgttgctgg cgttttttcca taggctccgc cccctgacg agcatcacaa aaatcgacgc   4800
tcaagtcaga ggtggcgaaa cccgacagga ctataaagat accaggcgtt ccccctgga    4860
agctccctcg tgcgctctcc tgttccgacc ctgccgctta ccggatacct gtccgccttt   4920
ctcccttcgg gaagcgtggc gctttctcat agctcacgct gtaggtatct cagttcggtg   4980
taggtcgttc gctccaagct gggctgtgtg cacgaacccc ccgttcagcc cgaccgctgc   5040
gccttatccg gtaactatcg tcttgagtcc aacccggtaa gacacgactt atcgccactg   5100
gcagcagcca ctggtaacag gattagcaga gcgaggtatg taggcggtgc tacagagttc   5160
ttgaagtggt ggcctaacta cggctacact agaagaacag tatttggtat ctgcgctctg   5220
ctgaagccag ttaccttcgg aaaaagagtt ggtagctctt gatccggcaa acaaaccacc   5280
gctggtagcg gtggtttttt tgtttgcaag cagcagatta cgcgcagaaa aaaggatct    5340
caagaagatc ctttgatctt ttctacgggg tctgacgctc agtggaacga aaactcacgt   5400
taagggattt tggtcatgag attatcaaaa aggatcttca cctagatcct ttaaattaa    5460
aaatgaagtt ttaaatcaat ctaaagtata tatgagtaaa cttggtctga cagttaccaa   5520
tgcttaatca gtgaggcacc tatctcagcg atctgtctat ttcgttcatc catagttgcc   5580
tgactcgggg ggggggggcg ctgaggtctg cctcgtgaag aagtgttgc tgactcatac    5640
```

-continued

```
caggcctgaa tcgccccatc atccagccag aaagtgaggg agccacggtt gatgagagct   5700
ttgttgtagg tggaccagtt ggtgattttg aacttttgct ttgccacgga acggtctgcg   5760
ttgtcgggaa gatgcgtgat ctgatccttc aactcagcaa aagttcgatt tattcaacaa   5820
agccgccgtc ccgtcaagtc agcgtaatgc tctgccagtg ttacaaccaa ttaaccaatt   5880
ctgattagaa aaactcatcg agcatcaaat gaaactgcaa tttattcata tcaggattat   5940
caataccata tttttgaaaa agccgtttct gtaatgaagg agaaaactca ccgaggcagt   6000
tccataggat ggcaagatcc tggtatcggt ctgcgattcc gactcgtcca acatcaatac   6060
aacctattaa tttcccctcg tcaaaaataa ggttatcaag tgagaaatca ccatgagtga   6120
cgactgaatc cggtgagaat ggcaaaagct tatgcatttc tttccagact tgttcaacag   6180
gccagccatt acgctcgtca tcaaaatcac tcgcatcaac caaaccgtta ttcattcgtg   6240
attgcgcctg agcgagacga aatacgcgat cgctgttaaa aggacaatta caaacaggaa   6300
tcgaatgcaa ccggcgcagg aacactgcca gcgcatcaac aatattttca cctgaatcag   6360
gatattcttc taatacctgg aatgctgttt tcccggggat cgcagtggtg agtaaccatg   6420
catcatcagg agtacggata aaatgcttga tggtcggaag aggcataaat tccgtcagcc   6480
agtttagtct gaccatctca tctgtaacat cattggcaac gctacctttg ccatgtttca   6540
gaaacaactc tggcgcatcg ggcttcccat acaatcgata gattgtcgca cctgattgcc   6600
cgacattatc gcgagcccat ttatacccat ataaatcagc atccatgttg gaatttaatc   6660
gcggcctcga gcaagacgtt tcccgttgaa tatggctcat aacacccctt gtattactgt   6720
ttatgtaagc agacagtttt attgttcatg atgatatatt tttatcttgt gcaatgtaac   6780
atcagagatt ttgagacaca acgtggcttt cccccccccc ccattattga agcatttatc   6840
agggttattg tctcatgagc ggatacatat ttgaatgtat ttagaaaaat aaacaaatag   6900
gggttccgcg cacatttccc cgaaaagtgc cacctgacgt ctaagaaacc attattatca   6960
tgacattaac ctataaaaat aggcgtatca cgaggccctt tcgtc                    7005
```

```
<210> SEQ ID NO 32
<211> LENGTH: 8256
<212> TYPE: DNA
<213> ORGANISM: Artificial Sequence
<220> FEATURE:
<223> OTHER INFORMATION: Synthetic Construct pAdApt Marburg GP(dTM)

<400> SEQUENCE: 32
```

```
ttaattaacc gcaattctca tgtttgacag cttatcatca tcaataatat accttatttt     60
ggattgaagc caatatgata atgagggggt ggagtttgtg acgtggcgcg gggcgtggga    120
acggggcggg tgacgtagta gtgtggcgga agtgtgatgt tgcaagtgtg gcggaacaca    180
tgtaagcgac ggatgtggca aaagtgacgt ttttggtgtg cgccggtgta cacaggaagt    240
gacaattttc gcgcggtttt aggcggatgt tgtagtaaat ttgggcgtaa ccgagtaaga    300
tttggccatt ttcgcgggaa aactgaataa gaggaagtga aatctgaata attttgtgtt    360
actcatagcg cgtaatattt gtctagggcc gcggggactt tgaccgttta cgtggagact    420
cgcccaggtg tttttctcag gtgttttccg cgttccgggt caaagttggc gttttattat    480
tatagtcagt acgtaccagt gcactggcct agagcggccc cattgcatac gttgtatcca    540
tatcataata tgtacattta tattggctca tgtccaacat taccgccatg ttgacattga    600
ttattgacta gttattaata gtaatcaatt acggggtcat tagttcatag cccatatatg    660
gagttccgcg ttacataact tacggtaaat ggcccgcctg gctgaccgcc caacgacccc    720
```

```
cgcccattga cgtcaataat gacgtatgtt cccatagtaa cgccaatagg gactttccat    780
tgacgtcaat gggtggagta tttacggtaa actgcccact tggcagtaca tcaagtgtat    840
catatgccaa gtacgccccc tattgacgtc aatgacggta atggcccgcc tggcattat    900
gcccagtaca tgaccttatg ggactttcct acttggcagt acatctacgt attagtcatc    960
gctattacca tggtgatgcg gttttggcag tacatcaatg ggcgtggata gcggtttgac   1020
tcacggggat ttccaagtct ccaccccatt gacgtcaatg ggagtttgtt ttggcaccaa   1080
aatcaacggg actttccaaa atgtcgtaac aactccgccc cattgacgca aatgggcggt   1140
aggcgtgtac ggtgggaggt ctatataagc agagctcgtt tagtgaaccg tcagatcgcc   1200
tggagacgcc atccacgctg ttttgacctc catagaagac accgggaccg atccagcctc   1260
cgtcaccgtc gtcgacacgt gtgatcagat atcgcggccg ctctagagtc gaatgaagaa   1320
cattaattgc tgggtaaaag tgattaattt ctttaaattt gaccagaata atattttgtc   1380
agtgaatata ttctcatatc acttgattaa aaacagaaaa ttaccctaac atgaagacca   1440
catgttttcct tatcagtctt atcttaattc aagggacaaa aaatctcccc attttagaga   1500
tagctagtaa taatcaaccc caaaatgtgg attcggtatg ctccggaact ctccagaaga   1560
cagaagacgt ccatctgatg ggattcacac tgagtgggca aaaagttgct gattccccttt   1620
tggaggcatc aagcgatgg gctttcagga caggtgtacc tcccaagaat gttgagtaca   1680
cagaggggga ggaagccaaa acatgctaca atataagtgt aacggatccc tctggaaaat   1740
ccttgctgtt agatcctcct accaacatcc gtgactatcc taaatgcaaa actatccatc   1800
atattcaagg tcaaacccct catgcacagg ggatcgccct tcatttatgg ggagcatttt   1860
ttctgtatga tcgcattgcc tccacaacaa tgtaccgagg caaagtcttc actgaaggga   1920
acatagcagc tatgattgtc aataagacag tgcacaaaat gattttctcg cggcaaggac   1980
aagggtaccg tcatatgaat ctgacttcta ctaataaata ttggacaagt agtaacggaa   2040
cgcaaacgaa tgacactgga tgtttcggcg ctcttcaaga atacaattct acaaagaacc   2100
aaacatgtgc tccgtccaaa atacctccac cactgcccac agcccgtccg gagatcaaac   2160
tcacaagcac cccaactgat gccaccaaac tcaataccac ggacccaagc agtgatgatg   2220
aggacctcgc aacatccggc tcagggtccg gagaacgaga accccacaca acttctgatg   2280
cggtcaccaa gcaagggctt catcaacaa tgccacccac tccctcacca caaccaagca   2340
cgccacagca aggaggaaac aacacaaacc attcccaaga tgctgtgact gaactagaca   2400
aaaataacac aactgcacaa ccgtccatgc cccctcataa cactaccaca atctctacta   2460
acaacacctc caaacacaac ttcagcactc tctctgcacc attacaaaac accaccaatg   2520
acaacacaca gagcacaatc actgaaaatg agcaaaccag tgcccccctcg ataacaaccc   2580
tgcctccaac gggaaatccc accacagcaa agagcaccag cagcaaaaaa ggccccgcca   2640
caacggcacc aaaacacgaca aatgagcatt tcaccagtcc tcccccccacc cccagctcga   2700
ctgcacaaca tcttgtatat ttcagaagaa agcgaagtat cctctggagg gaaggcgaca   2760
tgttcccttt tctggatggg ttaataaatg ctccaattga ttttgaccca gttccaaata   2820
caaaacaat ctttgatgaa tcctctagtt ctggtgcctc ggctgaggaa gatcaacatg   2880
cctccccccaa tattagttta actttatctt attttcctaa tataaatgag aacactgcct   2940
actctggaga aaatgagaat gattgtgatg cagagttaag aatttggagc gttcaggagg   3000
atgacctggc cgcagggctc agttggatac cgttttttgg ccctggaatt gaaggacttt   3060
```

```
acactgctgt tttaattaaa aatcaaaaca atttggtctg caggttgagg cgtctagcca    3120
atcaaactgc caaatccttg gaactcttat tgagagtcac aactgaggaa agaacattct    3180
ccttaatcaa tagacatgct attgactttc tactcacaag atggggagga acatgcaaag    3240
tgcttggacc tgattgttgc atcgggatag aagacttgtc caaaaatatt tcagagcaaa    3300
ttgaccaaat taaaaaggac gaacaaaaag aggggactgg ttggggtctg ggtggtaaat    3360
ggtggacatc cgactggggt taagatctgc tgtgccttct agttgccagc catctgttgt    3420
ttgcccctcc cccgtgcctt ccttgaccct ggaaggtgcc actcccactg tcctttccta    3480
ataaaatgag gaaattgcat cgcattgtct gagtaggtgt cattctattc tggggggtgg    3540
ggtggggcag cacagcaagg gggaggattg gaagacaat agcaggcatg ctggggatgc    3600
ggtgggctct atgggtaccc agggccgcat aacttcgtat aatgtatgct atacgaagtt    3660
ataagatctg tactgaaatg tgtgggcgtg gcttaagggt gggaaagaat atataaggtg    3720
ggggtcttat gtagttttgt atctgttttg cagcagccgc cgccgccatg agcaccaact    3780
cgtttgatgg aagcattgtg agctcatatt tgacaacgcg catgccccca tgggccgggg    3840
tgcgtcagaa tgtgatgggc tccagcattg atggtcgccc cgtcctgccc gcaaactcta    3900
ctaccttgac ctacgagacc gtgtctggaa cgccgttgga gactgcagcc tccgccgccg    3960
cttcagccgc tgcagccacc gcccgcggga ttgtgactga ctttgctttc ctgagcccgc    4020
ttgcaagcag tgcagcttcc cgttcatccg cccgcgatga caagttgacg gctcttttgg    4080
cacaattgga ttctttgacc cgggaactta atgtcgtttc tcagcagctg ttggatctgc    4140
gccagcaggt ttctgccctg aaggcttcct cccctcccaa tgcggtttaa aacataaata    4200
aaaaaccaga ctctgtttgg atttggatca agcaagtgtc ttgctgtctt tatttagggg    4260
ttttgcgcgc gcggtaggcc cgggaccagc ggtctcggtc gttgagggtc ctgtgtattt    4320
tttccaggac gtggtaaagg tgactctgga tgttcagata catgggcata agcccgtctc    4380
tggggtggag gtagcaccac tgcagagctt catgctgcgg ggtggtgttg tagatgatcc    4440
agtcgtagca ggagcgctgg gcgtggtgcc taaaaatgtc tttcagtagc aagctgattg    4500
ccaggggcag gcccttggtg taagtgttta caaagcggtt aagctgggat gggtgcatac    4560
gtggggatat gagatgcatc ttggactgta ttttttaggtt ggctatgttc ccagccatat    4620
ccctccgggg attcatgttg tgcagaacca ccagcacagt gtatccggtg cacttgggaa    4680
atttgtcatg tagcttagaa ggaaatgcgt ggaagaactt ggagacgccc ttgtgacctc    4740
caagattttc catgcattcg tccataatga tggcaatggg cccacgggcg gcggcctggg    4800
cgaagatatt tctgggatca ctaacgtcat agttgtgttc caggatgaga tcgtcatagg    4860 ccattttttac aaagcgcggg cggagggtgc cagactgcgg tataatggtt ccatccggcc    4920
caggggcgta gttaccctca cagatttgca tttcccacgc tttgagttca gatgggggga    4980
tcatgtctac ctgcgggcg atgaagaaaa cggtttccgg ggtaggggag atcagctggg    5040
aagaaagcag gttcctgagc agctgcgact taccgcagcc ggtgggcccg taaatcacac    5100
ctattaccgg ctgcaactgg tagttaagag agctgcagct gccgtcatcc ctgagcaggg    5160
gggccacttc gttaagcatg tccctgactc gcatgttttc cctgaccaaa tccgccagaa    5220
ggcgctcgcc gcccagcgat agcagttctt gcaaggaagc aaagttttc aacgtttga    5280 gaccgtccgc cgtaggcatg cttttgagcg tttgaccaag cagttccagg cggtcccaca    5340
gctcggtcac ctgctctacg gcatctcgat ccagcatatc tcctcgtttc gcgggttggg    5400
gcggctttcg ctgtacggca gtagtcggtg ctcgtccaga cgggccaggg tcatgtcttt    5460
```

```
ccacgggcgc agggtcctcg tcagcgtagt ctgggtcacg gtgaaggggt gcgctccggg    5520
ctgcgcgctg gccagggtgc gcttgaggct ggtcctgctg gtgctgaagc gctgccggtc    5580
ttcgccctgc gcgtcggcca ggtagcattt gaccatggtg tcatagtcca gcccctccgc    5640
ggcgtggccc ttggcgcgca gcttgccctt ggaggaggcg ccgcacgagg ggcagtgcag    5700
acttttgagg gcgtagagct tgggcgcgag aaataccgat tccggggagt aggcatccgc    5760
gccgcaggcc ccgcagacgg tctcgcattc cacgagccag gtgagctctg gccgttcggg    5820
gtcaaaaacc aggtttcccc catgcttttt gatgcgtttc ttacctctgg tttccatgag    5880
ccggtgtcca cgctcggtga cgaaaaggct gtccgtgtcc ccgtatacag acttgagagg    5940
cctgtcctcg agcggtgttc cgcggtcctc ctcgtataga aactcggacc actctgagac    6000
aaaggctcgc gtccaggcca gcacgaagga ggctaagtgg gaggggtagc ggtcgttgtc    6060
cactaggggg tccactcgct ccagggtgtg aagacacatg tcgccctctt cggcatcaag    6120
gaaggtgatt ggtttgtagg tgtaggccac gtgaccgggt gttcctgaag gggggctata    6180 aaaggggggtg ggggcgcgtt cgtcctcact ctcttccgca tcgctgtctg cgagggccag    6240
ctgttggggt gagtcgacgc gaggctggat ggccttcccc attatgattc ttctcgcttc    6300
cggcggcatc gggatgcccg cgttgcaggc catgctgtcc aggcaggtag atgacgacca    6360
tcagggacag cttcaaggcc agcaaaaggc caggaaccgt aaaaaggccg cgttgctggc    6420 gttttttccat aggctccgcc ccctgacga gcatcacaaa aatcgacgct caagtcagag    6480
gtggcgaaac ccgacaggac tataaagata ccaggcgttt ccccctggaa gctccctcgt    6540
gcgctctcct gttccgaccc tgccgcttac cggatacctg tccgcctttc tcccttcggg    6600
aagcgtggcg ctttctcata gctcacgctg taggtatctc agttcggtgt aggtcgttcg    6660
ctccaagctg ggctgtgtgc acgaaccccc cgttcagccc gaccgctgcg ccttatccgg    6720
taactatcgt cttgagtcca acccggtaag acacgactta tcgccactgg cagcagccac    6780
tggtaacagg attagcagag cgaggtatgt aggcggtgct acagagttct tgaagtggtg    6840
gcctaactac ggctacacta aaggacagt atttggtatc tgcgctctgc tgaagccagt    6900
taccttcgga aaaagagttg gtagctcttg atccggcaaa caaaccaccg ctggtagcgg    6960 tggtttttttt gtttgcaagc agcagattac gcgcagaaaa aaaggatctc aagaagatcc    7020
tttgatcttt tctacggggt ctgacgctca gtggaacgaa aactcacgtt aagggatttt    7080
ggtcatgaga ttatcaaaaa ggatcttcac ctagatcctt ttaaattaaa aatgaagttt    7140
taaatcaatc taaagtatat atgagtaaac ttggtctgac agttaccaat gcttaatcag    7200
tgaggcacct atctcagcga tctgtctatt tcgttcatcc atagttgcct gactccccgt    7260
cgtgtagata actacgatac gggagggctt accatctggc cccagtgctg caatgatacc    7320
gcgagaccca cgctcaccgg ctccagattt atcagcaata aaccagccag ccggaagggc    7380
cgagcgcaga agtggtcctg caactttatc cgcctccatc cagtctatta attgttgccg    7440
ggaagctaga gtaagtagtt cgccagttaa tagtttgcgc aacgttgttg ccattgctgc    7500
aggcatcgtg gtgtcacgct cgtcgtttgg tatggcttca ttcagctccg gttcccaacg    7560
atcaaggcga gttacatgat cccccatgtt gtgcaaaaaa gcggttagct ccttcggtcc    7620
tccgatcgtt gtcagaagta agttggccgc agtgttatca ctcatggtta tggcagcact    7680
gcataattct cttactgtca tgccatccgt aagatgcttt tctgtgactg gtgagtactc    7740
aaccaagtca ttctgagaat agtgtatgcg gcgaccgagt tgctcttgcc cggcgtcaac    7800
```

-continued

| | |
|---|---|
| acgggataat accgcgccac atagcagaac tttaaaagtg ctcatcattg gaaaacgttc | 7860 |
| ttcggggcga aaactctcaa ggatcttacc gctgttgaga tccagttcga tgtaacccac | 7920 |
| tcgtgcaccc aactgatctt cagcatcttt tactttcacc agcgtttctg ggtgagcaaa | 7980 |
| aacaggaagg caaaatgccg caaaaaaggg aataagggcg acacggaaat gttgaatact | 8040 |
| catactcttc cttttttcaat attattgaag catttatcag ggttattgtc tcatgagcgg | 8100 |
| atacatattt gaatgtattt agaaaaataa acaaataggg gttccgcgca catttccccg | 8160 |
| aaaagtgcca cctgacgtct aagaaaccat tattatcatg acattaacct ataaaaatag | 8220 |
| gcgtatcacg aggccctttc gtcttcaaga attgtt | 8256 |

<210> SEQ ID NO 33
<211> LENGTH: 6447
<212> TYPE: DNA
<213> ORGANISM: Artificial Sequence
<220> FEATURE:
<223> OTHER INFORMATION: Synthetic Construct pVR1012x/s Lassa GP

<400> SEQUENCE: 33
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
ggggtcatta gttcatagcc catatatgga gttccgcgtt acataactta cggtaaatgg 420
cccgcctggc tgaccgccca acgacccccg cccattgacg tcaataatga cgtatgttcc 480
catagtaacg ccaataggga ctttccattg acgtcaatgg gtggagtatt tacggtaaac 540
tgcccacttg gcagtacatc aagtgtatca tatgccaagt acgcccccta ttgacgtcaa 600
tgacggtaaa tggcccgcct ggcattatgc ccagtacatg accttatggg actttcctac 660
ttggcagtac atctacgtat tagtcatcgc tattaccatg gtgatgcggt tttggcagta 720
catcaatggg cgtggatagc ggtttgactc acggggattt ccaagtctcc accccattga 780
cgtcaatggg agtttgtttt ggcaccaaaa tcaacgggac tttccaaaat gtcgtaacaa 840
ctccgcccca ttgacgcaaa tgggcggtag gcgtgtacgg tgggaggtct atataagcag 900
agctcgttta gtgaaccgtc agatcgcctg gagacgccat ccacgctgtt ttgacctcca 960
tagaagacac cgggaccgat ccagcctccg cggccgggaa cggtgcattg gaacgcggat 1020
tccccgtgcc aagagtgacg taagtaccgc ctatagactc tataggcaca cccctttggc 1080
tcttatgcat gctatactgt ttttggcttg gggcctatac acccccgctt ccttatgcta 1140
taggtgatgg tatagcttag cctataggtg tgggttattg accattattg accactcccc 1200
tattggtgac gatactttcc attactaatc cataacatgg ctctttgcca caactatctc 1260
tattggctat atgccaatac tctgtccttc agagactgac acggactctg tatttttaca 1320
ggatggggtc ccatttatta tttacaaatt cacatataca acaacgccgt cccccgtgcc 1380
cgcagttttt attaaacata gcgtgggatc tccacgcgaa tctcgggtac gtgttccgga 1440
catgggctct tctccggtag cggcggagct tccacatccg agccctggtc ccatgcctcc 1500
agcggctcat ggtcgctcgg cagctccttg ctcctaacag tggaggccag acttaggcac 1560
agcacaatgc ccaccaccac cagtgtgccg cacaaggccg tggcggtagg gtatgtgtct 1620

-continued

```
gaaaatgagc gtggagattg ggctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tcctttccat gggtcttttc    1860
tgcagtcacc gtcgtcgaca cgtgtgatca gatatcgcgg ccgctctaga atttaggatt    1920
gcgcttttag agattcacta ctagttagga attcctaaat catggggcag attattacat    1980
tctttcaaga agtgccacat gtaatagagg aagtcatgaa cattgtgcta attgcgcttt    2040
ctctattggc aatcttgaag ggcttgtata acatcgctac atgtgggatt attggattgg    2100
ttgccttttt attcttgtgt ggcaagtctt gttccctaac ccttaaaggg ggatatgagc    2160
tgcaaacctt agaattaaat atggagaccc taaacatgac catgccctta tcatgcacca    2220
agaacagcag tcatcattac ataagagtgg gcaatgagac tggattagaa ttgactttaa    2280
ctaacaccag cattataaat cacaaatttt gcaacttatc cgatgctcac aaaaagaatc    2340
tttatgatca tgctctcatg agcatcatct caacattcca tctatccatt ccaaacttca    2400
atcagtatga agccatgagt tgtgatttca atggagggaa aatcagtgtg caatacaacc    2460
tctctcattc ctatgctggg gatgcggccg aacactgtgg gacagttgcc aacggagtgt    2520
tgcaaacatt tatgagaatg gcctggggtg aagatacat tgcattagac tcaggaaagg    2580
gaaactggga ctgtataatg accagctacc agtacctgat aattcaaaat acaacatggg    2640
aggaccactg ccaattctca agaccgtctc ctatcgggta ccttggcctt tgtcacaaa    2700 ggacaagaga tatatatata agtaggaggc tcttggggac cttcacctgg acattgtcag    2760
attctgaggg caatgaaaca ccaggtggtt attgtttaac caggtggatg ctaattgaag    2820
cagaactcaa gtgttttggg aatacagctg tggcaaaatg caatgagaag catgatgagg    2880
agttttgtga catgctgaga ttgtttgatt caacaagca agcaatccgt aggttgaagg    2940
ctgaggccca gatgagtatt caattaataa ataaagccgt gaatgcctta atcaatgatc    3000
aattaatcat gaagaaccat ttaagagaca tcatgggcat tccctactgc aattacagca    3060
agtattggta ccttaatcat actagtagcg ggagaacatc actaccaaag tgttggctta    3120
tatccaatgg gtcatatcta aatgaaaccc agttctctga tgacatagaa cagcaagccg    3180
acaatatgat cacagagatg cttcagaaag aatacattga aagacaaggg aaaacgccct    3240
tgggactagt ggacatttc atcttttagca caagctttta tctgatcagc atttcttgc     3300 atttaattaa aatccctaca catcgacaca tcgttgggaa accctgtccc aaaccccata    3360
gactaaatca catgggagta tgttcctgtg gactgtacaa acaccctggt gttccaacaa    3420
agtggaagag ataggatcc agatctgctg tgccttctag ttgccagcca tctgttgttt     3480 gccctcccc cgtgccttcc ttgacccctgg aaggtgccac tcccactgtc ctttcctaat    3540
aaaatgagga aattgcatcg cattgtctga gtaggtgtca ttctattctg ggggtggg     3600 tggggcagga cagcaagggg gaggattggg aagacaatag caggcatgct ggggatgcgg    3660
tgggctctat gggtacccag gtgctgaaga attgacccgg ttcctcctgg gccagaaaga    3720
agcaggcaca tccccttctc tgtgacacac cctgtccacg ccctggttc ttagttccag     3780 ccccactcat aggacactca tagctcagga gggctccgcc ttcaatccca cccgctaaag    3840
tacttggagc ggtctctccc tccctcatca gcccaccaaa ccaaacctag cctccaagag    3900
tgggaagaaa ttaaagcaag ataggctatt aagtgcagag ggagagaaaa tgcctccaac    3960
```

```
atgtgaggaa gtaatgagag aaatcataga attttaaggc catcatggcc ttaatcttcc    4020
gcttcctcgc tcactgactc gctgcgctcg gtcgttcggc tgcggcgagc ggtatcagct    4080
cactcaaagg cggtaatacg gttatccaca gaatcagggg ataacgcagg aaagaacatg    4140
tgagcaaaag gccagcaaaa ggccaggaac cgtaaaaagg ccgcgttgct ggcgtttttc    4200
cataggctcc gcccccctga cgagcatcac aaaaatcgac gctcaagtca gaggtggcga    4260
aacccgacag gactataaag ataccaggcg tttccccctg gaagctccct cgtgcgctct    4320
cctgttccga ccctgccgct taccggatac ctgtccgcct ttctcccttc gggaagcgtg    4380
gcgctttctc atagctcacg ctgtaggtat ctcagttcgg tgtaggtcgt tcgctccaag    4440
ctgggctgtg tgcacgaacc ccccgttcag cccgaccgct gcgccttatc cggtaactat    4500
cgtcttgagt ccaacccggt aagacacgac ttatcgccac tggcagcagc cactggtaac    4560
aggattagca gagcgaggta tgtaggcggt gctacagagt tcttgaagtg gtggcctaac    4620
tacggctaca ctagaagaac agtatttggt atctgcgctc tgctgaagcc agttaccttc    4680
ggaaaaagag ttggtagctc ttgatccggc aaacaaacca ccgctggtag cggtggtttt    4740
tttgtttgca agcagcagat tacgcgcaga aaaaaaggat ctcaagaaga tcctttgatc    4800
ttttctacgg ggtctgacgc tcagtggaac gaaaactcac gttaagggat tttggtcatg    4860
agattatcaa aaaggatctt cacctagatc cttttaaatt aaaaatgaag ttttaaatca    4920
atctaaagta tatatgagta aacttggtct gacagttacc aatgcttaat cagtgaggca    4980
cctatctcag cgatctgtct atttcgttca tccatagttg cctgactcgg ggggggggg    5040
cgctgaggtc tgcctcgtga agaaggtgtt gctgactcat accaggcctg aatcgcccca    5100
tcatccagcc agaaagtgag ggagccacgg ttgatgagag ctttgttgta ggtggaccag    5160
ttggtgattt tgaacttttg ctttgccacg gaacggtctg cgttgtcggg aagatgcgtg    5220
atctgatcct tcaactcagc aaaagttcga tttattcaac aaagccgccg tcccgtcaag    5280
tcagcgtaat gctctgccag tgttacaacc aattaaccaa ttctgattag aaaaactcat    5340
cgagcatcaa atgaaactgc aatttattca tatcaggatt atcaatacca tattttgaa    5400
aaagccgttt ctgtaatgaa ggagaaaact caccgaggca gttccatagg atggcaagat    5460
cctggtatcg gtctgcgatt ccgactcgtc aacatcaat acaacctatt aatttcccct    5520
cgtcaaaaat aaggttatca agtgagaaat caccatgagt gacgactgaa tccggtgaga    5580
atggcaaaag cttatgcatt tctttccaga cttgttcaac aggccagcca ttacgctcgt    5640
catcaaaatc actcgcatca accaaaccgt tattcattcg tgattgcgcc tgagcgagac    5700
gaaatacgcg atcgctgtta aaaggacaat tacaaacagg aatcgaatgc aaccggcgca    5760
ggaacactgc cagcgcatca acaatatttt cacctgaatc aggatattct tctaatacct    5820
ggaatgctgt ttcccgggg atcgcagtgg tgagtaacca tgcatcatca ggagtacgga    5880
taaaatgctt gatggtcgga agaggcataa attccgtcag ccagtttagt ctgaccatct    5940
catctgtaac atcattggca acgctacctt tgccatgttt cagaaacaac tctggcgcat    6000
cgggcttccc atacaatcga tagattgtcg cacctgattg cccgacatta tcgcgagccc    6060
atttataccc atataaatca gcatccatgt tggaatttaa tcgcggcctc gagcaagacg    6120
tttcccgttg aatatggctc ataacacccc ttgtattact gtttatgtaa gcagacagtt    6180
ttattgttca tgatgatata ttttatctt gtgcaatgta acatcagaga ttttgagaca    6240
caacgtggct ttcccccccc ccccattatt gaagcattta tcagggttat tgtctcatga    6300
gcggatacat atttgaatgt atttagaaaa ataaacaaat aggggttccg cgcacatttc    6360
```
cccgaaaagt gccacctgac gtctaagaaa ccattattat catgacatta acctataaaa    6420
ataggcgtat cacgaggccc tttcgtc                                         6447

<210> SEQ ID NO 34
<211> LENGTH: 6258
<212> TYPE: DNA
<213> ORGANISM: Artificial Sequence
<220> FEATURE:
<223> OTHER INFORMATION: Synthetic Construct pVR1012x/s Lassa GP(dTM)

<400> SEQUENCE: 34
tcgcgcgttt cggtgatgac ggtgaaaacc tctgacacat gcagctcccg agacggtcay    60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt tgacctcca     960 tagaagacac cgggaccgat ccagcctccg cggccgggaa cggtgcattg gaacgcggat    1020
tccccgtgcc aagagtgacg taagtaccgc ctatagactc tataggcaca cccctttggc    1080
tcttatgcat gctatactgt ttttggcttg gggcctatac accccgctt ccttatgcta    1140 taggtgatgg tatagcttag cctataggtg tgggttattg accattattg accactcccc    1200
tattggtgac gatactttcc attactaatc cataacatgg ctctttgcca caactatctc    1260
tattggctat atgccaatac tctgtccttc agagactgac acggactctg tatttttaca    1320
ggatggggtc ccattattta tttacaaatt cacatataca acaacgccgt ccccgtgcc     1380 cgcagttttt attaaacata gcgtgggatc tccacgcgaa tctcgggtac gtgttccgga    1440
catgggctct tctccggtag cggcggagct tccacatccg agccctggtc ccatgcctcc    1500
agcggctcat ggtcgctcgg cagctccttg ctcctaacag tggaggccag acttaggcac    1560
agcacaatgc ccaccaccac cagtgtgccg cacaaggccg tggcgtaggg gtatgtgtct    1620
gaaaatgagc gtggagattg gctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tcctttccat gggtcttttc    1860
tgcagtcacc gtcgtcgaca cgtgtgatca gatatcgcgg ccgctctaga atttaggatt    1920

```
gcgcttttag agattcacta ctagttagga attcctaaat catggggcag attattacat    1980
tctttcaaga agtgccacat gtaatagagg aagtcatgaa cattgtgcta attgcgcttt    2040
ctctattggc aatcttgaag ggcttgtata acatcgctac atgtgggatt attggattgg    2100
ttgcctttt attcttgtgt ggcaagtctt gttccctaac ccttaaaggg ggatatgagc    2160
tgcaaacctt agaattaaat atggagaccc taaacatgac catgcccta tcatgcacca    2220
agaacagcag tcatcattac ataagagtgg gcaatgagac tggattagaa ttgactttaa    2280
ctaacaccag cattataaat cacaaatttt gcaacttatc cgatgctcac aaaaagaatc    2340
tttatgatca tgctctcatg agcatcatct caacattcca tctatccatt ccaaacttca    2400
atcagtatga agccatgagt tgtgatttca atggagggaa aatcagtgtg caatacaacc    2460
tctctcattc ctatgctggg gatgcggccg aacactgtgg gacagttgcc aacggagtgt    2520
tgcaaacatt tatgagaatg gcctggggtg aagatacat tgcattagac tcaggaaagg    2580
gaaactggga ctgtataatg accagctacc agtacctgat aattcaaaat acaacatggg    2640
aggaccactg ccaattctca agaccgtctc ctatcgggta ccttggcctt ttgtcacaaa    2700
ggacaagaga tatatatata agtaggaggc tcttgggac cttcacctgg acattgtcag    2760
attctgaggg caatgaaaca ccaggtggtt attgtttaac caggtggatg ctaattgaag    2820
cagaactcaa gtgttttggg aatacagctg tggcaaaatg caatgagaag catgatgagg    2880
agttttgtga catgctgaga ttgtttgatt tcaacaagca agcaatccgt aggttgaagg    2940
ctgaggccca gatgagtatt caattaataa ataaagccgt gaatgcctta atcaatgatc    3000
aattaatcat gaagaaccat ttaagagaca tcatgggcat tccctactgc aattacagca    3060
agtattggta ccttaatcat actagtagcg ggagaacatc actaccaaag tgttggctta    3120
tatccaatgg gtcatatcta aatgaaaccc agttctctga tgacatagaa cagcaagccg    3180
acaatatgat cacagagatg cttcagaaag aatacattga agacaagggg aaaacgccct    3240
tgtagggatc cagatctgct gtgccttcta gttgccagcc atctgttgtt tgcccctccc    3300
ccgtgccttc cttgaccctg gaaggtgcca ctcccactgt cctttcctaa taaaatgagg    3360
aaattgcatc gcattgtctg agtaggtgtc attctattct gggggtggg gtggggcagg    3420
acagcaaggg ggaggattgg gaagacaata gcaggcatgc tggggatgcg gtgggctcta    3480
tgggtaccca ggtgctgaag aattgacccg gttcctcctg ggccagaaag aagcaggcac    3540
atccccttct ctgtgacaca ccctgtccac gcccctggtt cttagttcca gccccactca    3600
taggacactc atagctcagg agggctccgc cttcaatccc acccgctaaa gtacttggag    3660
cggtctctcc ctccctcatc agcccaccaa accaaaccta gcctccaaga gtgggaagaa    3720
attaaagcaa gataggctat taagtgcaga gggagagaaa atgcctccaa catgtgagga    3780
agtaatgaga gaaatcatag aattttaagg ccatcatggc cttaatcttc gcttcctcg    3840
ctcactgact cgctgcgctc ggtcgttcgg ctgcggcgag cggtatcagc tcactcaaag    3900
gcggtaatac ggttatccac agaatcaggg gataacgcag gaaagaacat gtgagcaaaa    3960
ggccagcaaa aggccaggaa ccgtaaaaag gccgcgttgc tggcgttttt ccataggctc    4020
cgcccccctg acgagcatca caaaaatcga cgctcaagtc agaggtggcg aaacccgaca    4080
ggactataaa gataccaggc gtttccccct ggaagctccc tcgtgcgctc tcctgttccg    4140
accctgccgc ttaccggata cctgtccgcc tttctccctt cgggaagcgt ggcgctttct    4200
catagctcac gctgtaggta tctcagttcg gtgtaggtcg ttcgctccaa gctgggctgt    4260
gtgcacgaac cccccgttca gcccgaccgc tgcgccttat ccggtaacta tcgtcttgag    4320
```

-continued tccaacccgg taagacacga cttatcgcca ctggcagcag ccactggtaa caggattagc 4380
agagcgaggt atgtaggcgg tgctacagag ttcttgaagt ggtggcctaa ctacggctac 4440
actagaagaa cagtatttgg tatctgcgct ctgctgaagc cagttacctt cggaaaaaga 4500
gttggtagct cttgatccgg caaacaaacc accgctggta gcggtggttt ttttgtttgc 4560
aagcagcaga ttacgcgcag aaaaaaagga tctcaagaag atcctttgat cttttctacg 4620
gggtctgacg ctcagtggaa cgaaaactca cgttaaggga ttttggtcat gagattatca 4680
aaaaggatct tcacctagat ccttttaaat taaaaatgaa gttttaaatc aatctaaagt 4740
atatatgagt aaacttggtc tgacagttac caatgcttaa tcagtgaggc acctatctca 4800
gcgatctgtc tatttcgttc atccatagtt gcctgactcg gggggggggg gcgctgaggt 4860
ctgcctcgtg aagaaggtgt tgctgactca taccaggcct gaatcgcccc atcatccagc 4920
cagaaagtga gggagccacg gttgatgaga gctttgttgt aggtggacca gttggtgatt 4980
ttgaactttt gctttgccac ggaacggtct gcgttgtcgg gaagatgcgt gatctgatcc 5040
ttcaactcag caaaagttcg atttattcaa caaagccgcc gtcccgtcaa gtcagcgtaa 5100
tgctctgcca gtgttacaac caattaacca attctgatta gaaaaactca tcgagcatca 5160
aatgaaactg caatttattc atatcaggat tatcaatacc atatttttga aaaagccgtt 5220
tctgtaatga aggagaaaac tcaccgaggc agttccatag gatggcaaga tcctggtatc 5280
ggtctgcgat tccgactcgt ccaacatcaa tacaacctat taatttcccc tcgtcaaaaa 5340
taaggttatc aagtgagaaa tcaccatgag tgacgactga atccggtgag aatggcaaaa 5400
gcttatgcat ttctttccag acttgttcaa caggccagcc attacgctcg tcatcaaaat 5460
cactcgcatc aaccaaaccg ttattcattc gtgattgcgc ctgagcgaga cgaaatacgc 5520
gatcgctgtt aaaaggacaa ttacaaacag gaatcgaatg caaccggcgc aggaacactg 5580
ccagcgcatc aacaatattt tcacctgaat caggatattc ttctaatacc tggaatgctg 5640
ttttcccggg gatcgcagtg gtgagtaacc atgcatcatc aggagtacgg ataaaatgct 5700
tgatggtcgg aagaggcata aattccgtca gccagtttag tctgaccatc tcatctgtaa 5760
catcattggc aacgctacct ttgccatgtt tcagaaacaa ctctggcgca tcgggcttcc 5820
catacaatcg atagattgtc gcacctgatt gcccgacatt atcgcgagcc catttatacc 5880
catataaatc agcatccatg ttggaattta atcgcggcct cgagcaagac gtttcccgtt 5940
gaatatggct cataacaccc cttgtattac tgtttatgta agcagacagt tttattgttc 6000
atgatgatat atttttatct tgtgcaatgt aacatcagag attttgagac acaacgtggc 6060
tttccccccc cccccattat tgaagcattt atcagggtta ttgtctcatg agcggataca 6120
tatttgaatg tatttagaaa aataaacaaa taggggttcc gcgcacattt ccccgaaaag 6180
tgccacctga cgtctaagaa accattatta tcatgacatt aacctataaa aataggcgta 6240
tcacgaggcc ctttcgtc 6258

<210> SEQ ID NO 35
<211> LENGTH: 7711
<212> TYPE: DNA
<213> ORGANISM: Artificial Sequence
<220> FEATURE:
<223> OTHER INFORMATION: Synthetic Construct pAdApt Lassa GP

<400> SEQUENCE: 35
ttaattaacc gcaattctca tgtttgacag cttatcatca tcaataatat accttatttt 60

```
ggattgaagc caatatgata atgagggggt ggagtttgtg acgtggcgcg gggcgtggga      120
acggggcggg tgacgtagta gtgtggcgga agtgtgatgt tgcaagtgtg gcggaacaca      180
tgtaagcgac ggatgtggca aaagtgacgt ttttggtgtg cgccggtgta cacaggaagt      240
gacaattttc gcgcggtttt aggcggatgt tgtagtaaat ttgggcgtaa ccgagtaaga      300
tttggccatt ttcgcgggaa aactgaataa gaggaagtga aatctgaata attttgtgtt      360
actcatagcg cgtaatattt gtctagggcc gcggggactt tgaccgttta cgtggagact      420
cgcccaggtg tttttctcag gtgttttccg cgttccgggt caaagttggc gttttattat      480
tatagtcagt acgtaccagt gcactggcct agagcggccc cattgcatac gttgtatcca      540
tatcataata tgtacattta tattggctca tgtccaacat taccgccatg ttgacattga      600
ttattgacta gttattaata gtaatcaatt acggggtcat tagttcatag cccatatatg      660
gagttccgcg ttacataact tacggtaaat ggcccgcctg gctgaccgcc caacgacccc      720
cgcccattga cgtcaataat gacgtatgtt cccatagtaa cgccaatagg gactttccat      780
tgacgtcaat gggtggagta tttacggtaa actgcccact tggcagtaca tcaagtgtat      840
catatgccaa gtacgccccc tattgacgtc aatgacggta atggcccgc  ctggcattat      900 gcccagtaca tgaccttatg ggactttcct acttggcagt acatctacgt attagtcatc      960
gctattacca tggtgatgcg gttttggcag tacatcaatg ggcgtggata gcggtttgac     1020
tcacggggat ttccaagtct ccaccccatt gacgtcaatg ggagtttgtt ttggcaccaa     1080
aatcaacggg actttccaaa atgtcgtaac aactccgccc cattgacgca atgggcggt      1140 aggcgtgtac ggtgggaggt ctatataagc agagctcgtt tagtgaaccg tcagatcgcc     1200
tggagacgcc atccacgctg ttttgacctc catagaagac accgggaccg atccagcctc     1260
cgtcaccgtc gtcgacacgt gtgatcagat atcgcggccg ctctagaatt taggattgcg     1320
cttttagaga ttcactacta gttaggaatt cctaaatcat ggggcagatt attacattct     1380
ttcaagaagt gccacatgta atagaggaag tcatgaacat tgtgctaatt gcgctttctc     1440
tattggcaat cttgaagggc ttgtataaca tcgctacatg tgggattatt ggattggttg     1500 ccttttatt cttgtgtggc aagtcttgtt ccctaaccct taaaggggga tatgagctgc     1560
aaaccttaga attaaatatg gagaccctaa acatgaccat gcccttatca tgcaccaaga     1620
acagcagtca tcattacata agagtgggca atgagactgg attagaattg actttaacta     1680
acaccagcat tataaatcac aaattttgca acttatccga tgctcacaaa aagaatcttt     1740
atgatcatgc tctcatgagc atcatctcaa cattccatct atccattcca aacttcaatc     1800
agtatgaagc catgagttgt gatttcaatg gagggaaaat cagtgtgcaa tacaacctct     1860
ctcattccta tgctggggat gcggccgaac actgtggaca agttgccaac ggagtgttgc     1920
aaacatttat gagaatggcc tggggtggaa gatacattgc attagactca ggaaagggaa     1980
actgggacta tataatgacc agctaccagt acctgataat tcaaaataca acatgggagg     2040
accactgcca attctcaaga ccgtctccta tcgggtacct tggccttttg tcacaaagga     2100
caagagatat atatataagt aggaggctct tgggaccttt cacctggaca ttgtcagatt     2160
ctgagggcaa tgaaacacca ggtggttatt gtttaaccag gtggatgcta attgaagcag     2220
aactcaagtg ttttgggaat acagctgtgg caaaatgcaa tgagaagcat gatgaggagt     2280
tttgtgacat gctgagattg tttgatttca acaagcaagc aatccgtagg ttgaaggctg     2340
aggcccagat gagtattcaa ttaataaata agccgtgaa  tgccttaatc aatgatcaat     2400
taatcatgaa gaaccattta agagacatca tgggcatttc ctactgcaat tacagcaagt     2460
```

```
attggtacct taatcatact agtagcggga gaacatcact accaaagtgt tggcttatat    2520
ccaatgggtc atatctaaat gaaacccagt tctctgatga catagaacag caagccgaca    2580
atatgatcac agagatgctt cagaaagaat acattgaaag acaagggaaa acgcccttgg    2640
gactagtgga cattttcatc tttagcacaa gcttttatct gatcagcatt ttcttgcatt    2700
taattaaaat ccctcacacat cgacacatcg ttgggaaacc ctgtcccaaa ccccatagac    2760
taaatcacat gggagtatgt tcctgtggac tgtacaaaca ccctggtgtt ccaacaaagt    2820
ggaagagata gggatccaga tctgctgtgc cttctagttg ccagccatct gttgtttgcc    2880
cctcccccgt gccttccttg accctggaag gtgccactcc cactgtcctt tcctaataaa    2940
atgaggaaat tgcatcgcat tgtctgagta ggtgtcattc tattctgggg ggtggggtgg    3000
ggcagcacag caaggggag gattgggaag acaatagcag gcatgctggg gatgcggtgg    3060
gctctatggg tacccaggc cgcataactt cgtataatgt atgctatacg aagttataag    3120
atctgtactg aaatgtgtgg gcgtggctta agggtgggaa agaatatata aggtgggggt    3180
cttatgtagt tttgtatctg ttttgcagca gccgccgccg ccatgagcac caactcgttt    3240
gatggaagca ttgtgagctc atatttgaca acgcgcatgc ccccatgggc cggggtgcgt    3300
cagaatgtga tgggctccag cattgatggt cgccccgtcc tgcccgcaaa ctctactacc    3360
ttgacctacg agaccgtgtc tggaacgccg ttggagactg cagcctccgc cgccgcttca    3420
gccgctgcag ccaccgcccg cgggattgtg actgactttg cttttcctgag cccgcttgca    3480 agcagtgcag cttcccgttc atccgcccgc gatgacaagt tgacggctct tttggcacaa    3540
ttggattctt tgacccggga acttaatgtc gtttctcagc agctgttgga tctgcgccag    3600
caggtttctg ccctgaaggc ttcctcccct cccaatgcgg tttaaaacat aaataaaaaa    3660
ccagactctg tttggatttg gatcaagcaa gtgtcttgct gtctttattt aggggttttg    3720
cgcgcgcggt aggcccggga ccagcggtct cggtcgttga gggtcctgtg tattttttcc    3780
aggacgtggt aaaggtgact ctggatgttc agatacatgg gcataagccc gtctctgggg    3840
tggaggtagc accactgcag agcttcatgc tgcggggtgg tgttgtagat gatccagtcg    3900
tagcaggagc gctgggcgtg gtgcctaaaa atgtctttca gtagcaagct gattgccagg    3960 ggcaggcct tggtgtaagt gtttacaaag cggttaagct gggatgggtg catacgtggg    4020
gatatgagat gcatcttgga ctgtattttt aggttggcta tgttcccagc catatccctc    4080
cggggattca tgttgtgcag aaccaccagc acagtgtatc cggtgcactt gggaaatttg    4140
tcatgtagct tagaaggaaa tgcgtggaag aacttggaga cgcccttgtg acctccaaga    4200
ttttccatgc attcgtccat aatgatgca atgggcccac gggcggcggc ctgggcgaag    4260
atatttctgg gatcactaac gtcatagttg tgttccagga tgagatcgtc ataggccatt    4320
tttacaaagc gcgggcggag ggtgccgac tgcggtataa tggttccatc cggcccaggg    4380
gcgtagttac cctcacagat ttgcatttcc cacgctttga gttcagatgg ggggatcatg    4440
tctacctgcg gggcgatgaa gaaaacggtt ccggggtag gggagatcag ctgggaagaa    4500
agcaggttcc tgagcagctg cgacttaccg cagccggtgg gcccgtaaat cacacctatt    4560
accggctgca actggtagtt aagagagctg cagctgccgt catccctgag caggggggcc    4620
acttcgttaa gcatgtccct gactcgcatg ttttccctga ccaaatccgc cagaaggcgc    4680
tcgccgccca gcgatagcag ttcttgcaag gaagcaaagt ttttcaacgg tttgagaccg    4740
tccgccgtag gcatgctttt gagcgtttga ccaagcagtt ccaggcggtc ccacagctcg    4800
```

```
gtcacctgct ctacggcatc tcgatccagc atatctcctc gtttcgcggg ttggggcggc    4860
tttcgctgta cggcagtagt cggtgctcgt ccagacgggc cagggtcatg tctttccacg    4920
ggcgcagggt cctcgtcagc gtagtctggg tcacggtgaa ggggtgcgct ccgggctgcg    4980
cgctggccag ggtgcgcttg aggctggtcc tgctggtgct gaagcgctgc cggtcttcgc    5040
cctgcgcgtc ggccaggtag catttgacca tggtgtcata gtccagcccc tccgcgcgt    5100 ggcccttggc gcgcagcttg cccttggagg aggcgccgca cgaggggcag tgcagacttt    5160
tgagggcgta gagcttgggc gcgagaaata ccgattccgg ggagtaggca tccgcgccgc    5220
aggccccgca gacggtctcg cattccacga gccaggtgag ctctggccgt tcggggtcaa    5280
aaaccaggtt tccccatgc tttttgatgc gtttcttacc tctggtttcc atgagccggt    5340
gtccacgctc ggtgacgaaa aggctgtccg tgtccccgta tacagacttg agaggcctgt    5400
cctcgagcgg tgttccgcgg tcctcctcgt atagaaactc ggaccactct gagacaaagg    5460
ctcgcgtcca ggccagcacg aaggaggcta agtgggaggg gtagcggtcg ttgtccacta    5520
gggggtccac tcgctccagg gtgtgaagac acatgtcgcc ctcttcggca tcaaggaagg    5580
tgattggttt gtaggtgtag gccacgtgac cgggtgttcc tgaagggggg ctataaaagg    5640
gggtgggggc gcgttcgtcc tcactctctt ccgcatcgct gtctgcgagg ccagctgtt    5700 ggggtgagtc gacgcgaggc tggatggcct tccccattat gattcttctc gcttccggcg    5760
gcatcgggat gcccgcgttg caggccatgc tgtccaggca ggtagatgac gaccatcagg    5820
gacagcttca aggccagcaa aaggccagga accgtaaaaa ggccgcgttg ctggcgtttt    5880
tccataggct ccgcccccct gacgagcatc acaaaaatcg acgctcaagt cagaggtggc    5940
gaaacccgac aggactataa agataccagg cgtttccccc tggaagctcc ctcgtgcgct    6000
ctcctgttcc gaccctgccg cttaccggat acctgtccgc ctttctccct cgggaagcg    6060 tggcgctttc tcatagctca cgctgtaggt atctcagttc ggtgtaggtc gttcgctcca    6120
agctgggctg tgtgcacgaa ccccccgttc agcccgaccg ctgcgcctta ccggtaact    6180 atcgtcttga gtccaacccg gtaagacacg acttatcgcc actggcagca gccactggta    6240
acaggattag cagagcgagg tatgtaggcg gtgctacaga gttcttgaag tggtggccta    6300
actacggcta cactagaagg acagtatttg gtatctgcgc tctgctgaag ccagttacct    6360
tcggaaaaag agttggtagc tcttgatccg gcaaacaaac caccgctggt agcggtggtt    6420
tttttgtttg caagcagcag attacgcgca gaaaaaaagg atctcaagaa gatcctttga    6480
tcttttctac ggggtctgac gctcagtgga acgaaaactc acgttaaggg attttggtca    6540
tgagattatc aaaaaggatc ttcacctaga tccttttaaa ttaaaaatga agttttaaat    6600
caatctaaag tatatatgag taaacttggt ctgacagtta ccaatgctta atcagtgagg    6660
cacctatctc agcgatctgt ctatttcgtt catccatagt tgcctgactc cccgtcgtgt    6720
agataactac gatacgggag ggcttaccat ctggccccag tgctgcaatg ataccgcgag    6780
acccacgctc accggctcca gatttatcag caataaacca gccagccgga agggccgagc    6840
gcagaagtgg tcctgcaact ttatccgcct ccatccagtc tattaattgt tgccgggaag    6900
ctagagtaag tagttcgcca gttaatagtt tgcgcaacgt tgttgccatt gctgcaggca    6960
tcgtggtgtc acgctcgtcg tttggtatgg cttcattcag ctccggttcc caacgatcaa    7020
ggcgagttac atgatccccc atgttgtgca aaaaagcggt tagctccttc ggtcctccga    7080
tcgttgtcag aagtaagttg gccgcagtgt tatcactcat ggttatgcca gcactgcata    7140
attctcttac tgtcatgcca tccgtaagat gcttttctgt gactggtgag tactcaacca    7200
```

-continued

```
agtcattctg agaatagtgt atgcggcgac cgagttgctc ttgcccggcg tcaacacggg   7260
ataataccgc gccacatagc agaactttaa aagtgctcat cattggaaaa cgttcttcgg   7320
ggcgaaaact ctcaaggatc ttaccgctgt tgagatccag ttcgatgtaa cccactcgtg   7380
cacccaactg atcttcagca tcttttactt tcaccagcgt ttctgggtga gcaaaaacag   7440
gaaggcaaaa tgccgcaaaa aagggaataa gggcgacacg gaaatgttga atactcatac   7500
tcttcctttt tcaatattat tgaagcattt atcagggtta ttgtctcatg agcggataca   7560
tatttgaatg tatttagaaa aataaacaaa taggggttcc gcgcacattt ccccgaaaag   7620
tgccacctga cgtctaagaa accattatta tcatgacatt aacctataaa aataggcgta   7680
tcacgaggcc ctttcgtctt caagaattgt t                                  7711
```

<210> SEQ ID NO 36
<211> LENGTH: 7522
<212> TYPE: DNA
<213> ORGANISM: Artificial Sequence
<220> FEATURE:
<223> OTHER INFORMATION: Synthetic Construct pAdApt Lassa GP(dTM)

<400> SEQUENCE: 36

```
ttaattaacc gcaattctca tgtttgacag cttatcatca tcaataatat accttatttt     60
ggattgaagc caatatgata atgagggggt ggagtttgtg acgtggcgcg gggcgtggga    120
acggggcggg tgacgtagta gtgtggcgga agtgtgatgt tgcaagtgtg gcggaacaca    180
tgtaagcgac ggatgtggca aaagtgacgt ttttggtgtg cgccggtgta cacaggaagt    240
gacaattttc gcgcggtttt aggcggatgt tgtagtaaat ttgggcgtaa ccgagtaaga    300
tttggccatt ttcgcgggaa aactgaataa gaggaagtga aatctgaata attttgtgtt    360
actcatagcg cgtaatattt gtctagggcc gcggggactt tgaccgttta cgtggagact    420
cgcccaggtg tttttctcag gtgttttccg cgttccgggt caaagttggc gttttattat    480
tatagtcagt acgtaccagt gcactggcct agagcggccc cattgcatac gttgtatcca    540
tatcataata tgtacattta tattggctca tgtccaacat taccgccatg ttgacattga    600
ttattgacta gttattaata gtaatcaatt acggggtcat tagttcatag cccatatatg    660
gagttccgcg ttacataact tacggtaaat ggcccgcctg gctgaccgcc caacgacccc    720
cgcccattga cgtcaataat gacgtatgtt cccatagtaa cgccaatagg gactttccat    780
tgacgtcaat gggtggagta tttacggtaa actgcccact tggcagtaca tcaagtgtat    840
catatgccaa gtacgccccc tattgacgtc aatgacggta aatggcccgc ctggcattat    900
gcccagtaca tgaccttatg ggactttcct acttggcagt acatctacgt attagtcatc    960
gctattacca tggtgatgcg gttttggcag tacatcaatg ggcgtggata gcggtttgac   1020
tcacggggat ttccaagtct ccaccccatt gacgtcaatg ggagtttgtt ttggcaccaa   1080
aatcaacggg actttccaaa atgtcgtaac aactccgccc cattgacgca aatgggcggt   1140
aggcgtgtac ggtgggaggt ctatataagc agagctcgtt tagtgaaccg tcagatcgcc   1200
tggagacgcc atccacgctg ttttgacctc catagaagac accgggaccg atccagcctc   1260
cgtcaccgtc gtcgacacgt gtgatcagat atcgcggccg ctctagaatt taggattgcg   1320
cttttagaga ttcactacta gttaggaatt cctaaatcat ggggcagatt attacattct   1380
ttcaagaagt gccacatgta atagaggaag tcatgaacat tgtgctaatt gcgctttctc   1440
tattggcaat cttgaagggc ttgtataaca tcgctacatg tgggattatt ggattggttg   1500
```

```
ccttttttatt cttgtgtggc aagtcttgtt ccctaaccct taaaggggga tatgagctgc    1560
aaaccttaga attaaatatg gagaccctaa acatgaccat gcccttatca tgcaccaaga    1620
acagcagtca tcattacata agagtgggca atgagactgg attagaattg actttaacta   1680
acaccagcat tataaatcac aaattttgca acttatccga tgctcacaaa aagaatcttt    1740
atgatcatgc tctcatgagc atcatctcaa cattccatct atccattcca aacttcaatc    1800
agtatgaagc catgagttgt gatttcaatg gagggaaaat cagtgtgcaa tacaacctct    1860
ctcattccta tgctggggat gcggccgaac actgtgggac agttgccaac ggagtgttgc    1920
aaacatttat gagaatggcc tggggtgaa gatacattgc attagactca ggaaagggaa      1980
actgggactg tataatgacc agctaccagt acctgataat tcaaaataca acatgggagg    2040
accactgcca attctcaaga ccgtctccta tcgggtacct tggccttttg tcacaaagga    2100
caagagatat atatataagt aggaggctct tggggacctt cacctggaca ttgtcagatt    2160
ctgagggcaa tgaaacacca ggtggttatt gtttaaccag gtggatgcta attgaagcag    2220
aactcaagtg ttttgggaat acagctgtgg caaaatgcaa tgagaagcat gatgaggagt    2280
tttgtgacat gctgagattg tttgatttca caagcaagc aatccgtagg ttgaaggctg      2340
aggcccagat gagtattcaa ttaataaata aagccgtgaa tgccttaatc aatgatcaat    2400
taatcatgaa gaaccattta agagacatca tgggcattcc ctactgcaat tacagcaagt    2460
attggtacct taatcatact agtagcggga gaacatcact accaaagtgt tggcttatat    2520
ccaatgggtc atatctaaat gaaacccagt tctctgatga catagaacag caagccgaca    2580
atatgatcac agagatgctt cagaaagaat acattgaaag acaagggaaa acgcccttgt    2640
agggatccag atctgctgtg ccttctagtt gccagccatc tgttgtttgc ccctcccccg    2700
tgccttcctt gaccctggaa ggtgccactc ccactgtcct ttcctaataa aatgaggaaa    2760
ttgcatcgca ttgtctgagt aggtgtcatt ctattctggg gggtggggtg gggcagcaca    2820
gcaaggggga ggattgggaa gacaatagca ggcatgctgg ggatgcggtg ggctctatgg    2880
gtacccaggg ccgcataact tcgtataatg tatgctatac gaagttataa gatctgtact    2940
gaaatgtgtg ggcgtggctt aagggtggga agaatatat aaggtggggg tcttatgtag      3000
ttttgtatct gttttgcagc agccgccgcc gccatgagca ccaactcgtt tgatggaagc    3060
attgtgagct catatttgac aacgcgcatg cccccatggg ccggggtgcg tcagaatgtg    3120
atgggctcca gcattgatgg tcgccccgtc ctgcccgcaa actctactac cttgacctac    3180
gagaccgtgt ctggaacgcc gttggagact gcagcctccg ccgccgcttc agccgctgca    3240
gccaccgccc gcgggattgt gactgacttt gctttcctga gccgcttgc aagcagtgca      3300 gcttcccgtt catccgcccg cgatgacaag ttgacggctc ttttggcaca attggattct    3360
ttgacccggg aacttaatgt cgtttctcag cagctgttgg atctgcgcca gcaggtttct    3420
gccctgaagg cttcctcccc tcccaatgcg gtttaaaaca taaataaaaa accagactct    3480
gtttggattt ggatcaagca agtgtcttgc tgtctttatt tagggttttt gcgcgcgcgg    3540
taggcccggg accagcggtc tcggtcgttg agggtcctgt gtatttttc caggacgtgg      3600 taaaggtgac tctggatgtt cagatacatg gcataagcc cgtctctggg gtggaggtag      3660
caccactgca gagcttcatg ctgcggggtg tgttgtagaa tgatccagtc gtagcaggag    3720
cgctgggcgt ggtgcctaaa aatgtctttc agtagcaagc tgattgccag ggcaggccc     3780 ttggtgtaag tgtttacaaa gcggttaagc tgggatgggt gcatacgtgg ggatatgaga    3840
tgcatcttgg actgtatttt taggttggct atgttcccag ccatatccct ccggggattc    3900
```

```
atgttgtgca gaaccaccag cacagtgtat ccggtgcact tgggaaattt gtcatgtagc   3960
ttagaaggaa atgcgtggaa gaacttggag acgcccttgt gacctccaag attttccatg   4020
cattcgtcca taatgatggc aatgggccca cgggcggcgg cctgggcgaa gatatttctg   4080
ggatcactaa cgtcatagtt gtgttccagg atgagatcgt cataggccat ttttacaaag   4140
cgcgggcgga gggtgccaga ctgcggtata atggttccat ccggcccagg ggcgtagtta   4200
ccctcacaga tttgcatttc ccacgctttg agttcagatg gggggatcat gtctacctgc   4260
ggggcgatga agaaaacggt tccggggta ggggagatca gctgggaaga aagcaggttc    4320
ctgagcagct gcgacttacc gcagccggtg ggcccgtaaa tcacacctat taccggctgc   4380
aactggtagt taagagagct gcagctgccg tcatccctga gcaggggggc cacttcgtta   4440
agcatgtccc tgactcgcat gtttttcctg accaaatccg ccagaaggcg ctcgccgccc   4500
agcgatagca gttcttgcaa ggaagcaaag ttttcaacg gtttgagacc gtccgccgta    4560
ggcatgcttt tgagcgtttg accaagcagt tccaggcggt cccacagctc ggtcacctgc   4620
tctacggcat ctcgatccag catatctcct cgtttcgcgg gttggggcgg ctttcgctgt   4680
acggcagtag tcggtgctcg tccagacggg ccagggtcat gtctttccac gggcgcaggg   4740
tcctcgtcag cgtagtctgg gtcacggtga aggggtgcgc tccgggctgc gcgctggcca   4800
gggtgcgctt gaggctggtc ctgctggtgc tgaagcgctg ccggtcttcg ccctgcgcgt   4860
cggccaggta gcatttgacc atggtgtcat agtccagccc ctccgcggcg tggcccttgg   4920
cgcgcagctt gcccttggag gaggcgccgc acgaggggca gtgcagactt ttgagggcgt   4980
agagcttggg cgcgagaaat accgattccg gggagtaggc atccgcgccg caggccccgc   5040
agacggtctc gcattccacg agccaggtga gctctggccg ttcggggtca aaaccaggt    5100
ttcccccatg cttttgatg cgtttcttac ctctggtttc catgagccgg tgtccacgct    5160
cggtgacgaa aaggctgtcc gtgtccccgt atacagactt gagaggcctg tcctcgagcg   5220
gtgttccgcg gtcctcctcg tatagaaact cggaccactc tgagacaaag gctcgcgtcc   5280
aggccagcac gaaggaggct aagtgggagg ggtagcggtc gttgtccact aggggtcca    5340
ctcgctccag ggtgtgaaga cacatgtcgc cctcttcggc atcaaggaag gtgattggtt   5400
tgtaggtgta ggccacgtga ccgggtgttc ctgaagggg gctataaaag gggtgggg     5460
cgcgttcgtc ctcactctct tccgcatcgc tgtctgcgag ggccagctgt tggggtgagt   5520
cgacgcgagg ctggatggcc ttccccatta tgattcttct cgcttccggc ggcatcggga   5580
tgcccgcgtt gcaggccatg ctgtccaggc aggtagatga cgaccatcag ggacagcttc   5640
aaggccagca aaaggccagg aaccgtaaaa aggccgcgtt gctggcgttt ttccataggc   5700
tccgcccccc tgacgagcat cacaaaaatc gacgctcaag tcagaggtgg cgaaacccga   5760
caggactata agataccag gcgtttcccc ctggaagctc cctcgtgcgc tctcctgttc    5820
cgaccctgcc gcttaccgga tacctgtccg cctttctccc ttcgggaagc gtggcgcttt   5880
ctcatagctc acgctgtagg tatctcagtt cggtgtaggt cgttcgctcc aagctgggct   5940
gtgtgcacga accccccgtt cagcccgacc gctgcgcctt atccggtaac tatcgtcttg   6000
agtccaaccc ggtaagacac gacttatcgc cactggcagc agccactggt aacaggatta   6060
gcagagcgag gtatgtaggc ggtgctacag agttcttgaa gtggtggcct aactacggct   6120
acactagaag gacagtattt ggtatctgcg ctctgctgaa gccagttacc ttcggaaaaa   6180
gagttggtag ctcttgatcc ggcaaacaaa ccaccgctgg tagcggtggt ttttttgttt   6240
```

| | | | | |
|---|---|---|---|---|
| gcaagcagca | gattacgcgc | agaaaaaaag | gatctcaaga | agatcctttg atcttttcta | 6300 |
| cggggtctga | cgctcagtgg | aacgaaaact | cacgttaagg | gattttggtc atgagattat | 6360 |
| caaaaaggat | cttcacctag | atccttttaa | attaaaaatg | aagttttaaa tcaatctaaa | 6420 |
| gtatatatga | gtaaacttgg | tctgacagtt | accaatgctt | aatcagtgag gcacctatct | 6480 |
| cagcgatctg | tctatttcgt | tcatccatag | ttgcctgact | ccccgtcgtg tagataacta | 6540 |
| cgatacggga | gggcttacca | tctggcccca | gtgctgcaat | gataccgcga gacccacgct | 6600 |
| caccggctcc | agatttatca | gcaataaacc | agccagccgg | aagggccgag cgcagaagtg | 6660 |
| gtcctgcaac | tttatccgcc | tccatccagt | ctattaattg | ttgccgggaa gctagagtaa | 6720 |
| gtagttcgcc | agttaatagt | ttgcgcaacg | ttgttgccat | tgctgcaggc atcgtggtgt | 6780 |
| cacgctcgtc | gtttggtatg | gcttcattca | gctccggttc | ccaacgatca aggcgagtta | 6840 |
| catgatcccc | catgttgtgc | aaaaaagcgg | ttagctcctt | cggtcctccg atcgttgtca | 6900 |
| gaagtaagtt | ggccgcagtg | ttatcactca | tggttatggc | agcactgcat aattctctta | 6960 |
| ctgtcatgcc | atccgtaaga | tgcttttctg | tgactggtga | gtactcaacc aagtcattct | 7020 |
| gagaatagtg | tatgcggcga | ccgagttgct | cttgcccggc | gtcaacacgg gataataccg | 7080 |
| cgccacatag | cagaacttta | aaagtgctca | tcattggaaa | acgttcttcg gggcgaaaac | 7140 |
| tctcaaggat | cttaccgctg | ttgagatcca | gttcgatgta | acccactcgt gcacccaact | 7200 |
| gatcttcagc | atcttttact | ttcaccagcg | tttctgggtg | agcaaaaaca ggaaggcaaa | 7260 |
| atgccgcaaa | aaagggaata | agggcgacac | ggaaatgttg | aatactcata ctcttccttt | 7320 |
| ttcaatatta | ttgaagcatt | tatcagggtt | attgtctcat | gagcggatac atatttgaat | 7380 |
| gtatttagaa | aaataaacaa | ataggggttc | cgcgcacatt | tccccgaaaa gtgccacctg | 7440 |
| acgtctaaga | aaccattatt | atcatgacat | taacctataa | aaataggcgt atcacgaggc | 7500 |
| cctttcgtct | tcaagaattg | tt | | | 7522 |

<210> SEQ ID NO 37
<211> LENGTH: 6324
<212> TYPE: DNA
<213> ORGANISM: Artificial Sequence
<220> FEATURE:
<223> OTHER INFORMATION: Synthetic Construct CMV/R Ebola GP(Z) delta TM/h

<400> SEQUENCE: 37

| | | | | |
|---|---|---|---|---|
| tcgcgcgttt | cggtgatgac | ggtgaaaacc | tctgacacat | gcagctcccg gagacggtca | 60 |
| cagcttgtct | gtaagcggat | gccgggagca | gacaagcccg | tcagggcgcg tcagcgggtg | 120 |
| ttggcgggtg | tcggggctgg | cttaactatg | cggcatcaga | gcagattgta ctgagagtgc | 180 |
| accatatgcg | gtgtgaaata | ccgcacagat | gcgtaaggag | aaaataccgc atcagattgg | 240 |
| ctattggcca | ttgcatacgt | tgtatccata | tcataatatg | tacatttata ttggctcatg | 300 |
| tccaacatta | ccgccatgtt | gacattgatt | attgactagt | tattaatagt aatcaattac | 360 |
| ggggtcatta | gttcatagcc | catatatgga | gttccgcgtt | acataactta cggtaaatgg | 420 |
| cccgcctggc | tgaccgccca | acgacccccg | cccattgacg | tcaataatga cgtatgttcc | 480 |
| catagtaacg | ccaataggga | ctttccattg | acgtcaatgg | gtggagtatt tacggtaaac | 540 |
| tgcccacttg | gcagtacatc | aagtgtatca | tatgccaagt | acgcccccta ttgacgtcaa | 600 |
| tgacggtaaa | tggcccgcct | ggcattatgc | ccagtacatg | accttatggg actttcctac | 660 |
| ttggcagtac | atctacgtat | tagtcatcgc | tattaccatg | gtgatgcggt tttggcagta | 720 |

```
catcaatggg cgtggatagc ggtttgactc acggggattt ccaagtctcc accccattga      780
cgtcaatggg agtttgtttt ggcaccaaaa tcaacgggac tttccaaaat gtcgtaacaa      840
ctccgcccca ttgacgcaaa tgggcggtag gcgtgtacgg tgggaggtct atataagcag      900
agctcgttta gtgaaccgtc agatcgcctg gagacgccat ccacgctgtt ttgacctcca      960
tagaagacac cgggaccgat ccagcctcca tcggctcgca tctctccttc acgcgcccgc     1020
cgccttacct gaggccgcca tccacgccgg ttgagtcgcg ttctgccgcc tcccgcctgt     1080
ggtgcctcct gaactacgtc cgccgtctag gtaagtttag agctcaggtc gagaccgggc     1140 cttttgtccgg cgctcccttg gagcctacct agactcagcc ggctctccac gctttgcctg    1200
accctgcttg ctcaactcta gttaacggtg gagggcagtg tagtctgagc agtactcgtt     1260
gctgccgcgc gcgccaccag acataatagc tgacagacta acagactgtt cctttccatg     1320
ggtcttttct gcagtcaccg tcgtcgacga tatcgccgcc atgggcgtga ccggcatcct     1380
gcagctgccc agggacaggt tcaagaggac cagcttcttc ctgtgggtga tcatcctgtt     1440
ccagaggacc ttcagcatcc ccctgggcgt gatccacaac agcaccctgc aggtgagcga     1500
cgtggacaag ctggtgtgca gggacaagct gagcagcacc aaccagctga ggagcgtggg     1560
cctgaacctg gagggcaacg gcgtggccac cgacgtgccc agcgccacca agaggtgggg     1620
cttcaggagc ggcgtgcctc ccaaggtggt gaactacgag gccggcgagt gggccgagaa     1680
ctgctacaac ctggagatca agaagcccga cggcagcgag tgcctgcccg ccgcccctga     1740
cggcatcagg ggcttcccca ggtgcaggta cgtgcacaag gtgagcggca ccggcccctg     1800
cgccggcgac ttcgccttcc acaaggaggg cgccttcttc ctgtacgaca ggctggccag     1860
caccgtgatc tacaggggca ccaccttcgc cgagggcgtg gtggccttcc tgatcctgcc     1920
ccaggccaag aaggacttct tcagcagcca ccctctgagg gagcccgtga acgccaccga     1980 ggacccagc agcggctact acagcaccac catcaggtac caggccaccg gcttcggcac     2040
caacgagacc gagtacctgt cgaggtggaa caacctgacc tacgtgcagc tggagtctag     2100
attcacccct cagttcctgc tgcagctgaa cgagaccatc tacaccagcg gcaagaggag     2160
caacaccacc ggcaagctga tctggaaggt gaaccccgag atcgacacca ccatcggcga     2220
gtgggccttc tgggagacca agaagaacct gaccaggaag atcaggagcg aggagctgag     2280
cttcaccgtc gtgagcaacg gggccaagaa catcagcggc cagagccccg ccaggaccag     2340
cagcgacccc ggcaccaaca ccaccaccga ggaccacaag atcatggcca gcgagaacag     2400
cagcgccatg gtgcaggtgc acagccaggg cagggaggcc gccgtgagcc acctgaccac     2460
cctggccacc atcagcacca gccctcagtc tttaaccacc aagcccggcc ccgacaacag     2520
cacccacaac acccctgtgt acaagctgga catcagcgag gccacccagg tggagcagca     2580
ccacaggagg accgacaacg acagcaccgc cagcgacacc ccttccgcca ccaccgccgc     2640
cggccctccg aaggccgaga acaccaacac cagcaagagc accgactttc tggatcccgc     2700
caccaccacc agccctcaga accacagcga gaccgccggc aacaacaaca cccaccacca     2760
ggacaccggc gaggagagcg ccagcagcgg caagctgggc ctgatcacca acaccatcgc     2820
cggcgtggcc ggcctgatca ccggcggcag gaggaccagg agggaggcca tcgtgaacgc     2880
ccagcccaag tgcaacccca acctgcacta ctggaccacc caggacgagg cgccgccat     2940 cggcctggcc tggattccct acttcggccc cgccgccgag ggcatctaca tcgagggcct     3000
gatgcacaac caggacggcc tgatctgcgg cctgaggcag ctggccaacg agaccaccca     3060
ggccctgcag ctgttcctga gggccaccac cgagctgagg accttcagca tcctgaacag     3120
```

```
gaaggccatc gacttcctgc tgcagaggtg gggcggcacc tgccacatcc tgggccccga   3180
ctgctgcatc gagccccacg actggaccaa gaacatcacc gacaagatcg accagatcat   3240
ccacgacttc gtggacaaga ccctgcccga ccagggcgac aacgacaact ggtggaccgg   3300
ctgaacacgt ggaattcaga tctgctgtgc cttctagttg ccagccatct gttgtttgcc   3360
cctcccccgt gccttccttg accctggaag gtgccactcc cactgtcctt tcctaataaa   3420
atgaggaaat tgcatcgcat tgtctgagta ggtgtcattc tattctgggg ggtggggtgg   3480
ggcaggacag caaggggag gattgggaag acaatagcag gcatgctggg gatgcggtgg   3540
gctctatggg tacccaggtg ctgaagaatt gacccggttc ctcctgggcc agaaagaagc   3600
aggcacatcc ccttctctgt gacacaccct gtccacgccc ctggttctta gttccagccc   3660
cactcatagg acactcatag ctcaggaggg ctccgccttc aatcccaccc gctaaagtac   3720
ttggagcggt ctctccctcc ctcatcagcc caccaaacca aacctagcct caagagtgg    3780
gaagaaatta aagcaagata ggctattaag tgcagaggga gagaaaatgc ctccaacatg   3840
tgaggaagta atgagagaaa tcatagaatt ttaaggccat catggcctta atcttccgct   3900
tcctcgctca ctgactcgct gcgctcggtc gttcggctgc ggcgagcggt atcagctcac   3960
tcaaaggcgg taatacggtt atccacagaa tcagggata acgcaggaaa gaacatgtga   4020
gcaaaaggcc agcaaaaggc caggaaccgt aaaaaggccg cgttgctggc gttttttccat  4080
aggctccgcc cccctgacga gcatcacaaa atcgacgct caagtcagag gtggcgaaac    4140
ccgacaggac tataaagata ccaggcgttt ccccctggaa gctccctcgt gcgctctcct   4200
gttccgaccc tgccgcttac cggatacctg tccgccttc tcccttcggg aagcgtggcg    4260
ctttctcata gctcacgctg taggtatctc agttcggtgt aggtcgttcg ctccaagctg   4320
ggctgtgtgc acgaaccccc cgttcagccc gaccgctgcg ccttatccgg taactatcgt   4380
cttgagtcca acccggtaag acacgactta tcgccactgg cagcagccac tggtaacagg   4440
attagcagag cgaggtatgt aggcggtgct acagagttct tgaagtggtg cctaactac    4500
ggctacacta gaagaacagt atttggtatc tgcgctctgc tgaagccagt taccttcgga   4560
aaaagagttg gtagctcttg atccggcaaa caaaccaccg ctggtagcgg tggtttttt    4620
gtttgcaagc agcagattac gcgcagaaaa aaggatctc aagaagatcc tttgatcttt    4680
tctacggggt ctgacgctca gtggaacgaa aactcacgtt aagggatttt ggtcatgaga   4740
ttatcaaaaa ggatcttcac ctagatcctt ttaaattaaa aatgaagttt taaatcaatc   4800
taaagtatat atgagtaaac ttggtctgac agttaccaat gcttaatcag tgaggcacct   4860
atctcagcga tctgtctatt tcgttcatcc atagttgcct gactcggggg gggggggcgc   4920
tgaggtctgc ctcgtgaaga aggtgttgct gactcatacc aggcctgaat cgccccatca   4980
tccagccaga aagtgaggga gccacggttg atgagagctt tgttgtaggt ggaccagttg   5040
gtgattttga acttttgctt tgccacggaa cggtctgcgt tgtcgggaag atgcgtgatc   5100
tgatccttca actcagcaaa agttcgattt attcaacaaa gccgccgtcc cgtcaagtca   5160
gcgtaatgct ctgccagtgt tacaaccaat taaccaattc tgattagaaa aactcatcga   5220
gcatcaaatg aaactgcaat ttattcatat caggattatc aataccatat ttttgaaaaa   5280
gccgtttctg taatgaagga gaaaactcac cgaggcagtt ccataggatg caagatcct    5340
ggtatcggtc tgcgattccg actcgtccaa catcaataca acctattaat ttcccctcgt   5400
caaaaataag gttatcaagt gagaaatcac catgagtgac gactgaatcc ggtgagaatg   5460
```

-continued

| | |
|---|---|
| gcaaaagctt atgcatttct ttccagactt gttcaacagg ccagccatta cgctcgtcat | 5520 |
| caaaatcact cgcatcaacc aaaccgttat tcattcgtga ttgcgcctga gcgagacgaa | 5580 |
| atacgcgatc gctgttaaaa ggacaattac aaacaggaat cgaatgcaac cggcgcagga | 5640 |
| acactgccag cgcatcaaca atattttcac ctgaatcagg atattcttct aatacctgga | 5700 |
| atgctgtttt cccggggatc gcagtggtga gtaaccatgc atcatcagga gtacggataa | 5760 |
| aatgcttgat ggtcggaaga ggcataaatt ccgtcagcca gtttagtctg accatctcat | 5820 |
| ctgtaacatc attggcaacg ctacctttgc catgtttcag aaacaactct ggcgcatcgg | 5880 |
| gcttcccata caatcgatag attgtcgcac ctgattgccc gacattatcg cgagcccatt | 5940 |
| tatacccata taaatcagca tccatgttgg aatttaatcg cggcctcgag caagacgttt | 6000 |
| cccgttgaat atggctcata caccccttg tattactgtt tatgtaagca gacagttta | 6060 |
| ttgttcatga tgatatattt ttatcttgtg caatgtaaca tcagagattt tgagacacaa | 6120 |
| cgtggctttc cccccccccc cattattgaa gcatttatca gggttattgt ctcatgagcg | 6180 |
| gatacatatt tgaatgtatt tagaaaaata acaaataggg gttccgcgc acatttcccc | 6240 |
| gaaaagtgcc acctgacgtc taagaaacca ttattatcat gacattaacc tataaaaata | 6300 |
| ggcgtatcac gaggcccttt cgtc | 6324 |

<210> SEQ ID NO 38
<211> LENGTH: 6868
<212> TYPE: DNA
<213> ORGANISM: Artificial Sequence
<220> FEATURE:
<223> OTHER INFORMATION: Synthetic Construct pVR1012x/s Ebola GP(Z) delta TM/h (P87666)

<400> SEQUENCE: 38

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcagattgg | 240 |
| ctattggcca ttgcatacgt tgtatccata tcataatatg tacatttata ttggctcatg | 300 |
| tccaacatta ccgccatgtt gacattgatt attgactagt tattaatagt aatcaattac | 360 |
| ggggtcatta gttcatagcc catatatgga gttccgcgtt acataactta cggtaaatgg | 420 |
| cccgcctggc tgaccgccca acgacccccg cccattgacg tcaataatga cgtatgttcc | 480 |
| catagtaacg ccaataggga ctttccattg acgtcaatgg gtggagtatt tacggtaaac | 540 |
| tgcccacttg gcagtacatc aagtgtatca tatgccaagt acgccccta ttgacgtcaa | 600 |
| tgacggtaaa tggcccgcct ggcattatgc ccagtacatg accttatggg actttcctac | 660 |
| ttggcagtac atctacgtat tagtcatcgc tattaccatg gtgatgcggt tttggcagta | 720 |
| catcaatggg cgtggatagc ggtttgactc acggggattt ccaagtctcc accccattga | 780 |
| cgtcaatggg agtttgtttt ggcaccaaaa tcaacgggac tttccaaaat gtcgtaacaa | 840 |
| ctccgcccca ttgacgcaaa tgggcggtag gcgtgtacgg tgggaggtct atataagcag | 900 |
| agctcgttta gtgaaccgtc agatcgcctg gagacgccat ccacgctgtt ttgacctcca | 960 |
| tagaagacac cgggaccgat ccagcctccg cggccgggaa cggtgcattg gaacgcggat | 1020 |
| tccccgtgcc aagagtgacg taagtaccgc ctatagactc tataggcaca ccctttggc | 1080 |
| tcttatgcat gctatactgt ttttggcttg gggcctatac accccgctt ccttatgcta | 1140 |

```
taggtgatgg tatagcttag cctataggtg tgggttattg accattattg accactcccc    1200
tattggtgac gatactttcc attactaatc cataacatgg ctctttgcca caactatctc    1260
tattggctat atgccaatac tctgtccttc agagactgac acggactctg tattttttaca   1320 ggatggggtc ccatttatta tttacaaatt cacatataca acaacgccgt cccccgtgcc    1380
cgcagttttt attaaacata gcgtgggatc tccacgcgaa tctcgggtac gtgttccgga    1440
catgggctct tctccggtag cggcggagct tccacatccg agccctggtc ccatgcctcc    1500
agcggctcat ggtcgctcgg cagctccttg ctcctaacag tggaggccag acttaggcac    1560
agcacaatgc ccaccaccac cagtgtgccg cacaaggccg tggcggtagg gtatgtgtct    1620
gaaaatgagc gtggagattg ggctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tcctttccat gggtcttttc    1860
tgcagtcacc gtcgtcgacg atatcgccgc catggagggc ctgagcctgc tgcagctgcc    1920
cagggacaag ttcaggaaga gcagcttctt cgtgtgggtg atcatcctgt tccagaaggc    1980
cttcagcatg cccctgggcg tggtgaccaa cagcaccctg gaggtgaccg agatcgacca    2040
gctggtgtgc aaggaccacc tggccagcac cgaccagctg aagagcgtgg gcctgaacct    2100
ggagggcagc ggcgtgagca ccgacatccc cagcgccacc aagaggtggg gcttcaggag    2160
cggcgtgcct ccccaggtgg tgagctacga ggccggcgag tgggccgaga actgctacaa    2220
cctggagatc aagaagcccg acggcagcga gtgcctgcct cctcctcctg acggcgtgag    2280
gggcttcccc aggtgcaggt acgtgcacaa ggcccagggc accggcccct gccccggcga    2340
ctacgccttc cacaaggacg gcgccttctt cctgtacgac aggctggcca gcaccgtgat    2400
ctacaggggc gtgaacttcg ccgagggcgt gatcgccttc ctgatcctgg ccaagcccaa    2460
ggagaccttc ctgcagagcc ctcccatcag ggaggccgcc aactacaccg agaacaccag    2520
cagctactac gccaccagct atctagagta cgagatcgag aacttcggcg cccagcacag    2580
caccaccctg ttcaagatca acaacaacac cttcgtgctg ctggacaggc cccacacccc    2640
tcagttcctg ttccagctga cgacaccat ccagctgcac cagcagctga gcaacaccac    2700
cggcaagctg atctggaccc tggacgccaa catcaacgcc gacatcggcg agtgggcctt    2760
ctgggagaac aagaagaacc tgagcgagca gctgagggc gaggagctga gcttcgagac    2820
cctgagcctg aacgagaccg aggacgacga cgccaccagc agcaggacca ccaagggcag    2880
gatcagcgac agggccacca ggaagtacag cgacctggtg cccaaggaca gccccggcat    2940
ggtgagcctg cacgtgcccg agggcgagac caccctgccc agcagaaaca gcaccgaggg    3000
caggagggtg gacgtgaaca cccaggagac catcaccgag accaccgcca ccatcatcgg    3060
caccaacggc aacaacatgc agatcagcac catcggcacc ggcctgagca gcagccgat    3120 cctgagcagc agccccacca tggccccta gccccgagacc cagaccagca ccacctacac    3180
ccctaagctg cccgtgatga ccaccgagga gcccaccacc cctcccagga cagccccgg    3240 atccaccacc gaggccccta ccctgaccac cctgagaaac atcaccaccg ccgtgaagac    3300
cgtgtgggcc caggagagca ccagcaacgg cctgatcacc agcaccgtga ccggcatcct    3360
gggcagcctg ggcctgagga agaggagcag gaggcaggtg aacaccaggg ccaccggcaa    3420
gtgcaacccc aacctgcact actgaccgcc ccaggagcag cacaacgccg ccggcatcgc    3480
ctggattccc tacttcggcc ccggcgccga gggcatctac accgagggcc tgatgcacaa    3540
```

```
ccagaacgcc ctggtgtgcg gcctgaggca gctggccaac gagaccaccc aggccctgca    3600
gctgttcctg agggccacca ccgagctgag gacctacacc atcctgaaca ggaaggccat    3660
cgacttcctg ctgaggaggt ggggcggcac ctgcaggatt ctgggccccg actgctgcat    3720
cgagccccac gactggacca agaacatcac cgacaagatc aaccagatca tccacgactt    3780
catcgacaac cctctgccca accaggacaa cgacgacaac tggtggaccg gctgaacacg    3840
tggaattcag atctgctgtg ccttctagtt gccagccatc tgttgtttgc ccctcccccg    3900
tgccttcctt gaccctggaa ggtgccactc ccactgtcct ttcctaataa aatgaggaaa    3960
ttgcatcgca ttgtctgagt aggtgtcatt ctattctggg gggtggggtg gggcaggaca    4020
gcaaggggga ggattgggaa gacaatagca ggcatgctgg ggatgcggtg ggctctatgg    4080
gtacccaggt gctgaagaat tgacccggtt cctcctgggc cagaaagaag caggcacatc    4140
cccttctctg tgacacaccc tgtccacgcc cctggttctt agttccagcc ccactcatag    4200
gacactcata gctcaggagg gctccgcctt caatcccacc cgctaaagta cttggagcgg    4260
tctctccctc cctcatcagc ccaccaaacc aaacctagcc tccaagagtg ggaagaaatt    4320
aaagcaagat aggctattaa gtgcagaggg agagaaaatg cctccaacat gtgaggaagt    4380
aatgagagaa atcatagaat tttaaggcca tgatttaagg ccatcatggc cttaatcttc    4440
cgcttcctcg ctcactgact cgctgcgctc ggtcgttcgg ctgcggcgag cggtatcagc    4500
tcactcaaag gcggtaatac ggttatccac agaatcaggg gataacgcag gaaagaacat    4560
gtgagcaaaa ggccagcaaa aggccaggaa ccgtaaaaag gccgcgttgc tggcgttttt    4620
ccataggctc cgcccccctg acgagcatca caaaaatcga cgctcaagtc agaggtggcg    4680
aaacccgaca ggactataaa gataccaggc gtttccccct ggaagctccc tcgtgcgctc    4740
tcctgttccg accctgccgc ttaccggata cctgtccgcc tttctccctt cgggaagcgt    4800
ggcgctttct catagctcac gctgtaggta tctcagttcg gtgtaggtcg ttcgctccaa    4860
gctgggctgt gtgcacgaac cccccgttca gcccgaccgc tgcgccttat ccggtaacta    4920
tcgtcttgag tccaacccgg taagacacga cttatcgcca ctggcagcag ccactggtaa    4980
caggattagc agagcgaggt atgtaggcgg tgctacagag ttcttgaagt ggtggcctaa    5040
ctacggctac actagaagaa cagtatttgg tatctgcgct ctgctgaagc cagttacctt    5100
cggaaaaaga gttggtagct cttgatccgg caaacaaacc accgctggta gcggtggttt    5160
ttttgtttgc aagcagcaga ttacgcgcag aaaaaaagga tctcaagaag atcctttgat    5220
cttttctacg gggtctgacg ctcagtggaa cgaaaactca cgttaaggga ttttggtcat    5280
gagattatca aaaaggatct tcacctagat ccttttaaat taaaaatgaa gttttaaatc    5340
aatctaaagt atatatgagt aaacttggtc tgacagttac caatgcttaa tcagtgaggc    5400
acctatctca gcgatctgtc tatttcgttc atccatagtt gcctgactcg ggggggggg    5460 gcgctgaggt ctgcctcgtg aagaaggtgt tgctgactca taccaggcct gaatcgcccc    5520
atcatccagc cagaaagtga gggagccacg gttgatgaga gctttgttgt aggtggacca    5580
gttggtgatt ttgaactttt gctttgccac ggaacggtct gcgttgtcgg aagatgcgt    5640 gatctgatcc ttcaactcag caaaagttcg atttattcaa caaagccgcc gtcccgtcaa    5700
gtcagcgtaa tgctctgcca gtgttacaac caattaacca attctgatta gaaaaactca    5760
tcgagcatca aatgaaactg caatttattc atatcaggat tatcaatacc atattttga    5820 aaaagccgtt tctgtaatga aggagaaaac tcaccgaggc agttccatag gatggcaaga    5880
```

-continued

```
tcctggtatc ggtctgcgat tccgactcgt ccaacatcaa tacaacctat taatttcccc    5940
tcgtcaaaaa taaggttatc aagtgagaaa tcaccatgag tgacgactga atccggtgag    6000
aatggcaaaa gcttatgcat ttctttccag acttgttcaa caggccagcc attacgctcg    6060
tcatcaaaat cactcgcatc aaccaaaccg ttattcattc gtgattgcgc ctgagcgaga    6120
cgaaatacgc gatcgctgtt aaaaggacaa ttacaaacag gaatcgaatg caaccggcgc    6180
aggaacactg ccagcgcatc aacaatattt tcacctgaat caggatattc ttctaatacc    6240
tggaatgctg ttttcccggg gatcgcagtg gtgagtaacc atgcatcatc aggagtacgg    6300
ataaaatgct tgatggtcgg aagaggcata aattccgtca gccagtttag tctgaccatc    6360
tcatctgtaa catcattggc aacgctacct ttgccatgtt tcagaaacaa ctctggcgca    6420
tcgggcttcc catacaatcg atagattgtc gcacctgatt gcccgacatt atcgcgagcc    6480
catttatacc catataaatc agcatccatg ttggaattta atcgcggcct cgagcaagac    6540
gtttcccgtt gaatatggct cataacaccc cttgtattac tgtttatgta agcagacagt    6600
tttattgttc atgatgatat attttatct tgtgcaatgt aacatcagag attttgagac    6660
acaacgtggc tttcccccc ccccattat tgaagcattt atcagggtta ttgtctcatg    6720
agcggataca tatttgaatg tatttagaaa aataaacaaa taggggttcc gcgcacattt    6780
ccccgaaaag tgccacctga cgtctaagaa accattatta tcatgacatt aacctataaa    6840
aataggcgta tcacgaggcc ctttcgtc                                      6868
```

<210> SEQ ID NO 39
<211> LENGTH: 6322
<212> TYPE: DNA
<213> ORGANISM: Artificial Sequence
<220> FEATURE:
<223> OTHER INFORMATION: Synthetic Construct CMV/R-GP(S/G)(deltaTM)/h

<400> SEQUENCE: 39

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgacccccg cccattgacg tcaataatga cgtatgttcc     480
catagtaacg ccaataggga ctttccattg acgtcaatgg gtggagtatt tacggtaaac     540
tgcccacttg gcagtacatc aagtgtatca tatgccaagt acgccccta ttgacgtcaa     600 tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag     900
agctcgttta gtgaaccgtc agatcgcctg gagacgccat ccacgctgtt ttgacctcca     960
tagaagacac cgggaccgat ccagcctcca tcggctcgca tctctccttc acgcgcccgc    1020
cgccttacct gaggccgcca tccacgccgg ttgagtcgcg ttctgccgcc tcccgcctgt    1080
```

```
ggtgcctcct gaactacgtc cgccgtctag gtaagtttag agctcaggtc gagaccgggc    1140
ctttgtccgg cgctcccttg gagcctacct agactcagcc ggctctccac gctttgcctg    1200
accctgcttg ctcaactcta gttaacggtg gagggcagtg tagtctgagc agtactcgtt    1260
gctgccgcgc gcgccaccag acataatagc tgacagacta acagactgtt cctttccatg    1320
ggtcttttct gcagtcaccg tcgtcgacga tatcgccgcc atggagggcc tgagcctgct    1380
gcagctgccc agggacaagt tcaggaagag cagcttcttc gtgtgggtga tcatcctgtt    1440
ccagaaggcc ttcagcatgc ccctgggcgt ggtgaccaac agcaccctgg aggtgaccga    1500
gatcgaccag ctggtgtgca aggaccacct ggccagcacc gaccagctga gagcgtggg    1560 cctgaacctg gagggcagcg gcgtgagcac cgacatcccc agcgccacca gaggtgggg    1620 cttcaggagc ggcgtgcctc ccaaggtggt gagctacgag gccggcgagt gggccgagaa    1680
ctgctacaac ctggagatca agaagcccga cggcagcgag tgcctgcctc tcctcctga    1740 cggcgtgagg ggcttcccca ggtgcaggta cgtgcacaag gcccagggca ccggcccctg    1800
ccccggcgac tacgccttcc acaaggacgg cgccttcttc ctgtacgaca ggctggccag    1860
caccgtgatc tacaggggcg tgaacttcgc cgagggcgtg atcgccttcc tgatcctggc    1920
caagcccaag gagaccttcc tgcagagccc tcccatcagg gaggccgtga actacaccga    1980
gaacaccagc agctactacg ccaccagcta tctagagtac gagatcgaga acttcggcgc    2040
ccagcacagc accaccctgt tcaagatcga caacaacacc ttcgtgaggc tggacaggcc    2100 ccacaccct cagttcctgt tccagctgaa cgacaccatc cacctgcacc agcagctgag    2160
caacaccacc ggcaggctga tctggaccct ggacgccaac atcaacgccg acatcggcga    2220
gtgggccttc tgggagaaca agaagaacct gagcgagcag ctgaggggcg aggagctgag    2280
cttcgaggcc ctgagcctga acgagaccga ggacgacgac gccgccagca gcaggatcac    2340
caagggcagg atcagcgaca gggccaccag gaagtacagc gacctggtgc caagaacag    2400 ccccggcatg gtgcccctgc acatccccga gggcgagacc accctgccca gccagaacag    2460
caccgagggc aggagggtgg gcgtgaacac ccaggagacc atcaccgaga ccgccgccac    2520
catcatcggc accaacggca accacatgca gatcagcacc atcggcatca ggcccagcag    2580
cagccagatc cccagcagca gccccaccac cgccccagc cccgaggccc agaccccac    2640 cacccacacc agcggaccca cgtgatggc caccgaggag cccaccaccc ctcccggcag    2700
cagccccgga cccaccaccg aggccccta cctgaccacc cctgagaaca tcaccaccgc    2760
cgtgaagacc gtgctgcccc aggagagcac cagcaacggc ctgatcacca gcaccgtgac    2820
cggcatcctg ggcagcctgg gcctgaggaa gaggagcagg aggcagacca caccaaggc    2880 caccggcaag tgcaaccca acctgcacta ctggaccgcc caggagcagc aaacgccgc    2940 cggcatcgcc tggattccct acttcggccc cggcgccgag gcatctaca ccgagggcct    3000 gatgcacaac cagaacgccc tggtgtgcgg cctgaggcag ctggccaacg agaccaccca    3060
ggccctgcag ctgttcctga gggccaccac cgagctgagg acctaccca tcctgaacag    3120 gaaggccatc gacttcctgc tgaggaggtg gggcggcacc tgcaggattc tgggccccga    3180
ctgctgcatc gagcccacg actgaccaa gaacatcacc gacaagatca accagatcat    3240
ccacgacttc atcgacaacc tctgcccaa ccaggacaac gacgacaact ggtggaccgg    3300
ctgaacacgt ggaattgatc tgctgtgcct tctagttgcc agccatctgt tgtttgcccc    3360
tcccccgtgc cttccttgac cctggaaggt gccactccca ctgtcctttc ctaataaaat    3420
```

```
gaggaaattg catcgcattg tctgagtagg tgtcattcta ttctgggggg tggggtgggg    3480
caggacagca aggggagga ttgggaagac aatagcaggc atgctgggga tgcggtgggc    3540
tctatgggta cccaggtgct gaagaattga cccggttcct cctgggccag aaagaagcag    3600
gcacatcccc ttctctgtga cacaccctgt ccacgcccct ggttcttagt tccagcccca    3660
ctcataggac actcatagct caggagggct ccgccttcaa tcccacccgc taaagtactt    3720
ggagcggtct ctccctccct catcagccca ccaaaccaaa cctagcctcc aagagtggga    3780
agaaattaaa gcaagatagg ctattaagtg cagagggaga gaaaatgcct ccaacatgtg    3840
aggaagtaat gagagaaatc atagaatttt aaggccatca tggccttaat cttccgcttc    3900
ctcgctcact gactcgctgc gctcggtcgt tcggctgcgg cgagcggtat cagctcactc    3960
aaaggcggta atacggttat ccacagaatc aggggataac gcaggaaaga acatgtgagc    4020
aaaaggccag caaaaggcca ggaaccgtaa aaaggccgcg ttgctggcgt ttttccatag    4080
gctccgcccc cctgacgagc atcacaaaaa tcgacgctca gtcagaggt ggcgaaaccc    4140 gacaggacta taaagatacc aggcgtttcc ccctggaagc tccctcgtgc gctctcctgt    4200
tccgaccctg ccgcttaccg gatacctgtc cgcctttctc ccttcgggaa gcgtggcgct    4260
ttctcatagc tcacgctgta ggtatctcag ttcggtgtag gtcgttcgct ccaagctggg    4320
ctgtgtgcac gaaccccccg ttcagcccga ccgctgcgcc ttatccggta actatcgtct    4380
tgagtccaac ccggtaagac acgacttatc gccactggca gcagccactg gtaacaggat    4440
tagcagagcg aggtatgtag gcggtgctac agagttcttg aagtggtggc ctaactacgg    4500
ctacactaga agaacagtat ttggtatctg cgctctgctg aagccagtta ccttcggaaa    4560
aagagttggt agctcttgat ccggcaaaca aaccaccgct ggtagcggtg ttttttgt    4620 ttgcaagcag cagattacgc gcagaaaaaa aggatctcaa gaagatcctt tgatcttttc    4680 tacgggtct gacgctcagt ggaacgaaaa ctcacgttaa gggattttgg tcatgagatt    4740
atcaaaaagg atcttcacct agatcctttt aaattaaaaa tgaagtttta atcaatcta    4800 aagtatatat gagtaaactt ggtctgacag ttaccaatgc ttaatcagtg aggcaccta    4860 ctcagcgatc tgtctatttc gttcatccat agttgcctga ctcgggggg ggggcgctg    4920 aggtctgcct cgtgaagaag gtgttgctga ctcataccag gcctgaatcg ccccatcatc    4980
cagccagaaa gtgagggagc cacggttgat gagagctttg ttgtaggtgg accagttggt    5040
gattttgaac ttttgctttg ccacggaacg gtctgcgttg tcgggaagat gcgtgatctg    5100
atccttcaac tcagcaaaag ttcgatttat tcaacaaagc cgccgtcccg tcaagtcagc    5160
gtaatgctct gccagtgtta caaccaatta accaattctg attagaaaaa ctcatcgagc    5220
atcaaatgaa actgcaattt attcatatca ggattatcaa taccatattt tgaaaaagc    5280 cgtttctgta atgaaggaga aaactcaccg aggcagttcc ataggatggc aagatcctgg    5340
tatcggtctg cgattccgac tcgtccaaca tcaatacaac ctattaattt ccctcgtca    5400 aaaataaggt tatcaagtga gaaatcacca tgagtgacga ctgaatccgg tgagaatggc    5460
aaaagcttat gcatttcttt ccagacttgt tcaacaggcc agccattacg ctcgtcatca    5520
aaatcactcg catcaaccaa accgttattc attcgtgatt gcgcctgagc gagacgaaat    5580
acgcgatcgc tgttaaaagg acaattacaa acaggaatcg aatgcaaccg gcgcaggaac    5640
actgccagcg catcaacaat attttcacct gaatcaggat attcttctaa tacctggaat    5700
gctgttttcc cggggatcgc agtggtgagt aaccatgcat catcaggagt acggataaaa    5760
tgcttgatgg tcggaagagg cataaattcc gtcagccagt ttagtctgac catctcatct    5820
```

| | | | | |
|---|---|---|---|---|
| gtaacatcat | tggcaacgct | acctttgcca | tgtttcagaa | acaactctgg cgcatcgggc | 5880 |
| ttcccataca | atcgatagat | tgtcgcacct | gattgcccga | cattatcgcg agcccattta | 5940 |
| tacccatata | aatcagcatc | catgttggaa | tttaatcgcg | gcctcgagca agacgtttcc | 6000 |
| cgttgaatat | ggctcataac | accccttgta | ttactgttta | tgtaagcaga cagttttatt | 6060 |
| gttcatgatg | atatatttttt | atcttgtgca | atgtaacatc | agagattttg agacacaacg | 6120 |
| tggctttccc | ccccccccca | ttattgaagc | atttatcagg | gttattgtct catgagcgga | 6180 |
| tacatatttg | aatgtattta | gaaaaataaa | caaatagggg | ttccgcgcac atttccccga | 6240 |
| aaagtgccac | ctgacgtcta | agaaaccatt | attatcatga | cattaaccta taaaaatagg | 6300 |
| cgtatcacga | ggccctttcg | tc | | | 6322 |

<210> SEQ ID NO 40
<211> LENGTH: 6324
<212> TYPE: DNA
<213> ORGANISM: Artificial Sequence
<220> FEATURE:
<223> OTHER INFORMATION: Synthetic Construct CMV/R-GP(S, Q66798)(dTM)/h

<400> SEQUENCE: 40

| | | | | |
|---|---|---|---|---|
| tcgcgcgttt | cggtgatgac | ggtgaaaacc | tctgacacat | gcagctcccg gagacggtca | 60 |
| cagcttgtct | gtaagcggat | gccgggagca | gacaagcccg | tcagggcgcg tcagcgggtg | 120 |
| ttggcgggtg | tcggggctgg | cttaactatg | cggcatcaga | gcagattgta ctgagagtgc | 180 |
| accatatgcg | gtgtgaaata | ccgcacagat | gcgtaaggag | aaaataccgc atcagattgg | 240 |
| ctattggcca | ttgcatacgt | tgtatccata | tcataatatg | tacatttata ttggctcatg | 300 |
| tccaacatta | ccgccatgtt | gacattgatt | attgactagt | tattaatagt aatcaattac | 360 |
| ggggtcatta | gttcatagcc | catatatgga | gttccgcgtt | acataactta cggtaaatgg | 420 |
| cccgcctggc | tgaccgccca | acgacccccg | cccattgacg | tcaataatga cgtatgttcc | 480 |
| catagtaacg | ccaataggga | ctttccattg | acgtcaatgg | gtggagtatt tacggtaaac | 540 |
| tgcccacttg | gcagtacatc | aagtgtatca | tatgccaagt | acgccccccta ttgacgtcaa | 600 |
| tgacggtaaa | tggcccgcct | ggcattatgc | ccagtacatg | accttatggg actttcctac | 660 |
| ttggcagtac | atctacgtat | tagtcatcgc | tattaccatg | gtgatgcggt tttggcagta | 720 |
| catcaatggg | cgtggatagc | ggtttgactc | acggggattt | ccaagtctcc accccattga | 780 |
| cgtcaatggg | agtttgtttt | ggcaccaaaa | tcaacgggac | tttccaaaat gtcgtaacaa | 840 |
| ctccgcccca | ttgacgcaaa | tgggcggtag | gcgtgtacgg | tgggaggtct atataagcag | 900 |
| agctcgttta | gtgaaccgtc | agatcgcctg | gagacgccat | ccacgctgtt ttgacctcca | 960 |
| tagaagacac | cgggaccgat | ccagcctcca | tcggctcgca | tctctccttc acgcgcccgc | 1020 |
| cgccttacct | gaggccgcca | tccacgccgg | ttgagtcgcg | ttctgccgcc tcccgcctgt | 1080 |
| ggtgcctcct | gaactacgtc | cgccgtctag | gtaagtttag | agctcaggtc gagaccgggc | 1140 |
| ctttgtccgg | cgctcccttg | gagcctacct | agactcagcc | ggctctccac gctttgcctg | 1200 |
| accctgcttg | ctcaactcta | gttaacggtg | gagggcagtg | tagtctgagc agtactcgtt | 1260 |
| gctgccgcgc | gcgccaccag | acataatagc | tgacagacta | acagactgtt cctttccatg | 1320 |
| ggtcttttct | gcagtcaccg | tcgtcgacga | tatcgccgcc | atggagggcc tgagcctgct | 1380 |
| gcagctgccc | aggacaagt | tcaggaagag | cagcttcttc | gtgtgggtga tcatcctgtt | 1440 |
| ccagaaggcc | ttcagcatgc | ccctgggcgt | ggtgaccaac | agcaccctgg aggtgaccga | 1500 |

```
gatcgaccag ctggtgtgca aggaccacct ggccagcacc gaccagctga agagcgtggg    1560
cctgaacctg gagggcagcg gcgtgagcac cgacatcccc agcgccacca agaggtgggg    1620
cttcaggagc ggcgtgcctc cccaggtggt gagctacgag gccggcgagt gggccgagaa    1680
ctgctacaac ctggagatca agaagcccga cggcagcgag tgcctgcctc ctcctcctga    1740
cggcgtgagg ggcttcccca ggtgcaggta cgtgcacaag gcccagggca ccggcccctg    1800
ccccggcgac tacgccttcc acaaggacgg cgccttcttc ctgtacgaca ggctggccag    1860
caccgtgatc tacagggggcg tgaacttcgc cgagggcgtg atcgccttcc tgatcctggc    1920
caagcccaag gagaccttcc tgcagagccc tcccatcagg gaggccgcca actacaccga    1980
gaacaccagc agctactacg ccaccagcta tctagagtac gagatcgaga acttcggcgc    2040
ccagcacagc accaccctgt tcaagatcaa caacaacacc ttcgtgctgc tggacaggcc    2100
ccacacccct cagttcctgt tccagctgaa cgacaccatc cagctgcacc agcagctgag    2160
caacaccacc ggcaagctga tctggaccct ggacgccaac atcaacgccg acatcggcga    2220
gtgggccttc tgggagaaca agaagaacct gagcgagcag ctgaggggcg aggagctgag    2280
cttcgagacc ctgagcctga cgagaccga ggacgacgac gccaccagca gcaggaccac    2340
caagggcagg atcagcgaca gggccaccag gaagtacagc gacctggtgc caaggacag    2400 ccccggcatg gtgagcctgc acgtgcccga gggcgagacc accctgccca gccagaacag    2460
caccgagggc aggagggtgg acgtgaacac caggagacc atcaccgaga ccaccgccac    2520
catcatcggc accaacggca caacatgca gatcagcacc atcggcaccg gcctgagcag    2580
cagccagatc ctgagcagca gccccaccat ggcccctagc cccgagaccc agaccagcac    2640
cacctacacc cctaagctgc ccgtgatgac caccgaggag cccaccaccc ctcccaggaa    2700
cagccccgga tccaccaccg aggcccctac cctgaccacc cctgagaaca tcaccaccgc    2760
cgtgaagacc gtgtgggccc aggagagcac cagcaacggc ctgatcacca gcaccgtgac    2820
cggcatcctg ggcagcctgg gcctgaggaa gaggagcagg aggcaggtga acaccagggc    2880
caccggcaag tgcaacccca acctgcacta ctggaccgcc caggagcagc acaacgccgc    2940
cggcatcgcc tggattccct acttcggccc cggcgccgag ggcatctaca ccgagggcct    3000
gatgcacaac cagaacgccc tggtgtgcgg cctgaggcag ctggccaacg agaccaccca    3060
ggccctgcag ctgttcctga gggccaccac cgagctgagg acctacacca tcctgaacag    3120
gaaggccatc gacttcctgc tgaggaggtg gggcggcacc tgcaggattc tgggccccga    3180
ctgctgcatc gagccccacg actggaccaa gaacatcacc gacaagatca accagatcat    3240
ccacgacttc atcgacaacc ctctgcccaa ccaggacaac gacgacaact ggtggaccgg    3300
ctgaacacgt ggaattcaga tctgctgtgc cttctagttg ccagccatct gttgtttgcc    3360
cctcccccgt gccttccttg accctggaag gtgccactcc cactgtcctt tcctaataaa    3420
atgaggaaat tgcatcgcat tgtctgagta ggtgtcattc tattctgggg ggtggggtgg    3480
ggcaggacag caaggggagg gattgggaag acaatagcag gcatgctggg gatgcggtgg    3540
gctctatggg taccaggtg ctgaagaatt gacccggttc ctcctgggcc agaaagaagc    3600
aggcacatcc ccttctctgt gacacaccct gtccacgccc ctggttctta gttccagccc    3660
cactcatagg acactcatag ctcaggaggg ctccgccttc aatcccaccc gctaaagtac    3720
ttggagcggt ctctccctcc ctcatcagcc caccaaacca aacctagcct ccaagagtgg    3780
gaagaaatta aagcaagata ggctattaag tgcagaggga gagaaaatgc ctccaacatg    3840
tgaggaagta atgagagaaa tcatagaatt ttaaggccat catggcctta atcttccgct    3900
```

```
tcctcgctca ctgactcgct gcgctcggtc gttcggctgc ggcgagcggt atcagctcac   3960
tcaaaggcgg taatacggtt atccacagaa tcaggggata acgcaggaaa gaacatgtga   4020
gcaaaaggcc agcaaaaggc caggaaccgt aaaaaggccg cgttgctggc gtttttccat   4080
aggctccgcc cccctgacga gcatcacaaa aatcgacgct caagtcagag gtggcgaaac   4140
ccgacaggac tataaagata ccaggcgttt ccccctggaa gctccctcgt gcgctctcct   4200
gttccgaccc tgccgcttac cggatacctg tccgcctttc tcccttcggg aagcgtggcg   4260
ctttctcata gctcacgctg taggtatctc agttcggtgt aggtcgttcg ctccaagctg   4320
ggctgtgtgc acgaaccccc cgttcagccc gaccgctgcg ccttatccgg taactatcgt   4380
cttgagtcca acccggtaag acacgactta tcgccactgg cagcagccac tggtaacagg   4440
attagcagag cgaggtatgt aggcggtgct acagagttct tgaagtggtg cctaactacg   4500 gctacacta aagaacagt atttggtatc tgcgctctgc tgaagccagt taccttcgga   4560
aaaagagttg gtagctcttg atccggcaaa caaaccaccg ctggtagcgg tggtttttt   4620 gtttgcaagc agcagattac gcgcagaaaa aaaggatctc aagaagatcc tttgatcttt   4680
tctacggggt ctgacgctca gtggaacgaa aactcacgtt aagggatttt ggtcatgaga   4740
ttatcaaaaa ggatcttcac ctagatcctt ttaaattaaa aatgaagttt taaatcaatc   4800
taaagtatat atgagtaaac ttggtctgac agttaccaat gcttaatcag tgaggcacct   4860
atctcagcga tctgtctatt tcgttcatcc atagttgcct gactcggggg gggggggcgc   4920
tgaggtctgc ctcgtgaaga aggtgttgct gactcatacc aggcctgaat cgccccatca   4980
tccagccaga aagtgaggga gccacggttg atgagagctt tgttgtaggt ggaccagttg   5040
gtgattttga acttttgctt tgccacggaa cggtctgcgt tgtcgggaag atgcgtgatc   5100
tgatccttca actcagcaaa agttcgattt attcaacaaa gccgccgtcc cgtcaagtca   5160
gcgtaatgct ctgccagtgt tacaaccaat taaccaattc tgattagaaa aactcatcga   5220
gcatcaaatg aaactgcaat ttattcatat caggattatc aataccatat ttttgaaaaa   5280
gccgtttctg taatgaagga gaaaactcac cgaggcagtt ccataggatg caagatcct   5340 ggtatcggtc tgcgattccg actcgtccaa catcaataca acctattaat ttcccctcgt   5400
caaaaataag gttatcaagt gagaaatcac catgagtgac gactgaatcc ggtgagaatg   5460
gcaaaagctt atgcatttct ttccagactt gttcaacagg ccagccatta cgctcgtcat   5520
caaaatcact cgcatcaacc aaaccgttat tcattcgtga ttgcgcctga gcgagacgaa   5580
atacgcgatc gctgttaaaa ggacaattac aaacaggaat cgaatgcaac cggcgcagga   5640
acactgccag cgcatcaaca atattttcac ctgaatcagg atattcttct aatacctgga   5700
atgctgtttt cccggggatc gcagtggtga gtaaccatgc atcatcagga gtacggataa   5760
aatgcttgat ggtcggaaga ggcataaatt ccgtcagcca gtttagtctg accatctcat   5820
ctgtaacatc attggcaacg ctacctttgc catgtttcag aaacaactct ggcgcatcgg   5880
gcttcccata caatcgatag attgtcgcac ctgattgccc gacattatcg cgagcccatt   5940
tatacccata taaatcagca tccatgttgg aatttaatcg cggcctcgag caagacgttt   6000
cccgttgaat atggctcata caccccttg tattactgtt tatgtaagca gacagtttta   6060
ttgttcatga tgatatattt ttatcttgtg caatgtaaca tcagagattt tgagacacaa   6120
cgtggctttc ccccccccc cattattgaa gcatttatca gggttattgt ctcatgagcg   6180
gatacatatt tgaatgtatt tagaaaaata acaaataggg gttccgcgc acatttcccc   6240
```

-continued gaaaagtgcc acctgacgtc taagaaacca ttattatcat gacattaacc tataaaaata 6300
ggcgtatcac gaggcccttt cgtc 6324

<210> SEQ ID NO 41
<211> LENGTH: 6236
<212> TYPE: DNA
<213> ORGANISM: Artificial Sequence
<220> FEATURE:
<223> OTHER INFORMATION: Synthetic Construct pVR1012x/s Lassa (codon optimized)

<400> SEQUENCE: 41
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
ggggtcatta gttcatagcc catatatgga gttccgcgtt acataactta cggtaaatgg 420
cccgcctggc tgaccgccca acgacccccg cccattgacg tcaataatga cgtatgttcc 480
catagtaacg ccaataggga ctttccattg acgtcaatgg gtggagtatt tacggtaaac 540
tgcccacttg gcagtacatc aagtgtatca tatgccaagt acgcccccta ttgacgtcaa 600
tgacggtaaa tggcccgcct ggcattatgc ccagtacatg accttatggg actttcctac 660
ttggcagtac atctacgtat tagtcatcgc tattaccatg gtgatgcggt tttggcagta 720
catcaatggg cgtggatagc ggtttgactc acggggattt ccaagtctcc accccattga 780
cgtcaatggg agtttgtttt ggcaccaaaa tcaacgggac tttccaaaat gtcgtaacaa 840
ctccgcccca ttgacgcaaa tgggcggtag gcgtgtacgg tgggaggtct atataagcag 900
agctcgttta gtgaaccgtc agatcgcctg gagacgccat ccacgctgtt ttgacctcca 960
tagaagacac cgggaccgat ccagcctccg cggccgggaa cggtgcattg gaacgcggat 1020
tccccgtgcc aagagtgacg taagtaccgc ctatagactc tataggcaca cccctttggc 1080
tcttatgcat gctatactgt ttttggcttg gggcctatac acccccgctt ccttatgcta 1140
taggtgatgg tatagcttag cctataggtg tgggttattg accattattg accactcccc 1200
tattggtgac gatactttcc attactaatc cataacatgg ctctttgcca caactatctc 1260
tattggctat atgccaatac tctgtccttc agagactgac acggactctg tatttttaca 1320
ggatggggtc ccatttatta tttacaaatt cacatataca acaacgccgt cccccgtgcc 1380
cgcagttttt attaaacata gcgtgggatc tccacgcgaa tctcgggtac gtgttccgga 1440
catgggctct tctccggtag cggcggagct tccacatccg agccctggtc ccatgcctcc 1500
agcggctcat ggtcgctcgg cagctccttg ctcctaacag tggaggccag acttaggcac 1560
agcacaatgc ccaccaccac cagtgtgccg cacaaggccg tggcggtagg gtatgtgtct 1620
gaaaatgagc gtggagattg ggctcgcacg gctgacgcag atggaagact taaggcagcg 1680
gcagaagaag atgcaggcag ctgagttgtt gtattctgat aagagtcaga ggtaactccc 1740
gttgcggtgc tgttaacggt ggagggcagt gtagtctgag cagtactcgt tgctgccgcg 1800
cgcgccacca gacataatag ctgacagact aacagactgt tcctttccat gggtcttttc 1860
tgcagtcacc gtcgtcgaca cgtgtgatca gatatcgcgg ccgctctaga gatatcgccg 1920

```
ccatgggcca gatcgtgacc ttcttccagg aggtgcccca tgtgatcgag gaggtgatga    1980
acatcgtgct gatcgccctg agcgtgctgg ccgtgctgaa gggcctgtac aacttcgcca    2040
cctgcggcct ggtgggcctg gtgaccttcc tgctgctgtg cggcaggagc tgcaccacca    2100
gcctgtacaa gggcgtgtac gagctgcaga ccctggagct gaacatggag accctgaaca    2160
tgaccatgcc cctgagctgc accaagaaca acagccacca ctacatcatg gtgggcaacg    2220
agaccggcct ggagctaacc ctgaccaaca ccagcatcat caaccacaag ttctgcaacc    2280
tgagcgacgc ccacaagaag aacctgtacg accacgccct gatgagcatc atcagcacct    2340
tccacctgag catccccaac ttcaaccagt acgaggccga gctgcgac ttcaacggcg      2400
gcaagatcag cgtgcagtac aacctgagcc acagctacgc cggcgacgcc gccaaccact    2460
gcggcaccgt ggccaacggc gtgctgcaga ccttcatgag gatggcctgg ggcggcagct    2520
acatcgccct ggacagcggc aggggcaact gggactgcat catgaccagc taccagtacc    2580
tgatcatcca gaacaccacc tgggaggacc actgccagtt cagcaggccc agccccatcg    2640
gctacctggg cctgctgagc cagaggacca gggacatcta catcagcagg aggctgctgg    2700
gcaccttcac ctggaccctg agcgacgcg agggcaagga cacccggc ggctactgcc       2760
tgaccaggtg gatgctgatc gaggccgagc tgaagtgctt cggcaacacc gccgtggcca    2820
agtgcaacga gaagcacgac gaggagttct gcgacatgct gaggctgttc gacttcaaca    2880
agcaggccat ccagaggctg aaggccgagg cccagatgag catccagctg atcaacaagg    2940
ccgtgaacgc cctgatcaac gaccagctga tcatgaagaa ccacctgagg gacatcatgg    3000
gcatccccta ctgcaactac agcaagtact ggtacctgaa ccacaccacc accggcagga    3060
ccagcctgcc caagtgctgg ctggtgagca acggcagcta cctgaacgag acccacttca    3120
gcgacgacat cgagcagcag gccgacaaca tgatcaccga gatgctgcag aaggagtaca    3180
tggagaggca gggcaagacc tgaacacgtg ggatccagat ctgctgtgcc ttctagttgc    3240
cagccatctg ttgtttgccc ctcccccgtg ccttccttga ccctggaagg tgccactccc    3300
actgtccttt cctaataaaa tgaggaaatt gcatcgcatt gtctgagtag gtgtcattct    3360
attctggggg gtggggtggg gcaggacagc aaggggggagg attgggaaga caatagcagg    3420
catgctgggg atgcggtggg ctctatgggt acccaggtgc tgaagaattg acccggttcc    3480
tcctgggcca gaaagaagca ggcacatccc cttctctgtg acacaccctg tccacgcccc    3540
tggttcttag ttccagcccc actcatagga cactcatagc tcaggagggc tccgccttca    3600
atcccacccg ctaaagtact tggagcggtc tctccctccc tcatcagccc accaaaccaa    3660
acctagcctc caagagtggg aagaaattaa agcaagatag gctattaagt gcagagggag    3720
agaaaatgcc tccaacatgt gaggaagtaa tgagagaaat catagaattt taaggccatg    3780
atttaaggcc atcatggcct taatcttccg cttcctcgct cactgactcg ctgcgctcgg    3840
tcgttcggct gcggcgagcg gtatcagctc actcaaaggc ggtaatacgg ttatccacag    3900
aatcagggga taacgcagga aagaacatgt gagcaaaagg ccagcaaaag gccaggaacc    3960
gtaaaaaggc cgcgttgctg gcgtttttcc ataggctccg ccccctgac gagcatcaca    4020
aaaatcgacg ctcaagtcag aggtggcgaa acccgacagg actataaaga taccaggcgt    4080
ttccccctgg aagctccctc gtgcgctctc ctgttccgac cctgccgctt accggatacc    4140
tgtccgcctt tctcccttcg ggaagcgtgg cgctttctca tagctcacgc tgtaggtatc    4200
tcagttcggt gtaggtcgtt cgctccaagc tgggctgtgt gcacgaaccc cccgttcagc    4260
ccgaccgctg cgccttatcc ggtaactatc gtcttgagtc aacccggta agacacgact    4320
```

-continued

```
tatcgccact ggcagcagcc actggtaaca ggattagcag agcgaggtat gtaggcggtg   4380
ctacagagtt cttgaagtgg tggcctaact acggctacac tagaagaaca gtatttggta   4440
tctgcgctct gctgaagcca gttaccttcg gaaaaagagt tggtagctct tgatccggca   4500
aacaaaccac cgctggtagc ggtggttttt ttgtttgcaa gcagcagatt acgcgcagaa   4560
aaaaaggatc tcaagaagat cctttgatct tttctacggg gtctgacgct cagtggaacg   4620
aaaactcacg ttaagggatt ttggtcatga gattatcaaa aaggatcttc acctagatcc   4680
ttttaaatta aaaatgaagt tttaaatcaa tctaaagtat atatgagtaa acttggtctg   4740
acagttacca atgcttaatc agtgaggcac ctatctcagc gatctgtcta tttcgttcat   4800
ccatagttgc ctgactcggg ggggggggc gctgaggtct gcctcgtgaa gaaggtgttg   4860
ctgactcata ccaggcctga atcgccccat catccagcca gaaagtgagg gagccacggt   4920
tgatgagagc tttgttgtag gtggaccagt tggtgatttt gaacttttgc tttgccacgg   4980
aacggtctgc gttgtcggga agatgcgtga tctgatcctt caactcagca aaagttcgat   5040
ttattcaaca aagccgccgt cccgtcaagt cagcgtaatg ctctgccagt gttacaacca   5100
attaaccaat tctgattaga aaaactcatc gagcatcaaa tgaaactgca atttattcat   5160
atcaggatta tcaataccat atttttgaaa aagccgtttc tgtaatgaag gagaaaactc   5220
accgaggcag ttccatagga tggcaagatc ctggtatcgg tctgcgattc cgactcgtcc   5280
aacatcaata caacctatta atttcccctc gtcaaaaata aggttatcaa gtgagaaatc   5340
accatgagtg acgactgaat ccggtgagaa tggcaaaagc ttatgcattt ctttccagac   5400
ttgttcaaca ggccagccat tacgctcgtc atcaaaatca ctcgcatcaa ccaaaccgtt   5460
attcattcgt gattgcgcct gagcgagacg aaatacgcga tcgctgttaa aaggacaatt   5520
acaaacagga atcgaatgca accggcgcag gaacactgcc agcgcatcaa caatattttc   5580
acctgaatca ggatattctt ctaatacctg gaatgctgtt ttcccgggga tcgcagtggt   5640
gagtaaccat gcatcatcag gagtacggat aaaatgcttg atggtcggaa gaggcataaa   5700
ttccgtcagc cagtttagtc tgaccatctc atctgtaaca tcattggcaa cgctaccttt   5760
gccatgtttc agaaacaact ctggcgcatc gggcttccca tacaatcgat agattgtcgc   5820
acctgattgc ccgacattat cgcgagccca tttataccca tataaatcag catccatgtt   5880
ggaatttaat cgcggcctcg agcaagacgt ttcccgttga atatggctca taacacccct   5940
tgtattactg tttatgtaag cagacagttt tattgttcat gatgatatat ttttatcttg   6000
tgcaatgtaa catcagagat tttgagacac aacgtggctt tccccccccc cccattattg   6060
aagcatttat cagggttatt gtctcatgag cggatacata tttgaatgta tttagaaaaa   6120
taaacaaata ggggttccgc gcacatttcc ccgaaaagtg ccacctgacg tctaagaaac   6180
cattattatc atgacattaa cctataaaaa taggcgtatc acgaggccct ttcgtc       6236
```

<210> SEQ ID NO 42
<211> LENGTH: 6902
<212> TYPE: DNA
<213> ORGANISM: Artificial Sequence
<220> FEATURE:
<223> OTHER INFORMATION: Synthetic Construct pVR1012x/s Marburg (codon optimized)

<400> SEQUENCE: 42

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
```

-continued

```
ttggcgggtg tcggggctgg cttaactatg cggcatcaga gcagattgta ctgagagtgc      180
accatatgcg gtgtgaaata ccgcacagat gcgtaaggag aaaataccgc atcagattgg      240
ctattggcca ttgcatacgt tgtatccata tcataatatg tacatttata ttggctcatg      300
tccaacatta ccgccatgtt gacattgatt attgactagt tattaatagt aatcaattac      360
ggggtcatta gttcatagcc catatatgga gttccgcgtt acataactta cggtaaatgg      420
cccgcctggc tgaccgccca acgaccccg cccattgacg tcaataatga cgtatgttcc       480
catagtaacg ccaataggga ctttccattg acgtcaatgg gtggagtatt tacggtaaac      540
tgcccacttg gcagtacatc aagtgtatca tatgccaagt acgcccccta ttgacgtcaa      600
tgacggtaaa tggcccgcct ggcattatgc ccagtacatg accttatggg actttcctac      660
ttggcagtac atctacgtat tagtcatcgc tattaccatg gtgatgcggt tttggcagta      720
catcaatggg cgtggatagc ggtttgactc acggggattt ccaagtctcc accccattga      780
cgtcaatggg agtttgtttt ggcaccaaaa tcaacgggac tttccaaaat gtcgtaacaa      840
ctccgcccca ttgacgcaaa tgggcggtag gcgtgtacgg tgggaggtct atataagcag      900
agctcgttta gtgaaccgtc agatcgcctg gagacgccat ccacgctgtt ttgacctcca      960
tagaagacac cgggaccgat ccagcctccg cggccgggaa cggtgcattg gaacgcggat     1020
tccccgtgcc aagagtgacg taagtaccgc ctatagactc tataggcaca ccctttggc      1080 tcttatgcat gctatactgt ttttggcttg gggcctatac accccgctt ccttatgcta      1140 taggtgatgg tatagcttag cctataggtg tgggttattg accattattg accactcccc      1200
tattggtgac gatactttcc attactaatc cataacatgg ctctttgcca caactatctc      1260
tattggctat atgccaatac tctgtccttc agagactgac acggactctg tattttaca      1320 ggatggggtc ccatttatta tttacaaatt cacatataca acaacgccgt ccccgtgcc      1380 cgcagttttt attaaacata gcgtgggatc tccacgcgaa tctcgggtac gtgttccgga     1440
catgggctct tctccggtag cggcggagct tccacatccg agccctggtc ccatgcctcc     1500
agcggctcat ggtcgctcgg cagctccttg ctcctaacag tggaggccag acttaggcac     1560
agcacaatgc ccaccaccac cagtgtgccg cacaaggccg tggcggtagg gtatgtgtct     1620
gaaaatgagc gtggagattg ggctcgcacg gctgacgcag atggaagact taaggcagcg     1680
gcagaagaag atgcaggcag ctgagttgtt gtattctgat aagagtcaga ggtaactccc     1740
gttgcggtgc tgttaacggt ggagggcagt gtagtctgag cagtactcgt tgctgccgcg     1800
cgcgccacca gacataatag ctgacagact aacagactgt tcctttccat gggtcttttc     1860
tgcagtcacc gtcgtcgaca cgtgtgatca gatatcgcgg ccgctctaga gatatcgccg     1920
ccatgaagac cacctgcctg ttcatcagcc tgatcctgat ccagggcatc aagaccctgc     1980
ccatcctgga gatcgccagc aacaaccagc cccagaacgt ggacagcgtg tgcagcggca     2040
ccctgcagaa gaccgaggac gtgcacctga tgggcttcac cctgagcggc cagaaggtgg     2100
ccgacagccc tctggaggcc agcaagaggt gggccttcag gaccggcgtg ccccccaaga     2160
acgtggagta caccgagggc gaggaggcca agacctgcta caacatcagc gtgaccgacc     2220
ccagcggcaa gagcctgctg ctggaccctc cccaacat cagggactac cctaagtgca       2280
agaccatcca ccacatccag ggccagaacc ctcacgccca gggcatcgcc ctgcacctgt     2340
ggggcgcctt cttcctgtac gacaggatcc ccagcaccac catgtacagg gcagggtgt      2400 tcaccgaggg caacatcgcc gccatgatcg ttaacaagac cgtgcacaag atgatcttca     2460
```

```
gcaggcaggg ccagggctac aggcacatga acctgaccag caccaacaag tactggacca    2520
gcaacaacgg cacccagacc aacgacaccg gctgcttcgg cgccctgcag gagtacaaca    2580
gcaccaagaa ccagacctgc gcccccagca agatccccag cccctgccc accgccaggc     2640
ccgagatcaa gcccaccagc accccaccg acgccaccac cctgaacacc accgacccca    2700
acaacgacga cgaggacctg atcaccagcg gcagcggcag cggcgagcag gagccctaca    2760
ccaccagcga cgccgtgacc aagcagggcc tgagcagcac catgcctcct accctagcc     2820
ctcagcccag caccctcag caggagggca caacaccga ccacagccag ggcaccgtga      2880
ccgagcccaa caagaccaac accaccgccc agcccacgat gcctcctcac aacaccaccg    2940
ccatcagcac caacaacacc agcaagaaca acttcagcac cctgagcgtg agcctgcaga    3000
acaccaccaa ctacgacacc cagagcaccg ccaccgagaa cgagcagacc agcgccccta    3060
gcaagaccac cctgcctccc accggcaacc tgaccaccgc caagagcacc aacaacacca    3120
agggccccac caccaccgcc cctaacatga ccaacgccca cctgaccagc ccagccccca    3180
cccccaaccc caccacccag cacctggtgt acttcaggaa gaagaggagc atcctgtgga    3240
gggagggcga tatgttcccc ttcctggacg gcctgatcaa cgcccctatc gacttcgacc    3300
ccgtgcccaa caccaagacc atcttcgacg agagcagcag cagcggcgcc agcgccgagg    3360
aggaccagca cgccagcccc aacatcagcc tgaccctgag ctacttcccc aacatcaacg    3420
agaacaccgc ctacagcggc gagaacgaga cgactgcga cgccgagctg aggatctgga    3480
gcgtgcagga ggacgacctg gccgccggcc tgagctggat tcccttcttc ggcccccggca   3540
tcgagggcct gtacaccgcc ggcctgatca agaaccagaa caacctggtg tgcaggctga    3600
ggaggctggc caaccagacc gccaagagcc tggagctgct gctgagggtg accaccgagg    3660
agaggacctt cagcctgatc aacaggcacg ccatcgactt cctgctgacc aggtggggcg    3720
gcacctgcaa ggtgctgggc cccgactgct gcatcggcat cgaggacctg agcaggaaca    3780
tcagcgagca gatcgaccag atcaagaagg acgagcagaa ggagggcacc ggctggggcc    3840
tgggcggcaa gtggtggacc agcgactgaa cacgtgggat ccagatctgc tgtgccttct    3900
agttgccagc catctgttgt ttgcccctcc ccgtgccctt ccttgaccct ggaaggtgcc    3960
actcccactg tccttttccta ataaaatgag gaaattgcat cgcattgtct gagtaggtgt    4020
cattctattc tggggggtgg ggtggggcag gacagcaagg gggaggattg gaagacaat    4080
agcaggcatg ctggggatgc ggtgggctct atgggtaccc aggtgctgaa gaattgaccc    4140
ggttcctcct gggccagaaa gaagcaggca catcccttc tctgtgacac accctgtcca    4200
cgcccctggt tcttagttcc agccccactc ataggacact catagctcag gagggctccg    4260
ccttcaatcc caccccgctaa agtacttgga gcggtctctc cctccctcat cagcccacca    4320
aaccaaacct agcctccaag agtgggaaga aattaaagca agataggcta ttaagtgcag    4380
agggagagaa aatgcctcca acatgtgagg aagtaatgag agaaatcata gaattttaag    4440
gccatgattt aaggccatca tggccttaat cttccgcttc ctcgctcact gactcgctgc    4500
gctcggtcgt tcggctgcgg cgagcggtat cagctcactc aaaggcggta atacggttat    4560
ccacagaatc aggggataac gcaggaaaga acatgtgagc aaaaggccag caaaaggcca    4620
ggaaccgtaa aaaggccgcg ttgctggcgt ttttccatag gctccgcccc cctgacgagc    4680
atcacaaaaa tcgacgctca agtcagaggt ggcgaaaccc gacaggacta taaagatacc    4740
aggcgtttcc ccctggaagc tccctcgtgc gctctcctgt tccgaccctg ccgcttaccg    4800
gatacctgtc cgcctttctc ccttcgggaa gcgtggcgct ttctcatagc tcacgctgta    4860
```

```
ggtatctcag ttcggtgtag gtcgttcgct ccaagctggg ctgtgtgcac gaaccccccg    4920
ttcagcccga ccgctgcgcc ttatccggta actatcgtct tgagtccaac ccggtaagac    4980
acgacttatc gccactggca gcagccactg gtaacaggat tagcagagcg aggtatgtag    5040
gcggtgctac agagttcttg aagtggtggc ctaactacgg ctacactaga gaacagtat    5100 ttggtatctg cgctctgctg aagccagtta ccttcggaaa aagagttggt agctcttgat    5160
ccggcaaaca accaccgct ggtagcggtg ttttttgt ttgcaagcag cagattacgc       5220
gcagaaaaaa aggatctcaa gaagatcctt tgatcttttc tacggggtct gacgctcagt    5280
ggaacgaaaa ctcacgttaa gggattttgg tcatgagatt atcaaaaagg atcttcacct    5340
agatcctttt aaattaaaaa tgaagtttta aatcaatcta agtatatat gagtaaactt     5400 ggtctgacag ttaccaatgc ttaatcagtg aggcacctat ctcagcgatc tgtctatttc    5460
gttcatccat agttgcctga ctcgggggg ggggcgctg aggtctgcct cgtgaagaag      5520
gtgttgctga ctcataccag gcctgaatcg ccccatcatc cagccagaaa gtgagggagc    5580
cacggttgat gagagctttg ttgtaggtgg accagttggt gattttgaac ttttgctttg    5640
ccacggaacg gtctgcgttg tcgggaagat gcgtgatctg atccttcaac tcagcaaaag    5700
ttcgatttat tcaacaaagc cgccgtcccg tcaagtcagc gtaatgctct gccagtgtta    5760
caaccaatta accaattctg attagaaaaa ctcatcgagc atcaaatgaa actgcaattt    5820
attcatatca ggattatcaa taccatattt ttgaaaaagc cgtttctgta atgaaggaga    5880
aaactcaccg aggcagttcc ataggatggc aagatcctgg tatcggtctg cgattccgac    5940
tcgtccaaca tcaatacaac ctattaattt cccctcgtca aaataaggt tatcaagtga    6000 gaaatcacca tgagtgacga ctgaatccgg tgagaatggc aaaagcttat gcatttcttt    6060
ccagacttgt tcaacaggcc agccattacg ctcgtcatca aaatcactcg catcaaccaa    6120
accgttattc attcgtgatt gcgcctgagc gagacgaaat acgcgatcgc tgttaaaagg    6180
acaattacaa acaggaatcg aatgcaaccg gcgcaggaac actgccagcg catcaacaat    6240
attttcacct gaatcaggat attcttctaa tacctggaat gctgttttcc cggggatcgc    6300
agtggtgagt aaccatgcat catcaggagt acggataaaa tgcttgatgg tcggaagagg    6360
cataaattcc gtcagccagt ttagtctgac catctcatct gtaacatcat ggcaacgct    6420 acctttgcca tgtttcagaa acaactctgg cgcatcgggc ttcccataca atcgatagat    6480
tgtcgcacct gattgcccga cattatcgcg agcccattta tacccatata atcagcatc    6540 catgttggaa tttaatcgcg gcctcgagca agacgtttcc cgttgaatat ggctcataac    6600
accccttgta ttactgttta tgtaagcaga cagttttatt gttcatgatg atatattttt    6660
atcttgtgca atgtaacatc agagattttg agacacaacg tggctttccc ccccccccca    6720
ttattgaagc atttatcagg gttattgtct catgagcgga tacatatttg aatgtattta    6780
gaaaaataaa caaataggg ttccgcgcac atttccccga aaagtgccac ctgacgtcta    6840
agaaaccatt attatcatga cattaaccta taaaaatagg cgtatcacga ggcccttcg    6900 tc                                                                   6902
```

<210> SEQ ID NO 43
<211> LENGTH: 6625
<212> TYPE: DNA
<213> ORGANISM: Artificial Sequence
<220> FEATURE:
<223> OTHER INFORMATION: Synthetic Construct CMV/R Ebola NP

```
<400> SEQUENCE: 43
tcgcgcgttt cggtgatgac ggtgaaaacc tctgacacat gcagctcccg gagacggtca      60
cagcttgtct gtaagcggat gccgggagca gacaagcccg tcaggcgcgc tcagcgggtg     120
ttggcgggtg tcgggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgaccccg cccattgacg tcaataatga cgtatgttcc     480
catagtaacg ccaataggga cttcccattg acgtcaatgg gtggagtatt tacgtaaac     540
tgcccacttg gcagtacatc aagtgtatca tatgccaagt acgccccta ttgacgtcaa     600
tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag     900
agctcgttta gtgaaccgtc agatcgcctg gagacgccat ccacgctgtt tgacctcca     960
tagaagacac cgggaccgat ccagcctcca tcggctcgca tctctccttc acgcgcccgc    1020
cgccttacct gaggccgcca tccacgccgg ttgagtcgcg ttctgccgcc tcccgcctgt    1080
ggtgcctcct gaactacgtc cgccgtctag gtaagtttag agctcaggtc gagaccgggc    1140
cttgtccgg cgctcccttg gagcctacct agactcagcc ggctctccac gctttgcctg    1200
accctgcttg ctcaactcta gttaacggtg gagggcagtg tagtctgagc agtactcgtt    1260
gctgccgcgc gcgccaccag acataatagc tgacagacta acagactgtt cctttccatg    1320
ggtcttttct gcagtcaccg tcgtcgacac gtgtgatcag atatcgcggc cgctctagac    1380
caggccctgg atccagatcg atccgagtat ggattctcgt cctcagaaaa tctggatggc    1440
gccgagtctc actgaatctg acatggatta ccacaagatc ttgacagcag gtctgtccgt    1500
tcaacagggg attgttcggc aaagagtcat cccagtgtat caagtaaaca atcttgaaga    1560
aatttgccaa cttatcatac aggcctttga agcaggtgtt gatttcaag agagtgcgga    1620
cagtttcctt ctcatgcttt gtcttcatca tgcgtaccag ggagattaca aacttttctt    1680
ggaaagtggc gcagtcaagt atttggaagg gcacgggttc cgttttgaag tcaagaagcg    1740
tgatggagtg aagcgccttg aggaattgct gccagcagta tctagtggaa aaaacattaa    1800
gagaacactt gctgccatgc cggaagagga gacaactgaa gctaatgccg gtcagtttct    1860
ctcctttgca agtctattcc ttccgaaatt ggtagtagga gaaaaggctt gccttgagaa    1920
ggttcaaagg caaattcaag tacatgcaga gcaaggactg atacaatatc caacagcttg    1980
gcaatcagta ggacacatga tggtgatttt ccgtttgatg cgaacaaatt ttctgatcaa    2040
atttctccta atacaccaag ggatgcacat ggttgccggg catgatgcca acgatgctgt    2100
gatttcaaat tcagtggctc aagctcgttt ttcaggctta ttgattgtca aaacagtact    2160
tgatcatatc ctacaaaaga cagaacgagg agttcgtctc catcctcttg caaggaccgc    2220
caaggtaaaa aatgaggtga actccttttaa ggctgcactc agctccctgg ccaagcatgg    2280
agagtatgct cctttcgccc gacttttgaa ccttttctgga gtaaataatc ttgagcatgg    2340
```

```
tcttttccct caactatcgg caattgcact cggagtcgcc acagcacacg ggagtaccct    2400
cgcaggagta aatgttggag aacagtatca acaactcaga gaggctgcca ctgaggctga    2460
gaagcaactc caacaatatg cagagtctcg cgaacttgac catcttggac ttgatgatca    2520
ggaaaagaaa attcttatga acttccatca gaaaagaac gaaatcagct tccagcaaac    2580
aaacgctatg gtaactctaa gaaaagagcg cctggccaag ctgacagaag ctatcactgc    2640 tgccgtcactg cccaaaacaa gtggacatta cgatgatgat gacgacattc cctttccagg    2700
acccatcaat gatgacgaca atcctggcca tcaagatgat gatccgactg actcacagga    2760
tacgaccatt cccgatgtgg tggttgatcc cgatgatgga agctacggcg aataccagag    2820
ttactcggaa aacggcatga atgcaccaga tgacttggtc ctattcgatc tagacgagga    2880
cgacgaggac actaagccag tgcctaatag atcgaccaag ggtggacaac agaagaacag    2940
tcaaaagggc cagcatatag agggcagaca gacacaatcc aggccaattc aaaatgtccc    3000
aggccctcac agaacaatcc accacgccag tgcgccactc acggacaatg acagaagaaa    3060
tgaaccctcc ggctcaacca gccctcgcat gctgacacca attaacgaag aggcagaccc    3120
actggacgat gccgacgacg agacgtctag ccttccgccc ttggagtcag atgatgaaga    3180
gcaggacagg gacggaactt ccaaccgcac acccactgtc gccccaccgg ctcccgtata    3240
cagagatcac tctgaaaaga aagaactccc gcaagacgag caacaagatc aggaccacac    3300
tcaagaggcc aggaaccagg acagtgacaa cacccagtca gaacactctt ttgaggagat    3360
gtatcgccac attctaagat cacaggggcc atttgatgct gttttgtatt atcatatgat    3420
gaaggatgag cctgtagttt tcagtaccag tgatggcaaa gagtacacgt atccagactc    3480
ccttgaagag gaatatccac catggctcac tgaaaagag gctatgaatg aagagaatag    3540
atttgttaca ttggatggtc aacaatttta ttggccggtg atgaatcaca agaataaatt    3600
catggcaatc ctgcaacatc atcagctgtg ccttctagtt gccagccatc tgttgtttgc    3660
ccctcccccg tgccttcctt gaccctggaa ggtgccactc ccactgtcct ttcctaataa    3720
aatgaggaaa ttgcatcgca ttgtctgagt aggtgtcatt ctattctggg gggtggggtg    3780
gggcaggaca gcaagggga ggattgggaa gacaatagca ggcatgctgg ggatgcggtg    3840
ggctctatgg gtacccaggt gctgaagaat tgacccggtt cctcctgggc cagaagaag    3900 caggcacatc cccttctctg tgacacaccc tgtccacgcc cctggttctt agttccagcc    3960
ccactcatag gacactcata gctcaggagg gctccgcctt caatcccacc cgctaaagta    4020
cttggagcgg tctctccctc cctcatcagc ccaccaaacc aaacctagcc tccaagagtg    4080
ggaagaaatt aaagcaagat aggctattaa gtgcagaggg agagaaaatg cctccaacat    4140
gtgaggaagt aatgagagaa atcatagaat tttaaggcca tcatggcctt aatcttccgc    4200
ttcctcgctc actgactcgc tgcgctcggt cgttcggctg cggcgagcgg tatcagctca    4260
ctcaaaggcg gtaatacggt tatccacaga atcagggat aacgcaggaa agaacatgtg    4320
agcaaaaggc cagcaaaagg ccaggaaccg taaaaaggcc gcgttgctgg cgttttccca    4380
taggctccgc cccctgacg agcatcacaa aaatcgacgc tcaagtcaga ggtggcgaaa    4440
cccgacagga ctataaagat accaggcgtt tccccctgga agctccctcg tgcgctctcc    4500
tgttccgacc ctgccgctta ccggatacct gtccgccttt ctcccttcgg gaagcgtggc    4560
gctttctcat agctcacgct gtaggtatct cagttcggtg taggtcgttc gctccaagct    4620
gggctgtgtg cacgaacccc ccgttcagcc cgaccgctgc gccttatccg gtaactatcg    4680
```

-continued

| | |
|---|---|
| tcttgagtcc aacccggtaa gacacgactt atcgccactg gcagcagcca ctggtaacag | 4740 |
| gattagcaga gcgaggtatg taggcggtgc tacagagttc ttgaagtggt ggcctaacta | 4800 |
| cggctacact agaagaacag tatttggtat ctgcgctctg ctgaagccag ttaccttcgg | 4860 |
| aaaaagagtt ggtagctctt gatccggcaa acaaaccacc gctggtagcg gtggttttt | 4920 |
| tgtttgcaag cagcagatta cgcgcagaaa aaaaggatct caagaagatc ctttgatctt | 4980 |
| ttctacgggg tctgacgctc agtggaacga aaactcacgt taagggattt tggtcatgag | 5040 |
| attatcaaaa aggatcttca cctagatcct tttaaattaa aaatgaagtt ttaaatcaat | 5100 |
| ctaaagtata tatgagtaaa cttggtctga cagttaccaa tgcttaatca gtgaggcacc | 5160 |
| tatctcagcg atctgtctat ttcgttcatc catagttgcc tgactcgggg ggggggggcg | 5220 |
| ctgaggtctg cctcgtgaag aaggtgttgc tgactcatac caggcctgaa tcgccccatc | 5280 |
| atccagccag aaagtgaggg agccacggtt gatgagagct tgttgtagg tggaccagtt | 5340 |
| ggtgattttg aacttttgct tgccacggaa acggtctgcg ttgtcgggaa gatgcgtgat | 5400 |
| ctgatccttc aactcagcaa agttcgatt tattcaacaa agccgccgtc ccgtcaagtc | 5460 |
| agcgtaatgc tctgccagtg ttacaaccaa ttaaccaatt ctgattagaa aaactcatcg | 5520 |
| agcatcaaat gaaactgcaa tttattcata tcaggattat caataccata ttttgaaaa | 5580 |
| agccgtttct gtaatgaagg agaaaactca ccgaggcagt tccataggat ggcaagatcc | 5640 |
| tggtatcggt ctgcgattcc gactcgtcca acatcaatac aacctattaa ttttcccctcg | 5700 |
| tcaaaaataa ggttatcaag tgagaaatca ccatgagtga cgactgaatc cggtgagaat | 5760 |
| ggcaaaagct tatgcatttc tttccagact tgttcaacag gccagccatt acgctcgtca | 5820 |
| tcaaaatcac tcgcatcaac caaaccgtta ttcattcgtg attgcgcctg agcgagacga | 5880 |
| aatacgcgat cgctgttaaa aggacaatta caaacaggaa tcgaatgcaa ccggcgcagg | 5940 |
| aacactgcca gcgcatcaac aatattttca cctgaatcag gatattcttc taatacctgg | 6000 |
| aatgctgttt tcccggggat cgcagtggtg agtaaccatg catcatcagg agtacggata | 6060 |
| aaatgcttga tggtcggaag aggcataaat tccgtcagcc agtttagtct gaccatctca | 6120 |
| tctgtaacat cattggcaac gctacctttg ccatgtttca gaaacaactc tggcgcatcg | 6180 |
| ggcttcccat acaatcgata gattgtcgca cctgattgcc cgacattatc gcgagcccat | 6240 |
| ttatacccat ataaatcagc atccatgttg gaatttaatc gcggcctcga gcaagacgtt | 6300 |
| tcccgttgaa tatggctcat aacaccccct gtattactgt ttatgtaagc agacagtttt | 6360 |
| attgttcatg atgatatatt tttatcttgt gcaatgtaac atcagagatt ttgagacaca | 6420 |
| acgtggcttt ccccccccc ccattattga agcatttatc agggttattg tctcatgagc | 6480 |
| ggatacatat ttgaatgtat ttagaaaaat aaacaaatag ggttccgcg cacatttccc | 6540 |
| cgaaaagtgc cacctgacgt ctaagaaacc attattatca tgacattaac ctataaaaat | 6600 |
| aggcgtatca cgaggccctt tcgtc | 6625 |

<210> SEQ ID NO 44
<211> LENGTH: 22
<212> TYPE: DNA
<213> ORGANISM: Artificial Sequence
<220> FEATURE:
<223> OTHER INFORMATION: Ebola Sudan GP primer

<400> SEQUENCE: 44
atcttcagga tctcgccatg ga                                      22

```
<210> SEQ ID NO 45
<211> LENGTH: 24
<212> TYPE: DNA
<213> ORGANISM: Artificial Sequence
<220> FEATURE:
<223> OTHER INFORMATION: Ebola Sudan GP primer

<400> SEQUENCE: 45
gatattcaac aaagcagctt gcag                                              24

<210> SEQ ID NO 46
<211> LENGTH: 21
<212> TYPE: DNA
<213> ORGANISM: Artificial Sequence
<220> FEATURE:
<223> OTHER INFORMATION: Ebola Ivory Coast GP primer

<400> SEQUENCE: 46
ctaatcacag tcaccatggg a                                                 21

<210> SEQ ID NO 47
<211> LENGTH: 24
<212> TYPE: DNA
<213> ORGANISM: Artificial Sequence
<220> FEATURE:
<223> OTHER INFORMATION: Ebola Ivory Coast GP primer

<400> SEQUENCE: 47
aaagtatgat gctatattag ttca                                              24

<210> SEQ ID NO 48
<211> LENGTH: 10
<212> TYPE: PRT
<213> ORGANISM: Ebola Virus

<400> SEQUENCE: 48

Gln Arg Thr Phe Ser Ile Pro Leu Gly Val
 1               5                  10

<210> SEQ ID NO 49
<211> LENGTH: 10
<212> TYPE: PRT
<213> ORGANISM: Ebola Virus

<400> SEQUENCE: 49

Arg Arg Thr Arg Arg Glu Ala Ile Val Asn
 1               5                  10

<210> SEQ ID NO 50
<211> LENGTH: 16
<212> TYPE: PRT
<213> ORGANISM: Ebola Virus

<400> SEQUENCE: 50

Gly Ala Ala Ile Gly Leu Ala Trp Ile Pro Tyr Phe Gly Pro Ala Ala
 1               5                  10                  15

<210> SEQ ID NO 51
<211> LENGTH: 5
<212> TYPE: PRT
<213> ORGANISM: Ebola Virus

<400> SEQUENCE: 51

Arg Arg Thr Arg Arg
 1               5
```

<210> SEQ ID NO 52
<211> LENGTH: 1087
<212> TYPE: DNA
<213> ORGANISM: Artificial Sequence
<220> FEATURE:
<223> OTHER INFORMATION: The CMV Enhancer/Promoter, R Region (HTVL-1), CMVIE Splicing Acceptor sequence

<400> SEQUENCE: 52

```
ccattgcata cgttgtatcc atatcataat atgtacattt atattggctc atgtccaaca       60
ttaccgccat gttgacattg attattgact agttattaat agtaatcaat tacggggtca      120
ttagttcata gcccatatat ggagttccgc gttacataac ttacggtaaa tggcccgcct      180
ggctgaccgc ccaacgaccc ccgcccattg acgtcaataa tgacgtatgt tcccatagta      240
acgccaatag ggactttcca ttgacgtcaa tgggtggagt atttacggta aactgcccac      300
ttggcagtac atcaagtgta tcatatgcca agtacgcccc ctattgacgt caatgacggt      360
aaatggcccg cctggcatta tgcccagtac atgaccttat gggactttcc tacttggcag      420
tacatctacg tattagtcat cgctattacc atggtgatgc ggttttggca gtacatcaat      480
gggcgtggat agcggtttga ctcacgggga tttccaagtc tccaccccat tgacgtcaat      540
gggagtttgt tttggcacca aaatcaacgg gactttccaa aatgtcgtaa caactccgcc      600
ccattgacgc aaatgggcgg taggcgtgta cggtgggagg tctatataag cagagctcgt      660
ttagtgaacc gtcagatcgc ctggagacgc catccacgct gttttgacct ccatagaaga      720
caccgggacc gatccagcct ccatcggctc gcatctctcc ttcacgcgcc cgccgcctta      780
cctgaggccg ccatccacgc cggttgagtc gcgttctgcc gcctcccgcc tgtggtgcct      840
cctgaactac gtccgccgtc taggtaagtt tagagctcag gtcgagaccg ggcctttgtc      900
cggcgctccc ttggagccta cctagactca gccggctctc cacgctttgc ctgaccctgc      960
ttgctcaact ctagttaacg gtggagggca gtgtagtctg agcagtactc gttgctgccg     1020
cgcgcgccac cagacataat agctgacaga ctaacagact gttcctttcc atgggtcttt     1080
tctgcag                                                               1087
```

DEVELOPMENT OF A PREVENTIVE VACCINE FOR FILOVIRUS INFECTION IN PRIMATES

RELATED APPLICATIONS

This application represents the U.S. National Phase of International Application No. PCT/US02/30251 filed Sep. 24, 2002, designating the United States of America and published in English as WO 03/028632 on Apr. 10, 2003, which claims the benefit of priority of U.S. Provisional Application No. 60/326,476 filed Oct. 1, 2001, which is hereby expressly incorporated by reference in its entirety.

FIELD OF THE INVENTION

The present invention relates generally to viral vaccines and, more particularly, to filovirus vaccines and methods of eliciting an immune response against a filovirus or a disease caused by infection with filovirus.

BACKGROUND OF THE INVENTION

The Ebola viruses, and the genetically-related Marburg virus, are filoviruses associated with outbreaks of highly lethal hemorrhagic fever in humans and primates in North America, Europe, and Africa (Peters, C. J. et al. in: *Fields Virology*, eds. Fields, B. N. et al. 1161-1176, Philadelphia, Lippincott-Raven, 1996; Peters, C. J. et al. 1994 *Semin Virol* 5:147-154). Ebola viruses are negative-stranded RNA viruses comprised of four subtypes, including those described in the Zaire, Sudan, Reston, and Ivory Coast episodes (Sanchez, A. et al. 1996 *PNAS USA* 93:3602-3607). Although several subtypes have been defined, the genetic organization of these viruses is similar, each containing seven linearly arrayed genes. Among the viral proteins, the envelope glycoprotein exists in two alternative forms, a 50-70 kilodalton (kDa) secreted protein of unknown function encoded by the viral genome and a 130 kDa transmembrane glycoprotein generated by RNA editing that mediates viral entry (Peters, C. J. et al. in: *Fields Virology*, eds. Fields, B. N. et al. 1161-1176, Philadelphia, Lippincott-Raven, 1996; Sanchez, A. et al. 1996 *PNAS* USA 93:3602-3607). Other structural gene products include the nucleoprotein (NP), matrix proteins VP24 and VP40, presumed nonstructural proteins VP30 and VP35, and the viral polymerase (reviewed in Peters, C. J. et al. in: Fields Virology, eds. Fields, B. N. et al. 1161-1176, Philadelphia, Lippincott-Raven, 1996). Although spontaneous variation of its RNA sequence does occur in nature, there appears to be less nucleotide polymorphism within Ebola subtypes than among other RNA viruses (Sanchez, A. et al. 1996 PNAS USA 93:3602-3607), suggesting that immunization may be useful in protecting against this disease. Previous attempts to elicit protective immune responses against Ebola virus using traditional active and passive immunization approaches have, however, not succeeded in primates (Peters, C. J. et al. in: *Fields Virology*, eds. Fields, B. N. et al. 1161-1176, Philadelphia, Lippincott-Raven, 1996; Clegg, J. C. S. et al. 1997 *New Generation Vaccines*, eds.: Levine, M. M. et al. 749-765, New York, N.Y. Marcel Dekker, Inc.; Jalrling, P. B. et al. 1996 Arch Virol Suppl 11:135-140). It would thus be desirable to provide a vaccine to elicit an immune response against a filovirus or disease caused by infection with filovirus. It would further be desirable to provide methods of making and using said vaccine.

SUMMARY OF THE INVENTION

Outbreaks of hemorrhagic fever caused by the Ebola virus are associated with high mortality rates that are a distinguishing feature of this human pathogen. The highest lethality is associated with the Zaire subtype, one of four strains identified to date (Feldmann, H. et al. 1994 Virology 199:469-473; Sanchez, A. et al. 1996 *PNAS USA* 93:3602-3607). Its rapid progression allows little opportunity to develop natural immunity, and there is currently no effective anti-viral therapy. Therefore, vaccination offers a promising intervention to prevent infection and limit spread. Here we describe a highly effective vaccine strategy for Ebola virus infection in primates. A combination of DNA immunization and boosting with adenoviral vectors that encode viral proteins generated cellular and humoral immunity in cynomolgus macaques. Challenge with a lethal dose of the highly pathogenic, wild-type, 1976 Mayinga strain of Ebola Zaire virus resulted in uniform infection in controls, who progressed to a moribund state and death in less than one week. In contrast, all vaccinated animals were asymptomatic for more than six months, with no detectable virus after the initial challenge. These findings demonstrate that it is possible to develop a preventive vaccine against Ebola virus infection in primates.

BRIEF DESCRIPTION OF THE DRAWINGS

FIG. 2 shows VRC6001 (pVR1012x/s-GP(Z)) construct map (see, Ebola/Marburg/Lassa Plasmids, and Recombinant Adenoviruses in Table 2).

FIG. 4 shows VRC6003 (pVR1012-GP(Z) delta MUC delta FUR) construct map (see, Ebola/Marburg/Lassa Plasmids, and Recombinant Adenoviruses in Table 2).

FIG. 5 shows VRC6004 (pVR1012-GP(Z) delta GP2) construct map (see, Ebola/Marburg/Lassa Plasmids, and Recombinant Adenoviruses in Table 2).

FIG. 7 shows VRC6006 (pVR1012-GP(Z) delta GP2 delta C-term B) construct map (see, Ebola/Marburg/Lassa Plasmids, and Recombinant Adenoviruses in Table 2).

FIG. 8 shows VRC6007 (pVR1012-GP(Z) delta GP2 delta FUS) construct map (see, Ebola/Marburg/Lassa Plasmids, and Recombinant Adenoviruses in Table 2).

FIG. 9 shows VRC6008 (pVR1012-GP(Z) delta TM) construct map (see, Ebola/Marburg/Lassa Plasmids, and Recombinant Adenoviruses in Table 2).

FIG. 10 shows VRC 6052 (pVR1012-GP(Z) delta SGP) construct map (see, Ebola/Marburg/Lassa Plasmids, and Recombinant Adenoviruses in Table 2).

FIG. 11 shows VRC 6101 (pVR1012x/s Ebola GP(R) (dTM)) construct map (see, Ebola/Marburg/Lassa Plasmids, and Recombinant Adenoviruses in Table 2).

FIG. 12 shows VRC 6110 (pAdApt Ebola GP(R) (dTM)) construct map (see, Ebola/Marburg/Lassa Plasmids, and Recombinant Adenoviruses in Table 2).

FIG. 13 shows VRC6200 (pVR1012-GP(S)) construct map (see, Ebola/Marburg/Lassa Plasmids, and Recombinant Adenoviruses in Table 2).

FIG. 14 shows VRC 6201 (pVR1012x/s Ebola GP(S)) construct map (see, Ebola/Marburg/Lassa Plasmids, and Recombinant Adenoviruses in Table 2).

FIG. 15 shows VRC6202 (pVR1012-GP(S) delta TM) construct map (see, Ebola/Marburg/Lassa Plasmids, and Recombinant Adenoviruses in Table 2).

FIG. 16 shows VRC6300 (pVR1012-GP(IC)) construct map (see, Ebola/Marburg/Lassa Plasmids, and Recombinant Adenoviruses in Table 2).

FIG. 17 shows VRC6301 (pVRO12x/s-GP(IC)) construct map (see, Ebola/Marburg/Lassa Plasmids, and Recombinant Adenoviruses in Table 2).

FIG. 18 shows VRC6302 (pVRO12-GP(IC) delta TM) construct map (see, Ebola/Marburg/Lassa Plasmids, and Recombinant Adenoviruses in Table 2).

FIG. 19 shows VRC 6303 (pVR1012x/s Ebola GP (IC) (dTM)) construct map (see, Ebola/Marburg/Lassa Plasmids, and Recombinant Adenoviruses in Table 2).

FIG. 20 shows VRC 6310 (pAdApt Ebola GP (IC) (dTM)) construct map (see, Ebola/Marburg/Lassa Plasmids, and Recombinant Adenoviruses in Table 2).

FIG. 23 shows VRC6401 (pVR1012x/s-NP) construct map (see, Ebola/Marburg/Lassa Plasmids, and Recombinant Adenoviruses in Table 2).

FIG. 26 shows VRC6601 (pAdApt Ebola GP(S)) construct map (see, Ebola/Marburg/Lassa Plasmids, and Recombinant Adenoviruses in Table 2).

FIG. 27 shows VRC 6602 (pAdApt Ebola GP(S)(dTM)) construct map (see, Ebola/Marburg/Lassa Plasmids, and Recombinant Adenoviruses in Table 2).

Figure 28:
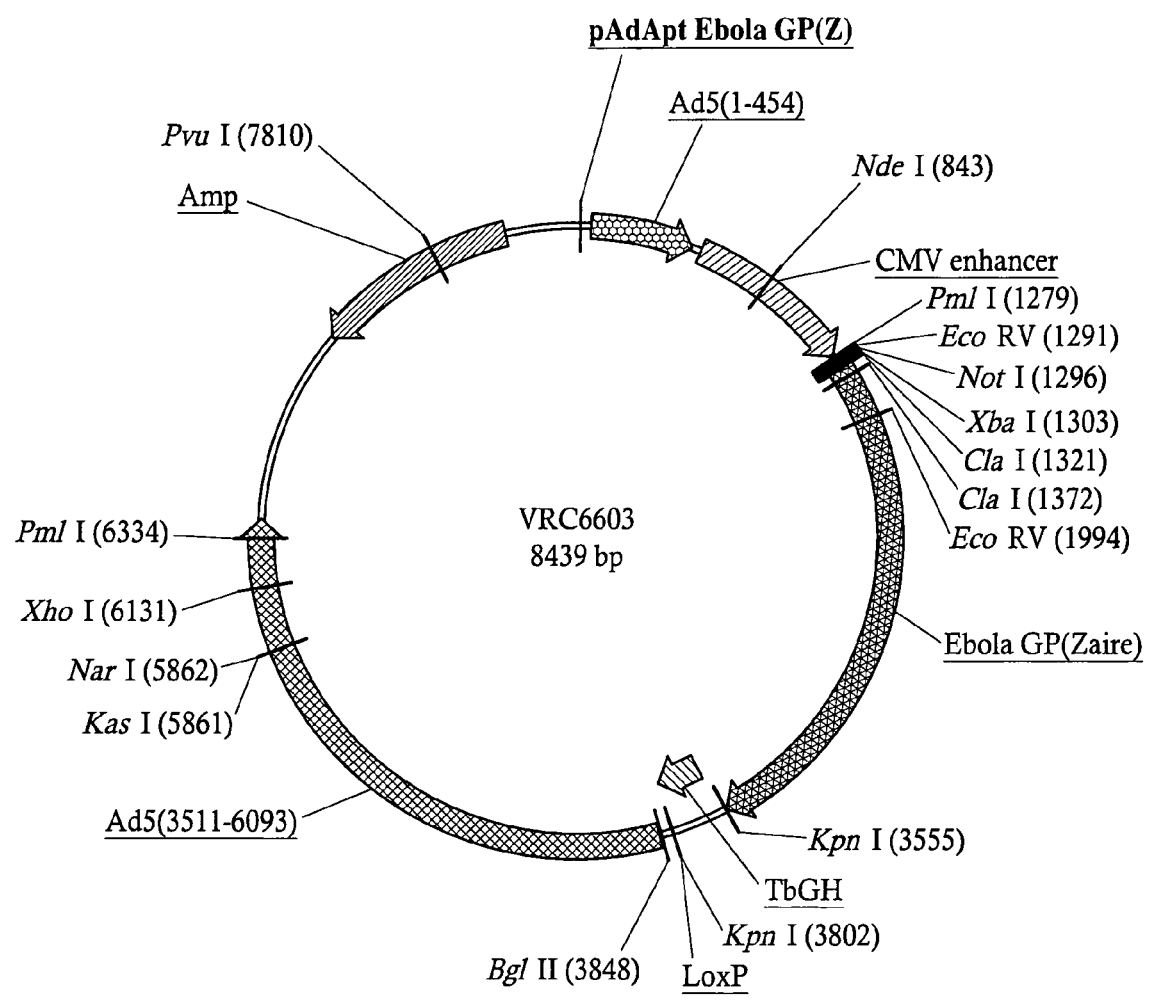

FIG. 28 shows VRC6603 (pAdApt Ebola GP(Z)) construct map (see, Ebola/Marburg/Lassa Plasmids, and Recombinant Adenoviruses in Table 2).

FIG. 29 shows VRC 6604 (pAdApt Ebola GP(Z)(dTM)) construct map (see, Ebola/Marburg/Lassa Plasmids, and Recombinant Adenoviruses in Table 2).

FIG. 30 shows VRC6701 (pVR1012-Marburg) construct map (see, Ebola/Marburg/Lassa Plasmids, and Recombinant Adenoviruses in Table 2).

FIG. 31 shows VRC 6702 (pVR1012x/s Marburg GP (dTM)) construct map (see, Ebola/Marburg/Lassa Plasmids, and Recombinant Adenoviruses in Table 2).

FIG. 32 shows VRC 6710 (pAdApt Marburg GP (dTM)) construct map (see, Ebola/Marburg/Lassa Plasmids, and Recombinant Adenoviruses in Table 2).

FIG. 33 shows VRC6800 (pVR1012x/s Lassa GP) construct map (see, Ebola/Marburg/Lassa Plasmids, and Recombinant Adenoviruses in Table 2).

FIG. 34 shows VRC6801 (pVR1012x/s Lassa GP (dTM) construct map (see, Ebola/Marburg/Lassa Plasmids, and Recombinant Adenoviruses in Table 2).

Figure 35:
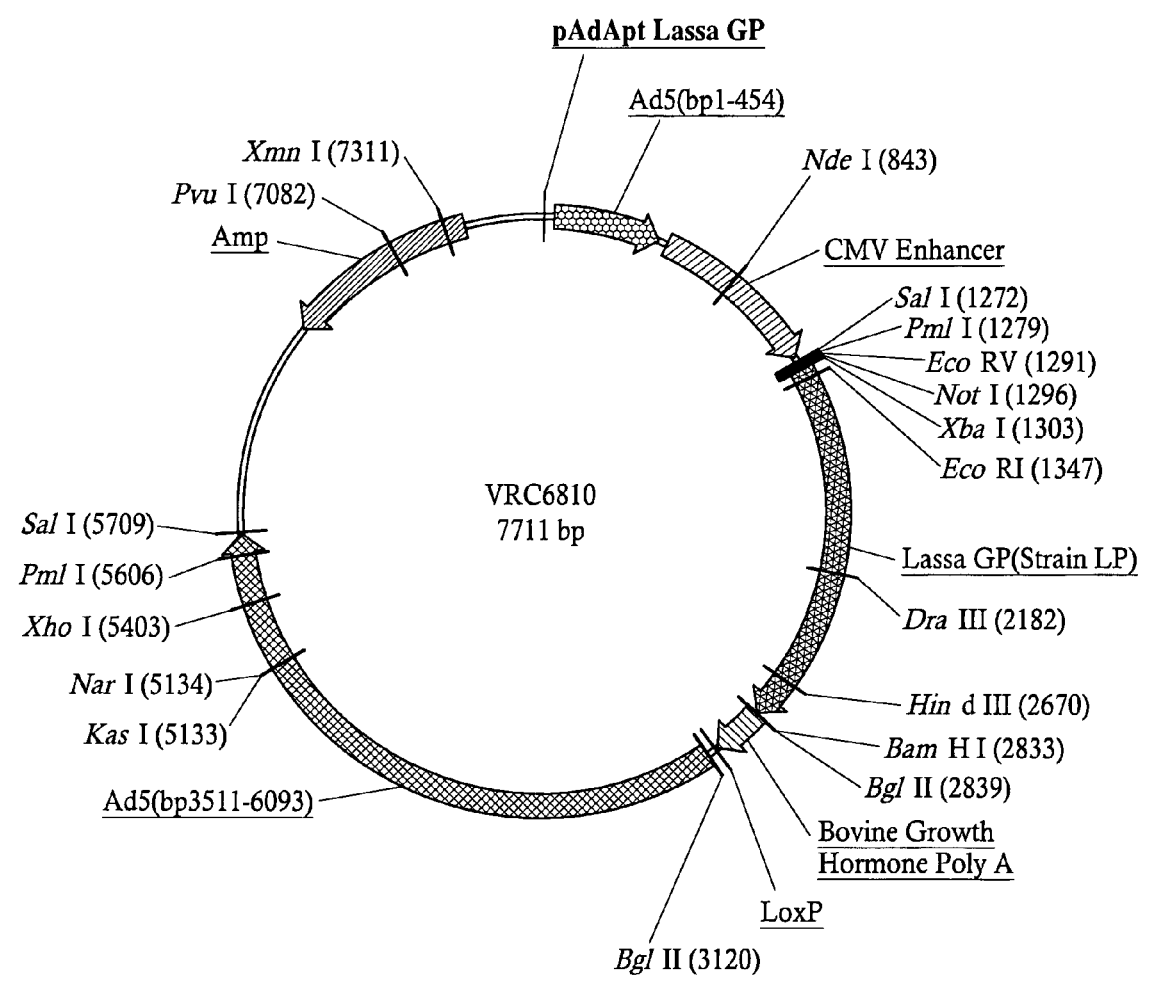

FIG. 35 shows VRC6810 (pAdApt Lassa GP) construct map (see, Ebola/Marburg/Lassa Plasmids, and Recombinant Adenoviruses in Table 2).

Figure 37:
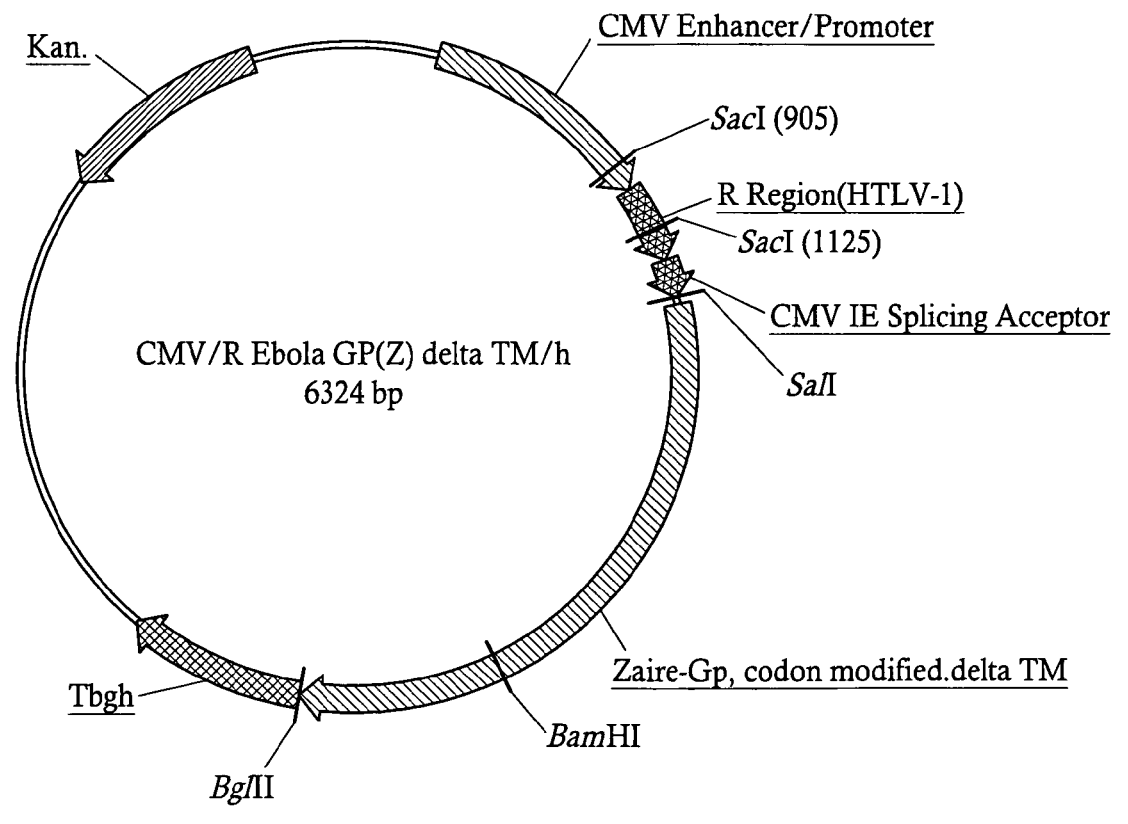

FIG. 37 shows CMV/R Ebola GP (Z) deltaTM/h (codon optimized) construct map (see, Ebola/Marburg/Lassa Plasmids, and Recombinant Adenoviruses in Table 2).

FIG. 38 shows pVR1012 Ebola GP (Z, P87666) delta TM/h (codon optimized) construct map (see, Ebola/Marburg/Lassa Plasmids, and Recombinant Adenoviruses in Table 2).

Figure 39:
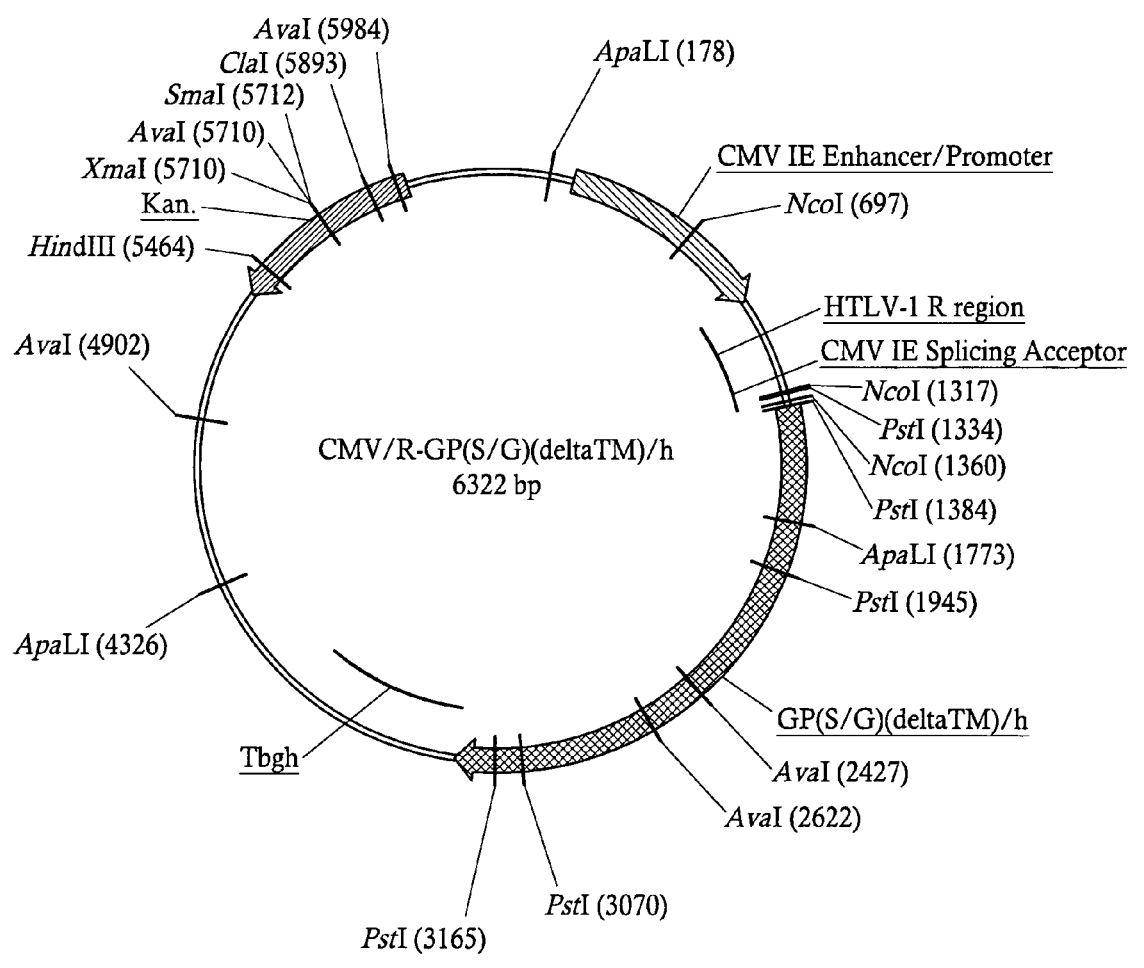

FIG. 39 shows CMV/R Ebola GP (S/Gulu) delta TM/h (codon optimized) construct map (see, Ebola/Marburg/Lassa Plasmids, and Recombinant Adenoviruses in Table 2).

FIG. 40 shows CMV/R Ebola GP (S,Q66798) delta TM/h (codon optimized) construct map (see, Ebola/Marburg/Lassa Plasmids, and Recombinant Adenoviruses in Table 2).

FIG. 41 shows VRC6802, pVR1012x/s Lassa delta TM/h (codon optimized) construct map (see, Ebola/Marburg/Lassa Plasmids, and Recombinant Adenoviruses in Table 2).

FIG. 42 shows VRC6703, pVR1012x/s Marburg delta TM/h (codon optimized) construct map (see, Ebola/Marburg/Lassa Plasmids, and Recombinant Adenoviruses in Table 2).

Figure 43:
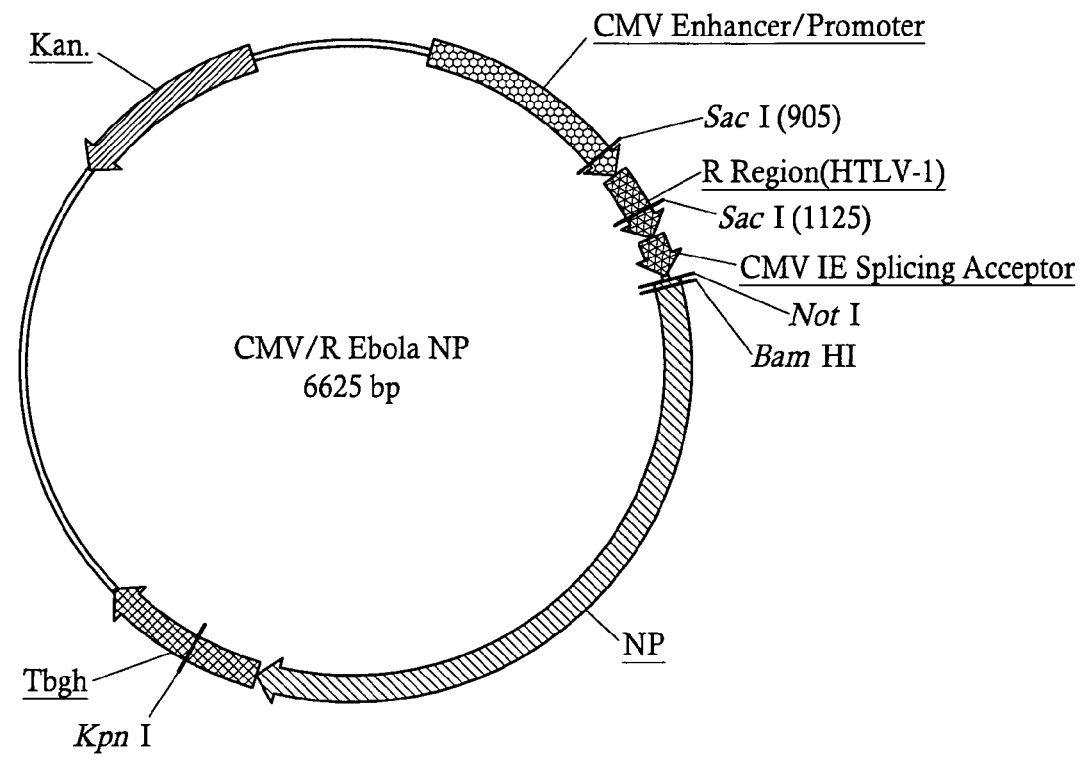

FIG. 43 shows CMV/R Ebola NP construct map (see, Ebola/Marburg/Lassa Plasmids, and Recombinant Adenoviruses in Table 2).

FIG. 46 shows induction of the cytopathic effects by Ebola virus glycoproteins and mapping of the molecular determinants of cytopathicity.

FIGS. 48 (A-D) shows DNA-Adenovirus immunization of cynomolgus macaques. A) Immunization schedule for DNA and/or adenovirus injections, and challenge with the wild-type Mayinga strain of the Zaire subtype of Ebola virus. B) Elisa titers of Ebola-specific antibodies in serum. Serum was collected at week 12 (open bar) and 2 days before the immunization at week 24 (closed bar). C) Lymphoproliferative responses to Ebola-secreted glycoprotein (SGP) following immunization. Bars represent the average fold-proliferation of all four blood samples for each subject. The standard deviation is not shown because the baseline level of induction varied between experiments. However, PBMC from all 8 animals were assayed within the same experiment for each time point, and the averages displayed in the figure are representative of the results obtained for any single time point. D) Lymphoproliferative responses to Ebola SGP in bulk PBMC following depletion of lymphocyte subsets. PBMC from week 24 were treated with Dynal magnetic beads coated with the indicated antibody to deplete $CD4^+$ or $CD8^+$ cell subsets. Cells remaining after depletion were normalized for input cell number and stimulated as described in the Example. Results are shown for two control (Subjects 2 and 3) and two vaccinated (Subjects 6 and 7) monkeys.

FIGS. 50 (A-B) shows enhanced expression of modified CMV expression vector, CMV/R.

TABLE 1

Figure 1:
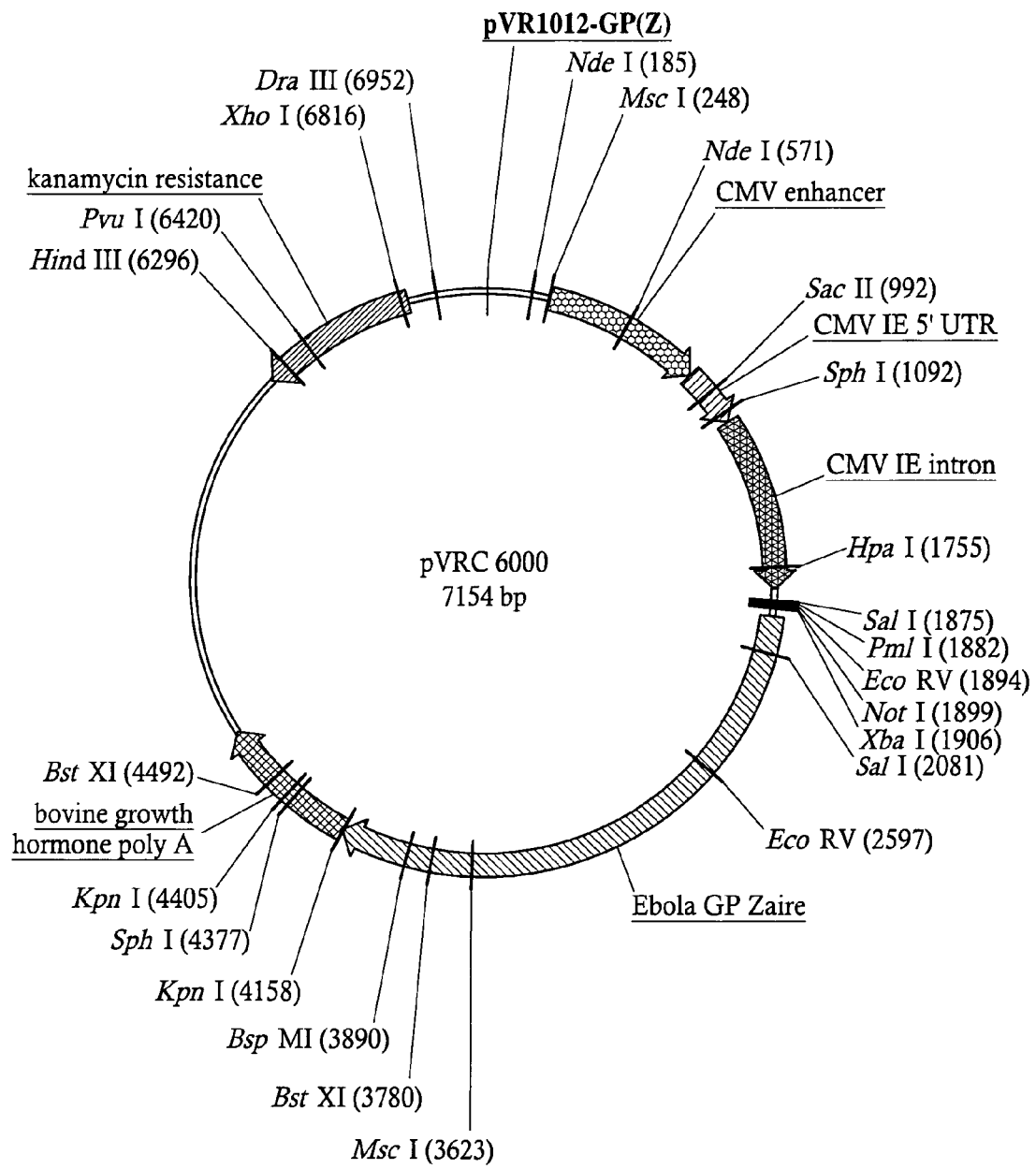
FIG. 1 shows VRC6000 (pVR1012-GP(Z)) construct map (see, Ebola/Marburg/Lassa Plasmids, and Recombinant Adenoviruses in Table 2).
Figure 3:
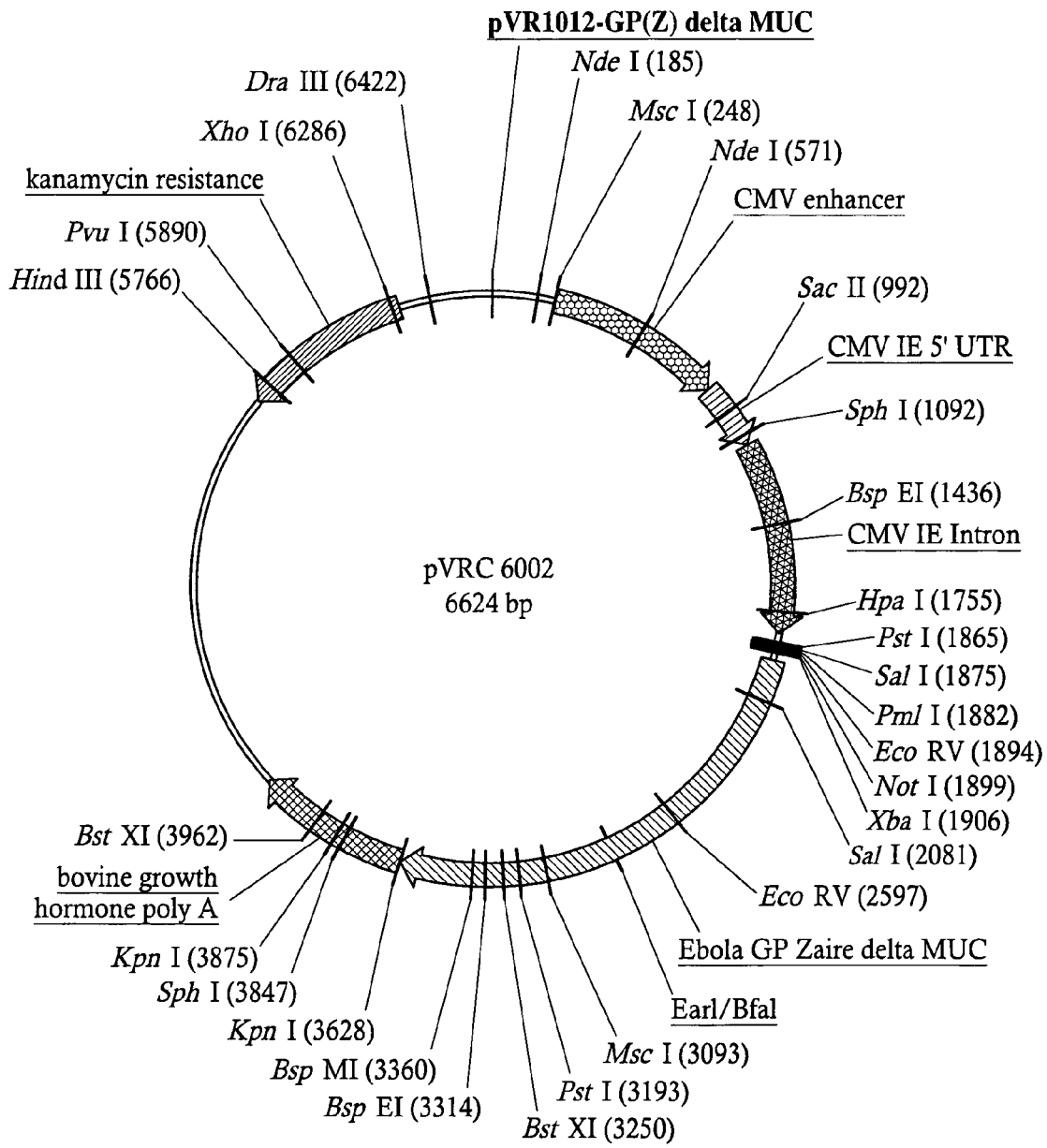
FIG. 3 shows VRC6002 (pVR1012-GP(Z) delta MUC) construct map (see, Ebola/Marburg/Lassa Plasmids, and Recombinant Adenoviruses in Table 2).
Figure 6:
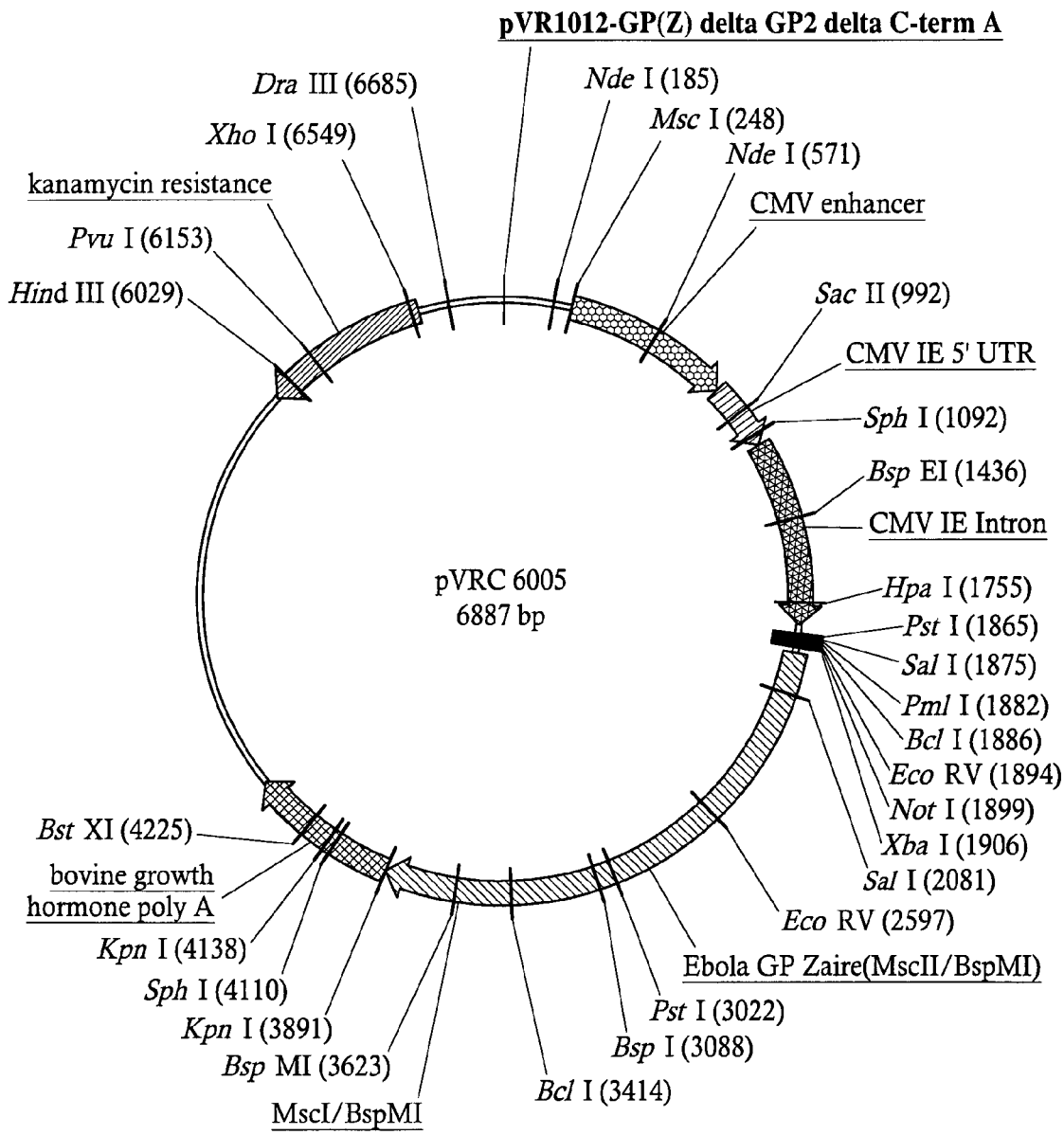
FIG. 6 shows VRC6005 (pVR1012-GP(Z) delta GP2 delta C-term A) construct map (see, Ebola/Marburg/Lassa Plasmids, and Recombinant Adenoviruses in Table 2).
Figure 21:
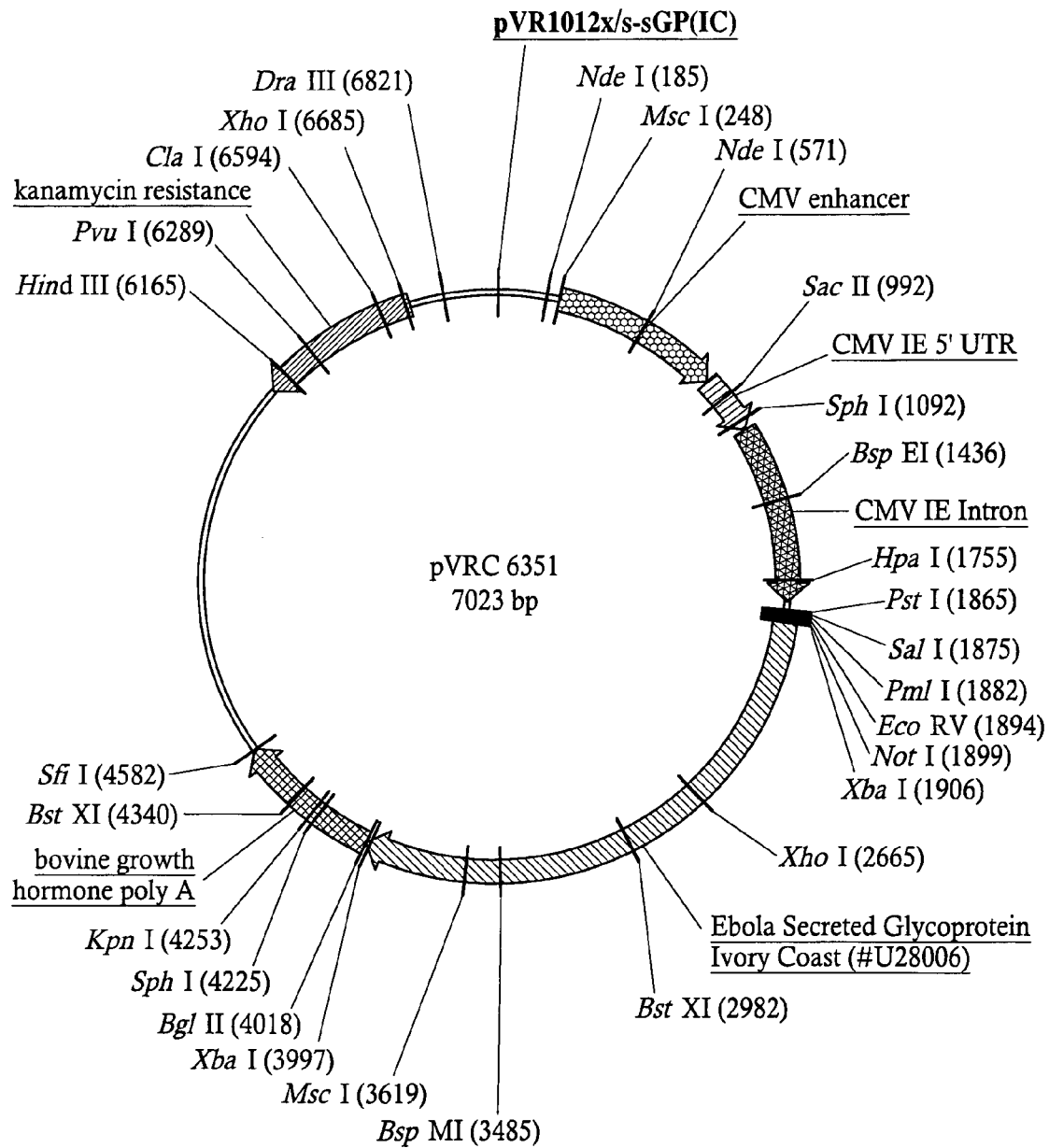
FIG. 21 shows VRC6351 (pVR1012x/s-SGP(IC)) construct map (see, Ebola/Marburg/Lassa Plasmids, and Recombinant Adenoviruses in Table 2).
Figure 22:
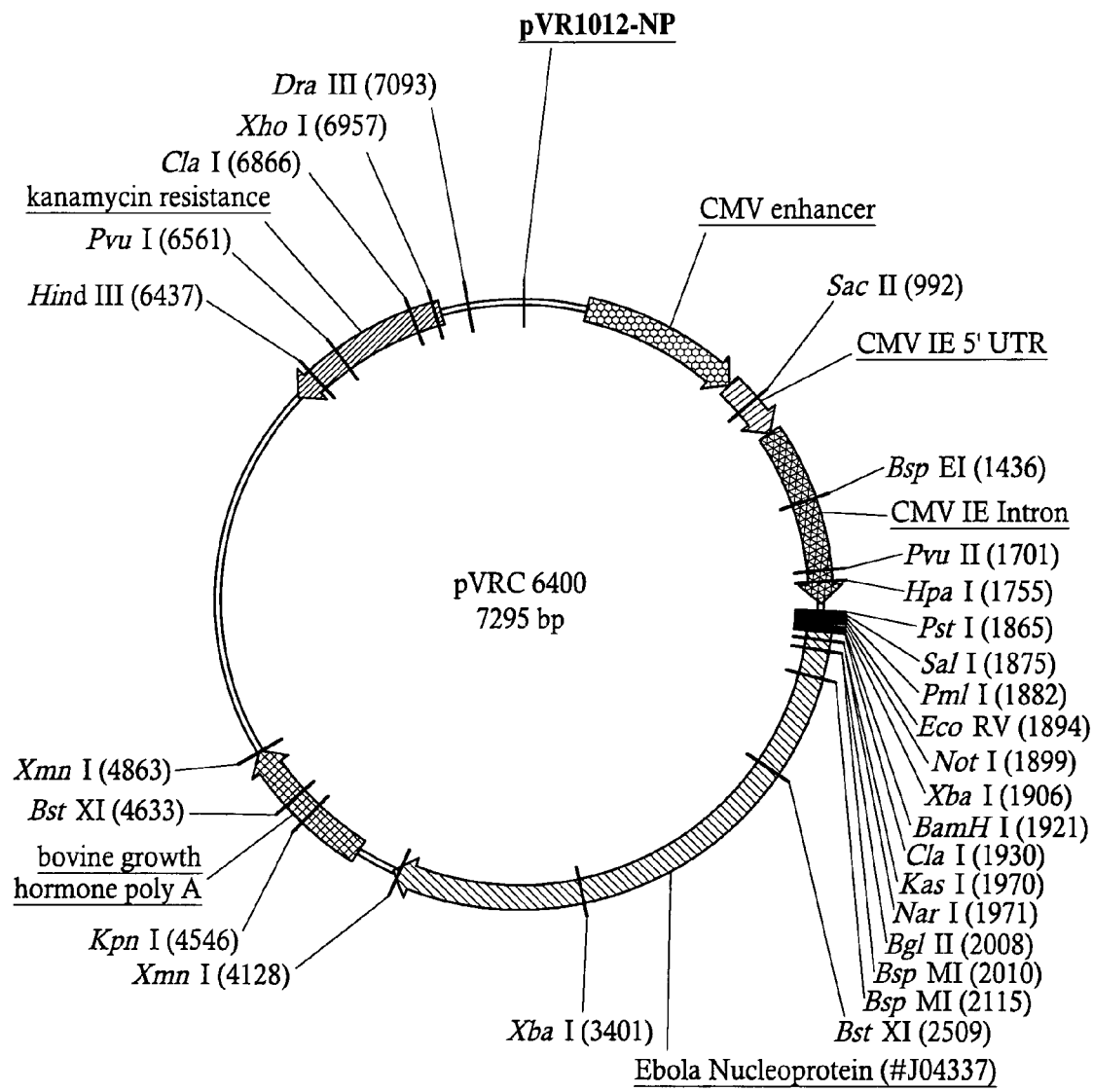
FIG. 22 shows VRC6400 (pVR1012-NP) construct map (see, Ebola/Marburg/Lassa Plasmids, and Recombinant Adenoviruses in Table 2).
Figure 24:
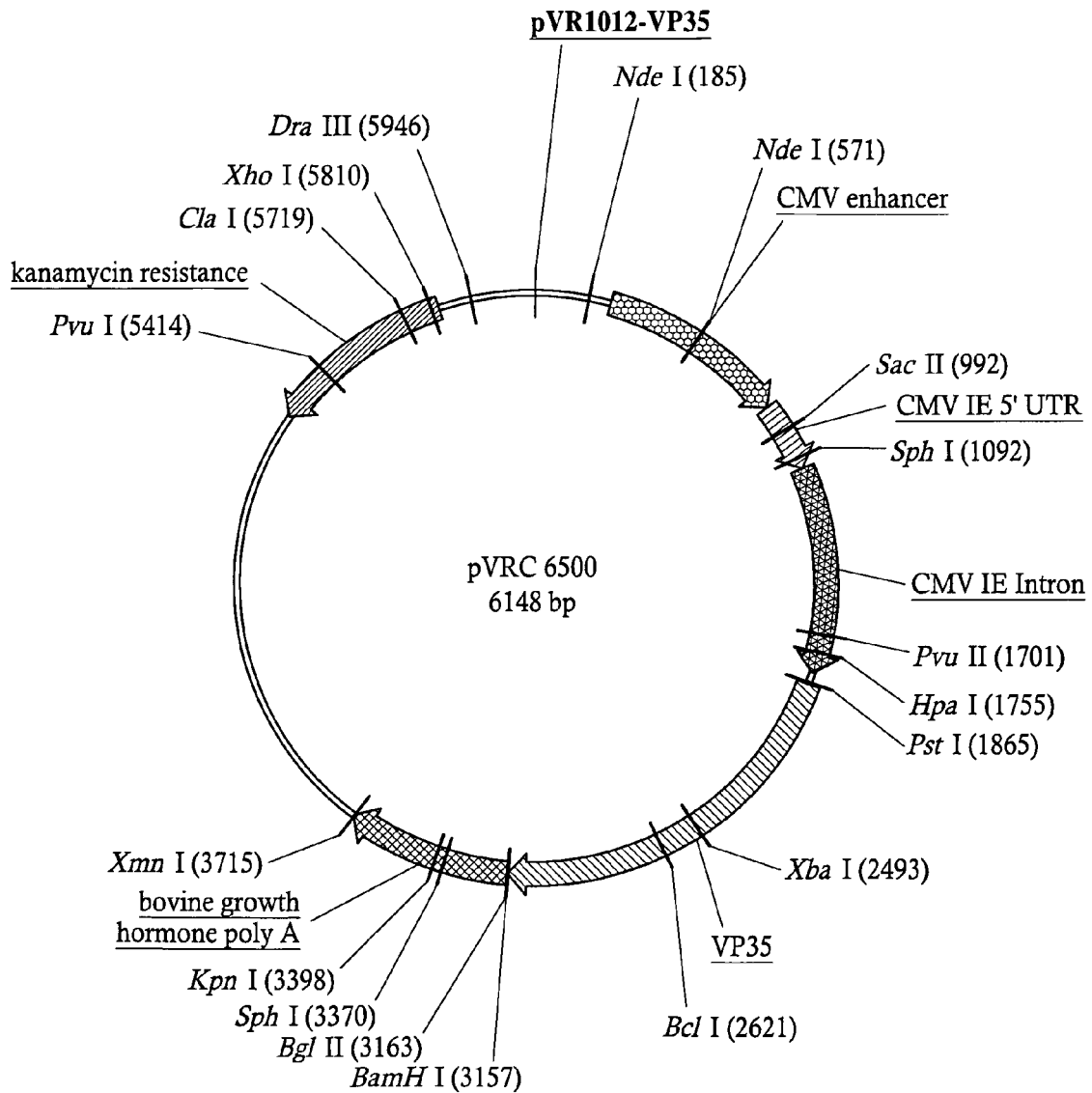
FIG. 24 shows VRC6500 (pVR1012-VP35) construct map (see, Ebola/Marburg/Lassa Plasmids, and Recombinant Adenoviruses in Table 2).
Figure 25:
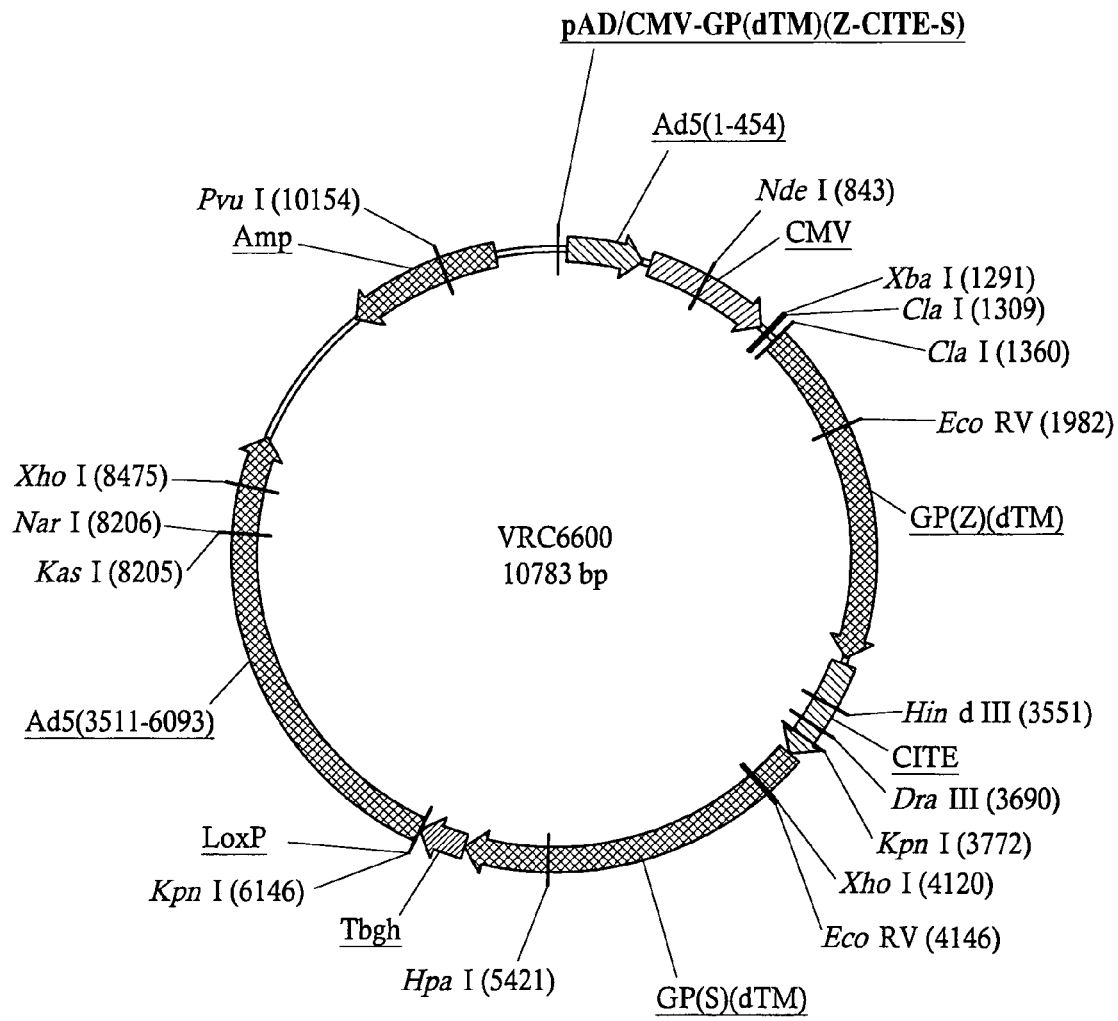
FIG. 25 shows VRC6600 (pAD/CMV-GP(dTM)(Z-CITE-S) construct map (see, Ebola/Marburg/Lassa Plasmids, and Recombinant Adenoviruses in Table 2).
Figure 36:
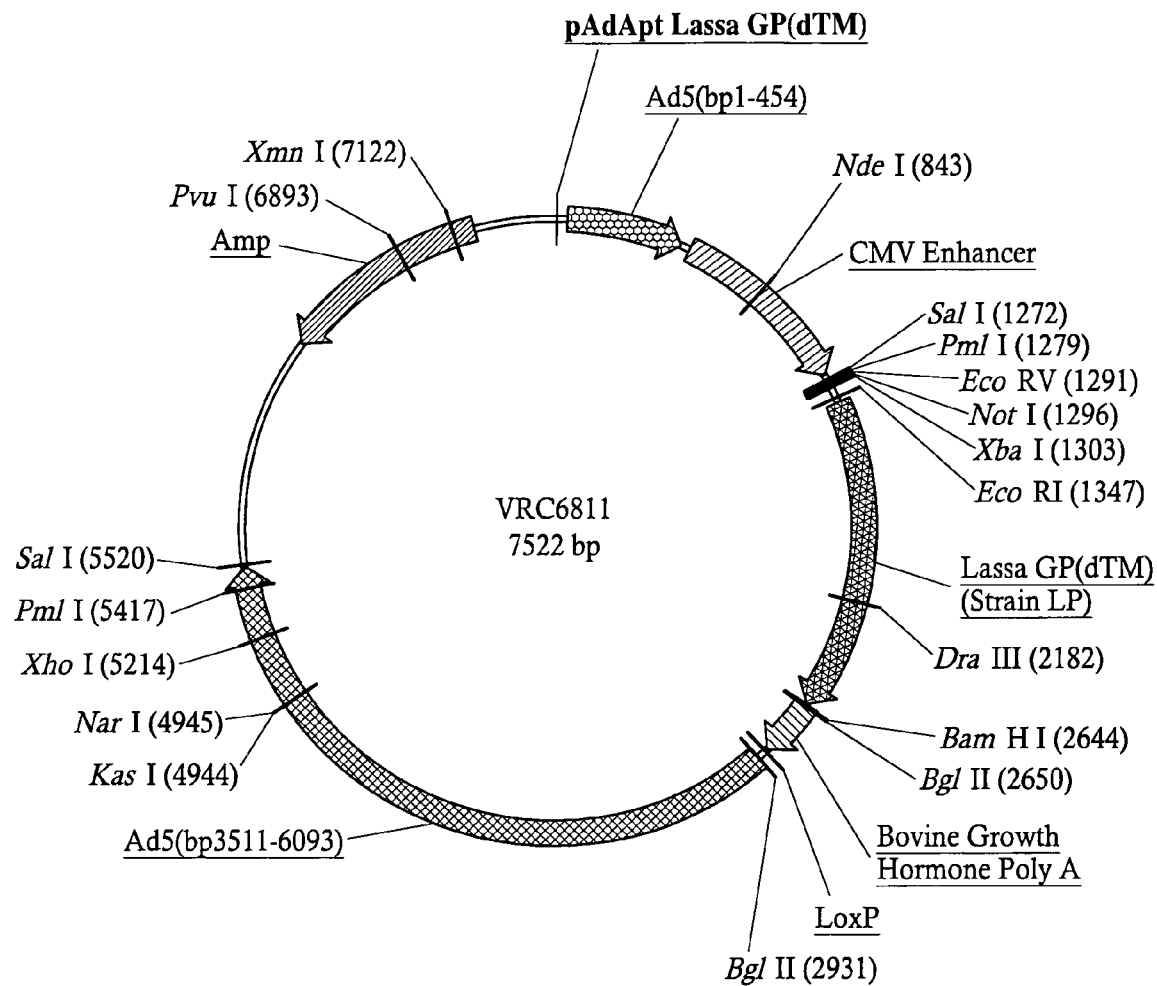
FIG. 36 shows VRC6811 (pAdApt Lassa GP (dTM)) construct map (see, Ebola/Marburg/Lassa Plasmids, and Recombinant Adenoviruses in Table 2).

Ebola/Marburg/Lassa GenBank Accession Numbers.

| Gene | GenBank Accession number |
|---|---|
| Ebola Zaire GP | U23187, P87666 |
| Ebola Zaire NP | J04337 |
| Ebola Sudan GP | U28134, Q66798 |
| Ebola Sudan NP | AF173836 |
| Ebola Ivory Coast GP | U28006 |
| Ebola Ivory Coast NP | JO4336 |
| Ebola Reston GP | U23152 |
| Ebola Reston NP | |
| Marburg GP | Z12132 |
| Marburg NP | X68495 |
| Lassa GP | AF181853 |
| Lassa NP | AF246121 |

TABLE 2

Ebola/Marburg/Lassa Plasmids, and Recombinant Adenoviruses

| Construct | Construct Name/Description | Construct Map Name | SEQ ID NO | Figure |
|---|---|---|---|---|
| VRC6000 | VRC6000 (pVR1012-GP(Z)) | pVR1012-GP(Z) | 1 | 1 |
| VRC6001 | VRC6001 (pVR1012x/s-GP(Z)) | pVR1012x/s Ebola GP(Z) | 2 | 2 |
| VRC6002 | VRC6002 (pVR1012-GP(Z) delta MUC) | pVR1012-GP(Z) delta MUC | 3 | 3 |
| VRC6003 | VRC6003 (pVR1012-GP(Z) delta MUC delta FUR) | pVR1012-GP(Z) delta MUC delta FUR | 4 | 4 |
| VRC6004 | VRC6004 (pVR1012-GP(Z) delta GP2) | pVR1042-GP(Z) delta GP2 | 5 | 5 |
| VRC6005 | VRC6005 (pVR1012-GP(Z) delta GP2 delta C-term A) | pVR1012-GP(Z) delta GP2 delta C-term A | 6 | 6 |
| VRC6006 | VRC6006 (pVR1012-GP(Z) delta GP2 delta C-term B) | pVR1012-GP(Z) delta GP2 delta C-term B | 7 | 7 |
| VRC6007 | VRC6007 (pVR1012-GP(Z) delta GP2 delta FUS) | pVR1012-GP(Z) delta GP2 delta FUS | 8 | 8 |
| VRC6008 | VRC6008 (pVR1012-GP(Z) delta TM) | pVR1012-GP(Z) delta TM | 9 | 9 |
| VRC6052 | VRC6052 (pVR1012-GP(Z) delta SGP) | pVR1012-GP(Z) delta SGP | 10 | 10 |
| VRC6101 | VRC6101 (pVR1012x/s Ebola GP(R) (dTM)) | pVR1012x/s Ebola GP(R)(dTM) | 11 | 11 |
| VRC6110 | VRC6110 (pAdApt Ebola GP(R) (dTM)) | pAdApt Ebola GP(R) (dTM) | 12 | 12 |
| VRC6200 | VRC6200 (pVR1012-GP(S)) | pVR1012-GP(S) | 13 | 13 |
| VRC6201 | VRC6201 (pVR1012x/s Ebola (GP(S)) | pVR1012x/s Ebola GP(S) | 14 | 14 |
| VRC6202 | VRC6202 (pVR1012-GP(S) delta TM) | pVR1012-GP(S) delta TM | 15 | 15 |
| VRC6300 | VRC6300 (pVR1012-GP(IC)) | pVR1012-GP(IC) | 16 | 16 |
| VRC6301 | VRC6301 (pVR1012x/s-GP(IC)) | pVR1012x/s Ebola GP(IC) | 17 | 17 |
| VRC6302 | VRC6302 (pVR1012-GP(IC) delta TM) | pVR1012-GP(IC) delta TM | 18 | 18 |
| VRC6303 | VRC6303 (pVR1012x/s Ebola GP (IC) (dTM)) | pVR1012x/s Ebola GP(IC)(dTM) | 19 | 19 |
| VRC6310 | VRC6310 (pAdApt Ebola GP (IC) (dTM)) | pAdApt Ebola GP(IC)(dTM) | 20 | 20 |
| VRC6351 | VRC6351 (pVR1012x/s-sGP(IC)) | pVR1012x/s-sGP(IC) | 21 | 21 |
| VRC6400 | VRC6400 (pVR1012-NP) | pVR1012-NP | 22 | 22 |
| VRC6401 | VRC6401 (pVR1012x/s-NP) | pVR1012x/s Ebola-NP | 23 | 23 |
| VRC6500 | VRC6500 (pVR1012-VP35) | pVR1012-VP35 | 24 | 24 |
| VRC6600 | VRC6600 (pAD/CMV-GP(dTM)(Z-CITE-S) | pAD/CMV-GP(dTM)(Z-CITE-S) | 25 | 25 |
| VRC6601 | VRC6601 (pAdApt Ebola GP(S)) | pAdApt Ebola GP(S) | 26 | 26 |
| VRC6602 | VRC6602 (pAdApt Ebola GP(S)(dTM)) | pAdApt Ebola GP(S)(dTM) | 27 | 27 |
| VRC6603 | VRC6603 (pAdApt Ebola GP(Z)) | pAdApt Ebola GP(Z) | 28 | 28 |
| VRC6604 | VRC6604 (pAdApt Ebola GP(Z)(dTM)) | pAdApt Ebola GP(Z)(dTM) | 29 | 29 |
| VRC6701 | VRC6701 (pVR1012-Marburg) | pVR1012 Marburg | 30 | 30 |
| VRC6702 | VRC6702 (pVR1012x/s Marburg GP (dTM)) | pVR1012x/s Marburg GP(dTM) | 31 | 31 |
| VRC6710 | VRC6710 (pAdApt Marburg GP (dTM)) | pAdApt Marburg GP (dTM) | 32 | 32 |
| VRC6800 | VRC6800 (pVR1012x/s Lassa GP) | pVR1012x/s Lassa GP | 33 | 33 |
| VRC6801 | VRC6801 (pVR1012x/s Lassa GP (dTM)) | pVR1012x/s Lassa GP (dTM) | 34 | 34 |
| VRC6810 | VRC6810 (pAdApt Lassa GP) | pAdApt Lassa GP | 35 | 35 |
| VRC6811 | VRC6811 (pAdApt Lassa GP (dTM)) | pAdApt Lassa GP (dTM) | 36 | 36 |
| | CMV/R Ebola GP (Z) deltaTM/h (codon optimized) | CMV/R Ebola GP(Z) delta TM/h | 37 | 37 |
| | pVR1012 Ebola GP(Z, P87666)delta TM/h (codon optimized) | pVR1012x/s Ebola GP(Z) delta TM/h (P87666) | 38 | 38 |
| | CMV/R Ebola GP (S/Gulu) delta TM/h (codon optimized) | CMV/R-GP(S/G)(delta TM)/h | 39 | 39 |
| | CMV/R Ebola GP (S, Q66798) delta TM/h (codon optimized) | CMV/R-GP(S, Q66798)(dTM)/h | 40 | 40 |
| VRC6802 | VRC6802, pVR1012x/s Lassa delta TM/h (codon optimized) | pVR1012x/s Lassa (codon optimized) | 41 | 41 |
| VRC6703 | VRC6703, pVR1012x/s Marburgdelta TM/h (codon optimized) | PVR1012x/s Marburg (codon optimized) | 42 | 42 |
| | CMV/R Ebola NP | CMV/R Ebola NP | 43 | 43 |

DETAILED DESCRIPTION OF THE INVENTION

Filovirus vaccines are provided comprising a nucleic acid molecule encoding a filoviral structural protein operatively-linked to a control sequence in a pharmaceutically acceptable excipient. In one embodiment, the nucleic acid molecule encodes the transmembrane form of the viral glycoprotein (GP). In another embodiment, the nucleic acid molecule encodes the secreted form of the viral glycoprotein (SGP). In yet another embodiment, the nucleic acid molecule encodes the viral nucleoprotein (NP).

The present invention further includes vaccines comprising nucleic acid molecules encoding filoviral structural proteins other than GP, SGP, and NP, e.g., other structural gene products which elicit an immune response against a filovirus or disease caused by infection with filovirus. The nucleic acid molecules of the vaccines of the present invention encode structural gene products of any Ebola viral strain including the Zaire, Sudan, Ivory Coast and Reston strains. Nucleic acid molecules encoding structural gene products of the genetically-related Marburg virus strains may also be employed. Moreover, the nucleic acid molecules of the present invention may be modified, e.g., the nucleic acid molecules set forth herein may be mutated, as long as the modified expressed protein elicits an immune response against a pathogen or disease. For example, the nucleic acid molecule may be mutated so that the expressed protein is less toxic to cells. The present invention also includes vaccines comprising a combination of nucleic acid molecules. For example, and without limitation, nucleic acid molecules encoding GP, SGP and NP of the Zaire, Sudan and Ivory Coast Ebola strains may be combined in any combination, in one vaccine composition.

The present invention also provides methods for immunizing a subject against disease caused by infection with filovirus comprising administering to the subject an immunoeffective amount of a filovirus vaccine. Methods of making and using filovirus vaccines are also provided by the present invention including the preparation of pharmaceutical compositions.

Biochemical Analysis of Secreted and Virion Glycoproteins of Ebola Virus.

Ebola (EBO) viruses are members of the Filoviridae and cause a severe, often fatal form of hemorrhagic fever disease in human and/or non-human primates. The glycoprotein (GP) gene of filoviruses is the fourth gene (of seven) from the 3' end of the negative-strand RNA genome. All EBO viruses characterized thus far have the same unconventional type of GP gene organization that results in the expression of a secreted, nonstructural glycoprotein (SGP) in preference to the structural GP. The SGP is encoded in a single frame (0 frame), while the GP is encoded in two frames (0 and −1 frames). Expression of the GP occurs when the two frames are connected through a transcriptional editing event that results in the insertion of a single extra adenosine (added to a run of seven adenosines).

Figure 44:
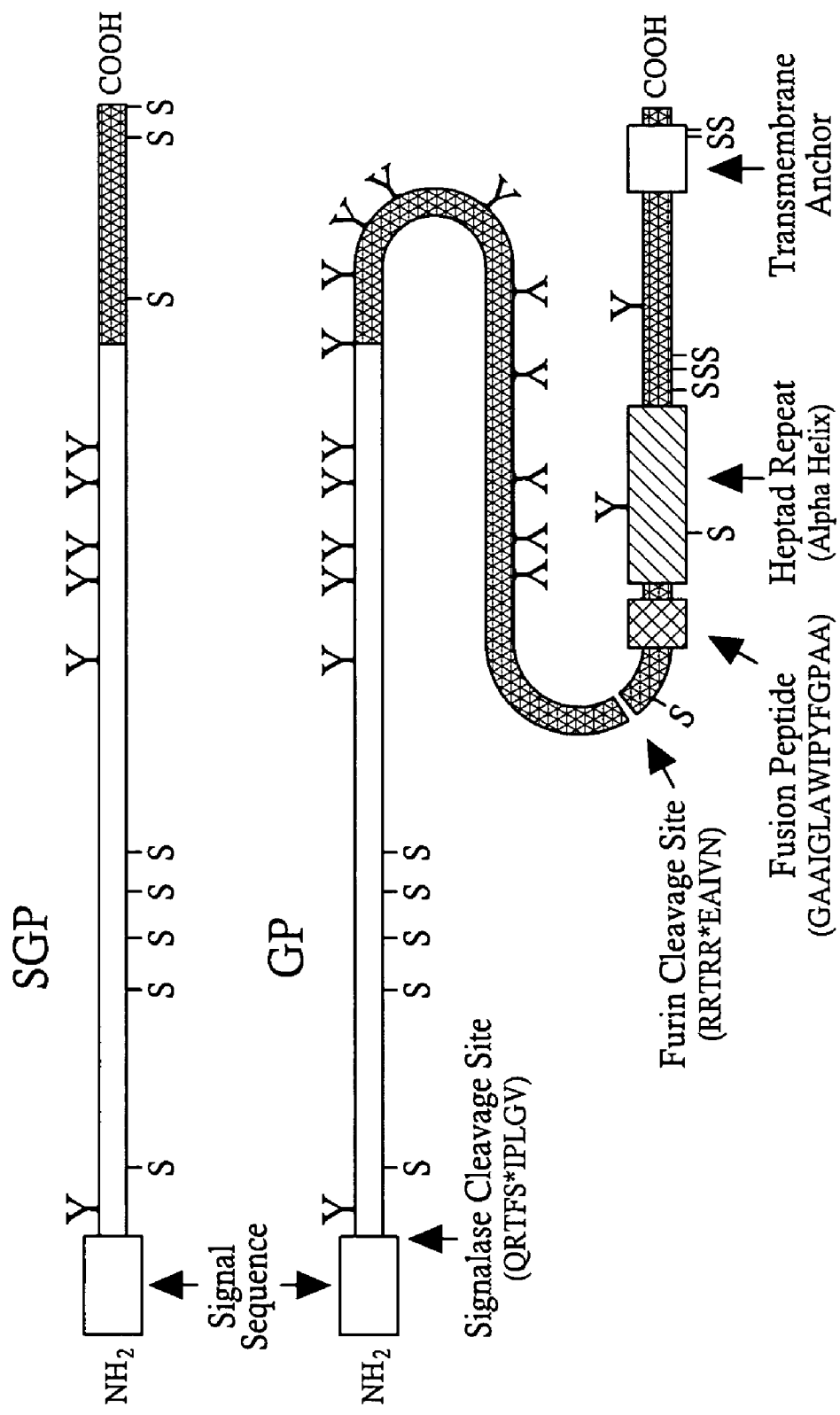
FIG. 44 is a diagrammatic representation of secreted glycoprotein (SGP) and glycoprotein (GP) molecules of Ebola virus (Zaire species isolated in 1976) showing important structural features. The white N-terminal regions of SGP and GP correspond to identical (shared) sequences, while the black C termini identify sequences unique to GP or SGP molecules. The common signalase cleavage sites for both SGP and GP and the furin cleavage site for GP0 (uncleaved form of GP) (↓) were determined by N-terminal sequencing. Also shown are cysteine residues (S), predicted N-linked glycosylation sites (Y-shaped projections), a predicted fusion peptide, a heptad repeat sequence, and a transmembrane anchor sequence. In Ebola viruses, the positions of these structures are conserved and their sequences are very similar or, in the case of N-linked glycosylation sites, are at least concentrated in the central region of GP. Signalase cleavage site is SEQ ID NO: 48, Furin cleavage site is SEQ ID NO: 49, and Fusion peptide is SEQ ID NO: 50.

Referring to FIG. 44, for Zaire species of EBO virus, the N-terminal 295 residues (including signal sequence) of the SGP (364 total residues) and GP (676 total residues) are identical, but the length and composition of their C-terminal sequences are unique. The GP, a type 1 transmembrane protein, is found on the surface of the infectious virion and functions in attachment structure in the binding and entry of the virus into susceptible cells. Comparisons of GP predicted amino acid sequences for all species of EBO virus show a general conservation in the N-terminal and C-terminal regions (each approximately one-third of the total sequence) and are separated by a highly variable middle section. This protein is highly glycosylated, containing large amounts of N- and O-linked glycans, and for Marburg (MB G) virus (another type of filovirus) has been shown to form trimers. Just N terminal to the transmembrane anchor sequence of the GP (residues 650 to 672) is a motif (residues 585 to 609) that is highly conserved in filoviruses. This sequence also has a high degree of homology with a motif in the glycoproteins of oncogenic retroviruses that has been shown to be immunosuppressive in vitro. Partially overlapping this motif is a heptad repeat sequence (53 residues; positions 541 to 593) that is thought to function in the formation of intermolecular coiled coils in the assembly of trimers, similar to structures predicted for the surface glycoproteins of other viruses. Immediately N terminal to this sequence is a predicted fusion peptide followed closely by a putative multibasic cleavage site for a subtilisin/kexin-like convertase, furin. Cleavage by furin has been indirectly demonstrated by use of specific inhibitors and is predicted to occur at the last arginine in the sequence RRTRR↓ (position 501 from the beginning of the open reading frame [ORF]). Although the role of the SGP is less defined, recent studies have shown that SGP can bind to neutrophils, while GP binds to endothelial cells. The different binding patterns of SGP and GP suggest that despite having identical N-terminal amino acid sequences (~280 residues), these glycoproteins are structurally very distinct from one another.

Figure 45:
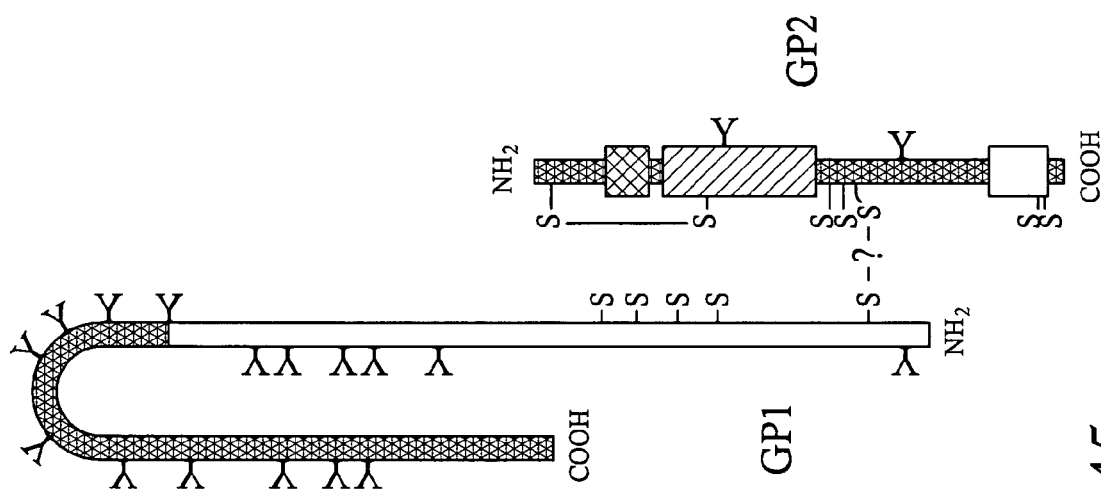
FIG. 45 is a diagrammatic representation of the structural GP. Shown is the predicted orientation of the GP1-GP2 heterodimer linked by undetermined disulfide bonding (indicated by the question mark). Intramolecular disulfide bonds that are shown come from prior predictions based on similarities to retrovirus glycoprotein structures. See FIG. 44 for other features of the amino acid sequence.

Referring to FIG. 45, the glycoproteins expressed by a Zaire species of Ebola virus were analyzed for cleavage, oligomerization, and other structural properties to better define their functions. The 50- to 70-kDa secreted and 150-kDa virion/structural glycoproteins (SGP and GP, respectively), which share the 295 N-terminal residues, are cleaved near the N terminus by signalase. A second cleavage event, occurring in GP at a multibasic site (RRTRR↓) (SEQ ID NO: 51) that is likely mediated by furin, results in two glycoproteins (GP1 and GP2) linked by disulfide bonding. This furin cleavage site is present in the same position in the GPs of all Ebola viruses (R[R/K]X[R/K]R→), and one is predicted for Marburg viruses (R[R/K]KR→), although in a different location. Based on the results of cross-linking studies, investigators were able to determine that Ebola virion peplomers are composed of trimers of GP1-GP2 heterodimers and that aspects of their structure are similar to those of retroviruses (including lentiviruses like HIV-1 and HIV-2), paramyxoviruses, and influenza viruses. Investigators also determined that SGP is secreted from infected cells almost exclusively in the form of a homodimer that is joined by disulfide bonding.

Referring to FIG. 46, investigators defined the main viral determinant of Ebola virus pathogenicity; synthesis of the virion glycoprotein (GP) of Ebola virus Zaire induced cytotoxic effects in human endothelial cells in vitro and in vivo. This effect mapped to a serine-threonine-rich, mucin-like domain of this type I transmembrane glycoprotein, one of seven gene products of the virus. Gene transfer of GP into explanted human or porcine blood vessels caused massive endothelial cell loss within 48 hours that led to a substantial increase in vascular permeability. Deletion of the mucin-like region of GP abolished these effects without affecting protein expression or function. GP derived from the Reston strain of virus, which causes disease in non-human primates but not in man, did not disrupt the vasculature of human blood vessels. In contrast, the Zaire GP induced endothelial cell disruption and cytotoxicity in both non-human primate and human blood vessels, and the mucin domain was required for this effect. These findings indicate that GP, through its mucin domain, is the viral determinant of Ebola pathogenicity and likely contributes to hemorrhage during infection.

Nucleic Acid Molecules

As indicated herein, nucleic acid molecules of the present invention may be in the form of RNA or in the form of DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Nucleic acid molecules of the present invention include DNA molecules comprising an open reading frame (ORF) encoding a wild-type filovirus structural gene product; and DNA molecules which comprise a sequence substantially different from those described above but which, due to the degeneracy of the genetic code, still encode an ORF of a wild-type filovirus structural gene product. Of course, the genetic code is well known in the art.

The present invention is further directed to fragments of the nucleic acid molecules described herein. By a fragment of a nucleic acid molecule having the nucleotide sequence of an ORF encoding a wild-type filovirus structural gene product is intended fragments at least about 15 nt., and more preferably at least about 20 nt., still more preferably at least about 30 nt., and even more preferably, at least about 40 nt. in length. Of course, larger fragments 50, 100, 150, 200, 250, 300, 350, 400, 450, or 500 nt. in length are also intended according to the present invention as are fragments corresponding to most, if not all, of the nucleotide sequence of the ORF encoding a wild-type filovirus structural gene product. By a fragment at least 20 nt. in length, for example, is intended fragments which include 20 or more contiguous bases from the nucleotide sequence of the ORF of a wild-type filovirus structural gene product.

Preferred nucleic acid fragments of the present invention include nucleic acid molecules encoding epitope-bearing portions of the filovirus structural protein. In particular, such nucleic acid fragments of the present invention include nucleic acid molecules encoding epitope-bearing domains of a filovirus structural protein, where the domain is the GP/SGP identity domain, the mucin-like domain, the furin cleavage site, the fusion peptide domain, the heptad repeat domain, the transmembrane anchor domain, and the intracellular domain, and any combination thereof, for example, a filovirus glycoprotein having a truncation at the carboxy terminus to delete the transmembrane anchor and intracellular domain, a filovirus glycoprotein having a truncation at the carboxy terminus to delete the heptad repeat domain and transmembrane anchor and intracellular domain, a filovirus glycoprotein having a truncation at the carboxy terminus to delete the fusion peptide domain, heptad repeat domain, and transmembrane anchor and intracellular domain, a filovirus glycoprotein having a truncation at the carboxy terminus to delete the furin cleavage site, fusion peptide domain, heptad repeat domain, and transmembrane anchor and intracellular domain, a filovirus glycoprotein having a truncation at the carboxy terminus to delete the mucin-like domain, furin cleavage site, fusion peptide domain, heptad repeat domain, and transmembrane anchor and intracellular domain. Another example is a filovirus glycoprotein having an amino, internal, or carboxy deletion to delete the mucin-like domain, the furin cleavage site, the fusion peptide domain, the heptad repeat domain, the transmembrane anchor domain, or the intracellular domain.

In another aspect, the invention provides a nucleic acid molecule comprising a polynucleotide which hybridizes under stringent hybridization conditions to a portion of the polynucleotide in a nucleic acid molecule of the invention described above. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5× Denhardt's solution, 10% dextran sulfate, and 20 µg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt.), and more preferably at least about 20 nt., still more preferably at least about 30 nt., and even more preferably about 30-70 nt. of the reference polynucleotide.

By a portion of a polynucleotide of "at least 20 nt. in length," for example, is intended 20 or more contiguous nucleotides from the nucleotide sequence of the reference polynucleotide. Of course, a polynucleotide which hybridizes only to a poly A sequence or a complementary stretch of T (or U) residues, would not be included in a polynucleotide of the invention used to hybridize to a portion of a nucleic acid of the invention, since such a polynucleotide would hybridize to any nucleic acid molecule containing a poly A stretch or the complement thereof (e.g., practically any double-stranded cDNA clone).

As indicated herein, nucleic acid molecules of the present invention which encode a filovirus structural gene product may include, but are not limited to those encoding the amino acid sequence of the full-length polypeptide, by itself, the coding sequence for the full-length polypeptide and additional sequences, such as those encoding a leader or secretory sequence, such as a pre-, or pro- or prepro-protein sequence, the coding sequence of the full-length polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example, ribosome binding and stability of mRNA; and additional coding sequence which codes for additional amino acids, such as those which provide additional functionalities.

The present invention further relates to variants of the nucleic acid molecules of the present invention, which encode portions, analogs or derivatives of the filovirus structural gene product. Variants may occur naturally, such as a natural allelic variant. By an "allelic variant" is intended one of several alternate forms of a gene occupying a given locus on a genome of an organism. (Genes II, Lewin, B., ed., John Wiley & Sons, 1985 New York). Non-naturally occurring variants may be produced using art-known mutagenesis techniques.

Such variants include those produced by nucleotide substitutions, deletions or additions, which may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the filovirus structural gene product or portions thereof. Also especially preferred in this regard are conservative substitutions.

Further embodiments of the invention include nucleic acid molecules comprising a polynucleotide having a nucleotide sequence at least 95% identical, and more preferably at least 96%, 97%, 98% or 99% identical to a nucleotide sequence encoding a polypeptide having the amino acid sequence of a wild-type filovirus structural gene product or fragment thereof or a nucleotide sequence complementary thereto.

By a polynucleotide having a nucleotide sequence at least, for example, 95% "identical" to a reference nucleotide sequence encoding a filovirus structural gene product is intended that the nucleotide sequence of the polynucleotide is identical to the reference sequence except that the polynucleotide sequence, may include up to five point mutations per each 100 nucleotides of the reference nucleotide sequence encoding the Ebola virus structural gene product. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to the reference nucleotide sequence can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, 1981 *Advances in Applied Mathematics* 2:482-489, to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 95%, 96%, 97%, 98% or 99% identical to the nucleic acid sequences shown herein in the Sequence Listing which encode a polypeptide having Ebola, Marburg, or Lassa virus polypeptide activity. By "a polypeptide having Ebola, Marburg, or Lassa virus polypeptide activity" is intended polypeptides exhibiting Ebola, Marburg, or Lassa virus polypeptide activity in a particular biological assay. For example, GP, SGP or NP protein activity can be measured for changes in immunological character by an appropriate immunological assay.

Of course, due to the degeneracy of the genetic code, one of ordinary skill in the art will immediately recognize that a large number of the nucleic acid molecules having a sequence at least 95%, 96%, 97%, 98%, or 99% identical to a nucleic acid sequence shown herein in the Sequence Listing will encode a polypeptide "having Ebola, Marburg, or Lassa virus polypeptide activity". In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having Ebola, Marburg, or Lassa virus polypeptide activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al. 1990 *Science* 247:1306-1310, wherein the authors indicate that proteins are surprisingly tolerant of amino acid substitutions.

Polypeptides and Fragments

The invention further provides a filovirus polypeptide having the amino acid sequence encoded by an open reading frame (ORF) of a wild-type filovirus structural gene, or a peptide or polypeptide comprising a portion thereof (e.g., SGP).

It will be recognized in the art that some amino acid sequences of the filovirus polypeptides can be varied without significant effect of the structure or function of the protein. If such differences in sequence are contemplated, it should be remembered that there will be critical areas on the protein which determine activity.

Thus, the invention further includes variations of the filovirus polypeptide which show substantial filovirus polypeptide activity or which include regions of filovirus protein such as the protein portions discussed below. Such mutants include deletions, insertions, inversions, repeats, and type substitutions. As indicated, guidance concerning which amino acid changes are likely to be phenotypically silent can be found in Bowie, J. U. et al. 1990 *Science* 247:1306-1310.

Thus, the fragment, derivative or analog of the polypeptide of the invention may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues include a substituent group, or (iii) one in which additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

As indicated, changes are preferably of a minor nature, such as conservative amino acid substitutions that do not significantly affect the folding or activity of the protein (see Table A).

TABLE A

Conservative Amino Acid Substitutions

| | |
|---|---|
| Aromatic | Phenylalanine |
| | Tryptophan |
| | Tyrosine |
| Ionizable: Acidic | Aspartic Acid |
| | Glutamic Acid |
| Ionizable: Basic | Arginine |
| | Histidine |
| | Lysine |

TABLE A-continued

Conservative Amino Acid Substitutions

| | |
|---|---|
| Nonionizable Polar | Asparagine |
| | Glutamine |
| | Selenocystine |
| | Serine |
| | Threonine |
| Nonpolar (Hydrophobic) | Alanine |
| | Glycine |
| | Isoleucine |
| | Leucine |
| | Proline |
| | Valine |
| Sulfur Containing | Cysteine |
| | Methionine |

Of course, the number of amino acid substitutions a skilled artisan would make depends on many factors, including those described above. Generally speaking, the number of amino acid substitutions for any given filovirus polypeptide will not be more than 50, 40, 30, 20, 10, 5 or 3.

Amino acids in the filovirus polypeptides of the present invention that are essential for function can be identified by methods known in the art, such as site-directed mutagenesis or alanine-scanning mutagenesis (Cunningham & Wells 1989 *Science* 244:1081-1085). The latter procedure introduces single alanine mutations at every residue in the molecule. The resulting mutant molecules are then tested for biological activity such as changes in immunological character.

The polypeptides of the present invention are conveniently provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell or a native source. For example, a recombinantly produced version of the filovirus polypeptide can be substantially purified by the one-step method described in Smith and Johnson 1988 *Gene* 67:31-40.

The polypeptides of the present invention include a polypeptide comprising a polypeptide having the amino acid sequence of a wild-type filovirus structural gene product or portion thereof or encoded by a nucleic acid sequence shown herein in the Sequence Listing; as well as polypeptides which are at least 95% identical, and more preferably at least 96%, 97%, 98%, or 99% identical to those described above.

By a polypeptide having an amino acid sequence at least, for example, 95% "identical" to a reference amino acid sequence of an filovirus polypeptide is intended that the amino acid sequence of the polypeptide is identical to the reference sequence except that the polypeptide sequence may include up to five amino acid alterations per each 100 amino acids of the reference amino acid of the filovirus polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 95%, 96%, 97%, 98%, or 99% identical to a reference amino acid sequence can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In another aspect, the invention provides portions of the polypeptides described herein with at least 30 amino acids and more preferably at least 50 amino acids. Preferred portions of the present invention include polypeptides comprising an epitope-bearing portion of a filovirus structural protein. In particular, preferred portions of the present invention include polypeptides comprising an epitope-bearing domain of a filovirus structural protein, where the domain is the GP/SGP identity domain, the mucin-like domain, the furin cleavage site, the fusion peptide domain, the heptad repeat domain, the transmembrane anchor domain, and the intracellular domain, and any combination thereof, for example, a filovirus glycoprotein having a truncation at the carboxy terminus to delete the transmembrane anchor and intracellular domain, a filovirus glycoprotein having a truncation at the carboxy terminus to delete the heptad repeat domain and transmembrane anchor and intracellular domain, a filovirus glycoprotein having a truncation at the carboxy terminus to delete the fusion peptide domain, heptad repeat domain, and transmembrane anchor and intracellular domain, a filovirus glycoprotein having a truncation at the carboxy terminus to delete the furin cleavage site, fusion peptide domain, heptad repeat domain, and transmembrane anchor and intracellular domain, and a filovirus glycoprotein having a truncation at the carboxy terminus to delete the mucin-like domain, furin cleavage site, fusion peptide domain, heptad repeat domain, and transmembrane anchor and intracellular domain. Another example is a filovirus glycoprotein having an amino, internal, or carboxy deletion to delete the mucin-like domain, the furin cleavage site, the fusion peptide domain, the heptad repeat domain, the transmembrane anchor domain, or the intracellular domain.

The polypeptides of the invention may be produced by any conventional means (Houghten, R. A. 1985 *PNAS USA* 82:5131-5135). The "Simultaneous Multiple Peptide Synthesis (SMPS)" process is described in U.S. Pat. No. 4,631,211 to Houghten et al. (1986).

The present invention also relates to vectors which include the nucleic acid molecules of the present invention, host cells which are genetically engineered with the recombinant vectors, and the production of filovirus polypeptides or fragments thereof by recombinant techniques.

The present invention relates to "prime and boost" immunization regimes in which the immune response induced by administration of a priming composition is boosted by administration of a boosting composition. The present invention is based on the inventors' experimental demonstration that effective boosting can be achieved using replication-defective adenovirus vectors, following priming with any of a variety of different types of priming compositions. The present invention employs replication-deficient adenovirus which, as the experiments described below show, has been found to be an effective means for providing a boost to an immune response primed to antigen using any of a variety of different priming compositions.

Replication-deficient adenovirus derived from human serotype 5 has been developed as a live viral vector by Graham and colleagues (Graham & Prevec 1995 *Mol Biotechnol* 3:207-20; Bett et al. 1994 *PNAS USA* 91:8802-6). Adenoviruses are non-enveloped viruses containing a linear double-stranded DNA genome of around 3600 bp. Recombinant viruses can be constructed by in vitro recombination between an adenovirus genome plasmid and a shuttle vector containing the gene of interest together with a strong eukaryotic promoter, in a permissive cell line which allows viral replication. High viral titres can be obtained from the permissive cell line, but the resulting viruses, although capable of infecting a wide range of cell types, do not replicate in any cells other than the permissive line, and are therefore a safe antigen delivery system. Recombinant adenoviruses have been shown to elicit protective immune responses against a number of antigens including tick-borne encephalitis virus NS1 protein (Jacobs et al. 1992 *J Virol* 66:2086-95) and measles virus nucleoprotein (Fooks et al. 1995 *Virology* 210:456-65).

Remarkably, the experimental work described below demonstrates that use of embodiments of the present invention allows for recombinant replication-defective adenovirus expressing an antigen to boost an immune response primed by a DNA vaccine. The replication-defective adenovirus was found to induce an immune response after intramuscular immunization. In prime/boost vaccination regimes the replication-defective adenovirus is also envisioned as being able to prime a response that can be boosted by a different recombinant virus or recombinantly produced antigen.

Non-human primates immunized with plasmid DNA and boosted with replication-defective adenovirus were protected against challenge. Both recombinant replication-deficient adenovirus and plasmid DNA are vaccines that are safe for use in humans. Advantageously, the inventors found that a vaccination regime used intramuscular immunization for both prime and boost can be employed, constituting a general immunization regime suitable for inducing an immune response, e.g., in humans.

The present invention in various aspects and embodiments employs a replication-deficient adenovirus vector encoding an antigen for boosting an immune response to the antigen primed by previous administration of the antigen or nucleic acid encoding the antigen.

A general aspect of the present invention provides for the use of a replication-deficient adenoviral vector for boosting an immune response to an antigen.

One aspect of the present invention provides a method of boosting an immune response to an antigen in an individual, the method including provision in the individual of a replication-deficient adenoviral vector including nucleic acid encoding the antigen operably linked to regulatory sequences for production of antigen in the individual by expression from the nucleic acid, whereby an immune response to the antigen previously primed in the individual is boosted.

An immune response to an antigen may be primed by genetic immunization, by infection with an infectious agent, or by recombinantly produced antigen.

A further aspect of the invention provides a method of inducing an immune response to an antigen in an individual, the method comprising administering to the individual a priming composition comprising the antigen or nucleic acid encoding the antigen and then administering a boosting composition which comprises a replication-deficient adenoviral vector including nucleic acid encoding the antigen operably linked to regulatory sequences for production of antigen in the individual by expression from the nucleic acid.

A further aspect provides for use of a replication-deficient adenoviral vector, as disclosed, in the manufacture of a medicament for administration to a mammal to boost an immune response to an antigen. Such a medicament is generally for administration following prior administration of a priming composition comprising the antigen.

The priming composition may comprise any viral vector, including adenoviral, or other than adenoviral, such as a vaccinia virus vector such as a replication-deficient strain such as modified virus Ankara (MVA) (Mayr et al. 1978 *Zentralbi Bakteriol* 167:375-90; Sutter and Moss 1992 *PNAS USA* 89:10847-51; Sutter et al. 1994 *Vaccine* 12:1032-40) or NYVAC (Tartaglia et al. 1992 *Virology* 118:217-32), an avipox vector such as fowlpox or canarypox, e.g., the strain known as ALVAC (Kanapox, Paoletti et al. 1994 *Dev Biol Stand* 1994 82:65-9), or a herpes virus vector.

The priming composition may comprise DNA encoding the antigen, such DNA preferably being in the form of a circular plasmid that is not capable of replicating in mammalian cells. Any selectable marker should not be resistant to an antibiotic used clinically, so for example Kanamycin resistance is preferred to Ampicillin resistance. Antigen expression should be driven by a promoter which is active in mammalian cells, for instance the cytomegalovirus immediate early (CMV IE) promoter.

In particular embodiments of the various aspects of the present invention, administration of a priming composition is followed by boosting with first and second boosting compositions, the first and second boosting compositions being the same or different from one another, e.g., as exemplified below. Still further boosting compositions may be employed without departing from the present invention. In one embodiment, a triple immunization regime employs DNA, then adenovirus (Ad) as a first boosting composition, and then MVA as a second boosting composition, optionally followed by a further (third) boosting composition or subsequent boosting administration of one or other or both of the same or different vectors. Another option is DNA then MVA then Ad, optionally followed by subsequent boosting administration of one or other or both of the same or different vectors.

The antigen to be included in respective priming and boosting compositions (however many boosting compositions are employed) need not be identical, but should share epitopes. The antigen may correspond to a complete antigen in a target pathogen or cell, or a fragment thereof. Peptide epitopes or artificial strings of epitopes may be employed, more efficiently cutting out unnecessary protein sequence in the antigen and encoding sequence in the vector or vectors. One or more additional epitopes may be included, for instance epitopes which are recognized by T helper cells, especially epitopes recognized in individuals of different HLA types.

Within the replication-deficient adenoviral vector, regulatory sequences for expression of the encoded antigen will include a promoter. By "promoter" is meant a sequence of nucleotides from which transportation may be initiated of DNA operably linked downstream (i.e. in the 3' direction on the sense strand of double-stranded DNA). "Operably linked" means joined as part of the same nucleic acid molecule, suitably positioned and oriented for transcription to be initiated from the promoter. DNA operably linked to a promoter is "under transcriptional initiation regulation" of the promoter. Other regulatory sequences including terminator fragments, polyadenylation sequences, enhancer sequences, marker genes, internal ribosome entry site (IRES) and other sequences may be included as appropriate, in accordance with the knowledge and practice of the ordinary person skilled in the art: see, for example, *Molecular Cloning: a Laboratory Manual*, 2$^{nd}$ edition, Sambrook et al. 1989 Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology*, Ausubel et al. eds., John Wiley & Sons, 1994.

Suitable promoters for use in aspects and embodiments of the present invention include the cytomegalovirus immediate early (CMV IE) promoter, with or without intron A, and any other promoter that is active in mammalian cells.

Either or both of the priming and boosting compositions may include an adjuvant or cytokine, such as alpha-interferon, gamma-interferon, platelet-derived growth factor (PDGF), granulocyte macrophage-colony stimulating factor (GM-CSF) granulocyte-colony stimulating factor (gCSF), tumor necrosis factor (TNF), epidermal growth factor (EGF), IL-1, IL-2, IL-4, IL-6, IL-8, IL-10 and IL-12, or encoding nucleic acid therefor.

Administration of the boosting composition is generally weeks or months after administration of the priming composition, preferably about 2-3 weeks or 4 weeks, or 8 weeks, or 16 weeks, or 20 weeks, or 24 weeks, or 28 weeks, or 32 weeks.

Preferably, administration of priming composition, boosting composition, or both priming and boosting compositions, is intramuscular immunization.

Intramuscular administration of adenovirus vaccines or plasmid DNA may be achieved by using a needle to inject a suspension of the virus or plasmid DNA. An alternative is the use of a needless injection device to administer a virus or plasmid DNA suspension (using, e.g., Biojector™) or a freeze-dried powder containing the vaccine (e.g., in accordance with techniques and products of Powderject), providing for manufacturing individually prepared doses that do not need cold storage. This would be a great advantage for a vaccine that is needed in rural areas of Africa.

Adenovirus is a virus with an excellent safety record in human immunizations. The generation of recombinant viruses can be accomplished simply, and they can be manufactured reproducibly in large quantities. Intramuscular administration of recombinant replication-deficient adenovirus is therefore highly suitable for prophylactic or therapeutic vaccination of humans against diseases which can be controlled by an immune response.

The individual may have a disease or disorder such that delivery of the antigen and generation of an immune response to the antigen is of benefit or has a therapeutically beneficial effect.

Most likely, administration will have prophylactic aim to generate an immune response against a pathogen or disease before infection or development of symptoms.

Diseases and disorders that may be treated or prevented in accordance with the present invention include those in which an immune response may play a protective or therapeutic role.

Components to be administered in accordance with the present invention may be formulated in pharmaceutical compositions. These compositions may comprise a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g., intravenous, cutaneous or subcutaneous, intramucosal (e.g., gut), intranasal, intramuscular, or intraperitoneal routes.

As noted, administration is preferably intradermal, subcutaneous or intramuscular.

Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required.

A slow-release formulation may be employed.

Following production of replication-deficient adenoviral particles and optional formulation of such particles into compositions, the particles may be administered to an individual, particularly human or other primate.

Administration may be to another mammal, e.g., rodent such as mouse, rat or hamster, guinea pig, rabbit, sheep, goat, pig, horse, cow, donkey, dog or cat.

Administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g., decisions on dosage etc., is within the responsibility of general practitioners and other medical doctors, or in a veterinary context a veterinarian, and typically takes account of the disorder to be treated, the condition of the individual patient, the site of delivery, the method of administration and other factors known to practitioners. Examples of the techniques and protocols mentioned above can be found in *Remington's Pharmaceutical Sciences*, 16$^{th}$ edition, Osol, A. ed., 1980.

In one preferred regimen, DNA is administered (preferably intramuscularly) at a dose of 10 micrograms to 50 milligrams/injection, followed by adenovirus (preferably intramuscularly) at a dose of $5 \times 10^7$-$1 \times 10^{12}$ particles/injection.

The composition may, if desired, be presented in a kit, pack or dispenser, which may contain one or more unit dosage forms containing the active ingredient. The kit, for example, may comprise metal or plastic foil, such as a blister pack. The kit, pack, or dispenser may be accompanied by instructions for administration.

A composition may be administered alone or in combination with other treatments, either simultaneously or sequentially dependent upon the condition to be treated.

Delivery to a non-human mammal need not be for a therapeutic purpose, but may be for use in an experimental context, for instance in investigation of mechanisms of immune responses to an antigen of interest, e.g., protection against disease.

Further aspects and embodiments of the present invention will be apparent to those of ordinary skill in the art, in view of the above disclosure and following experimental exemplifi- Development of a Preventive Vaccine for Ebola Virus Infection in Primates Genetic immunization has been shown to influence both humoral and cellular immune activation pathways and to protect against infection by human pathogens (Tang, D. C. et al. 1992 Nature 356:152-154; Ulmer, J. B. et al. 1993 Science 259:1745-1749; Wang, B. et al. 1993 PNAS USA 90:4156-4160; Sedegah, M. et al. 1994 PNAS USA 91:9866-9870). The effectiveness of plasmid vaccines is thought to result from host cell protein synthesis and endogenous presentation of the immunogen, and possibly to immunostimulatory effects of plasmid DNA itself (Krieg, A. M. et al. 1995 Nature 374:546-549; Sato, Y. et al. 1996 Science 273:352-354). DNA vaccines have been shown to elicit specific immune responses to Ebola virus antigens and to protect guinea pigs (Xu, L. et al. 1998 Nat Med 4:7-42) and mice (Vanderzanden, L. et al. 1998 Virology 246:134-144) against challenge with Ebola virus adapted to produce lethal infection in rodents (Connolly, B. M. et al. 1999 J Infect Dis 179:S203-S217; Bray, M. et al. 1998 J Infect Dis 178:651-661). Although both cell-mediated and humoral immune responses were elicited, antibody titer correlated with the degree of protection in animals immunized with plasmids encoding proteins from the Zaire subtype of Ebola virus.

A broadly effective vaccine would need to provide immunity to the multiple Ebola subtypes isolated in human infections (Zaire, Sudan and Ivory Coast), but a multivalent vaccine might dilute the specific immune response demonstrated for the single subtype vaccine. To address this concern, we analyzed the efficacy of the original Ebola Zaire DNA vaccine in comparison to its use in combination with DNA from Ebola subtypes Sudan and Ivory Coast. As in a previous study (Xu, L. et al. 1998 Nat Med 4:7-42), immunization with a single plasmid encoding Zaire subtype virion glycoprotein, GP(Z), generated a substantial virus-specific antibody response and conferred protective immunity in guinea pigs (Table I). Inclusion of a plasmid expressing Ebola nucleoprotein, NP, did not affect the antibody titer to Ebola GP(Z) or diminish its protective efficacy. Further broadening of the vaccine components to include NP and three subtypes of Ebola glycoprotein, Zaire, Ivory Coast and Sudan, GP(Z, IC, S)+NP, yielded a pre-challenge immune response comparable to the single-plasmid vaccine. Moreover, complete protection from infection with Ebola Zaire was achieved in guinea pigs that received the multivalent vaccine (Table I, subjects 13-16). Anamnestic antibody was not induced by the virus challenge, indicating that the vaccine itself provided an immune response sufficient to efficiently clear the virus. These findings show that multivalent plasmid immunization did not substantially diminish glycoprotein (GP)-specific antibody production and its protective efficacy in a rodent model.

TABLE I

Multivalent genetic immunization in guinea pigs

| ID | Immunization | ELISA IgG | Survival |
|---|---|---|---|
| 1 | Plasmid | 0 | No |
| 2 | Plasmid | 0 | No |
| 3 | Plasmid | 0 | No |
| 4 | Plasmid | 0 | No |
| 5 | GP(Z) | 6400 | Yes |
| 6 | GP(Z) | 6400 | Yes |
| 7 | GP(Z) | 6400 | Yes |
| 8 | GP(Z) | 3200 | Yes |
| 9 | GP(Z) + NP | 6400 | Yes |
| 10 | GP(Z) + NP | 6400 | Yes |
| 11 | GP(Z) + NP | 6400 | Yes |
| 12 | GP(Z) + NP | 6400 | Yes |
| 13 | GP(Z, IC, S) + NP | 6400 | Yes |
| 14 | GP(Z, IC, S) + NP | 1600 | Yes |
| 15 | GP(Z, IC, S) + NP | 6400 | Yes |
| 16 | GP(Z, IC, S) + NP | 6400 | Yes |

Table I. Comparison of multivalent vs. monovalent genetic immunization in guinea pigs. Guinea pigs were immunized intramuscularly three times at two-week intervals with 100 μg of DNA (Plasmid, 100 μg p1012; GP(Z), 100 μg pGP(Z); GP(Z)+NP, 75 μg pGP(Z) and 25 μg pNP; GP(Z, IC, S)+NP, 25 μg each of pGP(Z), pGP(IC), pGP(S) and pNP). Serum was collected 6 weeks after the first injection and pre-challenge titers for antibody to Ebola GP (ELISA IgG) were measured by ELISA (Ksiazek, T. G. et al. 1992 J Clin Microbiol 30:947-950) and are displayed as the reciprocal endpoint dilution. Three months after the final immunization the animals were challenged as described (Xu, L. et al. 1998 Nat Med 4:37-42).

Figure 47:
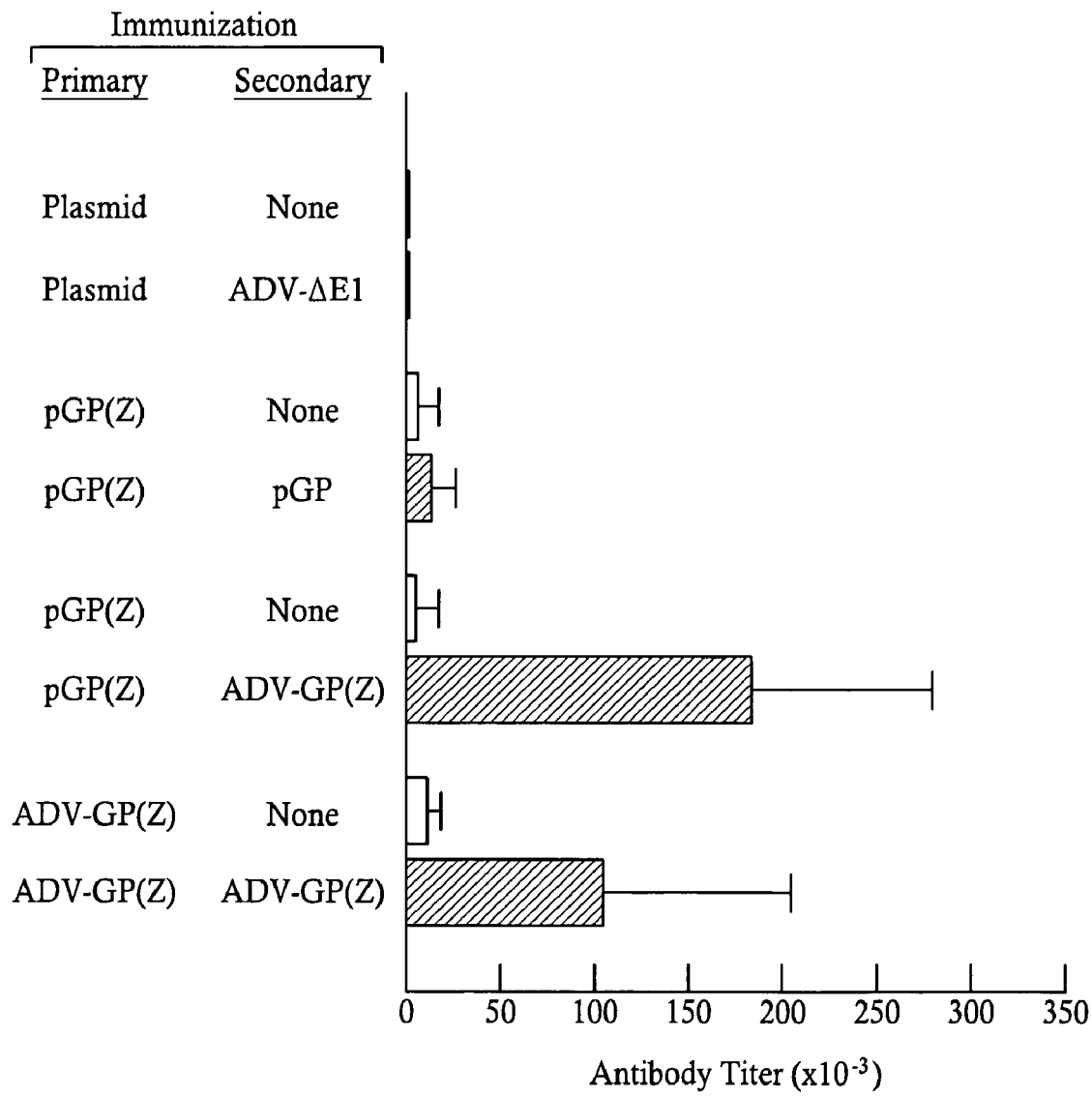
FIG. 47 shows Ebola-specific antibody responses generated by different DNA/adenovirus prime-boost combinations. Data are the means of the reciprocal endpoint dilution for each group of mice and error bars represent the standard deviation.

Because protection in the rodent model of Ebola virus infection correlated with antibody titers, and efficient humoral responses may influence clinical outcome in human disease (Baize, S. et al. 1999 Nat Med 5:423-426; Maruyama, T. et al. 1999 J Virol 73:6024-6030), we considered it important to elicit a strong humoral response for vaccines tested in primates, although cell-mediated immunity is coordinately induced and likely contributes to protection (Xu, L. et al. 1998 Nat Med 4:37-42). Recently, regimens of DNA priming followed by administration of viral vectors have demonstrated enhanced immune responses compared to vaccines using DNA alone (Sedegah, M. et al. 1998 PNAS USA 95:7648-7653; Hanke, T. et al. 1998 Vaccine 16:439-445; Robinson, H. L. et al. 1999 Nat Med 5:526-534; Schneider, J. et al. 1998 Nat Med 4:397-402). Recombinant, replication-deficient adenoviruses can be grown to high titer, infect antigen-presenting cells, and induce potent immune responses (Davis, A. R. et al. 1985 PNAS USA 82:7560-7564; Natuk, R. J. et al. 1992 PNAS USA 89:7777-7781; Xiang, Z. Q. et al. 1996 Virology 219:220-227). Adenoviruses have shown a boosting effect in mice (Xiang, Z. Q. et al. 1999 J Immunol 162:6716-6723), but the combination of DNA and adenovirus has not been tested for efficacy in an infectious challenge model, and the success of this approach in primates is yet unknown. We therefore developed a recombinant adenoviral vector that directs high level GP expression ADV-GP(Z) and used this vector to test whether a modified prime-boost strategy would augment the antibody response to Ebola virus obtained with naked DNA alone. Mice were injected with DNA and adenovirus vectors either singly or in combinations, and cell-mediated and humoral immune responses were assessed. A 10- to 100-fold increase in antibody titer was found in mice injected with DNA followed by an adenovirus boost, compared to DNA immunization alone (FIG. 47). An increase in cytotoxic T cell responses was also observed with this combination. Immunization with ADV-GP(Z) alone yielded antibody titers that were not significantly different from those obtained with the DNA prime, adenovirus boost immunization. These data suggest that immunogenicity of the Ebola GP DNA vaccine in mice is improved by boosting with recombinant adenovirus and that this strategy might represent a useful approach to enhance immune responses in non-human primates.

Whereas the rodent model has been useful in the development of a vaccine strategy, Ebola virus isolated directly from humans must first be adapted by multiple, sequential passage in rodents in order to produce a lethal infection in mice or guinea pigs (Connolly, B. M. et al. 1999 *J Infect Dis* 179: S203-S217; Bray, M. et al. 1998 *J Infect Dis* 178:651-661). Primate models of Ebola infection are thought to have a stronger predictive value for human disease and immune protection. We therefore conducted studies in non-human primates using a bimodal DNA/ADV vaccine and the multiple plasmid strategy that correlated with protection in guinea pigs. Cynomolgus macaques (*Macaca fascicularis*) received 3 injections of naked DNA vectors at 4-week intervals (FIG. 48A) and, after several months of rest which has been shown to boost immune responses (Letvin, N. L. et al. 1997 *PNAS USA* 94:9378-9383), were boosted with recombinant adenovirus expressing only the Zaire glycoprotein (FIG. 48A). Control animals received empty vectors (plasmid DNA and ADV-ΔE1 recombinant adenovirus), and vaccinated animals received the multicomponent DNA vaccine containing NP and three subtypes of Ebola GP (pGP/NP), followed by ADV-GP(Z). As expected, anti-Ebola serum antibodies could not be detected in control animals, but in animals receiving the Ebola vaccine, an antigen-specific antibody response was detected at week 12, one month after the third DNA injection (FIG. 48B). After boosting with recombinant adenovirus, antibody titers increased 10- to 20-fold over the levels obtained with DNA alone. Three months after the final immunization, antibody levels remained high, except for one animal (subject 8) whose titer dropped slightly from $5 \times 10^4$ to $1.3 \times 10^4$.

Primate cellular responses to Ebola antigens were next examined with an in vitro lymphocyte proliferation assay. In control monkeys, antigen-specific lymphocyte proliferation, measured by $^3$H-thymidine uptake, was equivalent to that in matched, unstimulated cells, resulting in a proliferation index near 1.0 for each animal (FIG. 48C). In contrast, peripheral blood mononuclear cells (PBMC) from animals immunized with the multivalent vaccine showed 9- to 20-fold increased stimulation, demonstrating a robust immune response to Ebola antigen at the cellular level. Depletion of CD4-positive lymphocytes reduced the antigen-stimulated proliferative response of PBMC from vaccinated monkeys to the level observed in control animals (FIG. 48D). Depletion of CD8-positive lymphocytes, however, did not affect Ebola antigen-specific lymphocyte proliferation. Therefore, the CD4-positive subset of lymphocytes, which provide the T cell help required for high antibody titers, contributes to the vaccine-induced cellular immune response.

Figure 49:
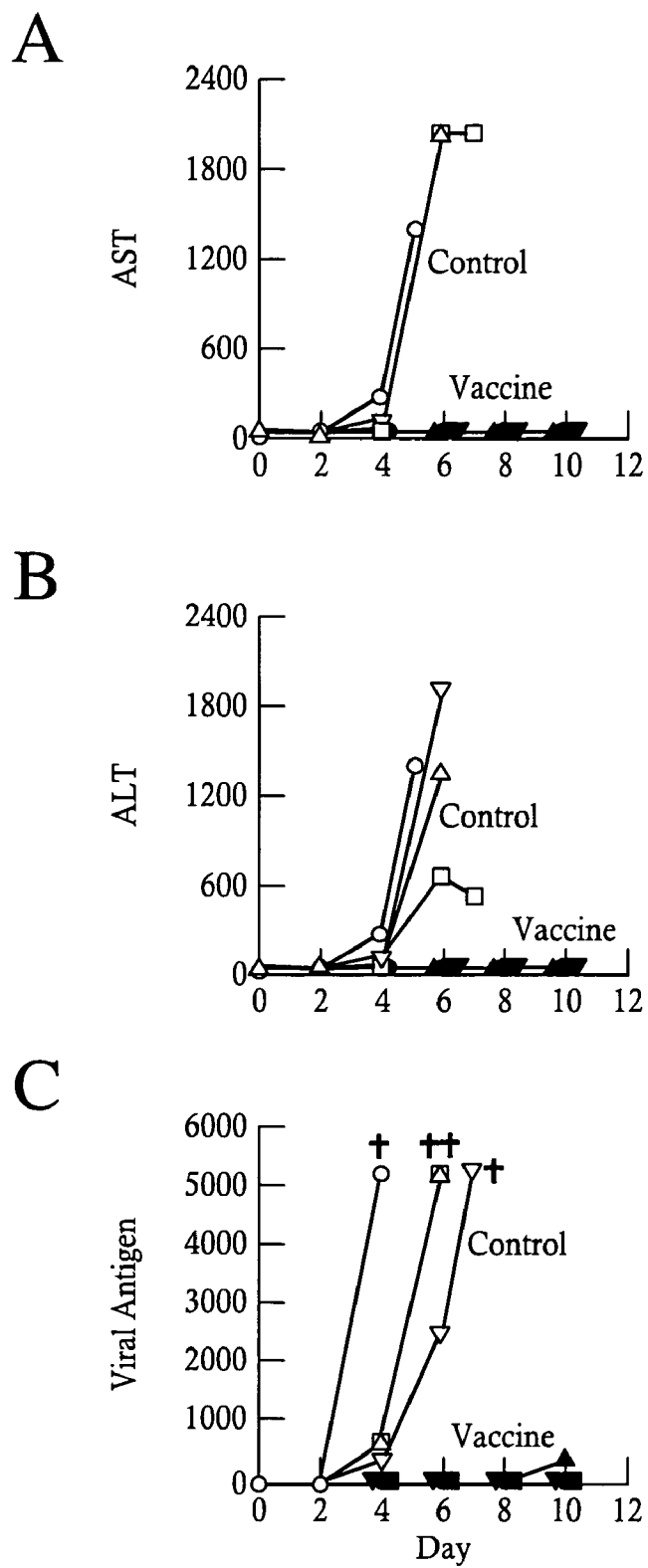
FIGS. 49 (A-C) shows protection of cynomolgus macaques against lethal challenge with Ebola virus after DNA-adenovirus immunization. A, B) Hepatic enzyme levels in monkeys after challenge with Ebola virus. Liver enzymes [alanine aminotransferase (ALT) and aspartate aminotransferase (AST)] levels in the non-human primate sera were measured by standard recommended procedures using General chemistry 12 reagent disk for the Piccolo™ Analyzer (Abaxis, Inc., Sunnyvale, Calif.). Results are shown for four immunized (closed symbols) and four control (open symbols) monkeys. C) Plasma viraemia in monkeys following infection with Ebola virus. Crosses represent time of death in control animals [days 5 (subject 1) and 6 (subjects 2 and 4)]. One control animal, subject 3, was euthanized on day 7 when it was moribund. One vaccinated animal that was resistant to infection, subject 5, was euthanized on day 10 for histological examination of tissues. By day 17, none of the animals had detectable viraemia, and they remained aviraemic for the duration of the observation period (6 months). Data are the reciprocal endpoint dilution of serum for each monkey. Results are shown for four immunized (closed symbols) and four control (open symbols) monkeys.

To determine the protective efficacy of this vaccination regimen, monkeys were challenged with a lethal dose of the wild-type Mayinga strain from the Zaire subtype of Ebola virus. In the control monkeys, blood chemistry revealed an increase in hepatic enzymes (FIG. 49A, B) that is characteristic for Ebola virus infection (Fisher-Hoch, S. P. et al. 1985 *J Infect Dis* 152:887-894). No such increase was observed in vaccinated subjects. The elevation of serum alanine aminotransferase (ALT) and aspartate aminotransferase (AST) was parallel to a dramatic increase in viraemia in all of the control animals (FIG. 49C). In contrast, no substantial increase in viral load was observed in vaccinated monkeys. The kinetics of disease progression was similar among the control animals, and the disease incidence was 100% in this group. Death occurred between days 5 and 6 for 3 animals, and the last monkey, moribund, was euthanized on day 7. In contrast, 4 out of 4 monkeys immunized with the combination DNA-adenovirus vaccine survived this lethal challenge of Ebola virus, and sterilizing immunity was achieved in 3 out of 4 subjects. The remaining animal showed a small transient rise in viral antigen; however, when followed long-term, all vaccinated animals showed no signs or symptoms of infection, and there was no detectable viraemia for more than 6 months after infection, as measured by ELISA detection of viral antigen (FIG. 49A) and end point titration analysis of cultured virus. The vaccine recipient (subject 8) that exhibited a transient low level of viraemia on day 10 returned to undetectable levels by day 17.

As the natural reservoir for Ebola virus is unknown, the potential for traditional public health measures to prevent future outbreaks is limited, thus increasing the urgency for the development of a vaccine and therapeutics in humans. The present findings demonstrate that primates can be immunized against the lethal effects of Ebola virus infection, and that sterilizing immunity can be achieved using a heterologous prime-boost strategy. A multicomponent genetic vaccine expressing Ebola virus structural proteins from diverse geographic isolates generated a strong antigen-specific immune response and resulted in the survival of immunized primates after challenge with a lethal dose of Ebola Zaire, the subtype of this virus associated with the highest number of deaths in human infections. The results of this study suggest that T-cell mediated and humoral immunity contribute to virus clearance in non-human primates, consistent with previous studies in rodents (Xu, L. et al. 1998 *Nat Med* 4:37-42; Wilson, J. et al. 2000 *Science* 287:1664 1666). Two immune parameters, antibody titer (1:75,000 vs. <1:100, P=0.001) and the cellular proliferative response (~12-fold vs. 1.4-fold, P=0.0014), provided highly significant immune correlates of protection. Studies investigating the correlates of immune protection from Ebola virus infection in humans are hampered by the aggressive nature of the virus and necessarily high level of biosafety containment. With the model of primate immunity presented here, it is envisioned as now being possible to elucidate the mechanisms of immune protection from Ebola virus infection, to advance immune-based anti-viral therapies, and to develop a human vaccine for this pathogen and even other infectious causes of hemorrhagic fever.

Descriptions of Ebola, Marburg, and Lassa Constructs

VRC 6000 VRC6000 (pVR1012-GP(Z)).
  Backbone, pVR1012 (#450) expressing Ebola Glycoprotein of Zaire Subtype. Orientation is BamHI/EcoRI/EcoRV/EcoRI/BglII)

VRC 6001 VRC6001 (pVR1012x/s-GP(Z)) No other description.
  This is the same as 6000, with the addition of an Sfi restriction site to the pVR1012 backbone.

VRC 6002 VRC6002 (PVR1012-GP(Z) delta MUC).
  The mucin-like domain of GP(Z) was deleted. 530 bp in the backbone, pVR1012 GP(Z) were deleted from EarI (2844) to BfaI(3374). This mutant can bind to the Ebola receptor.

VRC 6003 VRC6003 (pVR1012-GP(Z) delta MUC delta FUR).
  The mucin-like domain and furin-cleavage site of GP(Z) were deleted. 593 bp in the backbone, pVR1012 GP (Z) were deleted, from EarI(2844) to EarI(3437). The protein has properties similar to pVR1012-GP(Z) delta MUC.

VRC 6004 VRC6004 (pVR1012-GP(Z) delta GP2).
  A majority of the GP2 region in GP(Z) was deleted. 430 bp from the backbone, pVR1012-GP (Z) were deleted from BclI(3414) to BspEI(3844). The TM (transmembrane) region was retained.
VRC 6005 VRC6005 (pVR1012-GP(Z) delta GP2 delta C-term A).
  This is a C-terminal deletion of GP2. 267 bp were deleted from the pVR1012-GP (Z) backbone, from MscI(3623) to BspMI(3890).
VRC 6006 VRC6006 (pVR1012-GP(Z) delta GP2 delta C-term B).
  This is a smaller deletion of GP2 C-terminal. 110 bp of backbone pVR1012-GP(Z) were deleted from BstXI (3780) to BspMI(3890).
VRC 6007 VRC6007 (pVR1012-GP(Z) delta GP2 delta FUS).
  The fusion peptide in GP2 of GP(Z) was deleted in this mutant, using PCR. 47 bp from the backbone, pVR1012-GP(Z), was deleted from (3508-3555).
VRC 6008 VRC6008 (pVRO12-GP(Z) delta TM).
  The TM region of GP(Z) was truncated in this mutant. A stop codon (TGA) was added downstream of the BspMI site(3889). This protein is secreted and doesn't form a trimer.
VRC 6052 VRC 6052 (pVR1012-GP(Z) delta sGP).
  The majority of the SGP/GP homology region was deleted. 687 bp from the backbone, pVR1012-GP(Z), were deleted from HincII(2083) to HincII(2270).
VRC 6101 VRC 6101 (pVR1012x/s Ebola GP(R) (dTM)).
  The vector expresses Ebola glycoprotein (subtype Reston) without its transmembrane and intracellular domains. Using PCR, a stop codon was generated downstream of a.a. 650 of GP(R), followed by an XbaI site. This protein can be secreted and is termed GP(R)(dTM).
VRC 6110 VRC 6110 (pAdApt Ebola GP(R) (dTM)).
  An adenoviral shuttle vector expressing Ebola virus glycoprotein (Reston subtype) without its transmembrane and intracellular domains. Using PCR, a stop codon was generated downstream of a.a. 651 of GP(Reston), followed by an XbaI site. The resulting recombinant adenovirus expresses a 651 a.a. secreted glycoprotein termed GP(R)(dTM).
VRC 6200 VRC6200 (pVR1012-GP(S)).
  Backbone, pVR1012(#450), expressing Ebola Glycoprotein of the Sudan Subtype. Orientation is EcORI/EcORV/BamHI/BamHI/BamHI/XbaI.
VRC 6201 VRC 6201 (pVR1012x/s Ebola GP(S)).
  No other description, but this is the same as 6200 with the addition of an Sfi site to the 1012 backbone.
VRC 6202 VRC6202 (pVR1012-GP(S) delta TM).
  The TM region of GP(S) was truncated in this mutant. A stop codon (TGA) was added downstream of the BspMI site(xxx). This protein is secreted and doesn't form a trimer.
VRC 6300 VRC6300 (pVR1012-GP(IC)).
  Backbone, pVR1012(#450), expressing Ebola Glycoprotein of the Ivory Coast Subtype. Orientation is EcoRI/EcORV/BamHI/BamHI/BamHI/XbaI.
VRC 6301 VRC6301 (pVR1012x/s-GP(IC)).
  No other description, but this is the same as 6300 with the addition of an Sfi site to the 1012 backbone.
VRC 6302 VRC6302 (pVR1012-GP(IC) delta TM).
  The TM region of GP(IC) was truncated in this mutant. A stop codon (TGA) was added downstream of the BspMI site. This protein is secreted and doesn't form a trimer.

VRC 6303 VRC 6303 (pVR1012x/s Ebola GP (IC) (dTM)).
  A pVRC2000 based vector expressing Ebola glycoprotein (Ivory Coast subtype) without transmembrane and intracellular domains. Using PCR, a stop codon was generated downstream of a.a. 650, followed by a BglII site. The vector expresses a 650 a.a. secreted glycoprotein (a.a. 1-a.a. 650).
VRC 6310 VRC 6310 (pAdApt Ebola GP (IC) (dTM)).
  An adenoviral shuttle vector expressing Ebola glycoprotein (subtype Ivory Coast) without its transmembrane and intracellular domains. Using PCR, a stop codon was generated downstream of a.a. 651 of GP(IC). The resulting recombinant adenovirus expresses a 651 a.a secreted glycoprotein termed as GP(IC)(dTM).
VRC 6351 VRC6351 (pVR1012x/s-sGP(IC)). No other description.
VRC 6400 VRC6400 (pVR1012-NP).
  Backbone, pVR1012(#450) expressing Ebola Nucleoprotein of the Ivory Coast Subtype.
VRC 6401 VRC6401 (pVRO12x/s-NP).
  No other description, but this is the same as 6400 with the addition of an Sfi site to the 1012 backbone.
VRC 6500 VRC6500 (pVR1012-VP35).
  The backbone is pVR1012(#450). The insert is VP35 from Ebola cloned from pGEM 3Zf(+)VP35(#1213).
VRC 6600 VRC6600 (pAD/CMV-GP(dTM)(Z-CITE-S). No other description.
VRC 6601 VRC6601 (pAdApt Ebola GP(S)). No other description.
VRC 6602 VRC 6602 (pAdApt Ebola GP(S)(dTM)).
  An adenoviral shuttle vector expressing Ebola glycoprotein (Sudan subtype) without its transmembrane and intracellular domains. A stop codon was fused downstream of a.a. 650 of GP(S). The resulting recombinant adenovirus expresses a 654 a.a. secreted glycoprotein, termed as GP(S)(dTM).
VRC 6603 VRC6603 (pAdApt Ebola GP(Z)). No other description.
VRC 6604 VRC 6604 (pAdApt Ebola GP(Z)(dTM)).
  Adenoviral shuttle vector expressing Ebola glycoprotein (subtype Zaire) without its transmembrane and intracellular domains. A stop codon was fused downstream of a.a. 651 of GP(Z). The resulting recombinant adenovirus expresses a 655 a.a. secreted glycoprotein termed as GP(Z)(dTM).
VRC 6701 VRC6701 (pVR1012-Marburg).
  Marburg glycoprotein (GP) open reading frame, Musoke strain. Marburg was cloned into backbone #450(Bam (blunt)/XbaI) from VRC6700 (Xba/PvuII).
VRC 6702 VRC 6702 (pVR1012x/s Marburg GP (dTM)).
  This vector expresses the Marburg virus glycoprotein without its transmembrane and intracellular domains. Using PCR, a stop codon was generated downstream of a.a. 650 of GP(Marburg), followed by a BglII site. This protein can be secreted and termed as GP(Marburg) (dTM).
VRC 6710 VRC 6710 (pAdApt Marburg GP (dTM)).
  Adenoviral shuttle vector (pVRC1290) expressing Marburg virus glycoprotein without transmembrane and intracellular domains. Using PCR, a terminator codon was generated downstream of a.a. 650, followed by a BglII site. The resulting recombinant adenovirus expresses a 650 a.a. secreted protein (a.a. 1-a.a. 650).
VRC 6800 VRC6800 (pVR1012x/s Lassa GP). No other description.
VRC 6801 VRC6801 (pVR1012x/s Lassa GP (dTM). No other description.

VRC 6810 VRC6810 (pAdApt Lassa GP). No other description.

VRC 6811 VRC6811 (pAdApt Lassa GP (dTM)). No other description.

EXAMPLE 1

Vector construction. The construction of DNA vectors expressing Ebola Zaire glycoprotein (GP), secreted GP (SGP), and nucleoprotein (NP) has been described in Xu, L. et al. 1998 *Nat Med* 4:37-42. The GP Sudan and Ivory Coast expression vectors were constructed similarly. Briefly, GP open reading frames were generated from polymerase chain reaction after reverse transcription of RNA (RT-PCR) products of infected cell RNA using the following primers: 5' ATC TTC AGG ATC TCG CCA TGG A 3' (Sudan GP gene; NcoI>ATG; SEQ ID NO: 44), 5' GAT ATT CAA CAA AGC AGC TTG CAG 3' (Sudan GP gene; C-terminus GP stop; SEQ ID NO: 45), 5'CTA ATC ACA GTC ACC ATG GGA 3' (Ivory Coast GP gene; NcoI>ATG; SEQ ID NO: 46), 5' AAA GTA TGA TGC TAT ATT AGT TCA 3' (Ivory Coast GP gene; C-terminus GP stop; SEQ ID NO: 47) yielding the TA clones PCR2.1 Sudan and PCR2.1 Ivory Coast. The Sudan glycoprotein was digested from plasmid PCR2.1 with XbaI/HindIII, Klenow treated, and cloned into the XbaI site of p1012 (Xu, L. et al. 1998 Nat Med 4:37-42). Ivory Coast GP was digested from plasmid PCR2.1 with EcoRI, Klenow treated, and cloned into the XbaI site of p1012 (Xu, L. et al. 1998 *Nat Med* 4:37-42).

To make ADV-GP, the BamHI/EcoRI fragment of GP(Z) was digested from pGEM-3Zf(−)-GP, treated with Klenow, and inserted into HindIIIXbaI/Kle/CIP treated pRc/CMV plasmid. The resulting plasmid (PRC/CMV-GP(Z)) was digested by NruI/DraE and treated with Klenow. The NruI/DraIII/Kle fragment containing the CMV enhancer, GP(Z) DNA and bovine growth hormone polyadenylation signal was inserted into the BglII site of the adenoviral shuttle plasmid pAdBglII (Ohno, T. et al. 1994 Science 265:781-784). The adenovirus, a first generation dl 309-based Ad5 vector, contained a deletion in E1 to render the vector replication-defective and a partial deletion/substitution in E3, which disrupts the coding sequences for the E3 proteins with a relative molecular mass of 14.7 kD, 14.5 kD and 10.4 kD, respectively. The recombinant adenovirus expressing Zaire GP, ADV-GP(Z), was made according to previously published methods (Aoki, K. et al. 1999 Mol Med 5:224-231). The dose of adenovirus administered, $10^{10}$ plaque-forming units (PFU) per animal (approximately $3\times10^9$ PFU/kg), is within the range used safely in human gene therapy trials.

Animal study and safety. Eight cynomolgus macaques (*Macaca fascicularis*), 3 years of age and weighing 2-3 kg, obtained from Covance (Princeton, N.J.), were used for the immunization and challenge experiment. To obtain blood specimens and administer vaccines, the monkeys were anesthetized with Ketamine. The animals were housed singly and received regular enrichment according to the Guide for the Care and Use of Laboratory Animals (DHEW No. NIH 86-23). Just before the Ebola virus challenge and up to the end of the experiment, the animals were maintained in the Maximum Containment Laboratory (BSL-4) and fed and checked daily. One animal was euthanized that appeared moribund and was subsequently necropsied for pathologic examination. In addition, a single asymptomatic vaccinated animal was euthanized for pathologic and virologic analysis.

Mouse immunization. DNA and adenovirus vectors expressing Ebola Zaire GP or NP were constructed as described previously (Xu, L. et al. 1998 *Nat Med* 4:37-42; Ohno, T. et al. 1994 *Science* 265:781-784), with gene expression under the control of the cytomegalovirus enhancer and promoter. Mice were immunized intramuscularly with 100 µg of DNA (pGP or a p1012 plasmid control) or 10' PFU of adenovirus (ADV-GP or ADV-ΔE1 control virus) on days 0, 14, and 28 and blood was collected on day 28. On day 42, mice received an intramuscular boost with DNA or adenovirus and titers were re-measured on day 56. ELISA IgG titers were determined using 96-well plates coated with a preparation of Ebola virus antigen derived from purified virions and enriched for membrane-associated proteins (GP, VP40 and VP24) (Ksiazek, T. G. et al. 1992 *J Clin Microbiol* 30:947-950). Specific antigen binding was detected using a goat anti-human IgG(H+L)-horseradish peroxidase conjugate and ABTS/Peroxide (substrate/indicator).

Macaque immunization. For the DNA immunizations, animals received 1 mg each of DNA expressing GP(Zaire) [GP(Z)], GP(Ivory Coast) [pGP(IC)], GP(Sudan) [pGP(S)] and NP(Zaire) administered as a mixture [pGP/NP], or 4 mg empty [pGP(Z)] control plasmid bilaterally (2 mg per side) in the deltoid muscle. Immunization at weeks 0 and 4 were by IM injection, and at week 8 by Biojector. For the adenovirus boost, animals received $10^{10}$ PFU of ADV-GP (Zaire subtype) or ADV-ΔE1 (empty vector) divided into two doses administered bilaterally in the deltoid muscle. At week 32, all animals received an intraperitoneal injection of approximately 6 PFUs of Ebola virus (Zaire 1976 isolate; Mayinga strain) (Kiley, M. P. et al. 1980 *J Gen Virol* 49:333-341) in 1 ml Hanks' buffered salt solution. The virus was isolated directly from patient blood and used after a single passage in Vero cells.

ELISA IgG titers were determined as above for control (Plasmid: ADV-ΔEI) and immunized [pGP/NP: ADV-GP(Z)] monkeys. The reciprocal endpoint of dilution for each subject was at week 12 and week 24. Serum antibody levels were measured by ELISA as described (Ksiazek, T. G. et al. 1992 *J Clin Microbiol* 30:947-950).

Blood was collected from control (plasmid: ADV-AE1) or immunized [pGP/NP: ADV-GP(Z)] animals 1-3 days prior to the immunizations at weeks 4, 8 and 20, and at week 24. Blood was separated over a Percoll gradient to obtain the lymphocyte enriched population. Lymphocytes were stimulated as described (Xu, L. et al. 1998 *Nat Med* 4:37-42) for 5 days in vitro using supernatant from cells transfected with either Ebola secreted glycoprotein (SGP) or empty plasmid, and proliferation was measured by $^3$H-thymidine uptake. The proliferation index was calculated as the proliferation in wells receiving SGP divided by proliferation in wells receiving control supernatant.

Viral detection in macaques. The presence of circulating Ebola virus antigen was detected as described (Ksiazek, T. G. et al. 1992 *J Clin Microbiol* 30:947-950) by capturing VP40 protein from serial dilutions of monkey plasma. 96-well plates coated with antiVP40 mAb were used to capture antigen, and detection was with a rabbit anti-Ebola virus serum.

EXAMPLE 2

The amino acid sequences of Ebola GP(Zaire) and NP (Zaire) were obtained from Genbank: GP(Zaire), Genbank accession no. P87666; NP(Zaire), Genbank accession no. NC_002549; while GP(Sudan/Gulu) was obtained from the CDC. The amino acid sequences were then back-translated to DNA sequences using mammalian preferred codons. Serial 75 bp oligos with 25 bp overlapping were prepared to cover the entire gene. The oligos were then assembled into intact mammalian genes containing preferred codons using PCR. In the design, a stop codon was introduced in front of the predicted transmembrane domains of GP(Zaire) (a.a. 648-676) and GP (Sudan/Gulu) (a.a. 648-676) so that this region was excluded from these synthetically created genes. The deletions also led to the loss of a 4 a.a. cytoplasmic region in both constructs. Final sequencing of the Ebola GP (Zaire) sequence revealed 10 divergent amino acids from the laboratory GP sequence, which was used in our animal studies and these were corrected by site-directed mutagenesis. These inserts were cloned into p1012 x/s by XbaI/SalI.

Construction of CMV/R-GP(S/G)(ΔTM)/h

The codon-modified, transmembrane domain deleted form of the Ebola GP (Sudan/Gulu) gene was excised from p1012 (x/s)-GP(S/G)(ΔTM)/h using SalI/KpnI, and inserted into the SalI/KpnI digested CMV/R1MCS plasmid.

Construction of CMV/R GP(Z) (ΔTM)/h

The codon-modified, transmembrane domain deleted form of the Ebola GP (Zaire) gene was excised from p1012 x/s-GP (Z)(dTM)/h SalI/BglII sites and cloned into the SalI/BglII sites of the CMV/R plasmid.

Construction of CMV/R Ebola NP

The NotI-KpnI fragment from VRC6400 (pVR1012-NP) expressing Ebola nucleoprotein of Zaire Subtype was excised and cloned into the NotI/KpnI sites of the CMV/R plasmid.

EXAMPLE 3

Improved Non-Viral Mammalian Expression Vector

This invention provides an improved mammalian expression vector which generates a higher level of protein expression than vectors currently in use.

Initially, 3 new vectors, each containing a different enhancer, were developed and tested. The RSV enhancer, the mouse ubiquitin enhancer (mUBB), and the CMV enhancer (Xu et al. 1998 *Nature Med.* 4:37-42) were each combined with the HTLV-1 R region (Takebe et al. 1988 *Mol Cell Biol* 8:466-472) to create separate vectors. When these 3 vectors were compared to the backbone containing the CMV enhancer in combination with the CMV translational enhancer and intron (CMVint), which is currently the most effective vector, in vitro data showed that expression with the vector containing the CMV/R was increased 5-10 fold compared to CMV/int, and immunological studies showed induction of significantly higher CD4 and CD8 T cell responses compared to CMVint. Both in vivo and in vitro responses were markedly higher with this new vector. Neither of the other two vectors produced comparable results.

The expression vector is unique in that it uses a specific translational enhancer in combination with specific enhancer/promoters to yield high levels of expression and enhanced immunogenicity for DNA vaccines. This is particularly important because the potency of these vaccines in humans is marginal and generic improvements can serve as important platforms to make the technology practical for human use. The expression vector cassettes can be used in other gene based vaccines as well, or for production of recombinant proteins from eukaryotic expression vectors. The invention is useful in the production of genetic vaccines and gene therapies for a wide variety of diseases, including HIV and other viral diseases and cancer.

FIG. 50. Enhanced Expression of Modified CMV Expression Vector, CMV/R.

Mouse fibroblast 3T3 cells were transfected with (A) vector alone (lane 1), CMVint-gp-145(dCFI) (lane 2), CMV/R-gp145(dCFI) (lane 3) or (B) mUBB-gp145(dCFI) (lane 4), mUBB/R-gp145(dCFI) (lane 5) in 6-well tissue culture dishes with 0.5 ug of the corresponding plasmids using calcium phosphate. 24 hours after transfection, cells were harvested and lysed in lysis buffer (50 mM HEPES, 150 mM NaCl, 1% NP-40, Mini Complete protease inhibitor cocktail (Roche)). 10 μg of total protein of each sample were separated on a 4-15% gradient gel using SDS-PAGE, followed by protein transfer and Western blot analysis. Human HIV-IgG (1:5000) was used as the primary antibody, and HRP-conjugated goat anti-human IgG (1:5000) as the secondary antibody. The membrane was developed using the ECL Western blot developing system. The arrow indicates the specific band for the HIV Env gp145(ΔCFI) polyprotein.

Figure 51:
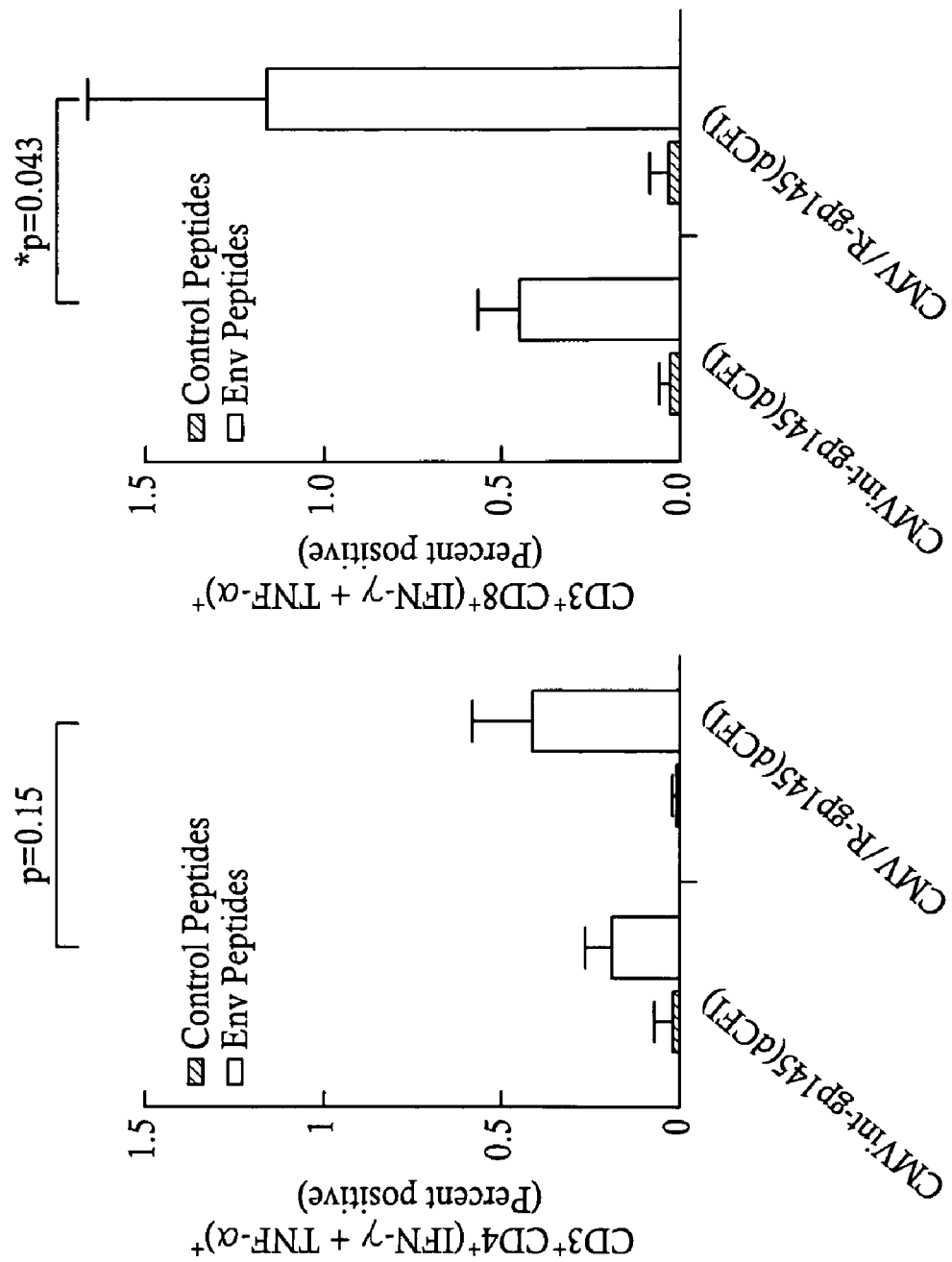
FIG. 51 shows enhanced immunogenicity of modified CMV expression vector, CMV/R, in mice.

FIG. 51. Enhanced Immunogenicity of Modified CMV Expression Vector, CMV/R, in Mice.

Five mice in each group were immunized with 50 μg of the indicated plasmid DNA at weeks 0, 2, and 6. 10 days after the last injection, splenocytes from each mouse were harvested and stimulated using a pool of control peptides (15 mer), or a pool of HIV Env peptides (15 mer) for 6 hours. The stimulated splenocytes were stained using a cocktail of antibodies containing PE-anti-mouse CD3, PerCP-anti-mouse CD4, APC-anti-mouse CD8, FITC-anti-mouse IFN-γ and FITC-anti-mouse TNF-α. The samples were analyzed by flow cytometry. CD3/CD4/IFN-γ/TNF-αand CD3/CD8/IFN-γ/TNF-α positive cell numbers were measured using FloJo software (Treestar).

The CMV Enhancer/Promoter. R Region (HTVL-1), CMV IE Splicing Acceptor Sequence

```
(SEQ ID NO: 52):

CCATTGCATACGTTGTATCCATATCATAATATGTACATTTATATTGGCTC

ATGTCCAACATTACCGCCATGTTGACATTGATTATTGACTAGTTATTAAT

AGTAATCAATTACGGGGTCATTAGTTCATAGCCCATATATGGAGTTCCGC

GTTACATAACTTACGGTAAATGGCCCGCCTGGCTGACCGCCCAACGACCC

CCGCCCATTGACGTCAATAATGACGTATGTTCCCATAGTAACGCCAATAG

GGACTTTCCATTGACGTCAATGGGTGGAGTATTTACGGTAAACTGCCCAC

TTGGCAGTACATCAAGTGTATCATATGCCAAGTACGCCCCCTATTGACGT

CAATGACGGTAAATGGCCCGCCTGGCATTATGCCCAGTACATGACCTTAT

GGGACTTTCCTACTTGGCAGTACATCTACGTATTAGTCATCGCTATTACC

ATGGTGATGCGGTTTTGGCAGTACATCAATGGGCGTGGATAGCGGTTTGA

CTCACGGGGATTTCCAAGTCTCCACCCCATTGACGTCAATGGGAGTTTGT

TTTGGCACCAAAATCAACGGGACTTTCCAAAATGTCGTAACAACTCCGCC

CCATTGACGCAAATGGGCGGTAGGCGTGTACGGTGGGAGGTCTATATAAG

CAGAGCTCGTTTAGTGAACCGTCAGATCGCCTGGAGACGCCATCCACGCT

GTTTTGACCTCCATAGAAGACACCGGGACCGATCCAGCCTCCATCGGCTC

GCATCTCTCCTTCACGCGCCCGCCGCCTTACCTGAGGCCGCCATCCACGC
```

-continued

```
CGGTTGAGTCGCGTTCTGCCGCCTCCCGCCTGTGGTGCCTCCTGAACTAC
GTCCGCCGTCTAGGTAAGTTTAGAGCTCAGGTCGAGACCGGGCCTTTGTC
CGGCGCTCCCTTGGAGCCTACCTAGACTCAGCCGGCTCTCCACGCTTTGC
CTGACCCTGCTTGCTCAACTCTAGTTAACGGTGGAGGGCAGTGTAGTCTG
AGCAGTACTCGTTGCTGCCGCGCGCGCCACCAGACATAATAGCTGACAGA
CTAACAGACTGTTCCTTTCCATGGGTCTTTTCTGCAG
```

1-741: CMV Enhancer/Promoter 742-972: HTLV-1 R region 973-1095: CMV/IE Splicing Acceptor While the present invention has been described in some detail for purposes of clarity and understanding, one skilled in the art will appreciate that various changes in form and detail can be made without departing from the true scope of the invention. All figures, tables, and appendices, as well as patents, applications and publications referred to above are hereby incorporated by reference.

What is claimed is:

1. A vaccine comprising an adenoviral vector comprising a sequence encoding Ebola Zaire glycoprotein and being at least 95% identical to the sequence encoding Ebola Zaire glycoprotein in the construct VRC6603 (SEQ ID NO:28).

2. The sequence in vaccine of claim 1 wherein the sequence encoding Ebola Zaire glycoprotein is VRC6603 (SEQ ID: NO:28).

3. A composition for boosting an immune response to a viral antigen in an individual, comprising an adenoviral vector comprising a sequence encoding Ebola Zaire glycoprotein and being at least 95% identical to the sequence encoding Ebola Zaire glycoprotein in the construct VRC6603 (SEQ ID NO:28).

4. The sequence in composition of claim 3 wherein the sequence encoding Ebola Zaire glycoprotein is VRC6603 (SEQ ID: NO:28).

5. A method of boosting an immune response to a viral antigen in an individual comprising administering to said individual a composition comprising an adenoviral vector comprising a sequence encoding Ebola Zaire glycoprotein and being at least 95% identical to the sequence encoding Ebola Zaire glycoprotein in the construct VRC6603 (SEQ ID NO:28).

6. The sequence in method of claim 5 wherein the sequence encoding Ebola Zaire glycoprotein is VRC6603 (SEQ ID: NO:28).

7. The method of claim 5 wherein the viral antigen is Ebola virus.

8. The method of claim 6 wherein the administration is by injection.

9. The method of claim 8 wherein VRC6603 is administered at a dose of $5 \times 10^7$ to $1 \times 10^{12}$ particles/injection.

* * * * *

UNITED STATES PATENT AND TRADEMARK OFFICE
CERTIFICATE OF CORRECTION

PATENT NO. : 7,635,688 B2
APPLICATION NO. : 10/491121
DATED : December 22, 2009
INVENTOR(S) : Nabel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 796 days.

Signed and Sealed this

Ninth Day of November, 2010

David J. Kappos
*Director of the United States Patent and Trademark Office*